United States Patent
Liotta et al.

(10) Patent No.: US 9,079,852 B2
(45) Date of Patent: Jul. 14, 2015

(54) NMDA RECEPTOR ANTAGONISTS FOR NEUROPROTECTION

(71) Applicants: Dennis C. Liotta, Atlanta, GA (US);
James P. Snyder, Atlanta, GA (US);
Stephen F. Traynelis, Decatur, GA (US); Lawrence Wilson, Atlanta, GA (US); Cara Mosley, Atlanta, GA (US);
Raymond J. Dingledine, Atlanta, GA (US); Scott Myers, Atlanta, GA (US);
Yesim Altas Tahirovic, Decatur, GA (US)

(72) Inventors: Dennis C. Liotta, Atlanta, GA (US);
James P. Snyder, Atlanta, GA (US);
Stephen F. Traynelis, Decatur, GA (US); Lawrence Wilson, Atlanta, GA (US); Cara Mosley, Atlanta, GA (US);
Raymond J. Dingledine, Atlanta, GA (US); Scott Myers, Atlanta, GA (US);
Yesim Altas Tahirovic, Decatur, GA (US)

(73) Assignees: Emory University, Atlanta, GA (US);
NeurOp, Inc., Atlanta, DE (US)

( * ) Notice: Subject to any disclaimer, the term of this patent is extended or adjusted under 35 U.S.C. 154(b) by 0 days.

(21) Appl. No.: 13/862,647

(22) Filed: Apr. 15, 2013

(65) Prior Publication Data
US 2014/0031363 A1    Jan. 30, 2014

Related U.S. Application Data

(63) Continuation of application No. 12/165,308, filed on Jun. 30, 2008, now Pat. No. 8,420,680.

(60) Provisional application No. 60/947,276, filed on Jun. 29, 2007, provisional application No. 60/949,120, filed on Jul. 11, 2007, provisional application No. 60/985,082, filed on Nov. 2, 2007, provisional application No. 61/127,105, filed on May 9, 2008.

(51) Int. Cl.
| | |
|---|---|
| A61K 31/421 | (2006.01) |
| A61K 31/4166 | (2006.01) |
| A61K 31/495 | (2006.01) |
| C07D 241/04 | (2006.01) |
| C07D 263/18 | (2006.01) |
| C07D 233/08 | (2006.01) |
| C07D 209/34 | (2006.01) |
| C07C 217/20 | (2006.01) |
| C07C 235/20 | (2006.01) |
| C07C 311/08 | (2006.01) |
| C07D 215/227 | (2006.01) |
| C07D 233/34 | (2006.01) |
| C07D 235/26 | (2006.01) |

(Continued)

(52) U.S. Cl.
CPC ............ *C07D 209/34* (2013.01); *C07C 217/20* (2013.01); *C07C 235/20* (2013.01); *C07C 311/08* (2013.01); *C07D 211/52* (2013.01); *C07D 213/74* (2013.01); *C07D 215/227* (2013.01); *C07D 233/32* (2013.01); *C07D 233/34* (2013.01); *C07D 235/26* (2013.01); *C07D 263/58* (2013.01); *C07D 295/088* (2013.01)

(58) Field of Classification Search
USPC ................... 514/386, 252.13, 376; 548/316.4, 548/225.1, 311.1; 544/358
See application file for complete search history.

(56) References Cited

U.S. PATENT DOCUMENTS 4,210,753 A * 7/1980 Tominaga et al. ............. 544/128
4,608,383 A   8/1986 Wiedemann et al.

(Continued)

FOREIGN PATENT DOCUMENTS

DE    19837386    2/1999
EP    1988077     11/2008

(Continued)

OTHER PUBLICATIONS

Wolff et al. (Burger's Medicinal Chemistry, 5th Ed., vol. 1, pp. 975-977, 1994).

(Continued)

*Primary Examiner* — Kamal Saeed
*Assistant Examiner* — Janet L Coppins
(74) *Attorney, Agent, or Firm* — King & Spalding

(57) ABSTRACT

Provided are compounds, pharmaceutical compositions and methods of treatment or prophylaxis of disorders associated with NMDA receptor activity, including neuropathic pain, stroke, traumatic brain injury, epilepsy, and related neurologic events or neurodegeneration. Compounds are of the general Formula I, or a pharmaceutically acceptable salt, ester, prodrug or derivative thereof are provided:

Formula I

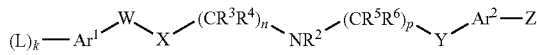

wherein:
each $(L)_k$-$Ar^1$ is a substituted or unsubstituted, mono or bicyclic aryl or heteroaryl; W is a bond, alkyl, or alkenyl; X is a bond, $NR^1$ or O and each $R^1$ and $R^2$ is independently H, alkyl, alkenyl or aralkyl or $R^1$ and $R^2$ taken together form a 5-8 membered ring; $R^3$-$R^6$ are selected from certain specific substituents or a carbonyl; Y is a bond, O, S, SO, $SO_2$, $CH_2$, NH, N(alkyl), or NHC(=O); and Z is OH, $NR^6R^7$, $NR^8SO_2(alkyl)$, $NR^8C(O)NR^6R^7$, $NR^8C(O)O(alkyl)$, $NR^8$-dihydrothiazole, or $NR^8$-dihydroimidazole or wherein Z can fuse with $Ar^2$ to form selected heterocycles.

23 Claims, No Drawings

(51) Int. Cl.

| | |
|---|---|
| C07D 263/58 | (2006.01) |
| C07D 295/088 | (2006.01) |
| C07D 211/52 | (2006.01) |
| C07D 213/74 | (2006.01) |
| C07D 233/32 | (2006.01) |

(56) References Cited

U.S. PATENT DOCUMENTS

| | | |
|---|---|---|
| 4,906,779 A | 3/1990 | Weber et al. |
| 4,924,008 A | 5/1990 | Abou-Gharbia et al. |
| 4,957,909 A | 9/1990 | Abou-Gharbia et al. |
| 4,959,366 A | 9/1990 | Cross et al. |
| 4,994,459 A | 2/1991 | Butera et al. |
| 4,994,467 A | 2/1991 | Zimmerman |
| 5,013,540 A | 5/1991 | Redburn |
| 5,034,400 A | 7/1991 | Olney |
| 5,039,528 A | 8/1991 | Olney |
| 5,093,525 A | 3/1992 | Weber |
| 5,095,009 A | 3/1992 | Whitten |
| 5,106,847 A | 4/1992 | Salituro |
| 5,118,675 A | 6/1992 | Jirkovsky |
| 5,124,319 A | 6/1992 | Baudy |
| 5,132,313 A | 7/1992 | Kozikowski |
| 5,179,085 A | 1/1993 | Bigge |
| 5,189,054 A | 2/1993 | Salituro |
| 5,190,976 A | 3/1993 | Weber |
| 5,192,751 A | 3/1993 | Thor |
| 5,194,430 A | 3/1993 | Whitten |
| 5,262,568 A | 11/1993 | Weber |
| 5,318,985 A | 6/1994 | McDonald |
| 5,321,012 A | 6/1994 | Mayer |
| 5,326,756 A | 7/1994 | Whitten |
| 5,336,689 A | 8/1994 | Weber et al. |
| 5,385,903 A | 1/1995 | Steppuhn |
| 5,385,947 A | 1/1995 | Godel |
| 5,395,822 A | 3/1995 | Izumi |
| 5,441,963 A | 8/1995 | McDonald |
| 5,470,844 A | 11/1995 | Whitten |
| 5,474,990 A | 12/1995 | Olney |
| 5,489,579 A | 2/1996 | McDonald |
| 5,491,153 A | 2/1996 | Salituro |
| 5,498,610 A | 3/1996 | Chenard |
| 5,502,058 A | 3/1996 | Mayer |
| 5,519,048 A | 5/1996 | Salituro |
| 5,538,958 A | 7/1996 | Whitten |
| 5,556,838 A | 9/1996 | Mayer |
| 5,559,154 A | 9/1996 | Weber |
| 5,563,157 A | 10/1996 | Harrison |
| 5,587,384 A | 12/1996 | Zhang |
| 5,594,007 A | 1/1997 | Chenard |
| 5,605,911 A | 2/1997 | Olney |
| 5,606,063 A | 2/1997 | Harrison |
| 5,614,509 A | 3/1997 | Turski |
| 5,616,580 A | 4/1997 | Olney |
| 5,629,307 A | 5/1997 | Olney |
| 5,633,379 A | 5/1997 | Allgeier |
| 5,637,622 A | 6/1997 | Weber |
| 5,654,281 A | 8/1997 | Mayer |
| 5,675,018 A | 10/1997 | Salituro |
| 5,703,107 A | 12/1997 | Salituro |
| 5,710,139 A | 1/1998 | Swahn |
| 5,710,168 A | 1/1998 | Chenard |
| 5,714,500 A | 2/1998 | Griffith |
| 5,753,657 A | 5/1998 | Aloup |
| 5,767,130 A | 6/1998 | Olney |
| 5,767,162 A | 6/1998 | Weber |
| 5,777,114 A | 7/1998 | Aloup |
| 5,783,572 A | 7/1998 | Mowbray |
| 5,783,700 A | 7/1998 | Nichols |
| 5,798,390 A | 8/1998 | Weber |
| 5,834,465 A | 11/1998 | Olney |
| 5,834,479 A | 11/1998 | Mayer |
| 5,840,731 A | 11/1998 | Mayer |
| 5,863,922 A | 1/1999 | Mayer |
| 5,866,585 A | 2/1999 | Fogel |
| 5,869,498 A | 2/1999 | Mayer |
| 5,888,996 A | 3/1999 | Farb |
| 5,889,026 A | 3/1999 | Alanine |
| 5,902,815 A | 5/1999 | Olney |
| 5,919,826 A | 7/1999 | Caruso |
| 5,922,716 A | 7/1999 | Aloup |
| 5,925,634 A | 7/1999 | Olney |
| 5,952,344 A | 9/1999 | Alanine |
| 5,958,919 A | 9/1999 | Olney |
| 5,962,472 A | 10/1999 | Bourson |
| RE36,397 E | 11/1999 | Zhang |
| 5,981,553 A | 11/1999 | Farr |
| 5,990,126 A | 11/1999 | Park |
| 6,007,841 A | 12/1999 | Caruso |
| 6,025,369 A | 2/2000 | Rosenquist |
| 6,034,134 A | 3/2000 | Gold |
| 6,054,451 A | 4/2000 | Caruso |
| 6,057,358 A | 5/2000 | Chung |
| 6,057,373 A | 5/2000 | Fogel |
| 6,071,929 A | 6/2000 | Alanine |
| 6,071,966 A | 6/2000 | Gold |
| 6,080,743 A | 6/2000 | Acklin |
| 6,083,941 A | 7/2000 | Farb |
| 6,096,743 A | 8/2000 | Shishikura |
| 6,177,434 B1 | 1/2001 | Kopke |
| 6,180,786 B1 | 1/2001 | Metz, Jr. |
| 6,184,236 B1 | 2/2001 | Alanine et al. |
| 6,187,338 B1 | 2/2001 | Caruso |
| 6,194,000 B1 | 2/2001 | Smith |
| 6,197,820 B1 | 3/2001 | Sontheimer |
| 6,200,990 B1 | 3/2001 | Namil |
| 6,242,456 B1 | 6/2001 | Shuster |
| 6,251,948 B1 | 6/2001 | Weber |
| 6,258,827 B1 | 7/2001 | Chenard |
| 6,265,426 B1 | 7/2001 | Alanine |
| 6,274,633 B1 | 8/2001 | Franks |
| 6,284,774 B1 | 9/2001 | Wright |
| 6,284,776 B1 | 9/2001 | Meltzer |
| 6,294,583 B1 | 9/2001 | Fogel |
| 6,339,093 B1 | 1/2002 | Alanine |
| 6,984,637 B2 | 1/2006 | Gong et al. |
| 7,375,136 B2 | 5/2008 | Traynelis et al. |
| 2004/0054013 A1 | 3/2004 | Tai et al. |
| 2006/0199864 A1 | 9/2006 | Traynelis et al. |
| 2006/0241121 A1 | 10/2006 | Greenlee et al. |

FOREIGN PATENT DOCUMENTS

| | | |
|---|---|---|
| GB | 1325876 | 8/1973 |
| GB | 1361863 | 7/1974 |
| WO | WO 91/13865 | 9/1991 |
| WO | WO 96/05174 | 8/1994 |
| WO | WO 96/00715 | 1/1996 |
| WO | WO 98/33771 | 1/1998 |
| WO | WO 01/02406 | 1/2001 |
| WO | WO 02/725242 | 9/2002 |
| WO | WO 2004/035534 | 4/2004 |
| WO | WO 2004/100956 | 11/2004 |
| WO | WO 2006/010968 | 2/2006 |
| WO | WO 2006/023957 | 3/2006 |
| WO | WO 2006/058753 | 6/2006 |
| WO | WO 2007/045893 | 4/2007 |
| WO | WO 2007/998282 | 9/2007 |
| WO | WO 2007/099828 | 3/2008 |

OTHER PUBLICATIONS

U.S. Appl. No. 12/151,633, Traynelis et al.
Bradford, H.R., "Glutamate, GABA, and Epilepsy," Progress in Neurobiology 47:477-511, 1995.
Claiborne, C.F. et al., "Orally efficacious NR2B-selective NMDA receptor antagonists," Bioorganic & Medicinal Chemistry Letters 13:697-700, 2003.
Curtis, N. R., "Novel N.sup.1-(benzyl)dinnamamidine derived NR2B subtype-selective NMDA receptor antagonists," Bioorganic & Medicinal Chemistry Letters 13:693-696, 2003.
Dingledine, R. et al., "The glutamate receptor ion channels," Pharmacological Reviews 51 (1):7-61, 1999.

(56) References Cited

OTHER PUBLICATIONS

McNamara, J. O., "Drugs effective in the therapy of the epilepsies," Chapter 21 In Goodman & Gliman's: The Pharmacological Basis of Therapeutics, J. G. Hardman and L.E. Limbird (eds.) McGraw Hill, New York, pp. 521-547, 2001.
Obrenovitch, T. P. et al., "Is high extracellular glutamate the key to excitotoxicity in traumatic brain injury?" J. Neurotrama 14(10):677-698, 1997.
http://www.emedicine.com/neuro/topic488.htm, Lutsep & Clark "Neuroprotective Agents in Stroke", Apr. 30, 2004.
Billups and Attwell (1996), Nature (Lond) 379:171-173.
Chester, M (1990), Prog Neurobiol 34:401-427.
Felsby et al. (1996), Pain 64:283-291.
Fischer et al. (1997), J Pharmacol Exp Ther 283:1285-1292.
Fletcher et al. (1995), Br J pharmacol 116(7):2791-2800.
Gray et al. (1997), J Neurosurg Anesthesiol 9:180-187.
Herrling, P.L., (1997) "Excitatory ammo acod clinical results with antagonists" Academic Press.
Hoyte L. et al (2004) "The Rise and Fall NMDA Antagonists for Ischemic Stroke Current Molecular Medicine" 4(2): 131-136.
Jendelova & Sykova (1991) Glia 4:56-63.
Kaku et al. (1993), Science 260:1516-1518.
Katsura et al (1992) Euro J Neurosci 4:166-176.
Kew et al. (1998), BrJ Pharmacol 123:463-472.
Kumamoto, E (1996), Magnes Res 9(4):317-327.
Lynch and Gallagher (1996), J Pharmacol Exp Ther 279:154-161.
McCool and Lovinger (1995), Neuropharmacology 34:621-629.
Menniti et al. (1997), Eur J Pharmacol 331:117-126, Ro 25-6981.
Munir and McGonigle (1995), J Neurosci 15:7847-7860.
Mutch & Hansen (1984) J Cereb Blood Flow Metab 4:17-27.
Nedergaard et al. (1991) Am J Physiol 260(Pt3): R581-588.
O'Donnell and Bickler (1994), Stroke 25:171-177.
Parsons et al. (1998) Drug News Perspective II:523 569.
Perrson et al. (1998), Acta Anaesthesiol Scand 42:750-758.
Pud et al. (1998), Pain 75:349-354.
Siesjo et al. (1985) J Cereb Blood Flow Metab 5:47-57.
Siesjo, BK (1985), Progr Brain Res 63:121-154.
Smith et al. (1986), J Cereb Blood Flow Metab 6:574-583.
Steece-Collier et al., (2002) Exper. Neurol., 163:239-243.
Stubhaug et al. (1997), Acta Anaesthesiol Scand 41:1124-1132.
Sykova & Sbvoboda (1990) Brain Res 512:181-189.
Sykova et al. (1992), Can J Physiol Pharamacol 70: Suppl S301-309.
Tombaugh and Sapolsky (1993), J Neurochem 61:793-803.
Traynelis et al. (1998), J Neurosci 18:6163-6175.
Velisek et al. (1994), Exp Brian Res 101:44-52.
Metman et al. (1998), Neurology 50:1323-1326.
Vornov et al. (1996), J Neurochem 67:2379-2389.
Xiong & Stringer (2000), J Neurophysiol 83:3519-3524.
Indian Journal of Chemistry, 1982, vol. 21B, p. 914-918.
Pharmazie, 1983, 38(6), p. 409-414.
Pharmazie, 1999, 54, p. 743-745.
J. Med. Chem., 1991, 34, p. 3212-3228.
J. Med. Chem., 1991, 34, p. 1570-1577.
Indian Journal of Chemistry, 1977, vol. 15B, p. 466-472.
Chinese Journal of Organic Chemistry, 2006, 26, 3, p. 364-367.
Journal of Enzyme Inhibition and Medicinal Chemistry, 2005, 20(6), p. 525-532.
Office Action for corresponding Japanese Patent Application No. 2010-515231; May 7, 2013.
Ettmayer, Peter. Medicinal Chemistry, Lessons Learned from Marketed and InvestigationalProdrugs, 47(10) (2004) 2394-2404.
Stella, Valentino J, Expert Opinion of Therapeutic Patents, Prodrugs as therapeutics, 2004 14(3): 277-280.
Testa, Bernard, Biochemical Pharmacology, Prodrug Research: Futile or Fertile? 68 (2004) 2097-2106.
Wolff et al. (Burger's Medicinal Chemistry, $5^{th}$Ed., vol. 1, pp. 975-977, 1994).
Yous et al. "Lipid-lowering properties of 6-benzothiazolone and structurally related compounds" Journal of Enzyme inhibitions and Medicinal Chemistry, Dec. 2005; 20 (6): 525-532.
Alanine, A. et al., "1-benzyloxy-4,5-dihydro-1H-imidzzol-2-yl-amines, a novel class of NR1/2B subtype selective NMDA receptor antagonists," Bioorganic & Medicinal Chemistry Letters 13:3155-3159, 2003.
Bradford, H.R., "Glutamate, GABA, and Epilepsy," Progress in Neurobiology 47:4'77-511, 1995.
Choi, D., "Antagonizing excitotoxicity: A therapeutic strategy for stroke?" Mount Sinai J. Med. 65(2):133-138, 1998.
Claiborne, C.F. et al., "Orally efficacious NR2B-selective NMDA receptor antagonists,"Bioorganic & Medicinal Chemistry Letters 13:697-700, 2003.
Curtis, N. R., "Novel $N^{1}$-(benzyl)dinnamarnidine derived NR2B subtype-selective NMDA receptor antagonists," Bioorganic & Medicinal Chemistry Letters 13:693-696, 2003.
Dingledine, R et al., "The glutamate receptor ion channels," Pharmacological Reviews 51 (1):7-61, 1999.
Dirnagl, U. et al., "Pathobiology of ischaemic stroke: an integrated view," TINS 22(9):391397, 1999.
McNamara, J 0 , "Drugs effective in the therapy of the epilepsies," Chapter 21 in Goodman & Gilman's: The Pharmacological Basis of Therapeutics, J. G. Hardman and L.E. Limbird (eds.) McGraw Hill, New York, pp. 521-547, 2001.
Mott, D. D. et al., "Phenyethanolamines inhibit NMDA receptors by enhancing proton inhibition," Nature Neuroscience 1(8):659-667, 1998.
Muir, K. W. et al., "Clinical experiences with excitatory amino acid antagonist drugs," Stroke 26:503-513, 1995.
Obrenovitch, T. P. et al., "Is high extracellular glutamate the key to excitotoxicity in traumatic brain injury?" J. Neurotrama 14(10):677698, 1997.
Rothstein, J. D. et al., "Excitotoxic destruction facilities brain tumor growth," Nature Medicine 7(9):994-995, 2001.
Rzeski, W. et al., "Glutamate antagonists limit tumor growth," Proc. Natl. Acad. Sci. 98(11):6372-6377, 2001.
Takano, T. et al., "Glutamate release promotes growth of malignant gliomas," Nature Medicine 7(9):1010-1015, 2001.
Traynelis, S. F. et al., "Proton inhibition of N-methyl-D-aspartate receptors in cerebellar neurons," Nature 345:347-350, 1990.
Traynelis, S. F. et al., "Control of proton sensitivity of the NMDA receptor by RNA splicing and polyamines," Science 268:873-876, 1995.
International Search Report of International Application No. PCT/US02/07053, date of mailing Sep. 11, 2002, 2 pages.
http://www.emedicine.comineuro/topic488.htm, Lutsep & Clark "Neuroprotective Agents in Stroke", Apr. 30, 2004.
Amato et al., (1994), J Neurophysiol 72:1686-1696.
Balestrino & Somjen (1988) J Physiol 396:247-266.
Barann et al., (1998), Naunyn Schmiedebergs Arch Pharmacol 358:145-152.
Billups and Attwell (1996), Nature (Loud) 379:171-173.
Blandini and Greenamyre (1998), Fundam Clin Pharmacol 12:4-12.
Blanpied et al., (1997), J Neurophys 77:309-323.
Brimecombe et al. (1998), J Pharmacol Exp Ther 286 (2):627-634.
Chester and Kaila (1992), Trends Neurosci 15:396-402.
Chesler, M (1990), Prog Neurobiol 34:401-427.

* cited by examiner

NMDA RECEPTOR ANTAGONISTS FOR NEUROPROTECTION

CROSS REFERENCE TO RELATED APPLICATIONS

This application is a continuation of U.S. Patent Application No. 12,/165,308, filed Jun. 30, 2008, which claims priority to U.S. Provisional Application No. 60/947,276, filed Jun. 29, 2007; U.S. Provisional Application No. 60/949,120, filed Jul. 11, 2007; U.S. Provisional Application No. 60/985,082, filed Nov. 2, 2007; and U.S. Provisional Application No. 61/127,105, filed May 9, 2008. The complete disclosure of each above-identified application is fully incorporated herein by reference.

This invention was made with government support from the National Institutes of Health under NIH Small Business Innovation Research (SBIR) Grant No. 2 R44 NS049666-02A1. The government has certain rights in the invention.

FIELD OF THE INVENTION

The present invention is in the area of NMDA receptor blockers, including pH-sensitive NMDA receptor blockers, as neuroprotective drugs, and includes methods and compositions for the treatment of neurodegeneration resulting from NMDA-receptor activation.

BACKGROUND OF THE INVENTION

The NMDA subtype of glutamate-gated ion channels mediates excitatory synaptic transmission between neurons in the central nervous system (Dingledine et al. (1999), Pharmacological Reviews 51:7-61). Animal models of stroke and brain trauma confirm that glutamate released from affected neurons can overstimulate N-methyl-D-aspartate (NMDA) receptors, which in turn causes neuronal death. Therefore, compounds that block NMDA receptors have been considered candidates for treatment of stroke and head injuries.

NMDA receptors are composed of NR1, NR2 (A, B, C, and D), and NR3 (A and B) subunits, which determine the functional properties of native NMDA receptors. Expression of the NR1 subunit alone does not produce a functional receptor. Co-expression of one or more NR2 subunits is required to form functional channels. In addition to glutamate, the NMDA receptor requires the binding of a co-agonist, glycine, to allow the receptor to function. A glycine binding site is found on the NR1 and NR3 subunits, whereas the glutamate binding site is found on NR2 subunits. At resting membrane potentials, NMDA receptors are largely inactive due to a voltage-dependent block of the channel pore by magnesium ions. Depolarization releases this channel block and permits passage of calcium as well as other ions.

The NMDA receptor is modulated by a number of endogenous and exogenous compounds including, sodium, potassium and calcium ions that can not only pass through the NMDA receptor channel but also modulate the activity of receptors. Zinc blocks the channel through NR2A- and NR2B-containing receptors noncompetitive and voltage-independent manner. Polyamines can also either potentiate or inhibit glutamate-mediated responses.

Stroke is the third leading cause of death in the United States and the most common cause of adult disability. In an ischemic stroke, which is the cause of approximately 80% of strokes, a blood vessel becomes occluded and the blood supply to part of the brain is blocked. Ischemic stroke is commonly divided into thrombotic stroke, embolic stroke, systemic hypoperfusion (Watershed or Border Zone stroke), or venous thrombosis. NMDA antagonists have been studied as neuroprotective agents for acute stroke. However, these agents, including Dextrorphan, Selfotel and aptiganel HCl (Cerestat) all showed certain toxicity profiles that required halting trials of these agents. Early clinical studies suggest that psychomimetic side effects occur less frequently with glycine site NMDA antagonists, however clinical studies have not supported a protective role for these agents (http://www.emedicine.com/neuro/topic488.htm, Lutsep & Clark "Neuroprotective Agents in Stroke", Apr. 30, 2004).

Epilepsy has also long been considered a potential therapeutic target for glutamate receptor antagonists. NMDA receptor antagonists are known to be anti-convulsant in many experimental models of epilepsy (Bradford (1995) Progress in Neurobiology 47:477-511; McNamara, J. O. (2001) Drugs effective in the therapy of the epilepsies. In Goodman & Gliman's: The pharmacological basis of therapeutics [Eds. J. G. Hardman and L. E. Limbird] McGraw Hill, New York).

NMDA receptor antagonists may also be beneficial in the treatment of chronic pain. Chronic pain, including neuropathic pain such as that due to injury of peripheral or central nerves, has often proved very difficult to treat. Treatment of chronic pain with ketamine and amantadine has proven beneficial, and it is believed that the analgesic effects of ketamine and amantadine are mediated by block of NMDA receptors. Several case reports have indicated that systemic administration of amantadine or ketamine substantially reduces the intensity of trauma-induced neuropathic pain. Small-scale double blind, randomized clinical trials corroborated that amantadine could significantly reduce neuropathic pain in cancer patients (Pud et al. (1998), Pain 75:349-354) and ketamine could reduce pain in patients with peripheral nerve injury (Felsby et al. (1996), Pain 64:283-291), peripheral vascular disease (Perrson et al. (1998), Acta Anaesthesiol Scand 42:750-758), or kidney donors (Stubhaug et al. (1997), Acta Anaesthesiol Scand 41:1124-1132). "Wind-up pain" produced by repeated pinpricking was also dramatically reduced. These findings suggest that central sensitization caused by nociceptive inputs can be prevented by administration of NMDA receptor antagonists.

NMDA receptor antagonists can also be beneficial in the treatment of Parkinson's Disease (Blandini and Greenamyre (1998), Fundam Clin Pharmacol 12:4-12). The anti-Parkinsonian drug, amantadine, is an NMDA receptor channel blocker (Blanpied et al. (1997), J Neurophys 77:309-323). In a small clinical trial, Amantadine reduced the severity of dyskinesias by 60% without reducing the antiparkinsonian effect of L-DOPA (Verhagen Metman et al. (1998), Neurology 50:1323-1326). Likewise, another NMDA receptor antagonist, CP-101,606, potentiated the relief of Parkinson's symptoms by L-DOPA in a monkey model (Steece-Collier et al., (2000) Exper. Neurol., 163:239-243).

NMDA receptor antagonists may in addition be beneficial in the treatment of brain cancers. Rapidly-growing brain gliomas can kill adjacent neurons by secreting glutamate and overactivating NMDA receptors such that the dying neurons make room for the growing tumor, and may release cellular components that stimulate tumor growth. Studies show NMDA receptor antagonists can reduce the rate of tumor growth in vivo as well as in some in vitro models (Takano, T., et al. (2001), Nature Medicine 7:1010-1015; Rothstein, J. D. and Bren, H. (2001) Nature Medicine 7:994-995; Rzeski, W., et al. (2001), Proc. Nat'l Acad. Sci. 98:6372).

While NMDA-receptor antagonists might be useful to treat a number of very challenging disorders, to date, dose-limiting side effects have prevented clinical use of NMDA receptor antagonists for these conditions. Thus, despite the tremendous potential for glutamate antagonists to treat many serious diseases, the severity of the side effects have caused many to abandon hope that a well-tolerated NMDA receptor antagonist could be developed (Hoyte L. et al (2004) "The Rise and Fall of NMDA Antagonists for Ischemic Stroke Current Molecular Medicine" 4(2): 131-136; Muir, K. W. and Lees, K. R. (1995) Stroke 26:503-513; Herrling, P. L., ed. (1997) "Excitatory amino acid clinical results with antagonists" Academic Press; Parsons et al. (1998) Drug News Perspective II: 523 569).

pH Sensitive NMDA Receptors

Two of the most prevalent subtypes of NMDA receptors (including the NR2A and NR2B subunits or an alternatively spliced NR1 subunit) have the unusual property of being normally inhibited by protons by about 50% at physiological pH (Traynelis, S. F. and Cull-Candy, S. G. (1990) Nature 345:347; Traynelis et al. (1995) Science 268: 873-876; Traynelis et al. (1998), J Neurosci 18:6163-6175).

The extracellular pH is highly dynamic in mammalian brain, and influences the function of a multitude of biochemical processes and proteins, including glutamate receptor function. The pH-sensitivity of the NMDA receptor has received increasing attention for at least two reasons. First, the $IC_{50}$ value for proton inhibition of pH 7.4 places the receptor under tonic inhibition at physiological pH. Second, pH changes are extensively documented in the central nervous system during synaptic transmission, glutamate receptor activation, glutamate receptor uptake, and prominently during pathological states such as ischemia and seizures (Siesjo, B K (1985), Progr Brain Res 63:121-154; Chesler, M (1990), Prog Neurobiol 34:401-427; Chesler and Kaila (1992), Trends Neurosci 15:396-402; Amato et al. (1994), J Neurophysiol 72:1686-1696).

During stroke, transient ischemia leads to a dramatic drop of pH to 6.4-6.5 in the core region of the infarct, with a modest drop in regions surrounding the core. The penumbral region, which surrounds the core and extends outward, suffers significant neuronal loss. The pH in this region drops to around pH 6.9. The pH-induced drops are exaggerated in presence of excess glutamate, and attenuated in hypoglycemic condition (see, for example, Mutch & Hansen (1984) J Cereb Blood Flow Metab 4: 17-27, Smith et al. (1986) J Cereb Blood Flow Metab 6: 574-583; Nedergaard et al. (1991) Am J Physiol 260 (Pt3): R581-588; Katsura et al (1992a) Euro J Neursci 4: 166-176; and Katsura & Siesjo (1998) "Acid base metabolism in ischemia" in pH and Brain function (Eds Kaila & Ransom) Wiley-Liss, New York).

In addition to ischemia, there are various other examples of conditions in which pH changes can be associated with pathological processes, including neuropathic pain, Parkinsons disease, epilepsy and traumatic brain injuries.

Neuropathic pain, which is due to hyperactivity of nerve fibers in the dorsal horn of the spinal chord can be associated with pH changes in the spinal cord. Single electrical stimulation of isolated spinal cord from rat pups produces an alkaline shift of 0.05 pH units, and a 0.1 pH unit shift following 10 Hz stimulation which is followed by acidification after cessation of the stimuli. This acidification is greater in older animals (Jendelova & Sykova (1991) Glia 4: 56-63), indicating an increased pH differential underlying the stimuli. Similarly, 30-40 Hz stimulation of the dorsal root in frog produced in vivo a transient extracellular acidification reaching a maximum ceiling of 0.25 pH unit reduction in the lower dorsal horn. Extracellular pH changes increased with stimulus intensity and frequency (Chvatal et al. (1988) Physiol Bohemoslov 37: 203-212). Further, high frequency (10-100 Hz) nerve stimulation in adult rat spinal cord in vivo produced triphasic alkaline-acid-alkaline shifts in extracellular pH (Sykova et al. (1992) Can J Physiol Pharmacol 70: Suppl 5301-309). Additionally, it has been shown that acute nociceptive stimuli (pinch, press, heat) applied to the rat hindpaw produced transient acidification of 0.01-0.05 pH units in the lower dorsal horn in vivo (laminae III-VII). Chemical or thermal peripheral injury produced prolonged 2 hour decreases in interstitial pH of 0.05-0.1 pH units. High frequency nerve stimulation produced an alkaline pH shift followed by a dominating 0.2 pH unit acid shift (Sykova & Svoboda (1990) Brain Res 512: 181-189). Thus, increased firing of pain fibers can cause a decrease in pH (acidification) of the dorsal horn of the spinal cord.

Subthalamic neurons are overactive in Parkinson's disease, which may result in a lower local pH. There is a correlation in brain regions between neuronal activity and extracellular pH, with activity causing acidification. High frequency stimulation of brain slices gives an initial acidification followed by an alkalinization, followed by a slow acidification (See, for example, Chesler (1990) Prog Neurobiol 34: 401-427, Chesler & Kaila (1992) Tr Neurosci 15: 396-402, and Kaila & Chesler (1998) "Activity evoked changes in extracellular pH" in pH and Brain function (eds Kaila and Ransom). Wiley-Liss, New York).

Acidification also occurs during seizures. Electrographic seizures in a wide range of preparations have been shown to cause a change in extracellular pH. For example, up to a 0.2-0.36 drop in pH can occur in cat fascia dentata or rat hippocampal CA1 or dentate during an electrically or chemically evoked seizure. Deeper drops in pH approaching 0.5 can occur under hypoxic conditions (Siesjo et al (1985) J Cereb Blood Flow Metab 5: 47-57; Balestrino & Somjen (1988) J Physiol 396: 247-266; and Xiong & Stringer (2000) J Neurophysiol 83: 3519-3524).

In addition, other types of brain injury can result in acidification. "Spreading depression" is a term used to describe a slowly moving wave of electrical inactivity that occurs following a number of traumatic insults to brain tissue. Spreading depression can occur during a concussion or migraine. Acidic pH changes occur with spreading depression. Systemic alkalosis can occur with reduction in overall carbon dioxide content (hypocapnia) through, for example, hyperventilation. Conversely, systemic acidosis can occur with an increase in blood carbon dioxide (hypercapnia) during respiratory distress or conditions that impair gas exchange or lung function. Diabetic ketoacidosis and lactic acidosis represent three of the most serious acute complications of diabetes and can result in brain acidification. Further, fetal asphyxia during parturition occurs in 25 per 1000 births at term. It involves hypoxia and brain damage that is similar but not identical to ischemia.

The acidification associated with pathological situations can partially inhibit NMDA receptors, which provides negative feedback that reduces their contribution to neurotoxicity and seizure maintenance (Kaku et al. (1993), Science 260: 1516-1518; Munir and McGonigle (1995), J Neurosci 15:7847-7860; Vornov et al. (1996), J Neurochem 67:2379-2389; Gray et al. (1997), J Neurosurg Anesthesiol 9:180-187; O'Donnell and Bickler (1994), Stroke 25:171-177; reviewed by Tombaugh and Sapolsky (1993), J Neurochem 61:793-803; (Balestrino and Somjen (1988), J Physiol (Lond) 396: 247-266; Velisek et al. (1994), Exp Brain Res 101:44-52). However, the pH sensitivity of glutamate transporters increases the likelihood that extracellular glutamate levels will be high during a period of acidification (Billups and Attwell (1996), Nature (Lond) 379:171-173), which enhances the opportunity for post-insult treatment of, for example, stroke with NMDA receptor antagonists (Tombaugh and Sapolsky (1993), J Neurochem 61:793-803).

Until 1995, it was not known whether the proton-sensitive property of the NMDA receptor could be exploited as a target for small molecule modulation of the receptor to develop therapeutics. Traynelis et al. (1995 Science 268:873) reported for the first time that the small molecule spermine could modulate NMDA receptor function through relief of proton inhibition. Spermine, a polyamine, shifts the pKa of the proton sensor to acidic values, reducing the degree of tonic inhibition at physiological pH, which appears as a potentiation of function (Traynelis et al. (1995), Science 268:873-876; Kumamoto, E (1996), Magnes Res 9(4):317-327).

In 1998, it was determined that the mechanism of action of the phenylethanolamine NMDA antagonists involved the proton sensor. Ifenprodil and CP-101,606 increased the sensitivity of the receptor to protons, thereby enhancing the proton inhibition. By shifting the pKa for proton block of NMDA receptors to more alkaline values, ifenprodil binding causes a larger fraction of receptors to be protonated at physiological pH and, thus, inhibited. In addition, ifenprodil was found to be more potent at lower pH (6.5) than higher pH (7.5) as tested in an in vitro model of NMDA-induced excitotoxicity in primary cultures of rat cerebral cortex (Mott et al. 1998 Nature Neuroscience 1:659). These compounds have exhibited neuroprotective properties in preclinical models and lack the severe side-effect liability of other types of NMDA antagonists (e.g. PCP-like psychotic symptoms and cardiovascular effects). Other NMDA receptor-selective derivatives of ifenprodil are being considered for clinical development, including CP101,606 (Menniti et al. (1997), Eur J Pharmacol 331:117-126), Ro 25-6981 (Fischer et al. (1997), J Pharmacol Exp Ther 283:1285-1292) and Ro 8-4304 (Kew et al. (1998), Br J Pharmacol 123:463-472). Unfortunately, ifenprodil and several of its analogs, including eliprodil and haloperidol (Lynch and Gallagher (1996), J Pharmacol Exp Ther 279:154-161; Brimecombe et al. (1998), Pharmacol Exp Ther 286(2):627-634), block certain serotonin receptors and calcium channels in addition to NMDA receptors, limiting their clinical usefulness (Fletcher et al. (1995), Br J Pharmacol 116(7):2791-2800; McCool and Lovinger (1995), Neuropharmacology 34:621-629; Barann et al. (1998), Naunyn Schmiedebergs Arch Pharmacol 358:145-152).

WO 02/072542 to Emory University describes a class of pH-dependent NMDA receptor antagonists that exhibit pH sensitivity tested in vitro using an oocyte assay and in an experimental model of epilepsy.

WO 06/023957 to Emory University describes processes for selection of a compound which may be useful in the treatment of an ischemic injury or a disorder that lowers the pH in a manner that activates the NMDA receptor antagonist.

There remains a need for improved neuroprotective compounds and methods for the treatment of neuropathologies that have reduced toxicity. In particular there is a need for improved treatments for neuropathic pain, inflammatory pain, stroke, traumatic brain injury, global ischemia, hypoxia, spinal cord trauma, epilepsy, and other neurodegenerative diseases and disorders.

It is therefore an object of the present invention to provide new compounds, pharmaceutical compositions and methods for the treatment of neuropathic and neurodegenerative diseases and disorders.

SUMMARY OF THE INVENTION

NMDA receptor antagonists of Formula I, II, III, IV and V are provided, as well as compositions and methods of use of these compounds in the treatment or prophylaxis of neuropathic pain, stroke, traumatic brain injury, epilepsy, and neurologic events or neurodegeneration resulting from NMDA receptor activation. In particular, the compounds described herein are useful as neuroprotective agents. In one embodiment, the compounds, compositions and methods are useful in the treatment of neuropathic pain. Compounds described herein are also useful in preventing neurodegeneration in patients with Parkinson's, Alzheimer's, Huntington's chorea, ALS, and other neurodegenerative conditions known to the art to be responsive to treatment using NMDA receptor antagonists.

In particular embodiments, certain NMDA receptor antagonists described herein have enhanced activity in brain tissue having lower-than-normal pH due to pathological conditions. Conditions that can alter the regional pH include hypoxia resulting from stroke, traumatic brain injury, global ischemia that may occur during cardiac surgery, hypoxia that may occur following cessation of breathing, pre-eclampsia, spinal cord trauma, epilepsy, status epilepticus, neuropathic pain, inflammatory pain, chronic pain, vascular dementia or glioma tumors.

In one embodiment, compounds, pharmaceutical compositions and methods of treatment or prophylaxis of neuropathic pain, stroke, traumatic brain injury, epilepsy, and other neurologic events or neurodegeneration resulting from NMDA receptor activation comprising administering a compound to a host in need thereof are provided, wherein the compounds is of Formula I, or a pharmaceutically acceptable salt, ester, prodrug or derivative thereof:

Formula I

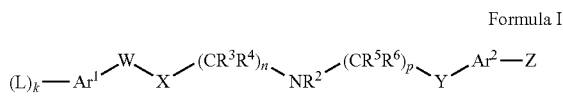

wherein:

each L is independently $C_1$-$C_6$ alkyl, $C_1$-$C_6$ alkoxy, C(=O)—($C_1$-$C_6$)-alkyl, $C_1$-$C_6$ haloalkyl, hydroxy, fluoro, chloro, bromo, iodo, nitro, or cyano; or two L groups may be taken together with $Ar^1$ to form: a dioxolane ring or a cyclobutane ring;

k=0, 1, 2, 3, 4 or 5;

each $Ar^1$ and $Ar^2$ is independently aryl or heteroaryl;

W is a bond, $C_1$-$C_4$ alkyl, or $C_2$-$C_4$ alkenyl;

X is a bond, $NR^1$ or O;

each $R^1$ and $R^2$ is independently H, $C_1$-$C_6$ alkyl, $C_2$-$C_6$ alkenyl or $C_6$-$C_{12}$ aralkyl; or $R^1$ and $R^2$ can be taken together to form a 5-8 membered ring;

each $R^3$ and $R^4$ is independently H, $C_1$-$C_6$ alkyl, $C_1$-$C_6$ alkoxy, C(=O)—($C_1$-$C_6$)-alkyl, $C_1$-$C_6$ haloalkyl, hydroxy, fluoro, chloro, bromo, iodo, nitro, or cyano; or $CR^3R^4$ is C=O;

n=1, 2, 3 or 4;

each $R^5$ and $R^6$ is independently H, $C_1$-$C_6$ alkyl, $C_1$-$C_6$ alkoxy, C(=O)—($C_1$-$C_6$)-alkyl, $C_1$-$C_6$ haloalkyl, hydroxy, fluoro, chloro, bromo, iodo, nitro, or cyano; or $CR^5R^6$ is C=O or C=$CH_2$;

or wherein —NR²—(CR⁵R⁶)$_p$— can be

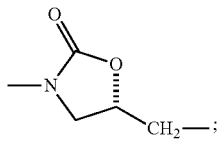

Y is a bond, O, S, SO, SO₂, CH₂, NH, N(C₁-C₆ alkyl), or NHC(=O);

Z is OH, NR⁶R⁷, NR⁸SO₂(C₁-C₆ alkyl), NR⁸C(O)NR⁶R⁷, NR⁸C(S)NR⁶R⁷, NR⁸C(O)O(C₁-C₆ alkyl), NR⁸-dihydrothiazole, or NR⁸-dihydroimidazole; wherein each R⁶, R⁷ and R⁸ is independently H, C₁-C₆ alkyl or C₆-C₁₂ aralkyl; or

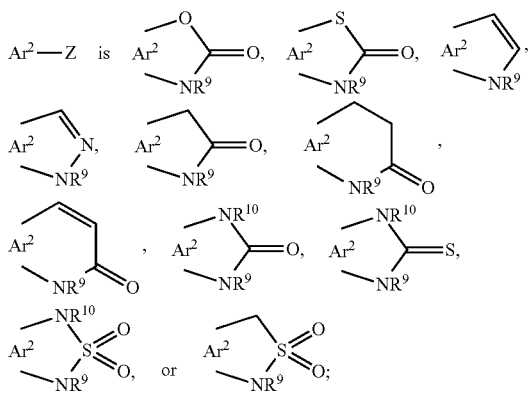

wherein R⁹ and R¹⁰ are each independently H, C₁-C₆ alkyl, aralkyl.

In certain embodiments, it has been found that certain aryl substitutions enhance activity and safety of tri-cyclic substituted amine NMDA receptor antagonist compounds by decreasing secondary effects such as hERG binding and α1 adrenergic receptor activation. Thus, in certain embodiments, compounds, pharmaceutical compositions and methods of treatment or prophylaxis of neuropathic pain, stroke, traumatic brain injury, epilepsy, and other neurologic events or neurodegeneration resulting from NMDA receptor activation are provided comprising administering a compound to a host in need thereof are provided, wherein the compound is of Formula V, or a pharmaceutically acceptable salt, ester, prodrug or derivative thereof:

Ar'—W'—B'—W"—Y'—Ar"—Z'     Formula V wherein B' is selected from the group consisting of:

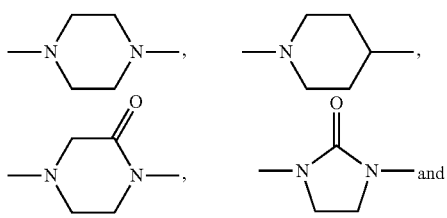

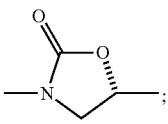

W' is a bond or C₁-C₄ alkyl;
W" is C₁-C₄ alkyl, C₁-C₄ hydroxyalkyl, C₁-C₄ haloalkyl or C(=O)—C₁-C₄ alkyl;
Y' is selected from a bond, O, S, CH₂ and N;
Ar' is an substituted or unsubstituted aromatic or nonaromatic cycloalkyl which optionally may include 0-3 heteroatoms;
Ar" is an aromatic or nonaromatic cycloalkyl which optionally may include 0-3 heteroatoms;
Z' is NRC(O)NR₂ wherein each R is independently selected from H, C₁-C₆ alkyl or C₆-C₁₂ aralkyl; or
Ar"—Z' are taken together and selected from the group consisting

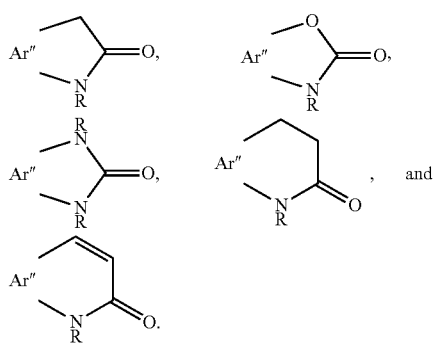

In one embodiment, Ar' is substituted by (L')$_{k'}$ wherein each L' is independently C₁-C₆ alkyl, C₁-C₆ alkoxy, C(=O)—(C₁-C₆)-alkyl, C₁-C₆ haloalkyl, alkaryl, hydroxy, —O-alkyl, —O-aryl, —SH, —S-alkyl, —S-aryl, fluoro, chloro, bromo, iodo, nitro, or cyano; or two L' groups may be taken together with Ar' to form a dioxolane ring or a cyclobutane ring; and k'=1, 2, 3, 4 or 5.

In certain embodiments, the compounds are used for the treatment of neuropathic pain, stroke, traumatic brain injury, epilepsy, other neurologic events or neurodegeneration resulting from NMDA receptor activation, Parkinson's disease, Alzheimer's disease, Huntington's chorea, ALS, and other neurodegenerative conditions known to the art to be responsive to treatment using NMDA receptor blockers. In particular embodiments, the compounds are used for the prophylaxis of neuropathic pain, stroke, traumatic brain injury, epilepsy, other neurologic events or neurodegeneration resulting from NMDA receptor activation, Parkinson's disease, Alzheimer's disease, Huntington's chorea, ALS, and other neurodegenerative conditions known to the art to be responsive to treatment using NMDA receptor blockers. The compounds can be administered on a prophylactic basis to a patient at risk of a disorder associated with NMDA receptor overactivation, and in particular a disorder associated with a reduced pH. In particular embodiments, the compounds act as neuroprotective agents.

In certain embodiments, the compounds are administered to a host in need thereof. In certain other embodiments, the compounds are administered in combination or alternation with other compounds that are useful in the treatment or prophylaxis of other neurologic events or neurodegeneration resulting from NMDA receptor activation, Parkinson's disease, Alzheimer's disease, Huntington's chorea, ALS, and other neurodegenerative conditions known to the art to be responsive to treatment using NMDA receptor blockers.

DETAILED DESCRIPTION OF THE INVENTION

It has been discovered that certain NMDA receptor antagonists are useful in the treatment or prophylaxis of neuropathic pain, stroke, traumatic brain injury, epilepsy, and other neurologic events or neurodegeneration resulting from NMDA receptor activation as well as Parkinson's disease, Alzheimer's disease, Huntington's chorea, ALS, and other neurodegenerative conditions known in the art to be responsive to treatment using NMDA receptor blockers. In particular, compounds described below are useful as neuroprotective agents. In one specific embodiment, the compounds, compositions and methods are useful in the treatment of neuropathic pain. In certain embodiments, the compounds provided herein are allosteric NMDA inhibitors.

In one embodiment, the $IC_{50}$ value of the compound is 0.01 to 10 µM, 0.01 to 9 µM, 0.01 to 8 µM, 0.01 to 7 µM, 0.01 to 6 µM, 0.01 to 5 µM, 0.01 to 4 µM, 0.01 to 3 µM, 0.01 to 2 µM, 0.01 to 1 µM, 0.05 to 7 µM, 0.05 to 6 µM, 0.05 to 5 µM, 0.05 to 4 µM, 0.05 to 3 µM, 0.05 to 2 µM, 0.05 to 1 µM, 0.05 to 0.5 µM, 0.1 to 7 µM, 0.1 to 6 µM, 0.1 to 5 µM, 0.1 to 4 µM, 0.1 to 3 µM, 0.1 to 2 µM, 0.1 to 1 µM, 0.1 to 0.5 µM, 0.1 to 0.4 µM, 0.1 to 0.3 µM, or 0.1 to 0.2 µM.

Certain NMDA receptor antagonists described herein have enhanced activity in tissue having lower-than-normal pH. The acidic environment generated by ischemic tissue during stroke or by other disorders is harnessed as a switch to activate the neuroprotective agents described herein. In this way side effects are minimized in unaffected tissue since drug at these sites are less active.

In particular embodiments, the compound is pH sensitive. In specific embodiments, the compound exhibits a potency boost of at least 2, at least 3, at least 4, at least 5, at least 6, at least 7, at least 8, at least 9, at least 10, at least 15 or at least 20 when comparing the $IC_{50}$ at physiological pH versus the $IC_{50}$ diseased pH (i.e., ($IC_{50}$ at phys pH/$IC_{50}$ at Dis pH)). In certain embodiments, the compound exhibits at least a 30%, 35%, 40%, 45%, 50%, 55%, or 60% decrease in infarct volume when a patient is suffering from a stroke or related condition.

In one embodiment, the compound has an $IC_{50}$ value of less than 10 µM at a pH of about 6 to about 9. In one embodiment, the compound has an $IC_{50}$ value of less than 10 µM at a pH of about 6.9. In another embodiment, the compound has an $IC_{50}$ value of less than 10 µM at a pH of about 7.6. In one embodiment, the compound has an $IC_{50}$ value of less than 10 µM at physiological pH. In one embodiment, the compound has an $IC_{50}$ value of less than 10 µM at diseased pH.

In one embodiment, the $IC_{50}$ value of the compound at pH 6.9 is 0.01 to 10 µM, 0.01 to 9 µM, 0.01 to 8 µM, 0.01 to 7 µM, 0.01 to 6 µM, 0.01 to 5 µM, 0.01 to 4 µM, 0.01 to 3 µM, 0.01 to 2 µM, 0.01 to 1 µM, 0.05 to 7 µM, 0.05 to 6 µM, 0.05 to 5 µM, 0.05 to 4 µM, 0.05 to 3 µM, 0.05 to 2 µM, 0.05 to 1 µM, 0.05 to 0.5 µM, 0.1 to 7 µM, 0.1 to 6 µM, 0.1 to 5 µM, 0.1 to 4 µM, 0.1 to 3 µM, 0.1 to 2 µM, 0.1 to 1 µM, 0.1 to 0.5 µM, 0.1 to 0.4 µM, 0.1 to 0.3 µM, or 0.1 to 0.2 µM, and the ratio of the $IC_{50}$ values at pH 7.6 to pH 6.9 for the compound is greater than 1, 2, 3, 4, 5, 6, 7, 8, 9, 10, 15, 20, 25, 30, 40, 50, 60, 70, 80, 90, or 100.

In one embodiment, the $IC_{50}$ value of the compound at pH 6.9 is 0.01 to 10 µM, 0.01 to 9 µM, 0.01 to 8 µM, 0.01 to 7 µM, 0.01 to 6 µM, 0.01 to 5 µM, 0.01 to 4 µM, 0.01 to 3 µM, 0.01 to 2 µM, 0.01 to 1 µM, 0.05 to 7 µM, 0.05 to 6 µM, 0.05 to 5 µM, 0.05 to 4 µM, 0.05 to 3 µM, 0.05 to 2 µM, 0.05 to 1 µM, 0.05 to 0.5 µM, 0.1 to 7 µM, 0.1 to 6 µM, 0.1 to 5 µM, 0.1 to 4 µM, 0.1 to 3 µM, 0.1 to 2 µM, 0.1 to 1 µM, 0.1 to 0.5 µM, 0.1 to 0.4 µM, 0.1 to 0.3 µM, or 0.1 to 0.2 µM, and the ratio of the $IC_{50}$ values at pH 7.6 to pH 6.9 for the compound is between 1 and 100, 2 and 100, 3 and 100, 4 and 100, 5 and 100, 6 and 100, 7 and 100, 8 and 100, 9 and 100, 10 and 100, 15 and 100, 20 and 100, 25 and 100, 30 and 100, 40 and 100, 50 and 100, 60 and 100, 70 and 100, 80 and 100, or 90 and 100.

In other embodiments, the $IC_{50}$ value of the compound at pH about 7.6 is 0.01 to 10 µM, 0.01 to 9 04, 0.01 to 8 µM, 0.01 to 7 µM, 0.01 to 6 µM, 0.01 to 5 µM, 0.01 to 4 µM, 0.01 to 3 µM, 0.01 to 2 µM, 0.01 to 1 µM, 0.05 to 7 µM, 0.05 to 6 µM, 0.05 to 5 µM, 0.05 to 4 µM, 0.05 to 3 µM, 0.05 to 2 µM, 0.05 to 1 µM, 0.05 to 0.5 µM, 0.1 to 7 µM, 0.1 to 6 µM, 0.1 to 5 µM, 0.1 to 4 µM, 0.1 to 3 µM, 0.1 to 2 µM, 0.1 to 1 µM, 0.1 to 0.5 µM, 0.1 to 0.4 µM, 0.1 to 0.3 µM, or 0.1 to 0.2 µM, In certain of these embodiments, the compound exhibits a ratio of the $IC_{50}$ values at pH 7.6 to pH 6.9 between 1 and 100, 2 and 100, 3 and 100, 4 and 100, 5 and 100, 6 and 100, 7 and 100, 8 and 100, 9 and 100, 10 and 100, 15 and 100, 20 and 100, 25 and 100, 30 and 100, 40 and 100, 50 and 100, 60 and 100, 70 and 100, 80 and 100, or 90 and 100. In certain other embodiments, the compound exhibits a ratio below 10, or below 5, or 4, 3, 2 or 1.

Compounds
Formula I

In one embodiment, compounds, pharmaceutical compositions and methods of treatment or prophylaxis of neuropathic pain, stroke, traumatic brain injury, epilepsy, and other neurologic events or neurodegeneration resulting from NMDA receptor activation, comprising administering to a host in need thereof a compound of Formula I, or a pharmaceutically acceptable salt, ester, prodrug or derivative thereof are provided:

Formula I

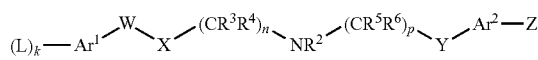

wherein:
each L is independently $C_1$-$C_6$ alkyl, $C_1$-$C_6$ alkoxy, C(═O)—($C_1$-$C_6$)-alkyl, $C_1$-$C_6$ haloalkyl, alkaryl, hydroxy, —O-alkyl, —O-aryl, —SH, —S-alkyl, —S-aryl, fluoro, chloro, bromo, iodo, nitro, or cyano; or two L groups may be taken together with $Ar^1$ to form: a dioxolane ring or a cyclobutane ring;
k=0, 1, 2, 3, 4 or 5;
each $Ar^1$ and $Ar^2$ is independently aryl or heteroaryl;
W is a bond, $C_1$-$C_4$ alkyl, or $C_2$-$C_4$ alkenyl;
X is a bond, $NR^1$ or O;
each $R^1$ and $R^2$ is independently H, $C_1$-$C_6$ alkyl, $C_2$-$C_6$ alkenyl or $C_6$-$C_{12}$ aralkyl; or
$R^1$ and $R^2$ can be taken together to form a 5-8 membered ring;
each $R^3$ and $R^4$ is independently H, $C_1$-$C_6$ alkyl, $C_1$-$C_6$ alkoxy, C(═O)—($C_1$-$C_6$)-alkyl, $C_1$-$C_6$ haloalkyl, hydroxy, fluoro, chloro, bromo, iodo, nitro, or cyano; or $CR^3R^4$ is C═O;
n=1, 2, 3 or 4;
each $R^5$ and $R^6$ is independently H, $C_1$-$C_6$ alkyl, $C_1$-$C_6$ alkoxy, C(═O)—($C_1$-$C_6$)-alkyl, $C_1$-$C_6$ haloalkyl, hydroxy, fluoro, chloro, bromo, iodo, nitro, or cyano; or $CR^5R^6$ is C═O or C═$CH_2$;

or wherein —NR$^2$—(CR$^5$R$^6$)$_p$— can be

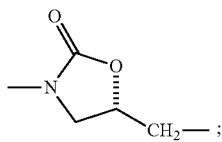

Y is a bond, O, S, SO, SO$_2$, CH$_2$, NH, N(C$_1$-C$_6$ alkyl), or NHC(=O);

Z is OH, NR$^6$R$^7$, NR$^8$SO$_2$(C$_1$-C$_6$ alkyl), NR$^8$C(O)NR$^6$R$^7$, NR$^8$C(S)NR$^6$R$^7$, NR$^8$C(O)O(C$_1$-C$_6$ alkyl), NR$^8$-dihydrothiazole, or NR$^8$-dihydroimidazole; wherein each R$^6$, R$^7$ and R$^8$ is independently H, C$_1$-C$_6$ alkyl or C$_6$-C$_{12}$ aralkyl; or

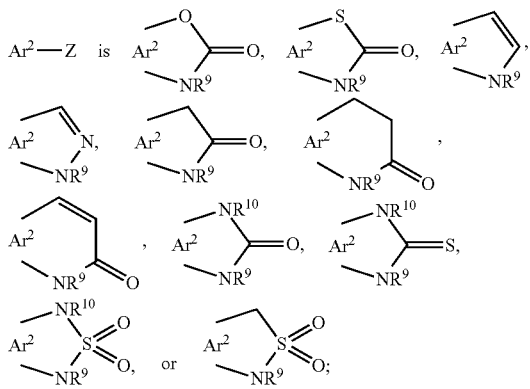

wherein R$^9$ and R$^{10}$ are each independently H, C$_1$-C$_6$ alkyl, aralkyl.

In specific embodiments of the Formula I when X is a bond, Y is O and Ar$^2$ is phenyl, Z is not NR$^8$SO$_2$(C$_1$-C$_6$ alkyl); and when X is O, —NR$^2$—(CR$^5$R$^6$)$_p$— is not —NH—C(=O)—.

In one embodiment, when Y is NHC(=O), Z is not OH or NR$^8$SO$_2$(C$_1$-C$_6$ alkyl). In one subembodiment, when R$^1$ and R$^2$ are taken together to form a 5-8 membered ring so that —NR$^1$—(CR$^3$R$^4$)$_n$—NR$^2$— is

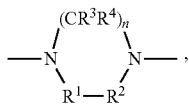

Y—Ar$^2$ is not NH-heteroaryl. In another subembodiment, when R$^1$ and R$^2$ are taken together to form a 5-8 membered ring so that —NR$^1$—(CR$^3$R$^4$)$_n$—NR$^2$— is

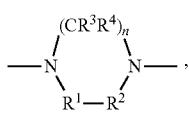

Y is not NHC(=O).

In one embodiment, X is NR$^1$. In another embodiment, X is O. In another embodiment, X is a bond. In a particular subembodiment, X is a bond, n is 1, R$^3$ and R$^4$ are both H, and W is C$_2$ alkenyl. In certain embodiments, X is not a bond.

In particular subembodiment, Ar$^1$ is phenyl, pyridyl, pyrimidinyl, thiophenyl, imidazolyl, furanyl, indolyl, benzothiophenyl, benzofuranyl, or benzoimidazolyl.

In another particular subembodiment, L is C$_1$-C$_4$ alkyl, C$_1$-C$_4$ alkoxy, C(=O)—(C$_1$-C$_4$)-alkyl, C$_1$-C$_6$ haloalkyl, hydroxy, fluoro, chloro, bromo, iodo, nitro, or cyano. In a further subembodiment, L is methyl, trifluoromethyl, methoxy, nitro, fluoro, chloro or hydroxy. In one further subembodiment, there are one, two or three L groups substituting Ar$^1$. In one subembodiment, Ar$^1$ is substituted with one fluoro group. In one subembodiment, Ar$^1$ is substituted with two fluoro groups. In one subembodiment, Ar$^1$ is substituted with one fluoro group and one chloro group. In one subembodiment, Ar$^1$ is substituted with one chloro group. In one subembodiment, Ar$^1$ is substituted with two chloro groups. In one subembodiment, Ar$^1$ is substituted with one methyl group. In one subembodiment, Ar$^1$ is substituted with one trifluoromethyl group.

In one subembodiment, Ar$^1$ is phenyl. In one subembodiment, Ar$^1$ is phenyl and is substituted with an L group at the 2, 3, or 4 position. In another subembodiment, Ar$^1$ is phenyl and is substituted with L groups at the 2 and 4 positions. In another subembodiment, Ar$^1$ is phenyl and is substituted with L groups at the 3 and 4 positions.

In one subembodiment, Ar$^1$ is pyridyl. In another subembodiment, Ar$^1$ is 2-pyridyl, 3-pyridyl, or 4-pyridyl.

In one embodiment, Ar$^1$ is a bicyclic group wherein the W group is attached to the heterocyclic ring.

In one embodiment, W is a bond. In another embodiment, W is CH$_2$. In another embodiment, W is C$_2$-C$_4$ alkenyl.

In one embodiment, each R$^1$ and R$^2$ is independently H or C$_1$-C$_4$ alkyl, for example, methyl, ethyl, n-propyl, isopropyl, n-butyl, sec-butyl or tert-butyl. In one embodiment, R$^1$ and R$^2$ are both H. In one embodiment, R$^1$ and R$^2$ are both C$_1$-C$_4$ alkyl, for example n-butyl. In another embodiment, R$^1$ and R$^2$ can be taken together to form a 5-8 membered ring so that —NR$^1$—(CR$^3$R$^4$)$_n$—NR$^2$— is

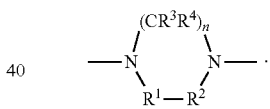

In one subembodiment, when R$^1$ and R$^2$ are taken together to form a 5-8 membered ring so that —NR$^1$—(CR$^3$R$^4$)$_n$—NR$^2$— is

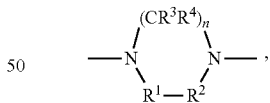

Y—Ar$^2$ is not NH-heteroaryl. In another subembodiment, when R$^1$ and R$^2$ are taken together to form a 5-8 membered ring so that —NR$^1$—(CR$^3$R$^4$)$_n$—NR$^2$— is

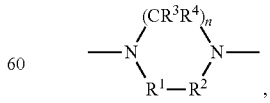

Y is not NHC(=O). In one embodiment, n is 2. In one embodiment, n is 3. In another embodiment, R$^1$ and R$^2$ are each CH$_2$. In a subembodiment, CR$^3$R$^4$ is CH$_2$ and n is 2. In a subembodiment, CR$^3$R$^4$ in CH$_2$ and n is 3. In a subembodiment, CR$^3$R$^4$ is C=O and n is 1.

In one embodiment,

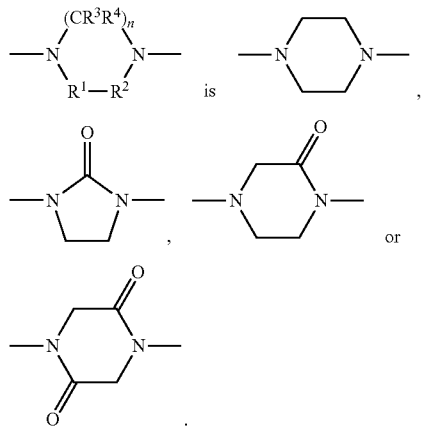

In one embodiment,

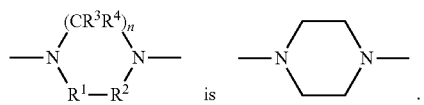

In another embodiment,

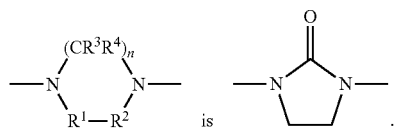

In one embodiment, each $R^5$ and $R^6$ is independently H, $C_1$-$C_4$ alkyl, $C_1$-$C_4$ alkoxy, C(=O)—($C_1$-$C_4$)-alkyl, $C_1$-$C_4$ haloalkyl, hydroxy, fluoro, chloro, bromo, iodo, nitro, or cyano. In one embodiment, $CR^5R^6$ is C=O or C=$CH_2$. In one embodiment, p is 2, 3, or 4. In another embodiment, p is 3. In one embodiment, $R^5$ and $R^6$ are H. In another embodiment, one of $R^5$ and $R^6$ is hydroxy. In another embodiment, $CR^5R^6$ is C=$CH_2$. In another embodiment, $CR^5R^6$ is C=O. In one embodiment, $(CR^5R^6)_p$ is selected from the group consisting of

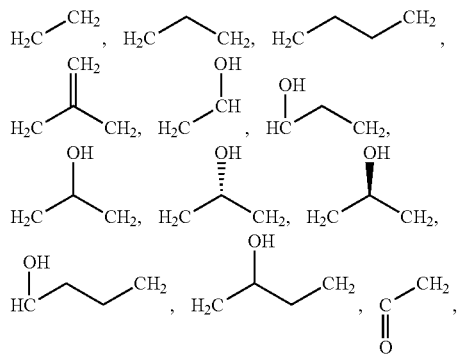

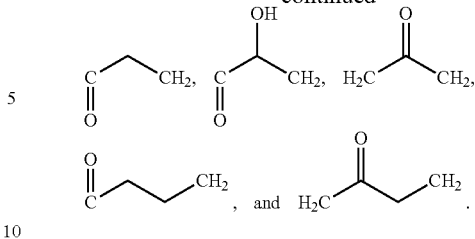

Compounds of Formula I can include compounds wherein when p is greater than 1, each $(CR^5R^6)$ can be independently selected, for example, in one embodiment p is 2 and one $(CR^5R^6)$ is C=O and the other $(CR^5R^6)$ is $CH_2$. In one embodiment, $R^5$ is not fluoro. In another embodiment, $R^6$ is not fluoro.

In one embodiment, —$NR^2$—$(CR^5R^6)_p$— is

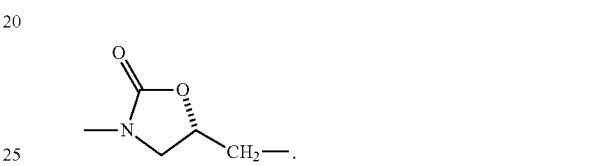

In a particular subembodiment, the compound is

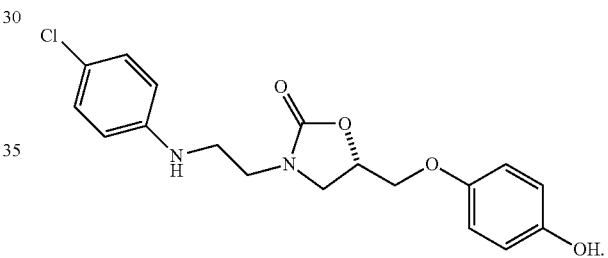

In another particular subembodiment, the compound is

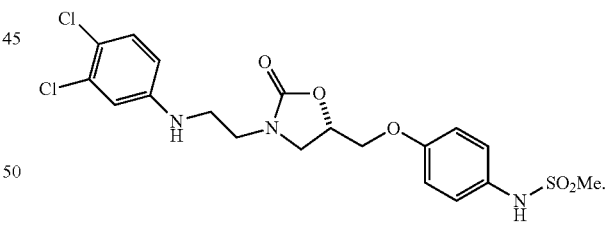

In one embodiment, Y is a bond, O or $CH_2$. In one embodiment, Y is O. In another embodiment, Y is $CH_2$. In one embodiment, Y is not NH. In another embodiment, Y is not NHC(=O).

In one embodiment, $Ar^2$ is aryl. In one embodiment, $Ar^2$ is aryl, but not phenyl or heteroaryl. In one embodiment $Ar^2$ is phenyl. In one subembodiment, $Ar^2$ is phenyl and is substituted with a Z group at the 4 position. In one embodiment, $Ar^2$ is not heteroaryl. In one embodiment, $Ar^2$ is aryl, but not phenyl or heteroaryl.

In one embodiment, Z is OH, $NR^6R^7$, $NR^8SO_2(C_1$-$C_6$ alkyl), $NR^8C(O)NR^6R^7$, $NR^8C(S)NR^6R^7$, $NR^8C(O)O(C_1$-$C_6$ alkyl), $NR^8$-dihydrothiazole, or $NR^8$-dihydroimidazole.

In one embodiment,

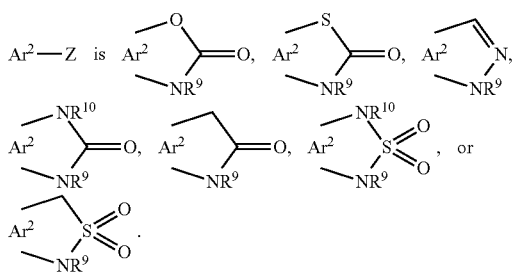

In one subembodiment,

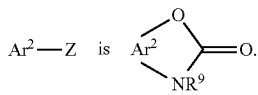

In one subembodiment,

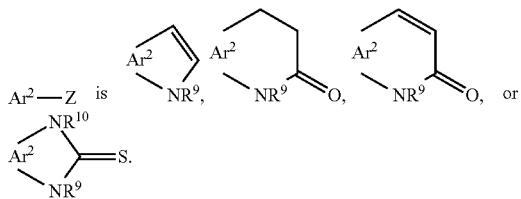

In one subembodiment, $R^9$ and $R^{10}$ are each H.

In one embodiment, Z is $NR^8C(O)NR^6R^7$, for example $NHC(O)NH_2$ or $NHC(O)N(CH_3)_2$.

In another embodiment, Z and $Ar^2$ are taken together and selected from the group consisting of:

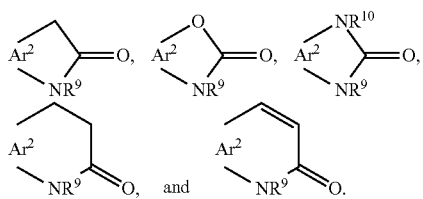

In one embodiment, the compound is a compound of Formula I, or a pharmaceutically acceptable salt, ester, prodrug or derivative thereof, wherein:
L is $C_1$-$C_6$ alkyl, $C_1$-$C_6$ alkoxy, C(=O)—($C_1$-$C_6$)-alkyl, $C_1$-$C_6$ haloalkyl, alkaryl, hydroxy, —O-alkyl, —O-aryl, —SH, —S-alkyl, —S-aryl, fluoro, chloro, bromo, iodo, nitro, or cyano; or two L groups may be taken together with $Ar^1$ to form a dioxolane ring or a cyclobutane ring;
k=0, 1, 2, 3, 4 or 5;
$Ar^1$ is phenyl, pyridyl, pyrimidinyl, thiophenyl, imidazolyl, furanyl, indolyl, benzothiophenyl, benzofuranyl, benzoimidazolyl;
$Ar^2$ is phenyl;
W is a bond, $C_1$-$C_4$ alkyl, or $C_2$-$C_4$ alkenyl;
each $R^1$ and $R^2$ is independently H, $C_1$-$C_4$ alkyl; or
$R^1$ and $R^2$ can be taken together to form a 5-8 membered ring;
each $R^3$ and $R^4$ is independently H, $C_1$-$C_6$ alkyl, $C_1$-$C_6$ alkoxy, C(=O)—($C_1$-$C_6$)-alkyl, $C_1$-$C_6$ haloalkyl, hydroxy, fluoro, chloro, bromo, iodo, nitro, or cyano; or $CR^3R^4$ is C=O;
n=1, 2, 3 or 4;
each $R^5$ and $R^6$ is independently H, $C_1$-$C_6$ alkyl, $C_1$-$C_6$ alkoxy, C(=O)—($C_1$-$C_6$)-alkyl, $C_1$-$C_6$ haloalkyl, hydroxy, fluoro, chloro, bromo, iodo, nitro, or cyano; or $CR^5R^6$ is C=O, C=$CH_2$;
Y is a bond, O, S, SO, $SO_2$, $CH_2$, NH, N($C_1$-$C_6$ alkyl), NHC(=O);
Z is OH, $NH_2$, $NHSO_2$($C_1$-$C_4$ alkyl), $NHC(O)NR^6R^7$, $NR^8C(S)NR^6R^7$, $NHC(O)O(C_1$-$C_4$ alkyl), NH-dihydrothiazole, or NH-dihydroimidazole; wherein each $R^6$ and $R^7$ is independently H, $C_1$-$C_6$ alkyl; or

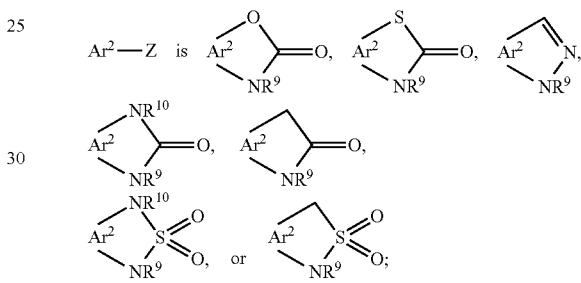

wherein $R^9$ and $R^{10}$ are each independently H or $C_1$-$C_4$ alkyl.

In one embodiment, the compound is a compound of Formula I, or a pharmaceutically acceptable salt, ester, prodrug or derivative thereof, wherein:
L is $C_1$-$C_6$ alkyl, $C_1$-$C_6$ alkoxy, C(=O)—($C_1$-$C_6$)-alkyl, $C_1$-$C_6$ haloalkyl, alkaryl, hydroxy, —O-alkyl, —O-aryl, —SH, —S-alkyl, —S-aryl, fluoro, chloro, bromo, iodo, nitro, or cyano; or two L groups may be taken together with $Ar^1$ to form a dioxolane ring or a cyclobutane ring;
k=0, 1, 2, 3, 4 or 5;
$Ar^1$ is phenyl, pyridyl, pyrimidinyl, thiophenyl, imidazolyl, furanyl, indolyl, benzothiophenyl, benzofuranyl, benzoimidazolyl;
$Ar^2$ is phenyl;
W is a bond, $C_1$-$C_4$ alkyl, or $C_2$-$C_4$ alkenyl;
each $R^1$ and $R^2$ is independently H, $C_1$-$C_4$ alkyl; or
$R^1$ and $R^2$ can be taken together to form a 5-8 membered ring;
each $R^3$ and $R^4$ is independently H, $C_1$-$C_6$ alkyl, $C_1$-$C_6$ alkoxy, C(=O)—($C_1$-$C_6$)-alkyl, $C_1$-$C_6$ haloalkyl, hydroxy, fluoro, chloro, bromo, iodo, nitro, or cyano; or $CR^3R^4$ is C=O;
n=1, 2, 3 or 4;
each $R^5$ and $R^6$ is independently H, $C_1$-$C_6$ alkyl, $C_1$-$C_6$ alkoxy, C(=O)—($C_1$-$C_6$)-alkyl, $C_1$-$C_6$ haloalkyl, hydroxy, fluoro, chloro, bromo, iodo, nitro, or cyano; or $CR^5R^6$ is C=O, C=$CH_2$;

Y is a bond, O, S, SO, SO$_2$, CH$_2$, NH, N(C$_1$-C$_6$ alkyl), NHC(=O);

Z is OH, NH$_2$, NHSO$_2$(C$_1$-C$_4$ alkyl), NHC(O)NR$^6$R$^7$, NR$^8$C(S)NR$^6$R$^7$, NHC(O)O(C$_1$-C$_4$ alkyl), NH-dihydrothiazole, or NH-dihydroimidazole; wherein each R$^6$ and R$^7$ is independently H, C$_1$-C$_6$ alkyl; or

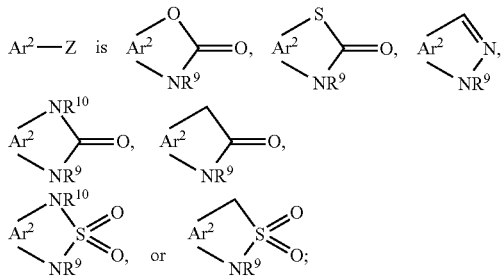

wherein R$^9$ and R$^{10}$ are each independently H or C$_1$-C$_4$ alkyl.

In one embodiment, the compound is a compound of Formula I, or a pharmaceutically acceptable salt, ester, prodrug or derivative thereof, wherein:

L is C$_1$-C$_4$ alkyl, C$_1$-C$_4$ alkoxy, C(=O)—(C$_1$-C$_4$)-alkyl, C$_1$-C$_4$ haloalkyl, alkaryl, hydroxy, —O-alkyl, —O-aryl, —SH, —S-alkyl, —S-aryl, fluoro, chloro, bromo, iodo, or nitro; or two L groups may be taken together to form a dioxolane ring with Ar$^1$;

k=0, 1, 2, 3, 4 or 5;
Ar$^1$ is phenyl or pyridyl;
Ar$^2$ is phenyl;
W is a bond or C$_1$-C$_4$ alkyl;
X is NR$^1$;
each R$^1$ and R$^2$ is independently H or C$_1$-C$_4$ alkyl; or
R$^1$ and R$^2$ can be taken together to form a 5-8 membered ring;
each R$^3$ and R$^4$ is independently H or C$_1$-C$_4$ alkyl; or CR$^3$R$^4$ is C=O;
n=2 or 3;
each R$^5$ and R$^6$ is independently H, C$_1$-C$_4$ alkyl or OH; or CR$^4$R$^5$ is C=O or C=CH$_2$;
Y is O or CH$_2$;
Z is OH, NH$_2$, NHSO$_2$(C$_1$-C$_4$ alkyl), NHC(O)NR$^6$R$^7$, NR$^8$C(S)NR$^6$R$^7$, NHC(O)O(C$_1$-C$_4$ alkyl), NH-dihydrothiazole, or NH-dihydroimidazole; wherein each R$^6$ and R$^7$ is independently H or C$_1$-C$_4$ alkyl; or

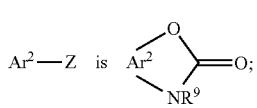

R$^9$ is H or C$_1$-C$_4$ alkyl.

In one embodiment, the compound is a compound of Formula I, or a pharmaceutically acceptable salt, ester, prodrug or derivative thereof, wherein:

L is C$_1$-C$_4$ alkyl, C$_1$-C$_4$ alkoxy, C(=O)—(C$_1$-C$_4$)-alkyl, C$_1$-C$_4$ haloalkyl, alkaryl, hydroxy, —O-alkyl, —O-aryl, —SH, —S-alkyl, —S-aryl, fluoro, chloro, bromo, iodo, or nitro; or two L groups may be taken together to form a dioxolane ring with Ar$^1$;

k=0, 1, 2, 3, 4 or 5;
Ar$^1$ is phenyl or pyridyl;
Ar$^2$ is phenyl;
W is a bond or C$_1$-C$_4$ alkyl;
X is O;
R$^2$ is H or C$_1$-C$_4$ alkyl;
each R$^3$ and R$^4$ is independently H or C$_1$-C$_4$ alkyl; or CR$^3$R$^4$ is C=O;
n=2 or 3;
each R$^5$ and R$^6$ is independently H, C$_1$-C$_4$ alkyl or OH; or CR$^4$R$^5$ is C=O or C=CH$_2$;
Y is O or CH$_2$;
Z is OH, NH$_2$, NHSO$_2$(C$_1$-C$_4$ alkyl), NHC(O)NR$^6$R$^7$, NHC(O)O(C$_1$-C$_4$ alkyl), NH-dihydrothiazole, or NH-dihydroimidazole; wherein each R$^6$ and R$^7$ is independently H or C$_1$-C$_4$ alkyl; or

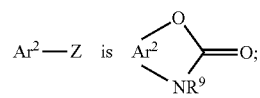

R$^9$ is H or C$_1$-C$_4$ alkyl.

In one embodiment, the compound is a compound of Formula I, or a pharmaceutically acceptable salt, ester, prodrug or derivative thereof, wherein:

L is C$_1$-C$_4$ alkyl, C$_1$-C$_4$ alkoxy, C(=O)—(C$_1$-C$_4$)-alkyl, C$_1$-C$_4$ haloalkyl, hydroxy, fluoro, chloro, bromo, iodo, or nitro; or two L groups may be taken together to form a dioxolane ring with Ar$^1$;

k=0, 1, 2, 3, 4 or 5;
Ar$^1$ is phenyl or pyridyl;
Ar$^2$ is phenyl;
W is C$_2$-C$_4$ alkenyl;
X is a bond;
R$^2$ is H or C$_1$-C$_4$ alkyl;
each R$^3$ and R$^4$ is independently H or C$_1$-C$_4$ alkyl; or CR$^3$R$^4$ is C=O;
n=1, 2 or 3;
each R$^5$ and R$^6$ is independently H, C$_1$-C$_4$ alkyl or OH; or CR$^4$R$^5$ is C=O or C=CH$_2$;
Y is O or CH$_2$;
Z is OH, NH$_2$, NHSO$_2$(C$_1$-C$_4$ alkyl), NHC(O)NR$^6$R$^7$, NR$^8$C(S)NR$^6$R$^7$, NHC(O)O(C$_1$-C$_4$ alkyl), NH-dihydrothiazole, or NH-dihydroimidazole; wherein each R$^6$ and R$^7$ is independently H or C$_1$-C$_4$ alkyl; or

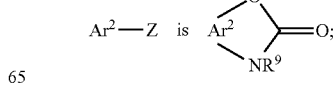

R$^9$ is H or C$_1$-C$_4$ alkyl.

In one embodiment, the compound is selected from the compounds in Table 1.

TABLE 1

| Compound | NAME |
|---|---|
| | N-(4-{3-[4-(3,4-Dichloro-phenyl)-piperazin-1-yl]-2-(S)-hydroxy-propoxy}-phenyl)-methanesulfonamide |
| | N-(4-{3-[4-(4-Chloro-phenyl)-piperazin-1-yl]-2-(S)-hydroxy-propoxy}-phenyl)-methanesulfonamide |
| | N-(4-{3-[4-phenyl-piperazin-1-yl]-2-(S)-hydroxy-propoxy}-phenyl)-methanesulfonamide |
| | N-(4-{3-[4-(4-Hydroxy-phenyl)-piperazin-1-yl]-2-(S)-hydroxy-propoxy}-phenyl)-methanesulfonamide |
| | N-(4-{3-4-(2-Pyridyl)-piperazin-1-yl]-2-(S)-hydroxy-propoxy}-phenyl)-methanesulfonamide |
| | N-(4-{3-[4-(4-Pyridyl)-piperazin-1-yl]-2-(S)-hydroxy-propoxy}-phenyl)-methanesulfonamide |

TABLE 1-continued

| Compound | NAME |
|---|---|
| | N-{4-[2-(S)-Hydroxy-3-(2-phenylamino-ethylamino)-propoxy]-phenyl}-methanesulfonamide |
| | N-{4-[2-(S)-Hydroxy-3-(2-(3,4-difluoro-phenyl)amino-ethylamino)-propoxy]-phenyl}-methanesulfonamide |
| | N-(4-{3-[3-(3,4-Dichloro-phenyl)-allylamino]-2-(S)-hydroxy-propoxy}-phenyl)-methanesulfonamide |
| | N-[4-(3-{Butyl-[3-(3,4-dichloro-phenyl)-allyl]-amino}-2-(S)-hydroxy-propoxy)-phenyl]-methanesulfonamide |
| | N-(4-{3-[3-(3,4-Difluoro-phenyl)-allylamino]-2-(S)-hydroxy-propoxy}-phenyl)-methanesulfonamide |

In one embodiment, the compound is selected from the compounds in Table 2.

TABLE 2

| Compound | NAME |
|---|---|
| | 6-{3-[4-(3,4-Difluoro-phenyl)-piperazin-1-yl]-2-(S)-hydroxy-propoxy}-3H-benzooxazol-2-one |
| | 6-{3-[4-(3,4-Dichloro-phenyl)-piperazin-1-yl]-2-(S)-hydroxy-propoxy}-3H-benzooxazol-2-one |
| | 6-{3-[4-(4-Methyl-phenyl)-piperazin-1-yl]-2-(S)-hydroxy-propoxy}-3H-benzooxazol-2-one |
| | 6-{3-[2-(4-Chloro-phenylamino)-ethylamino]-2-(S)-hydroxy-propoxy}-3H-benzooxazol-2-one |

In one embodiment, the compound is selected from the compounds in Table 3.

TABLE 3

| Compound | NAME |
|---|---|
| | 4-{3-[4-(3,4-Dichloro-phenyl)-piperazin-1-yl]-2-(S)-hydroxy-propoxy}-phenol |

TABLE 3-continued

| Compound | NAME |
| --- | --- |
| | 4-{3-[4-(3,4-Difluoro-phenyl)-piperazin-1-yl]-2-(S)-hydroxy-propoxy}-phenol |
| | 4-{3-[4-(3,4-Difluoro-phenyl)-piperazin-1-yl]-2-(R)-hydroxy-propoxy}-phenol |
| | 4-{3-[4-(4-Fluoro-phenyl)-piperazin-1-yl]-2-(S)-hydroxy-propoxy}-phenol |
| | 4-{3-[4-(3,4-Dimethyl-phenyl)-piperazin-1-yl]-2-(S)-hydroxy-propoxy}-phenol |
| | 4-{3-[4-(4-Methyl-phenyl)-piperazin-1-yl]-2-(S)-hydroxy-propoxy}-phenol |
| | 4-{3-[4-(4-Cyano-phenyl)-piperazin-1-yl]-2-(S)-hydroxy-propoxy}-phenol |

TABLE 3-continued

| Compound | NAME |
|---|---|
| | 4-{3-[4-(4-Bromo-phenyl)-piperazin-1-yl]-2-(S)-hydroxy-propoxy}-phenol |
| | 4-{3-[4-(4-Hydroxy-phenyl)-piperazin-1-yl]-2-(S)-hydroxy-propoxy}-phenol |
| | 4-{3-[4-(4-Methoxy-phenyl)-piperazin-1-yl]-2-(S)-hydroxy-propoxy}-phenol |
| | 4-{3-[4-(4-Trifluoromethyl-phenyl)-piperazin-1-yl]-2-(S)-hydroxy-propoxy}-phenol |
| | 4-{3-[4-(4-Biphenyl)-piperazin-1-yl]-2-(S)-hydroxy-propoxy}-phenol |
| | 4-{3-[4-(2,4-Difluoro-phenyl)-piperazin-1-yl]-2-(S)-hydroxy-propoxy}-phenol |

TABLE 3-continued

| Compound | NAME |
|---|---|
| | 4-{3-[4-(2-Fluoro-phenyl)-piperazin-1-yl]-2-(S)-hydroxy-propoxy}-phenol |
| | 4-{3-[4-(2-Chloro-phenyl)-piperazin-1-yl]-2-(S)-hydroxy-propoxy}-phenol |
| | 4-{3-[4-(2-Chloro-phenyl)-piperazin-1-yl]-2-(S)-hydroxy-propoxy}-phenol |
| | 4-{3-[4-(2-Cyano-phenyl)-piperazin-1-yl]-2-(S)-hydroxy-propoxy}-phenol |
| | 4-{3-[4-Phenyl-piperazin-1-yl]-2-(S)-hydroxy-propoxy}-phenol |
| | 4-{3-[4-(3-Fluoro-phenyl)-piperazin-1-yl]-2-(S)-hydroxy-propoxy}-phenol |

TABLE 3-continued

| Compound | NAME |
|---|---|
| | 4-{3-[4-(3-Chloro-phenyl)-piperazin-1-yl]-2-(S)-hydroxy-propoxy}-phenol |
| | 4-{3-[4-(3-Methyl-phenyl)-piperazin-1-yl]-2-(S)-hydroxy-propoxy}-phenol |
| | 4-{3-[4-(3-Trifluoromethyl-phenyl)-piperazin-1-yl]-2-(S)-hydroxy-propoxy}-phenol |
| | |

In one embodiment, the compound is selected from the compounds in Table 4.

TABLE 4

| Compound | NAME |
|---|---|
| | (4-{2-[4-(3,4-Difluoro-phenyl)-piperazin-1-ylmethyl]-allyloxy}-phenyl)-urea |

TABLE 4-continued

| Compound | NAME |
|---|---|
| | (4-{3-[4-(4-Fluoro-phenyl)-piperazin-1-yl]-propoxy}-phenyl)-urea |
| | (4-{3-[4-(4-Chloro-phenyl)-piperazin-1-yl]-2-hydroxy-propoxy}-phenyl)-urea |
| | 1-Ethyl-3-(4-{3-[4-(4-fluoro-phenyl)-piperazin-1-yl]-propoxyl}-phenyl)-urea |
| | (4-{3-[4-(4-Fluoro-phenyl)-piperazin-1-yl]-propoxy}-phenyl)-carbamic acid methyl ester |
| | (S)-1-(4-(3-(4-(3,4-dichlorophenyl)piperazin-1-yl)-2-hydroxypropoxy)phenyl)urea |
| | (S)-1-(4-(3-(4-(3,4-difluorophenyl)piperazin-1-yl)-2-hydroxypropoxy)phenyl)urea |

TABLE 4-continued

| Compound | NAME |
|---|---|
| | (R)-1-(4-(3-(4-(3,4-difluorophenyl)piperazin-1-yl)-2-hydroxypropoxy)phenyl)urea |
| | (S)-1-(4-(3-(4-(4-fluorophenyl)piperazin-1-yl)-2-hydroxypropoxy)phenyl)urea |
| | (S)-1-(4-(3-(4-(3,4-dimethylphenyl)piperazin-1-yl)-2-hydroxypropoxy)phenyl)urea |
| | (S)-1-(4-(2-hydroxy-3-(4-p-tolylpiperazin-1-yl)propoxy)phenyl)urea |
| | (S)-1-(4-(3-(4-(4-cyanophenyl)piperazin-1-yl)-2-hydroxypropoxy)phenyl)urea |
| | (S)-1-(4-(3-(4-(4-bromophenyl)piperazin-1-yl)-2-(S)-hydroxypropoxy)phenyl)urea |

TABLE 4-continued

| Compound | NAME |
|---|---|
| (structure) | (S)-1-(4-(2-hydroxy-3-(4-(4-hydroxyphenyl)piperazin-1-yl)propoxy)phenyl)urea |
| (structure) | (S)-1-(4-(2-hydroxy-3-(4-(4-methoxyphenyl)piperazin-1-yl)propoxy)phenyl)urea |
| (structure) | (S)-1-(4-(2-hydroxy-3-(4-(4-(trifluoromethyl)phenyl)piperazin-1-yl)propoxy)phenyl)urea |
| (structure) | (S)-1-(4-(3-(4-(biphenyl-4-yl)piperazin-1-yl)-2-hydroxypropoxy)phenyl)urea |
| (structure) | (S)-1-(4-(3-(4-(2,4-difluorophenyl)piperazin-1-yl)-2-hydroxypropoxy)phenyl)urea |
| (structure) | (S)-1-(4-(3-(4-(2-fluorophenyl)piperazin-1-yl)-2-hydroxypropoxy)phenyl)urea |

TABLE 4-continued

| Compound | NAME |
|---|---|
| | (S)-1-(4-(3-(4-(2-chlorophenyl)piperazin-1-yl)-2-hydroxypropoxy)phenyl)urea |
| | (S)-1-(4-(2-hydroxy-3-(4-o-tolylpiperazin-1-yl)propoxy)phenyl)urea |
| | (S)-1-(4-(3-(4-(2-cyanophenyl)piperazin-1-yl)-2-hydroxypropoxy)phenyl)urea |
| | (S)-1-(4-(2-hydroxy-3-(4-phenylpiperazin-1-yl)propoxy)phenyl)urea |
| | (S)-1-(4-(3-(4-(3-fluorophenyl)piperazin-1-yl)-2-hydroxypropoxy)phenyl)urea |
| | (S)-1-(4-(3-(4-(3-chlorophenyl)piperazin-1-yl)-2-(S)-hydroxypropoxy)phenyl)urea |

TABLE 4-continued

| Compound | NAME |
|---|---|
| 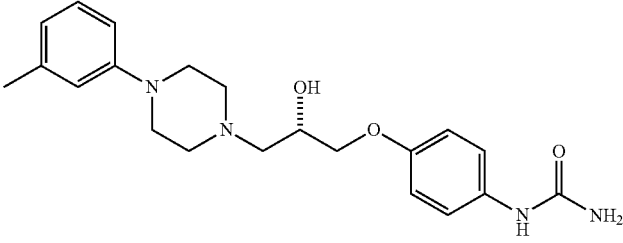 [SMILES: Cc1cccc(N2CCN(C[C@H](O)COc3ccc(NC(N)=O)cc3)CC2)c1] | (S)-1-(4-(2-hydroxy-3-(4-m-tolypiperazin-1-yl)propoxy)phenyl)urea |
| 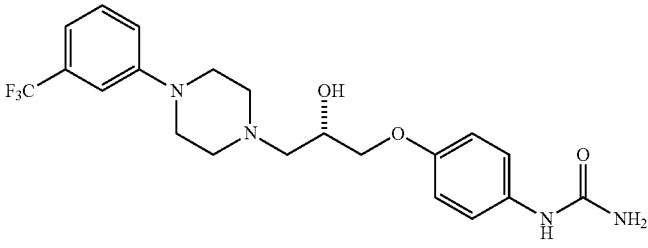 [SMILES: NC(=O)Nc1ccc(OC[C@@H](O)CN2CCN(c3cccc(C(F)(F)F)c3)CC2)cc1] | (S)-1-(4-(2-hydroxy-3-(4-(3-(trifluoromethyl)phenyl)piperazin-1-yl)propoxy)phenyl)urea |
| 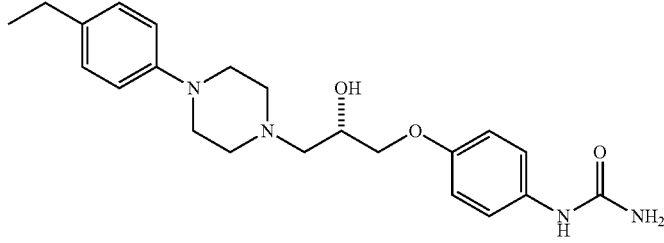 [SMILES: CCc1ccc(N2CCN(C[C@H](O)COc3ccc(NC(N)=O)cc3)CC2)cc1] | (S)-1-(4-(3-(4-(4-ethylphenyl)piperazin-1-yl)-2-hydroxypropoxy)phenyl)urea |
| 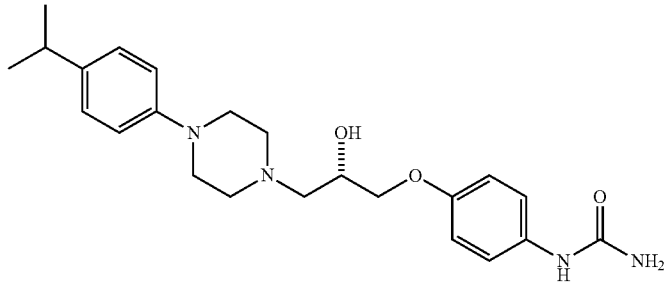 [SMILES: CC(C)c1ccc(N2CCN(C[C@H](O)COc3ccc(NC(N)=O)cc3)CC2)cc1] | (S)-1-(4-(3-(4-(4-isopropylphenyl)piperazin-1-yl)-2-hydroxypropoxy)phenyl)urea |
| 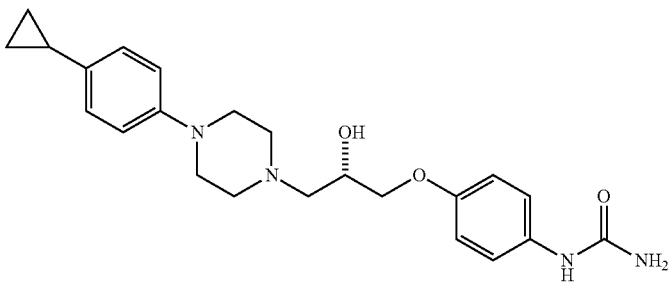 [SMILES: NC(=O)Nc1ccc(OC[C@@H](O)CN2CCN(c3ccc(C4CC4)cc3)CC2)cc1] | (S)-1-(4-(3-(4-(4-cyclopropylphenyl)piperazin-1-yl)-2-hydroxypropoxy)phenyl)urea |
| 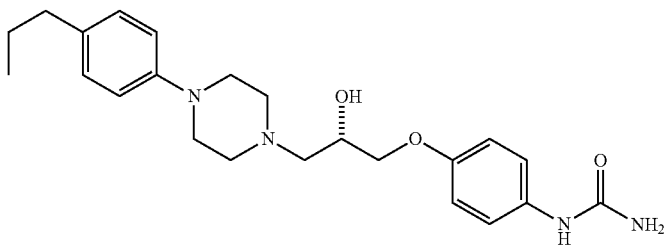 [SMILES: CCCc1ccc(N2CCN(C[C@H](O)COc3ccc(NC(N)=O)cc3)CC2)cc1] | (S)-1-(4-(3-(4-(4-propylphenyl)piperazin-1-yl)-2-hydroxypropoxy)phenyl)urea |

TABLE 4-continued

| Compound | NAME |
|---|---|
| | (S)-1-(4-(3-(4-(4-butylphenyl)piperazin-1-yl)-2-hydroxypropoxy)phenyl)urea |
| | (S)-1-(4-(3-(4-(4-isobutylphenyl)piperazin-1-yl)-2-hydroxypropoxy)phenyl)urea |
| | (S)-1-(4-(2-hydroxy-3-(4-(4-(prop-1-ynyl)phenyl)piperazin-1-yl)propoxy)phenyl)urea |
| | (S)-1-(4-(3-(4-(2-naphthyl)piperazin-1-yl)-2-hydroxypropoxy)phenyl)urea |
| | 1-(4-((S)-3-((R)-4-(4-chlorophenyl)-2-methylpiperazin-1-yl)-2-hydroxypropoxy)phenyl)urea |
| | 1-(4-((S)-3-((S)-4-(4-chlorophenyl)-2-methylpiperazin-1-yl)-2-hydroxypropoxy)phenyl)urea |

TABLE 4-continued

| Compound | NAME |
|---|---|
| | 1-(4-((S)-3-4-(4-chlorophenyl)-cis-2,6-dimethylpiperazin-1-yl)-2-hydroxypropoxy)phenyl)urea |
| | 1-(4-((S)-3-(cis-2,6-dimethyl-4-p-tolylpiperazin-1-yl)-2-hydroxypropoxy)phenyl)urea |
| | (R)-1-(4-(3-(4-(4-chlorophenyl)piperazin-1-yl)-2-hydroxypropoxy)phenyl)urea |
| | (R)-1-(4-(3-(4-(3,4-dichlorophenyl)piperazin-1-yl)-2-hydroxypropoxy)phenyl)urea |
| | (R)-1-(4-(3-(4-(4-ethylphenyl)piperazin-1-yl)-2-hydroxypropoxy)phenyl)urea |
| | (R)-1-(4-(3-(4-(4-isopropylphenyl)piperazin-1-yl)-2-hydroxypropoxy)phenyl)urea |

TABLE 4-continued

| Compound | NAME |
|---|---|
| | (R)-1-(4-(3-(4-(4-cyclopropylphenyl)piperazin-1-yl)-2-hydroxypropoxy)phenyl)urea |
| | (R)-1-(4-(3-(4-(4-propylphenyl)piperazin-1-yl)-2-hydroxypropoxy)phenyl)urea |
| | (R)-1-(4-(3-(4-(4-butylphenyl)piperazin-1-yl)-2-hydroxypropoxy)phenyl)urea |
| | (R)-1-(4-(3-(4-(4-isobutylphenyl)piperazin-1-yl)-2-hydroxypropoxy)phenyl)urea |
| | (R)-1-(4-(2-hydroxy-3-(4-(4-(prop-1-ynyl)phenyl)piperazin-1-yl)propoxy)phenyl)urea |
| | (R)-1-(4-(3-(4-(2-naphthyl)piperazin-1-yl)-2-hydroxypropoxy)phenyl)urea |

TABLE 4-continued

| Compound | NAME |
|---|---|
|  | (R)-1-(4-(3-(4-(4-methylphenyl)piperazin-1-yl)-2-hydroxypropoxy)phenyl)urea |
|  | (R)-1-(4-(3-(4-phenyl-piperazin-1-yl)-2-hydroxypropoxy)phenyl)urea |
|  | (R)-1-(4-(3-(4-(4-fluorophenyl)piperazin-1-yl)-2-hydroxypropoxy)phenyl)urea |

In one embodiment, the compound is selected from the compounds in Table 5.

TABLE 5

| Compound | Name |
|---|---|
|  | N-[2-(3,4-Dichloro-phenylamino)-ethyl]-2-(4-methanesulfonylamino-phenoxy)-acetamide |
|  | N-(4-{2-[2-(3,4-Dichloro-phenylamino)-ethylamino]-ethoxy}-phenyl)-methanesulfonamide |
|  | N-(4-{3-[4-(3,4-Dichloro-phenyl)-piperazin-1-yl]-3-oxo-propyl}-phenyl)-methanesulfonamide |

TABLE 5-continued

| Compound | Name |
|---|---|
| | N-(4-{3-[4-(3,4-DiFluoro-phenyl)-piperazin-1-yl]-3-oxo-propyl}-phenyl)-methanesulfonamide |
| | N-(4-{3-[4-(3,4-Dichloro-phenyl)-piperazin-1-yl]-propyl}-phenyl)-methanesulfonamide |
| | N-(4-{2-[4-(3,4-Dichloro-phenyl)-piperazin-1-yl]-2-oxo-ethoxy}-phenyl)-methanesulfonamide |
| | 6-{2-[4-(3,4-Dichloro-phenyl)-piperazin-1-yl]-2-oxo-ethoxy}-3H-benzooxazol-2-one |
| | 6-{2-[4-(3,4-DiFluoro-phenyl)-piperazin-1-yl]-2-oxo-ethoxy}-3H-benzooxazol-2-one |
| | 6-{2-[4-(4-Chloro-phenyl)-piperazin-1-yl]-2-oxo-ethoxy}-3H-benzooxazol-2-one |
| | N-[2-(3,4-Dichloro-phenylamino)-ethyl]-2-(2-oxo-2,3-dihydro-benzooxazol-6-yloxy)-acetamide |

TABLE 5-continued

| Compound | Name |
|---|---|
| | N-[2-(3,4-Dichloro-phenylamino)-ethyl]-2-(4-hydroxy-phenoxy)-acetamide |
| | N-[2-(3,4-Dichloro-phenylamino)-ethyl-(4-hydroxy-phenyl)-propionamide |
| | N-[2-(3,4-Dichloro-phenylamino)-ethyl]-2-(3-fluoro-4-hydroxy-phenoxy)-acetamide |
| | N-[3-(3,4-Dichloro-phenyl)-allyl]-2-(4-methanesulfonylamino-phenoxy)-acetamide |
| | N-[2-(3,4-Dichloro-phenoxy)-ethyl]-2-(4-methanesulfonylamino-phenoxy)-acetamide |
| | N-[2-(3,4-Dichloro-phenoxy)-ethyl]-2-(4-hydroxy-phenoxy)-acetamide |
| | N-[2-(3,4-Dichloro-phenoxy)-ethyl]-2-(4-ureido-phenoxy)-acetamide |
| | (S)-1-(4-chlorophenyl)-3-(2-hydroxy-3-(4-hydroxyphenoxy)propyl)imidazolidin-2-one |
| | (S)-N-(4-(3-(3-(3,4-dichlorophenyl)-2-oxoimidazolidin-1-yl)-2-hydroxypropoxy)phenyl)methanesulfonamide |

TABLE 5-continued

| Compound | Name |
|---|---|
| (structure) | (S)-3-(2-(4-chlorophenylamino)ethyl)-5-((4-hydroxyphenoxy)methyl)oxazolidin-2-one |
| (structure) | (S)-N-(4-((3-(2-(3,4-dichlorophenylamino)ethyl)-2-oxooxazolidin-5-yl)methoxy)phenyl)methanesulfonamide |

In one embodiment, the compound is selected from Table 6.

TABLE 6

| Compound | NAME |
|---|---|
| (structure) | (S)-5-(3-(4-(3,4-dichlorophenyl)piperazin-1-yl)-2-hydroxypropoxy)indolin-2-one |
| (structure) | (S)-5-(3-(4-(3,4-difluorophenyl)piperazin-1-yl)-2-hydroxypropoxy)indolin-2-one |
| (structure) | (R)-5-(3-(4-(3,4-difluorophenyl)piperazin-1-yl)-2-hydroxypropoxy)indolin-2-one |

TABLE 6-continued

| Compound | NAME |
|---|---|
| | (S)-5-(3-(4-(4-fluorophenyl)piperazin-1-yl)-2-hydroxypropoxy)indolin-2-one |
| | (S)-5-(3-(4-(3,4-dimethylphenyl)piperazin-1-yl)-2-hydroxypropoxy)indolin-2-one |
| | (S)-5-(2-hydroxy-3-(4-p-tolylpiperazin-1-yl)propoxy)indolin-2-one |
| | (S)-4-(4-(2-hydroxy-3-(2-oxoindolin-5-yloxy)propyl)piperazin-1-yl)benzonitrile |
| | (S)-5-(3-(4-(4-bromophenyl)piperazin-1-yl)-2-hydroxypropoxy)indolin-2-one |
| | (S)-5-(2-hydroxy-3-(4-(4-hydroxyphenyl)piperazin-1-yl)propoxy)indolin-2-one |

TABLE 6-continued

| Compound | NAME |
|---|---|
| 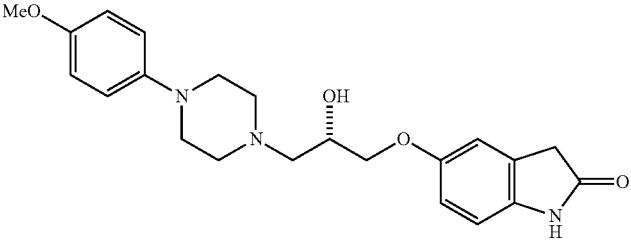 | (S)-5-(2-hydroxy-3-(4-(4-methoxyphenyl)piperazin-1-yl)propoxy)indolin-2-one |
| 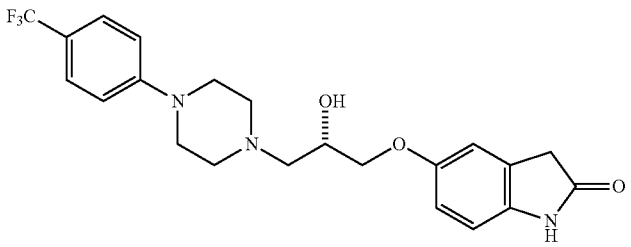 [SMILES: O=C1Cc2cc(OC[C@@H](O)CN3CCN(c4ccc(O)cc4)CC3)ccc2N1] | (S)-5-(2-hydroxy-3-(4-(4-(trifluoromethyl)phenyl)piperazin-1-yl)propoxy)indolin-2-one |
| 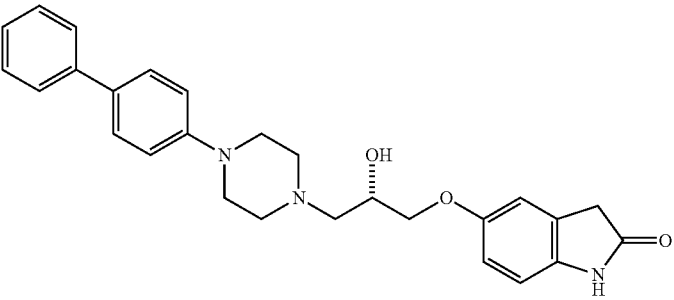 [SMILES: O=C1Cc2cc(OC[C@@H](O)CN3CCN(c4ccc(-c5ccccc5)cc4)CC3)ccc2N1] | (S)-5-(3-(4-(biphenyl-4-yl)piperazin-1-yl)-2-hydroxypropoxy)indolin-2-one |
| 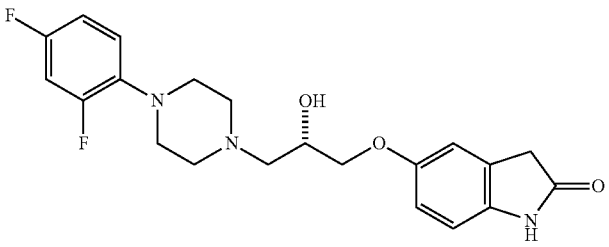 [SMILES: O=C1Cc2cc(OC[C@@H](O)CN3CCN(c4ccc(F)cc4F)CC3)ccc2N1] | (S)-5-(3-(4-(2,4-difluorophenyl)piperazin-1-yl)-2-hydroxypropoxy)indolin-2-one |
| 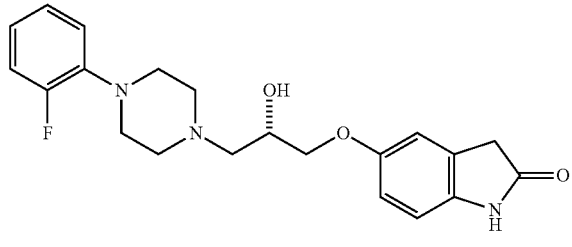 | (S)-5-(3-(4-(2-fluorophenyl)piperazin-1-yl)-2-hydroxypropoxy)indolin-2-one |
| 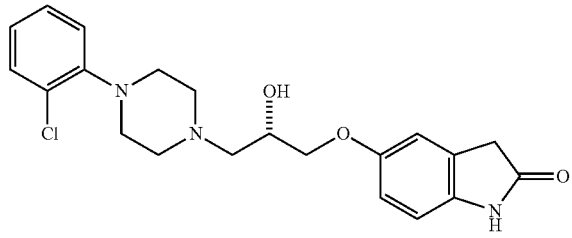 [SMILES: O=C1Cc2cc(OC[C@@H](O)CN3CCN(c4ccccc4Cl)CC3)ccc2N1] | (S)-5-(3-(4-(2-chlorophenyl)piperazin-1-yl)-2-hydroxypropoxy)indolin-2-one |

TABLE 6-continued

| Compound | NAME |
|---|---|
| | (S)-5-(2-hydroxy-3-(4-o-tolylpiperazin-1-yl)propoxy)indolin-2-one |
| | (S)-2-(4-(2-hydroxy-3-(2-oxoindolin-5-yloxy)propyl)piperazin-1-yl)benzonitrile |
| | (S)-5-(2-hydroxy-3-(4-phenylpiperazin-1-yl)propoxy)indolin-2-one |
| | (S)-5-(3-(4-(3-fluorophenyl)piperazin-1-yl)-2-hydroxypropoxy)indolin-2-one |
| | (S)-5-(3-(4-(3-chlorophenyl)piperazin-1-yl)-2-hydroxypropoxy)indolin-2-one |
| | (S)-5-(2-hydroxy-3-(4-m-tolylpiperazin-1-yl)propoxy)indolin-2-one |

TABLE 6-continued

| Compound | NAME |
|---|---|
| 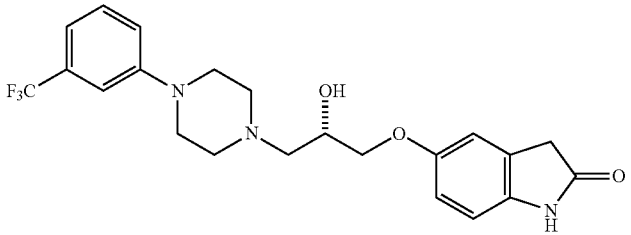 [SMILES: O=C1Cc2cc(OC[C@@H](O)CN3CCN(c4cccc(C(F)(F)F)c4)CC3)ccc2N1] | (S)-5-(2-hydroxy-3-(4-(3-(trifluoromethyl)phenyl)piperazin-1-yl)propoxy)indolin-2-one |
| 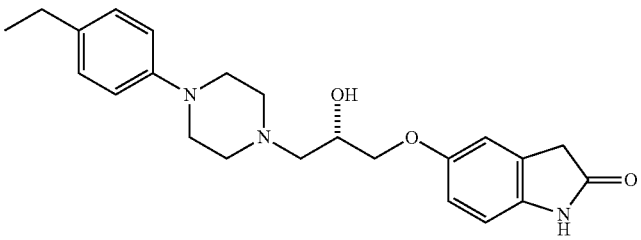 [SMILES: CCc1ccc(N2CCN(C[C@H](O)COc3ccc4c(c3)CC(=O)N4)CC2)cc1] | (S)-(3-(4-(4-ethylphenyl)piperazin-1-yl)hydroxypropoxy)indolin-2-one |
| 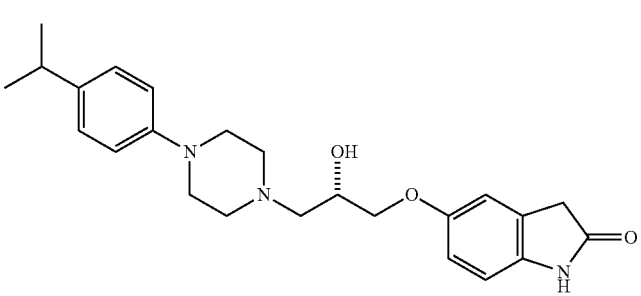 [SMILES: CC(C)c1ccc(N2CCN(C[C@H](O)COc3ccc4c(c3)CC(=O)N4)CC2)cc1] | (S)-5-(2-hydroxy-3-(4-(4-isopropylphenyl)piperazin-1-yl)propoxy)indolin-2-one |
| 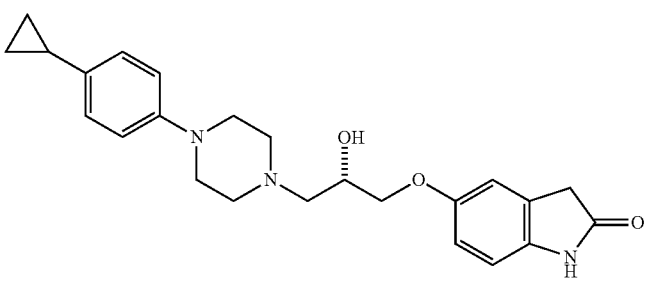 [SMILES: O=C1Cc2cc(OC[C@@H](O)CN3CCN(c4ccc(C5CC5)cc4)CC3)ccc2N1] | (S)-5-(3-(4-(4-cyclopropylphenyl)piperazin-1-yl)-2-hydroxypropoxy)indolin-2-one |
| 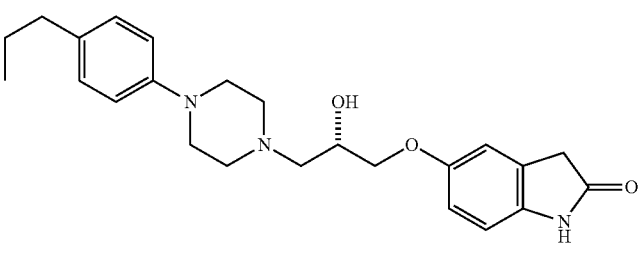 [SMILES: CCCc1ccc(N2CCN(C[C@H](O)COc3ccc4c(c3)CC(=O)N4)CC2)cc1] | (S)-5-(2-hydroxy-3-(4-(4-propylphenyl)piperazin-1-yl)propoxy)indolin-2-one |
| 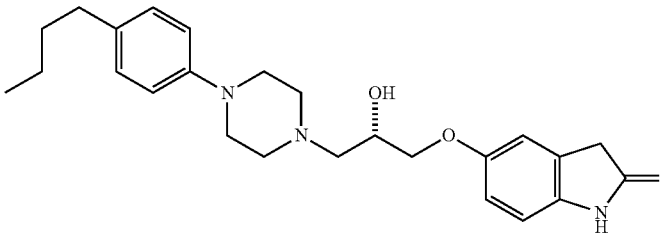 | (S)-5-(3-(4-(4-butylphenyl)piperazin-1-yl)-2-hydroxypropoxy)indolin-2-one |

TABLE 6-continued

| Compound | NAME |
|---|---|
| | (S)-5-(2-hydroxy-(3-(4-(4-isobutylphenyl)piperazin-1-yl)propoxy)indolin-2-one |
| | (S)-5-(2-hydroxy-3-(4-(4-(prop-1-ynyl)phenyl)piperazin-1-yl)propoxy)indolin-2-one |
| | (S)-5-(2-hydroxy-3-(4-(naphthalen-2-yl)piperazin-1-yl)propoxy)indolin-2-one |
| | 5-((S)-3-((R)-4-(4-chlorophenyl)-2-methylpiperazin-1-yl)-2-hydroxypropoxy)indolin-2-one |
| | 5-((S)-3-((S)-4-(4-chlorophenyl)-2-methylpiperazin-1-yl)-2-hydroxypropoxy)indolin-2-one |
| | 5-((S)-3-((2S,6R)-4-(4-chlorophenyl)-2,6-dimethylpiperazin-1-yl)-2-hydroxypropoxy)indolin-2-one |

TABLE 6-continued

| Compound | NAME |
|---|---|
| 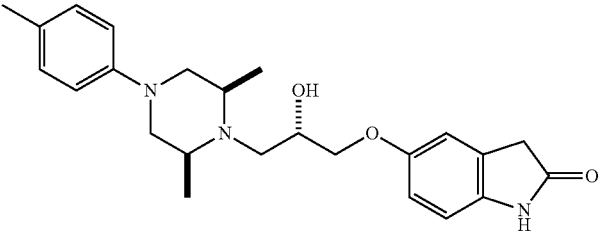 [SMILES: Cc1ccc(N2C[C@@H](C)N(C[C@H](O)COc3ccc4c(c3)CC(=O)N4)[C@@H](C)C2)cc1] | 5-((S)-3-((2S,6R)-2,6-dimethyl-4-p-tolylpiperazin-1-yl)-2-hydroxypropoxy)indolin-2-one |
| 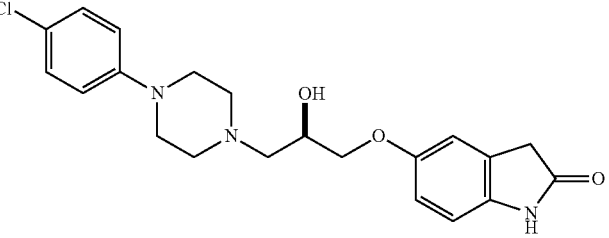 | (R)-5-(3-(4-(4-chlorophenyl)piperazin-1-yl)-2-hydroxypropoxy)indolin-2-one |
| 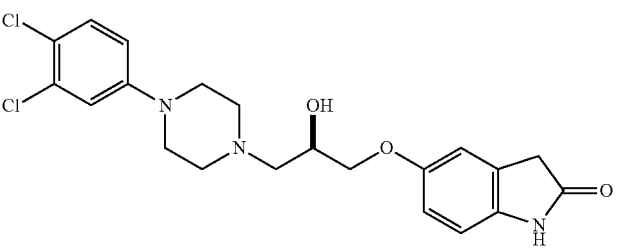 [SMILES: O=C1Cc2cc(OC[C@H](O)CN3CCN(c4ccc(Cl)c(Cl)c4)CC3)ccc2N1] | (R)-5-(3-(4-(3,4-dichlorophenyl)piperazin-1-yl)-2-hydroxypropoxy)indolin-2-one |
| 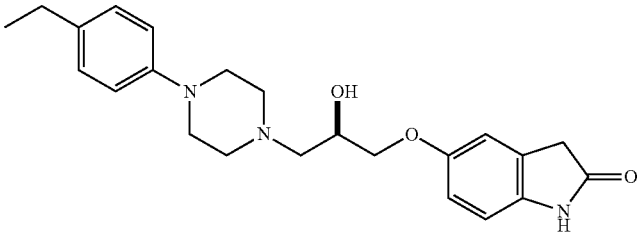 | (R)-5-(3-(4-(4-ethylphenyl)piperazin-1-yl) hydroxypropoxy)indolin-2-one |
| 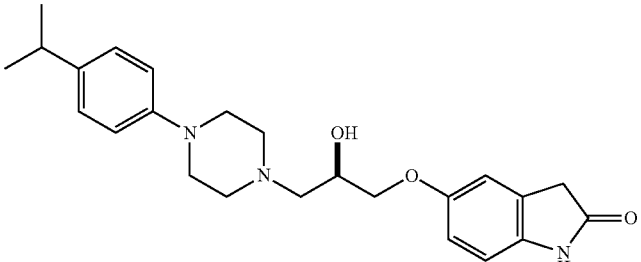 | (R)-5-(2-hydroxy-3-(4-(4-isopropylphenyl)piperazin-1-yl)propoxy)indolin-2-one |
| 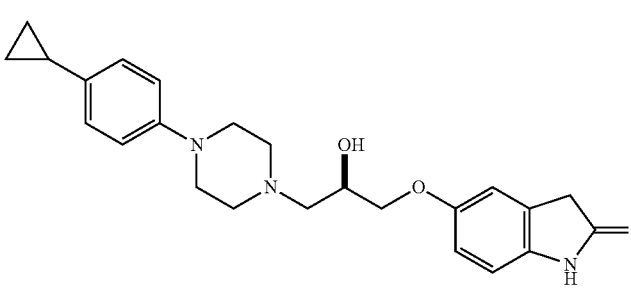 | (R)-5-(3-(4-(4-cyclopropylphenyl)piperazin-1-yl)-2-hydroxypropoxy)indolin-2-one |

TABLE 6-continued

| Compound | NAME |
|---|---|
| 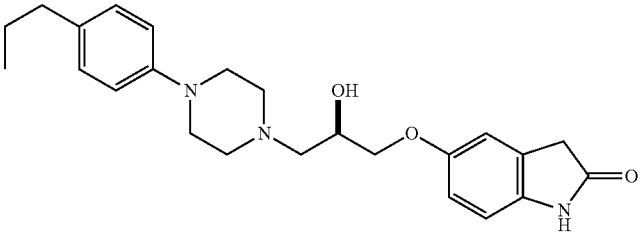 [SMILES: CCCc1ccc(N2CCN(C[C@@H](O)COc3ccc4c(c3)CC(=O)N4)CC2)cc1] | (R)-5-(2-hydroxy-3-(4-(4-propylphenyl)piperazin-1-yl)propoxy)indolin-2-one |
| 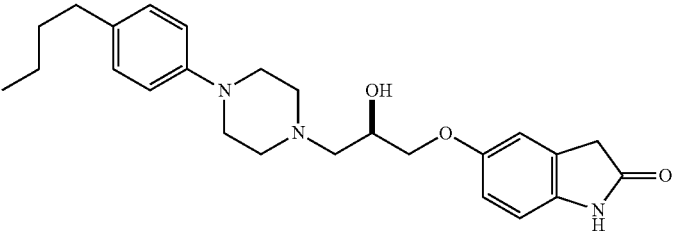 [SMILES: CCCCc1ccc(N2CCN(C[C@@H](O)COc3ccc4c(c3)CC(=O)N4)CC2)cc1] | (R)-5-(3-(4-(4-butylphenyl)piperazin-1-yl)-2-hydroxypropoxy)indolin-2-one |
| 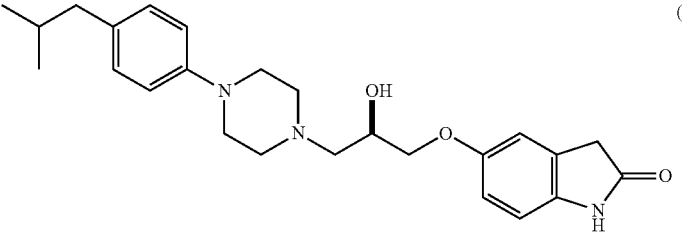 | (R)-5-(2-hydroxy-3-(4-(4-isobutylphenyl)piperazin-1-yl)propoxy)indolin-2-one |
| 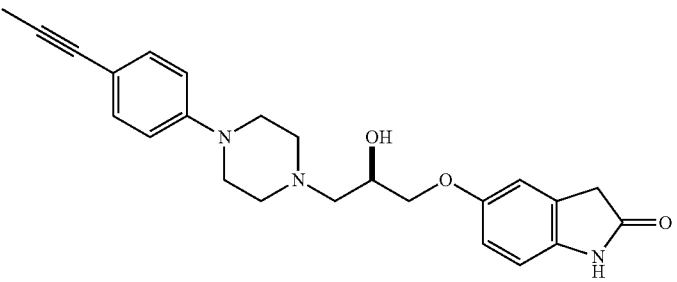 [SMILES: CC#Cc1ccc(N2CCN(C[C@@H](O)COc3ccc4c(c3)CC(=O)N4)CC2)cc1] | (R)-5-(2-hydroxy-3-(4-(4-(prop-1-ynyl)phenyl)piperazin-1-yl)propoxy)indolin-2-one |
| 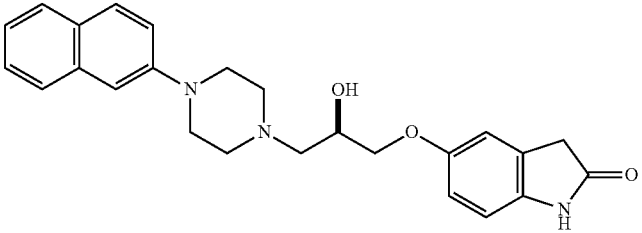 [SMILES: O=C1Cc2cc(OC[C@H](O)CN3CCN(c4ccc5ccccc5c4)CC3)ccc2N1] | (R)-5-(2-hydroxy-3-(4-(naphthalen-2-yl)piperazin-1-yl)propoxy)indolin-2-one |
| 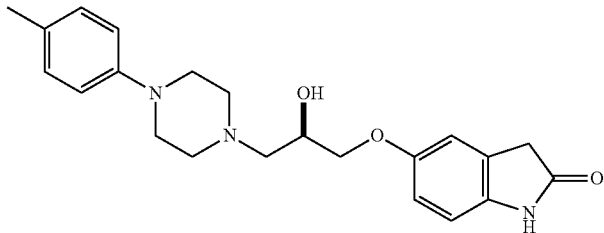 [SMILES: Cc1ccc(N2CCN(C[C@@H](O)COc3ccc4c(c3)CC(=O)N4)CC2)cc1] | (R)-5-(2-hydroxy-(3-(4-p-tolylpiperazin-1-yl)propoxy)indolin-2-one |

TABLE 6-continued

| Compound | NAME |
| --- | --- |
| | (R)-5-(2-hydroxy-3-(4-phenylpiperazin-1-yl)propoxy)indolin-2-one |
| | (R)-5-(3-(4-(4-fluorophenyl)piperazin-1-yl)-2-hydroxypropoxy)indolin-2-one |

In one embodiment, the compound is selected from Table 7.

TABLE 7

| Compound | NAME |
| --- | --- |
| | (S)-6-(3-(4-(3,4-dichlorophenyl)piperazin-1-yl)-2-hydroxypropoxy)-3,4-dihydroquinolin-2(1H)-one |
| | (S)-6-(3-(4-(3,4-difluorophenyl)piperazin-1-yl)-2-hydroxypropoxy)-3,4-dihydroquinolin-2(1H)-one |
| | (S)-6-(3-(4-(3,4-difluorophenyl)piperazin-1-yl)-2-hydroxypropoxy)-3,4-dihydroquinolin-2(1H)-one |

TABLE 7-continued

| Compound | NAME |
|---|---|
| | (S)-6-(3-(4-(4-fluorophenyl)piperazin-1-yl)-2-hydroxypropoxy)-3,4-dihydroquinolin-2(1H)-one |
| | (S)-6-(3-(4-(3,4-dimethylphenyl)piperazin-1-yl)-2-hydroxypropoxy)-3,4-dihydroquinolin-2(1H)-one |
| | (S)-6-(2-hydroxy-3-(4-p-tolylpiperazin-1-yl)propoxy)-3,4-dihydroquinolin-2(1H)-one |
| | (S)-4-(4-(2-hydroxy-3-(2-oxo-1,2,3,4-tetrahydroquinolin-6-yloxy)propyl)piperazin-1-yl)benzonitrile |
| | (S)-6-(3-(4-(4-bromophenyl)piperazin-1-yl)-2-hydroxypropoxy)-3,4-dihydroquinolin-2(1H)-one |
| | (S)-6-(2-hydroxy-3-(4-(4-hydroxyphenyl)piperazin-1-yl)propoxy)-3,4-dihydroquinolin-2(1H)-one |

TABLE 7-continued

| Compound | NAME |
|---|---|
| (structure) | (S)-6-(2-hydroxy-3-(4-(4-methoxyphenyl)piperazin-1-yl)propoxy)-3,4-dihydroquinolin-2(1H)-one |
| (structure) | (S)-6-(2-hydroxy-3-(4-(4-(trifluoromethyl)phenyl)piperazin-1-yl)propoxy)-3,4-dihydroquinolin-2(1H)-one |
| (structure) | (S)-6-(3-(4-(biphenyl-4-yl)piperazin-1-yl)-2-hydroxypropoxy)-3,4-dihydroquinolin-2(1H)-one |
| (structure) | (S)-6-(3-(4-(2,4-difluorophenyl)piperazin-1-yl)-2-hydroxypropoxy)-3,4-dihydroquinolin-2(1H)-one |
| (structure) | (S)-6-(3-(4-(2-fluorophenyl)piperazin-1-yl)-2-hydroxypropoxy)-3,4-dihydroquinolin-2(1H)-one |
| (structure) | (S)-6-(3-(4-(2-chlorophenyl)piperazin-1-yl)-2-hydroxypropoxy)-3,4-dihydroquinolin-2(1H)-one |

TABLE 7-continued

| Compound | NAME |
|---|---|
| | (S)-6-(2-hydroxy-3-(4-o-tolylpiperazin-1-yl)propoxy)-3,4-dihydroquinolin-2(1H)-one |
| | (S)-2-(4-(2-hydroxy-3-(2-oxo-1,2,3,4-tetrahydroquinolin-6-yloxy)propyl)piperazin-1-yl)benzonitrile |
| | (S)-6-(2-hydroxy-3-(4-phenylpiperazin-1-yl)propoxy)-3,4-dihydroquinolin-2(1H)-one |
| | (S)-6-(3-(4-(3-fluorophenyl)piperazin-1-yl)-2-hydroxypropoxy)-3,4-dihydroquinolin-2(1H)-one |
| | (S)-6-(3-(4-(3-chlorophenyl)piperazin-1-yl)-2-hydroxypropoxy)-3,4-dihydroquinolin-2(1H)-one |
| | (S)-6-(2-hydroxy-3-(4-m-tolypiperazin-1-yl)propoxy)-3,4-dihydroquinolin-2(1H)-one |

TABLE 7-continued

| Compound | NAME |
|---|---|
|  | (S)-6-(2-hydroxy-3-(4-(3-(trifluoromethyl)phenyl)piperazin-1-yl)propoxy)-3,4-dihydroquinolin-2(1H)-one |
|  | (S)-6-(3-(4-(4-ethylphenyl)piperazin-1-yl)-2-hydroxypropoxy)-3,4-dihydroquinolin-2(1H)-one |
|  | (S)-6-(2-hydroxy-3-(4-(4-isopropylphenyl)piperazin-1-yl)propoxy)-3,4-dihydroquinolin-2(1H)-one |
|  | (S)-6-(3-(4-(4-cyclopropylphenyl)piperazin-1-yl)-2-hydroxypropoxy)-3,4-dihydroquinolin-2(1H)-one |
|  | (S)-6-(2-hydroxy-3-(4-(4-propylphenyl)piperazin-1-yl)propoxy)-3,4-dihydroquinolin-2(1H)-one |
|  | (S)-6-(3-(4-(4-butylphenyl)piperazin-1-yl)-2-hydroxypropoxy)-3,4-dihydroquinolin-2(1H)-one |

TABLE 7-continued

| Compound | NAME |
|---|---|
| | (S)-6-(2-hydroxy-3-(4-(4-isobutylphenyl)piperazin-1-yl)propoxy)-3,4-dihydroquinolin-2(1H)-one |
| | (S)-6-(2-hydroxy-3-(4-(4-(prop-1-ynyl)phenyl)piperazin-1-yl)propoxy)-3,4-dihydroquinolin-2(1H)-one |
| | (S)-6-(2-hydroxy-3-(4-(naphthalen-2-yl)-piperazin-1-yl)propoxy)-3,4-dihydroquinolin-2(1H)-one |
| | 6-((S)-3-((R)-4-(4-chlorophenyl)-2-methylpiperazin-1-yl)-2-hydroxypropoxy)-3,4-dihydroquinolin-2(1H)-one |
| | 6-((S)-3-((S)-4-(4-chlorophenyl)-2-methylpiperazin-1-yl)-2-hydroxypropoxy)-3,4-dihydroquinolin-2(1H)-one |
| | 6-((S)-3-((2S,6R)-4-(4-chlorophenyl)-2,6-dimethylpiperazin-1-yl)-2-hydroxypropoxy)-3,4-dihydroquinolin-2(1H)-one |

TABLE 7-continued

| Compound | NAME |
| --- | --- |
|  | 6-((S)-3-((2S,6R)-2,6-dimethyl-4-p-tolylpiperazin-1-yl)-2-hydroxypropoxy)-3,4-dihydroquinolin-2(1H)-one |
|  | (R)-6-(3-(4-(4-chlorophenyl)piperazin-1-yl)-2-hydroxypropoxy)-3,4-dihydroquinolin-2(1H)-one |
|  | (R)-6-(3-(4-(3,4-dichlorophenyl)piperazin-1-yl)-2-hydroxypropoxy)-3,4-dihydroquinolin-2(1H)-one |
|  | (R)-6-(3-(4-(4-ethylphenyl)piperazin-1-yl)-2-hydroxypropoxy)-3,4-dihydroquinolin-2(1H)-one |
|  | (R)-6-(2-hydroxy-3-(4-(4-isopropylphenyl)piperazin-1-yl)propoxy)-3,4-dihydroquinolin-2(1H)-one |
|  | (R)-6-(3-(4-(4-cyclopropylphenyl)piperazin-1-yl)-2-hydroxypropoxy)-3,4-dihydroquinolin-2(1H)-one |

TABLE 7-continued

| Compound | NAME |
|---|---|
|  | (R)-6-(2-hydroxy-3-(4-(4-propylphenyl)piperazin-1-yl)propoxy)-3,4-dihydroquinolin-2(1H)-one |
|  | (R)-6-(3-(4-(4-butylphenyl)piperazin-1-yl)-2-hydroxypropoxy)-3,4-dihydroquinolin-2(1H)-one |
|  | (R)-6-(2-hydroxy-3-(4-(4-isobutylphenyl)piperazin-1-yl)propoxy)-3,4-dihydroquinolin-2(1H)-one |
|  | (R-6-(2-hydroxy-3-(4-(4-(prop-1-ynyl)phenyl)piperazin-1-yl)propoxy)-3,4-dihydroquinolin-2(1H)-one |
|  | (R)-6-(2-hydroxy-3-(4-(naphthalen-2yl)piperazin-1-yl)propoxy)-3,4-dihydroquinolin-2(1H)-one |
|  | (R)-6-(2-hydroxy-3-(4-p-tolylpiperazin-1-yl)propoxy)-3,4-dihydroquinolin-2(1H)-one |

TABLE 7-continued

| Compound | NAME |
|---|---|
| (structure) | (R)-6-(2-hydroxy-3-(4-phenylpiperazin-1-yl)propoxy)-3,4-dihydroquinolin-2(1H)-one |
| (structure) | (R)-6-(3-(4-(4-fluorophenyl)piperazin-1-yl)-2-hydroxypropoxy)-3,4-dihydroquinolin-2(1H)-one |

In another embodiment, the compound is selected from Table 8.

TABLE 8

| Compound | NAME |
|---|---|
| (structure) | (S)-6-(3-(4-(3,4-dichlorophenyl)piperazin-1-yl)-2-hydroxypropoxy)quinolin-2(1H)-one |
| (structure) | (S)-6-(3-(4-(3,4-difluorophenyl)piperazin-1-yl)-2-hydroxypropoxy)quinolin-2(1H)-one |
| (structure) | (R)-6-(3-(4-(3,4-difluorophenyl)piperazin-1-yl)-2-hydroxypropoxy)quinolin-2(1H)-one |

TABLE 8-continued

| Compound | NAME |
|---|---|
| | (S)-6-(3-(4-(4-fluorophenyl)piperazin-1-yl)-2-hydroxypropoxy)quinolin-2(1H)-one |
| | (S)-6-(3-(4-(3,4-dimethylphenyl)piperazin-1-yl)-2-hydroxypropoxy)quinolin-2(1H)-one |
| | (S)-6-(2-hydroxy-3-(4-p-tolylpiperazin-1-yl)propoxy)quinolin-2(1H)-one |
| | (S)-4-(4-(2-hydroxy-3-(2-oxo-1,2-dihydroquinolin-6-yloxy)propyl)piperazin-1-yl)benzonitrile |
| | (S)-6-(3-(4-(4-bromophenyl)piperazin-1-yl)-2-hydroxypropoxy)quinolin-2(1H)-one |
| | (S)-6-(2-hydroxy-3-(4-(4-hydroxyphenyl)piperazin-1-yl)propoxy)quinolin-2(1H)-one |

TABLE 8-continued

| Compound | NAME |
|---|---|
| | (S)-6-(2-hydroxy-3-(4-(4-methoxyphenyl)piperazin-1-yl)propoxy)quinolin-2(1H)-one |
| | (S)-6-(2-hydroxy-3-(4-(4-(trifluoromethyl)phenyl)piperazin-1-yl)propoxy)quinolin-2(1H)-one |
| | (S)-6-(3-(4-(biphenyl-4-yl)piperazin-1-yl)-2-hydroxypropoxy)quinolin-2(1H)-one |
| | (S)-6-(3-(4-(2,4-difluorophenyl)piperazin-1-yl)-2-hydroxypropoxy)quinolin-2(1H)-one |
| | (S)-6-(3-(4-(2-fluorophenyl)piperazin-1-yl)-2-hydroxypropoxy)quinolin-2(1H)-one |
| | (S)-6-(3-(4-(2-chlorophenyl)piperazin-1-yl)-2-hydroxypropoxy)quinolin-2(1H)-one |

TABLE 8-continued

| Compound | NAME |
|---|---|
| | (S)-6-(2-hydroxy-3-(4-o-tolylpiperazin-1-yl)propoxy)quinolin-2(1H)-one |
| | (S)-2-(4-(2-hydroxy-3-(2-oxo-1,2-dihydroquinolin-6-yloxy)propyl)piperazin-1-yl)benzonitrile |
| | (S)-6-(2-hydroxy-3-(4-phenylpiperazin-1-yl)propoxy)quinolin-2(1H)-one |
| | (S)-6-(3-(4-(3-fluorophenyl)piperazin-1-yl)-2-hydroxypropoxy)quinolin-2(1H)-one |
| | (S)-6-(3-(4-(3-chlorophenyl)piperazin-1-yl)-2-hydroxypropoxy)quinolin-2(1H)-one |
| | (S)-6-(2-hydroxy-3-(4-m-tolypiperazin-1-yl)propoxy)quinolin-2(1H)-one |

TABLE 8-continued

| Compound | NAME |
|---|---|
| | (S)-6-(2-hydroxy-3-(4-(3-(trifluoromethyl)phenyl)piperazin-1-yl)propoxy)quinolin-2(1H)-one |
| | (S)-6-(3-(4-(4-ethylphenyl)piperazin-1-yl)-2-hydroxypropoxy)quinolin-2(1H)-one |
| | (S)-6-(2-hyroxy-3-(4-(4-isoproylphenyl)piperazin-1-yl)propoxy)quinolin-2(1H)-one |
| | (S)-6-(3-(4-(4-cyclopropylphenyl)piperazin-1-yl)-2-hydroxypropoxy)quinolin-2(1H)-one |
| | (S)-6-(2-hydroxy-3-(4-(4-propylphenyl)piperazin-1-yl)propoxy)quinolin-2(1H)-one |
| | (S)-6-(3-(4-(4-butylphenyl)piperazin-1-yl)-2-hydroxypropoxy)quinolin-2(1H)-one |

TABLE 8-continued

| Compound | NAME |
|---|---|
| | (S)-6-(2-hydroxy-3-(4-(4-isobutylphenyl)piperazin-1-yl)propoxy)quinolin-2(1H)-one |
| | (S)-6-(2-hydroxy-3-(4-(4-(prop-1-ynyl)phenyl)piperazin-1-yl)propoxy)quinolin-2(1H)-one |
| | (S)-6-(2-hydroxy-3-(4-(naphthalen-2-yl)piperazin-1-yl)propoxy)quinolin-2(1H)-one |
| | 6-((S)-3-((R)-4-(4-chlorophenyl)-2-methylpiperazin-1-yl)-2-hydroxypropoxy)quinolin-2(1H)-one |
| | 6-((S)-3-((S)-4-(4-chlorophenyl)-2-methylpiperazin-1-yl)-2-hydroxypropoxy)quinolin-2(1H)-one |
| | 6-((S)-3-((2S,6R)-4-(4-chlorophenyl)-2,6-dimethylpiperazin-1-yl)-2-hydroxypropoxy)quinolin-2(1H)-one |

TABLE 8-continued

| Compound | NAME |
|---|---|
| | 6((S)-3-((2S,6R)-2,6-dimethyl-4-p-tolylpiperazin-1-yl)-2-hydroxypropoxy)quinolin-2(1H)-one |
| | (R)-6-(3-(4-(4-chlorophenyl)piperazin-1-yl)-2-hydroxypropoxy)quinolin-2(1H)-one |
| | (R)-6-(3-(4-(3,4-dichlorophenyl)piperazin-1-yl)-2-hydroxypropoxy)quinolin-2(1H)-one |
| | (R)-6-(3-(4-(4-ethylphenyl)piperazin-1-yl)-2-hydroxypropoxy)quinolin-2(1H)-one |
| | (R)-6-(2-hydroxy-3-(4-(4-isopropylphenyl)piperazin-1-yl)propoxy)quinolin-2(1H)-one |
| | (R)-6-(3-(4-(4-cyclopropylphenyl)piperazin-1-yl)-2-hydroxypropoxy)quinolin-2(1H)-one |

TABLE 8-continued

| Compound | NAME |
|---|---|
| | (R)-6-(2-hydroxy-3-(4-(4-propylphenyl)piperazin-1-yl)propoxy)quinolin-2(1H)-one |
| | (R)-6-(3-(4-(4-butylphenyl)piperazin-1-yl)-2-hydroxypropoxy)quinolin-2(1H)-one |
| | (R)-6-(2-hydroxy-3-(4-(4-isobutylphenyl)piperazin-1-yl)propoxy)quinolin-2(1H)-one |
| | (R)-6-(2-hydroxy-3-(4-(4-(prop-1-ynyl)phenyl)piperazin-1-yl)propoxy)quinolin-2(1H)-one |
| | (R)-6-(2-hydroxy-3-(4-(naphthalen-2-yl)piperazin-1-yl)propoxy)quinolin-2(1H)-one |
| | (R)-6-(2-hydroxy-3-(4-p-tolylpiperazin-1-yl)propoxy)quinolin-2(1H)-one |

TABLE 8-continued

| Compound | NAME |
|---|---|
| | (R)-6-(2-hydroxy-3-(4-phenylpiperazin-1-yl)propoxy)quinolin-2(1H)-one |
| | (R)-6-(3-(4-(fluorophenyl)piperazin-1-yl)-2-hydroxypropoxy)quinolin-2(1H)-one |
| | (S)-6-(3-(4-benzyl-4-hydroxypiperidin-1-yl)-2-hydroxypropoxy)quinolin-2(1H)-one |
| | (R)-6-(3-(4-benzyl-4-hydroxypiperidin-1-yl)-2-hydroxypropoxy)quinolin-2(1H)-one |
| | (S)-6-(2-hydroxy-3-(4-hydroxy-4-phenylpiperidin-1-yl)propoxy)quinolin-2(1H)-one |

In another embodiment, the compound is selected from Table 9.

TABLE 9

| Compound | Name |
|---|---|
| | N-(4-(2-(3-(3,4-dichlorophenyl)-2-oxoimidazolidin-1-yl)ethoxy)phenyl)methanesulfonamide |

TABLE 9-continued

| Compound | Name |
|---|---|
| | N-(4-(3-(3-(3,4-dichlorophenyl)-2-oxoimidazolidin-1-yl)propyl)phenyl)methanesulfonamide |
| | (S)-N-(4-(3-(3-(3,4-dichlorophenyl)-2-oxoimidazolidin-1-yl)-2-hydroxypropoxy)phenyl)methanesulfonamide |
| | (S)-N-(4-(3-(3-(4-chlorophenyl)-2-oxoimidazolidin-1-yl)-2-hydroxypropoxy)phenyl)methanesulfonamide |
| | (S)-1-(4-chlorophenyl)-3-(2-hydroxy-3-(4-hydroxyphenoxy)propyl)imidazolidin-2-one |
| | 1-(4-chlorophenyl)-3-(3-(4-hydroxyphenoxy)propyl)imidazolidin-2-one |
| | (S)-1-(4-(3-(3-(4-chlorophenyl)-2-oxoimidazolidin-1-yl)-2-hydroxypropoxy)phenyl)urea |

In another embodiment, the compound is selected from Table 10.

TABLE 10

| Compound | Name |
|---|---|
| | N-(2-(3,4-difluorophenylamino)ethyl)-2-(4-(methylsulfonamido)phenoxy)acetamide |

TABLE 10-continued

| Compound | Name |
|---|---|
| | N-(2-(3,4-dichlorophenylamino)ethyl)-2-(4-(methylsulfonamido)phenoxy)acetamide |
| | N-(2-(3,4-dichlorophenylthio)ethyl)-2-(4-(methylsulfonamido)phenoxy)acetamide |
| | N-(2-(3,4-dichlorophenoxy)ethyl)-2-(4-(methylsulfonamido)phenoxy)acetamide |
| | (E)-N-(3-(3,4-dichlorophenyl)allyl)-2-(4-(methylsulfonamido)phenoxy)acetamide |
| | N-(3-(3,4-dichlorophenyl)propyl)-2-(4-(methylsulfonamido)phenoxy)acetamide |
| | N-(2-(3,4-dichlorophenylamino)ethyl)-3-(4-(methylsulfonamido)phenyl)propanamide |
| | N-(2-(3,4-dichlorophenylthio)ethyl)-3-(4-(methylsulfonamido)phenyl)propanamide |

TABLE 10-continued

| Compound | Name |
|---|---|
| | N-(2-(3,4-dichlorophenoxy)ethyl)-3-(4-(methylsulfonamido)phenyl)propanamide |
| | (E)-N-(3-(3,4-dichlorophenyl)allyl)-3-(4-(methylsulfonamido)phenyl)propanamide |
| | N-(3-(3,4-dichlorophenyl)propyl)-3-(4-(methylsulfonamido)phenyl)propanamide |
| | N-(4-(3-(4-(3,4-dichlorophenyl)piperazin-1-yl)-3-oxopropyl)phenyl)methanesulfonamide |
| | N-(4-(2-(4-(3,4-dichlorophenyl)piperazin-1-yl)-2-oxoethoxy)phenyl)methanesulfonamide |
| | N-(4-(3-(4-(3,4-dichlorophenyl)-2-oxopiperazin-1-yl)propyl)phenyl)methanesulfonamide |

TABLE 10-continued

| Compound | Name |
|---|---|
| | N-(4-(2-(4-(3,4-dichlorophenyl)-2-oxopiperazin-1-yl)ethoxy)phenyl)methanesulfonamide |
| | (S)-N-(4-(3-(4-(4-chlorophenyl)-2-oxopiperazin-1-yl)-2-hydroxypropoxy)phenyl)methanesulfonamide |
| | (S)-N-(4-(3-(4-(3,4-difluorophenyl)-2-oxopiperazin-1-yl)-2-hydroxypropoxy)phenyl)methanesulfonamide |
| | N-(4-(3-(4-(3,4-difluorophenyl)-2-oxopiperazin-1-yl)propoxy)phenyl)methanesulfonamide |
| | N-(4-(3-(4-(3,4-difluorophenyl)piperazin-1-yl)-3-oxopropyl)phenyl)methanesulfonamide |
| | N-(4-(2-(4-(3,4-difluorophenyl)piperazin-1-yl)-2-oxoethoxy)phenyl)methanesulfonamide |

TABLE 10-continued

| Compound | Name |
|---|---|
| | 6-(2-(4-3,4-difluorophenyl)piperazin-1-yl)-2-oxoethoxy)benzo[d]oxazol-2(3H)-one |
| | 6-(2-(4-(3,4-dichlorophenyl)piperazin-1-yl)-2-oxoethoxy)benzo[d]oxazol-2(3H)-one |
| | 6-(2-(4-(4-Chlorophenyl)piperazin-1-yl)-2-oxoethoxy)benzo[d]oxazol-2(3H)-one |
| | 5-(2-(4-(3,4-difluorophenyl)piperazin-1-yl)-2-oxoethoxy)indolin-2-one |
| | 5-(2-(4-(4-chlorophenyl)piperazin-1-yl)-2-oxoethoxy)indolin-2-one |
| | 5-(2-(4-(3,4-dichlorophenyl)piperazin-1-yl)-2-oxoethoxy)indolin-2-one |

TABLE 10-continued

| Compound | Name |
|---|---|
| | 6-(2-(4-(3,4-dichlorophenyl)piperazin-1-yl)-2-oxoethoxy)-3,4-dihydroquinolin-2(1H)-one |
| | 6-(2-(4-(4-chlorophenyl)piperazin-1-yl)-2-oxoethoxy)-3,4-dihydroquinolin-2(1H)-one |
| | 6-(2-(4-(3,4-difluorophenyl)piperazin-1-yl)-2-oxoethoxy)-3,4-dihydroquinolin-2(1H)-one |
| | 6-(2-(4-(3,4-dichlorophenyl)piperazin-1-yl)-2-oxoethoxy)quinolin-2(1H)-one |
| | 6-(2-(4-(4-chlorophenyl)piperazin-1-yl)-2-oxoethoxy)quinolin-2(1H)-one |
| | 6-(2-(4-(3,4-difluorophenyl)piperazin-1-yl)-2-oxoethoxy)quinolin-2(1H)-one |

TABLE 10-continued

| Compound | Name |
|---|---|
| | 6-(3-(4-(3,4-difluorophenyl)piperazin-1-yl)-3-oxopropoxy)benzo[d]oxazol-2(3H)-one |
| | 6-(3-(4-(3,4-dichlorophenyl)piperazin-1-yl)-3-oxopropoxy)benzo[d]oxazol-2(3H)-one |
| | 6-(3-(4-(4-chlorophenyl)piperazin-1-yl)-3-oxopropoxy)benzo[d]oxazol-2(3H)-one |
| | 5-(3-(4-(3,4-difluorophenyl)piperazin-1-yl)-3-oxopropoxy)indolin-2-one |
| | 5-(3-(4-(3,4-dichlorophenyl)piperazin-1-yl)-3-oxopropoxy)indolin-2-one |

TABLE 10-continued

| Compound | Name |
|---|---|
| | 5-(3-(4-(4-chlorophenyl)piperazin-1-yl)-3-oxopropoxy)indolin-2-one |
| | 6-(3-(4-(3,4-difluorophenyl)piperazin-1-yl)-3-oxopropoxy)-3,4-dihydroquinolin-2(1H)-one |
| | 6-(3-(4-(4-chlorophenyl)piperazin-1-yl)-3-oxopropoxy)-3,4-dihydroquinolin-2(1H)-one |
| | 6-(3-(4-(3,4-dichlorophenyl)piperazin-1-yl)-3-oxopropoxy)-3,4-dihydroquinolin-2(1H)-one |
| | 6-(3-(4-(3,4-difluorophenyl)piperazin-1-yl)-3-oxopropoxy)quinolin-2(1H)-one |

TABLE 10-continued

| Compound | Name |
|---|---|
| | 6-(3-(4-(4-chlorophenyl)piperazin-1-yl)-3-oxopropoxy)quinolin-2(1H)-one |
| | 6-(3-(4-(3,4-dichlorophenyl)piperazin-1-yl)-3-oxopropoxy)quinolin-2(1H)-one |
| | 5-(2-(4-(3,4-dichlorophenyl)-2-oxopiperazin-1-yl)ethoxy)indolin-2-one |
| | 5-(2-(4-(4-chlorophenyl)-2-oxopiperazin-1-yl)ethoxy)indolin-2-one |
| | 5-(2-(4-3,4-difluorophenyl)-2-oxopiperazin-1-yl)ethoxy)indolin-2-one |
| | 5-(3-(4-(3,4-difluorophenyl)-2-oxopiperazin-1-yl)propoxy)indolin-2-one |

TABLE 10-continued

| Compound | Name |
|---|---|
| 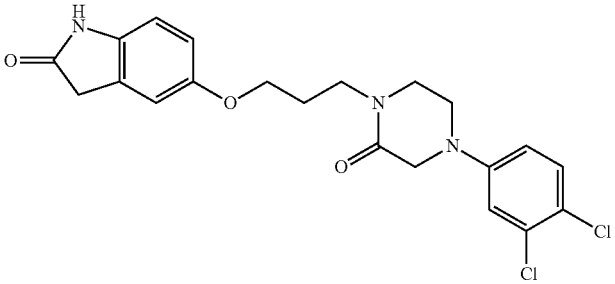 [SMILES: O=C1Cc2cc(OCCCN3CCN(c4ccc(Cl)c(Cl)c4)CC3=O)ccc2N1] | 5-(3-(4-(3,4-dichlorophenyl)-2-oxopiperazin-1-yl)propoxy)indolin-2-one |
| 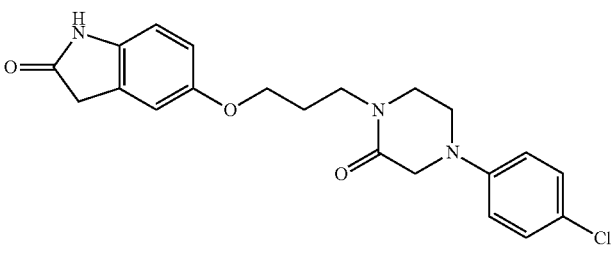 [SMILES: O=C1Cc2cc(OCCCN3CCN(c4ccc(Cl)cc4)CC3=O)ccc2N1] | 5-(3-(4-(4-chlorophenyl)-2-oxopiperazin-1-yl)propoxy)indolin-2-one |
| 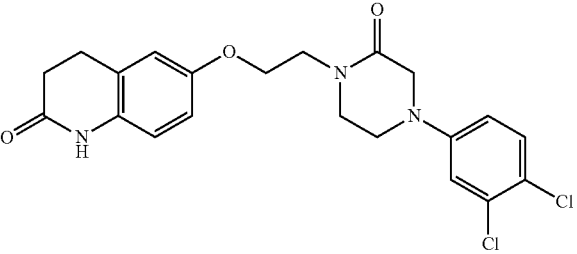 [SMILES: O=C1CCc2cc(OCCN3CCN(c4ccc(Cl)c(Cl)c4)CC3=O)ccc2N1] | 6-(2-(4-(3,4-dichlorophenyl)-2-oxopiperazin-1-yl)ethoxy)-3,4-dihydroquinolin-2(1H)-one |
| 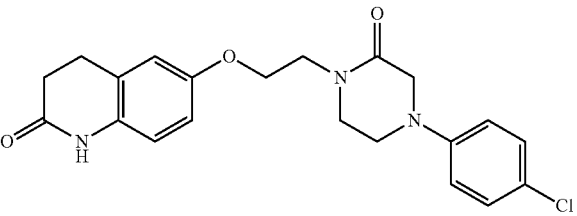 [SMILES: O=C1CCc2cc(OCCN3CCN(c4ccc(Cl)cc4)CC3=O)ccc2N1] | 6-(2-(4-(4-chlorophenyl)-2-oxopiperazin-1-yl)ethoxy)-3,4-dihydroquinolin-2(1H)-one |
| 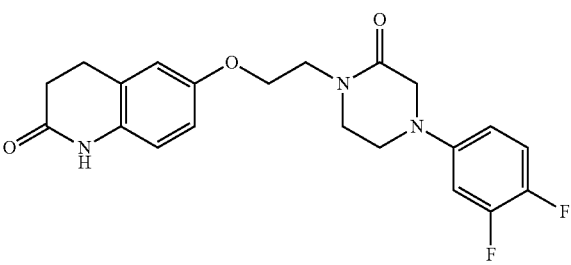 [SMILES: O=C1CCc2cc(OCCN3CCN(c4ccc(F)c(F)c4)CC3=O)ccc2N1] | 6-(2-(4-(3,4-difluorophenyl)-2-oxopiperazin-1-yl)ethoxy)-3,4-dihydroquinolin-2(1H)-one |
| 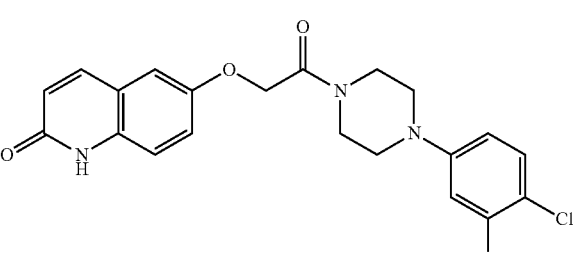 | 6-(2-(4-(3,4-dichlorophenyl)piperazin-1-yl)-2-oxoethoxy)quinolin-2(1H)-one |

TABLE 10-continued

| Compound | Name |
| --- | --- |
| | 6-(2-(4-(4-chlorophenyl)piperazin-1-yl)-2-oxoethoxy)quinolin-2(1H)-one |
| | 6-(2-(4-(3,4-difluorophenyl)piperazin-1-yl)-2-oxoethoxy)quinolin-2(1H)-one |
| | N-(2-(3,4-dichlorophenylamino)ethyl)-2-(2-oxo-2,3-dihydrobenzo[d]oxazol-6-yloxy)acetamide |
| | N-(2-(3,4-difluorophenylamino)ethyl)-2-(2-oxo-2,3-dihydrobenzo[d]oxazol-6-yloxy)acetamide |
| | N-(2-(3,4-difluorophenylamino)ethyl-2-(4-hydroxyphenoxy)acetamide |
| | N-(2-(3,4-difluorophenylamino)ethyl)-3-(4-hydroxyphenyl)propanamide |

TABLE 10-continued

| Compound | Name |
|---|---|
| [structure: 2-fluoro-4-hydroxyphenoxy-CH2-C(=O)-NH-CH2CH2-NH-3,4-difluorophenyl] | N-(2-(3,4-difluorophenylamino)ethyl)-2-(3-fluoro-4-hydroxyphenoxy)acetamide |

In one embodiment, the compound is not

[structure: 4-hydroxyphenoxy-CH2-CH(OH)-CH2-piperazine-N-biphenyl]

In another embodiment, the compound is not

[structure: MeO2SHN-phenyl-O-CH2-CH(OH)-CH2-piperazine-N-pyridin-4-yl]

In one embodiment, the compound has an IC$_{50}$ value of 600 nM or less. In one embodiment, the compound has an IC$_{50}$ value of 600 nM or less at pH 6.9 or an ischemic pH. In one embodiment, the compound is selected from Table 11.

TABLE 11

[structure: MeO2SHN-phenyl-O-CH2-CH(OH)-CH2-piperazine-N-(3,4-difluorophenyl)]

[structure: MeO2SHN-phenyl-O-CH2-CH(OH)-CH2-NH-CH2CH2-NH-(3,4-dichlorophenyl)]

TABLE 11-continued

[structure: MeO2SHN-phenyl-O-CH2-CH(OH)-CH2-piperazine-N-(3,4-dichlorophenyl)]

[structure: MeO2SHN-phenyl-O-CH2-CH(OH)-CH2-piperazine-N-(4-chlorophenyl)]

[structure: MeO2SHN-phenyl-O-CH2-CH(OH)-CH2-piperazine-N-phenyl]

[structure: MeO2SHN-phenyl-O-CH2-CH(OH)-CH2-NH-CH2CH2-NH-phenyl]

[structure: MeO2SHN-phenyl-O-CH2-CH(OH)-CH2-NH-CH2CH2-NH-(3,4-difluorophenyl)]

TABLE 11-continued
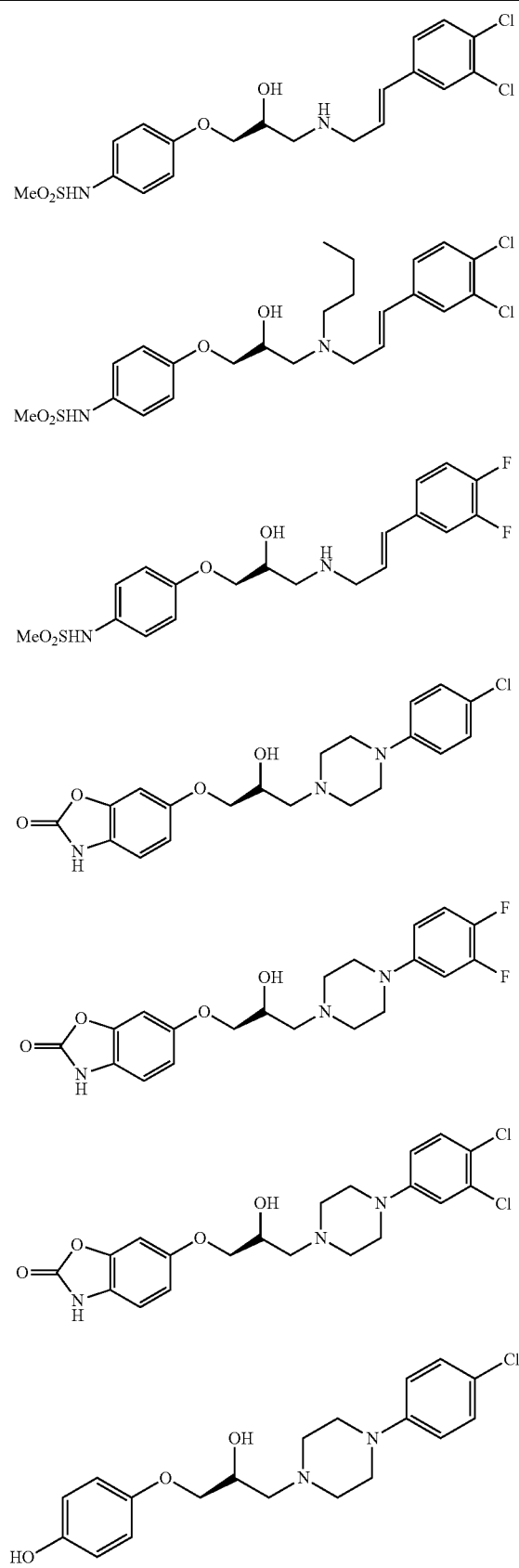
TABLE 11-continued
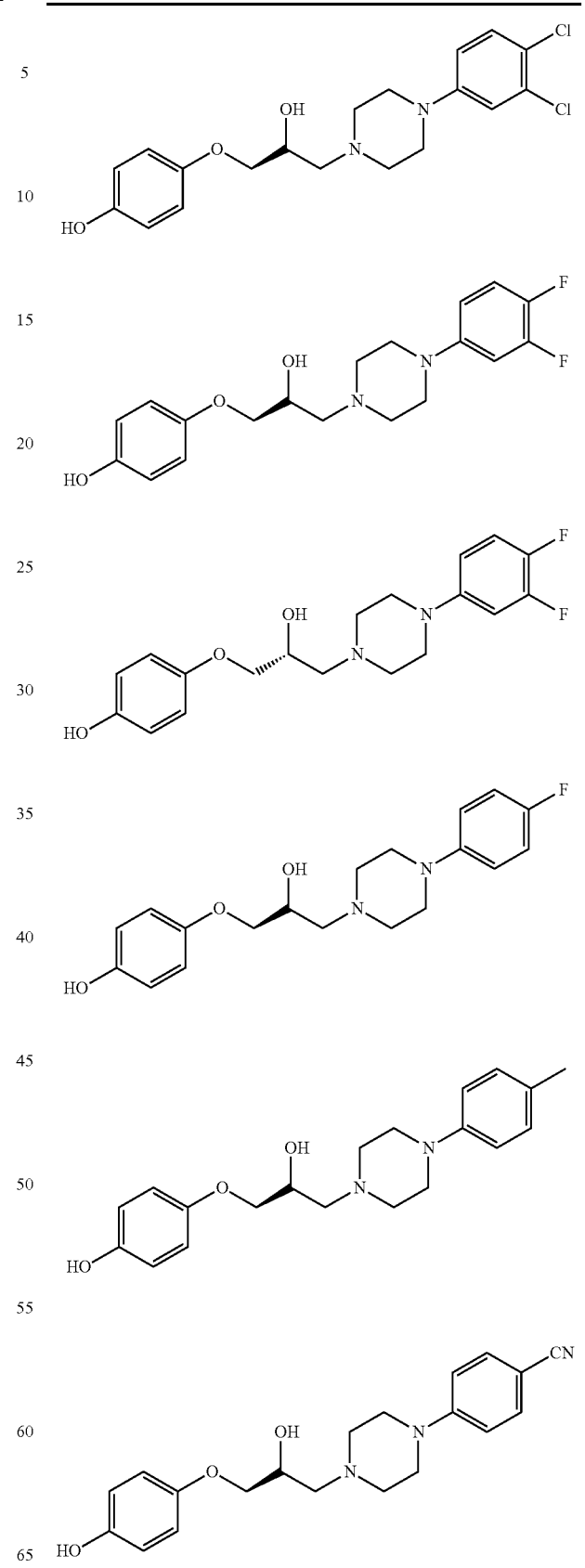

TABLE 11-continued
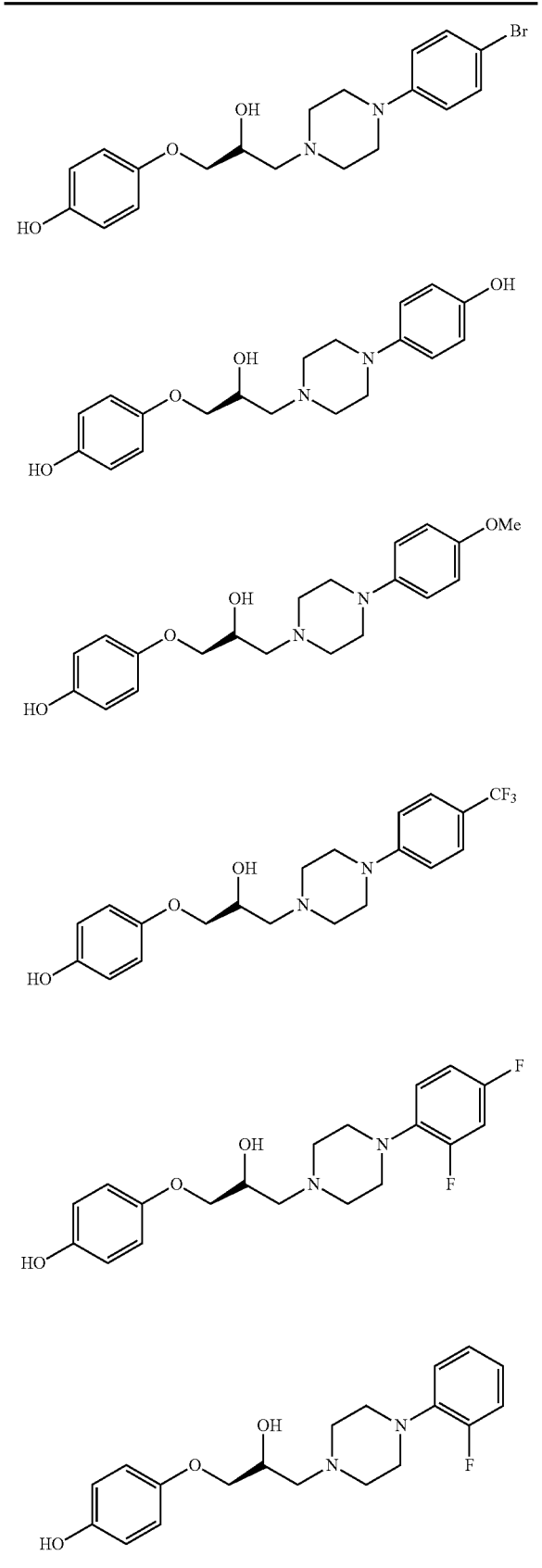
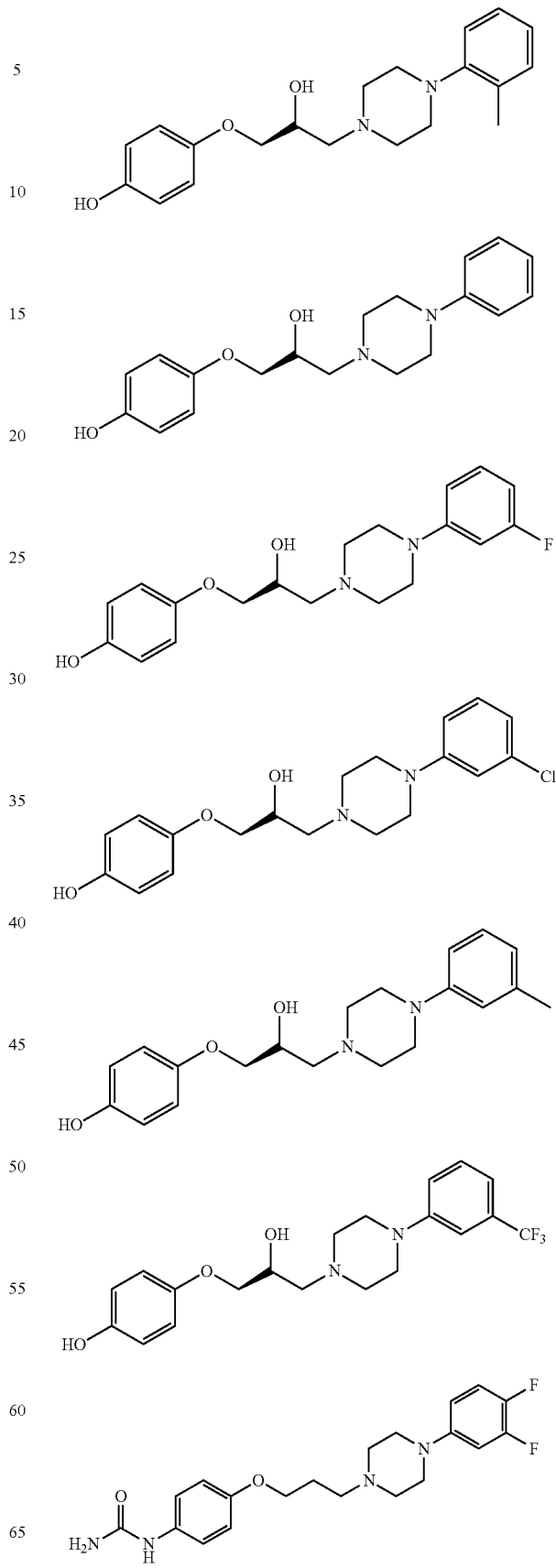

TABLE 11-continued
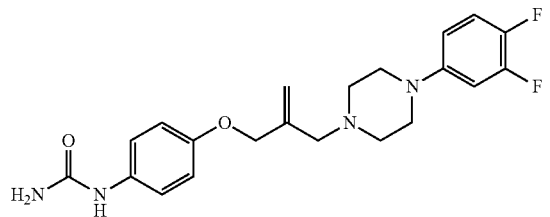 [SMILES: C=C(COc1ccc(NC(N)=O)cc1)CN1CCN(c2ccc(F)c(F)c2)CC1]
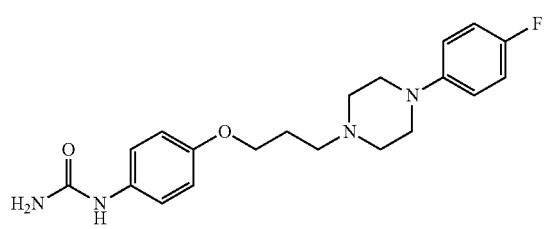 [SMILES: NC(=O)Nc1ccc(OCCCN2CCN(c3ccc(F)cc3)CC2)cc1]
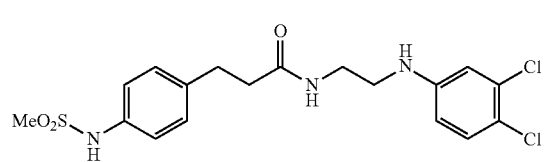 [SMILES: CS(=O)(=O)Nc1ccc(CCC(=O)NCCNc2ccc(Cl)c(Cl)c2)cc1]
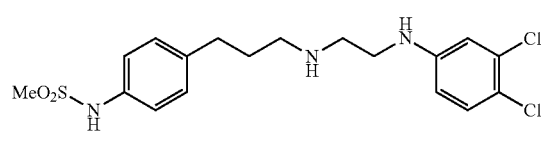 [SMILES: CS(=O)(=O)Nc1ccc(CCCNCCNc2ccc(Cl)c(Cl)c2)cc1]
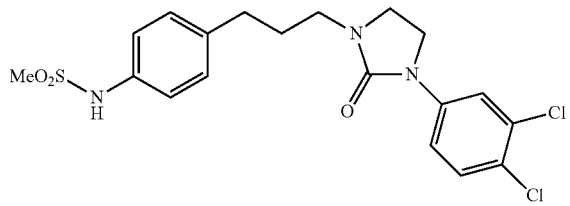 [SMILES: CS(=O)(=O)Nc1ccc(CCCN2CCN(c3ccc(Cl)c(Cl)c3)C2=O)cc1]
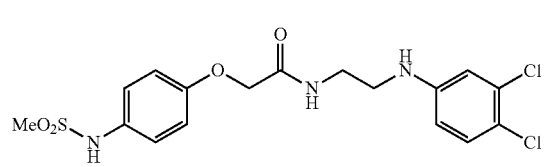 [SMILES: CS(=O)(=O)Nc1ccc(OCC(=O)NCCNc2ccc(Cl)c(Cl)c2)cc1]
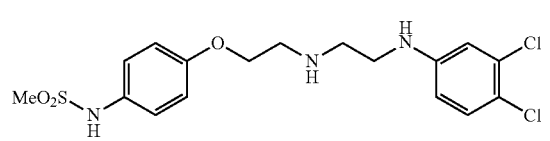 [SMILES: CS(=O)(=O)Nc1ccc(OCCNCCNc2ccc(Cl)c(Cl)c2)cc1]
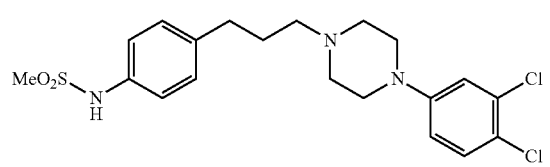 [SMILES: CS(=O)(=O)Nc1ccc(CCCN2CCN(c3ccc(Cl)c(Cl)c3)CC2)cc1]
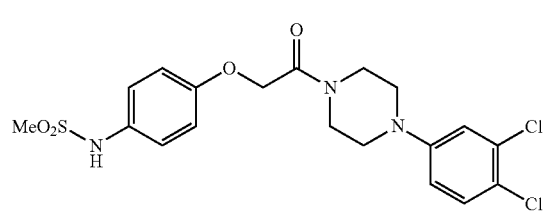
TABLE 11-continued
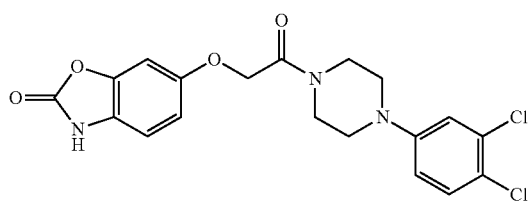 [SMILES: O=C(COc1ccc2[nH]c(=O)oc2c1)N1CCN(c2ccc(Cl)c(Cl)c2)CC1]
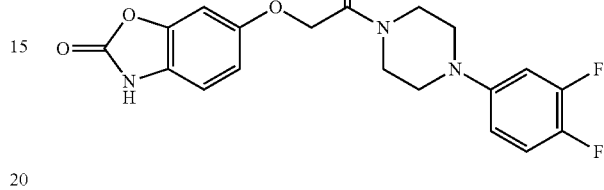
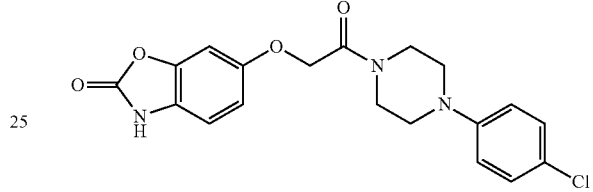
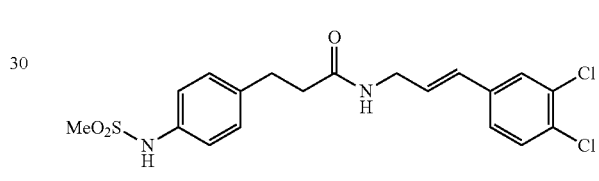
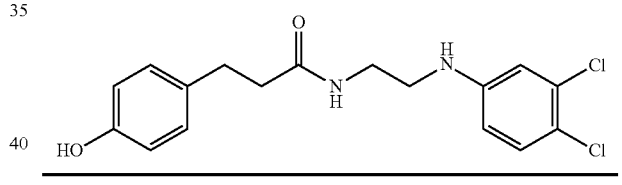
In one embodiment, the compound has an $IC_{50}$ value of 600 nM or less at pH 7.6 or a physiological pH. In one embodiment, the compound is selected from Table 12.
TABLE 12
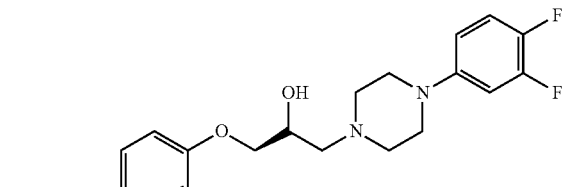
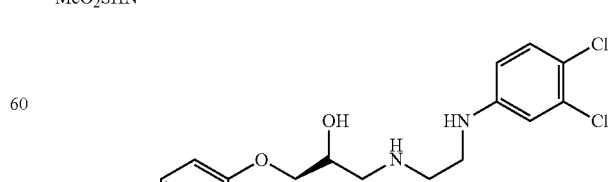

TABLE 12-continued
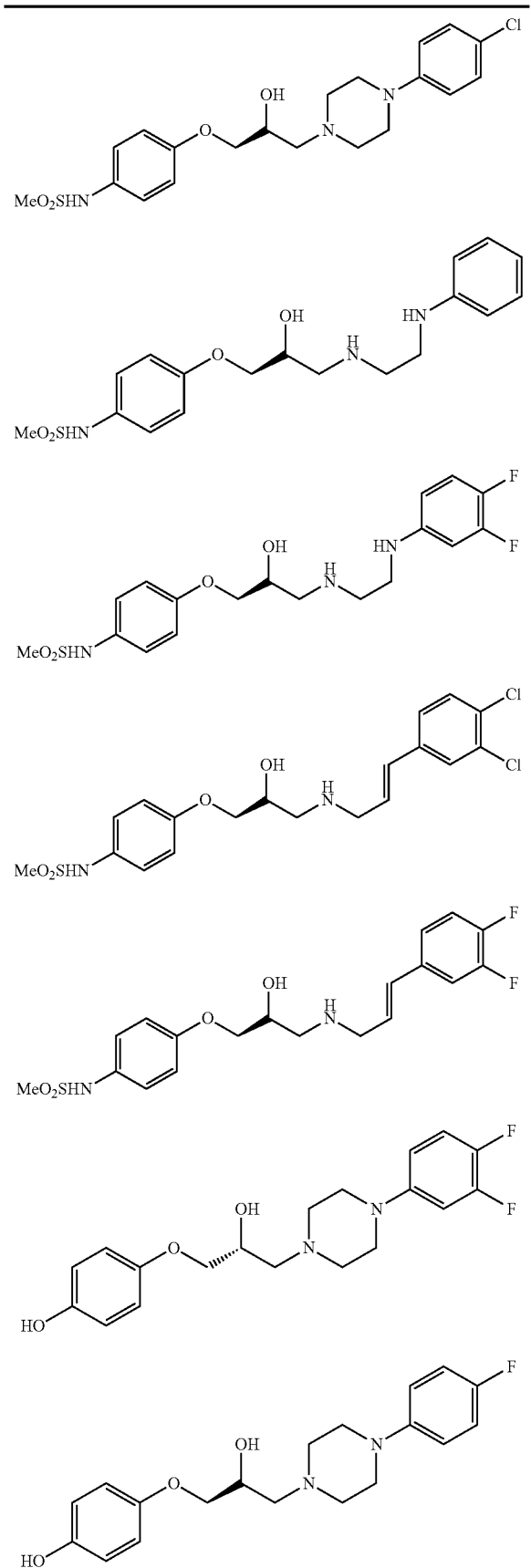
TABLE 12-continued
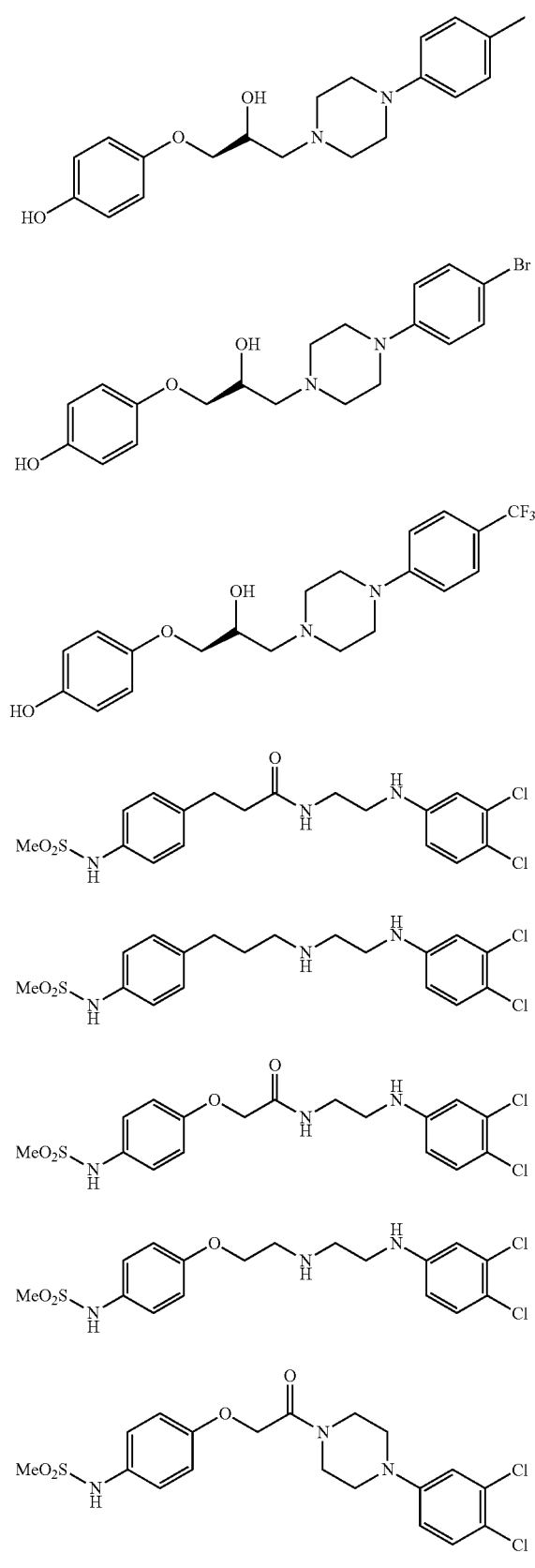

TABLE 12-continued
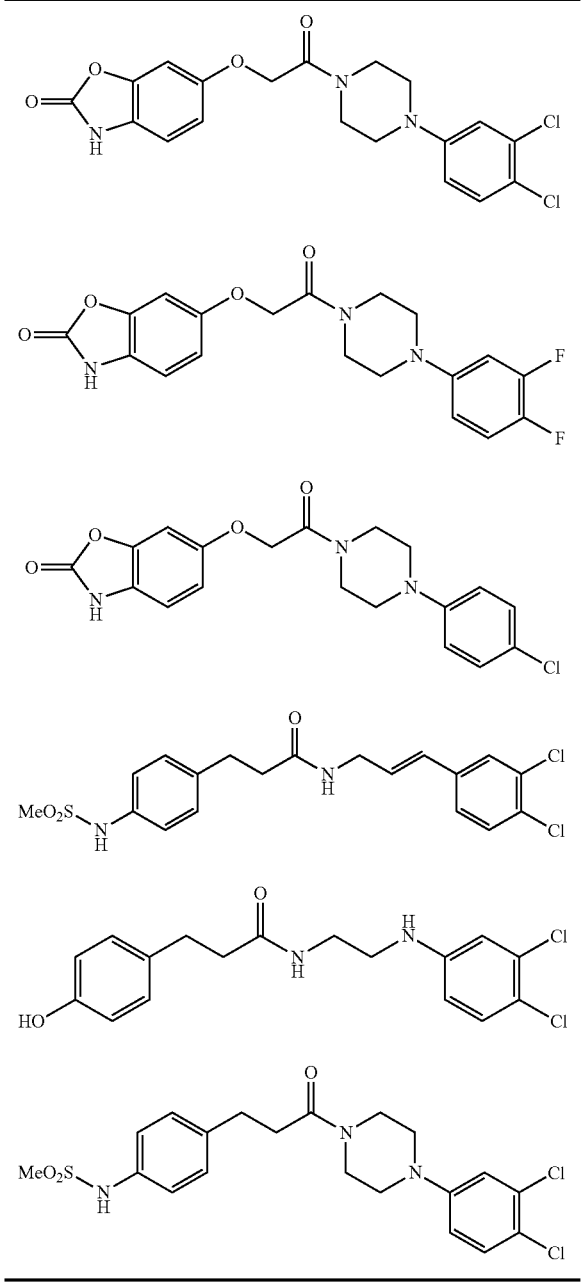
TABLE 13-continued
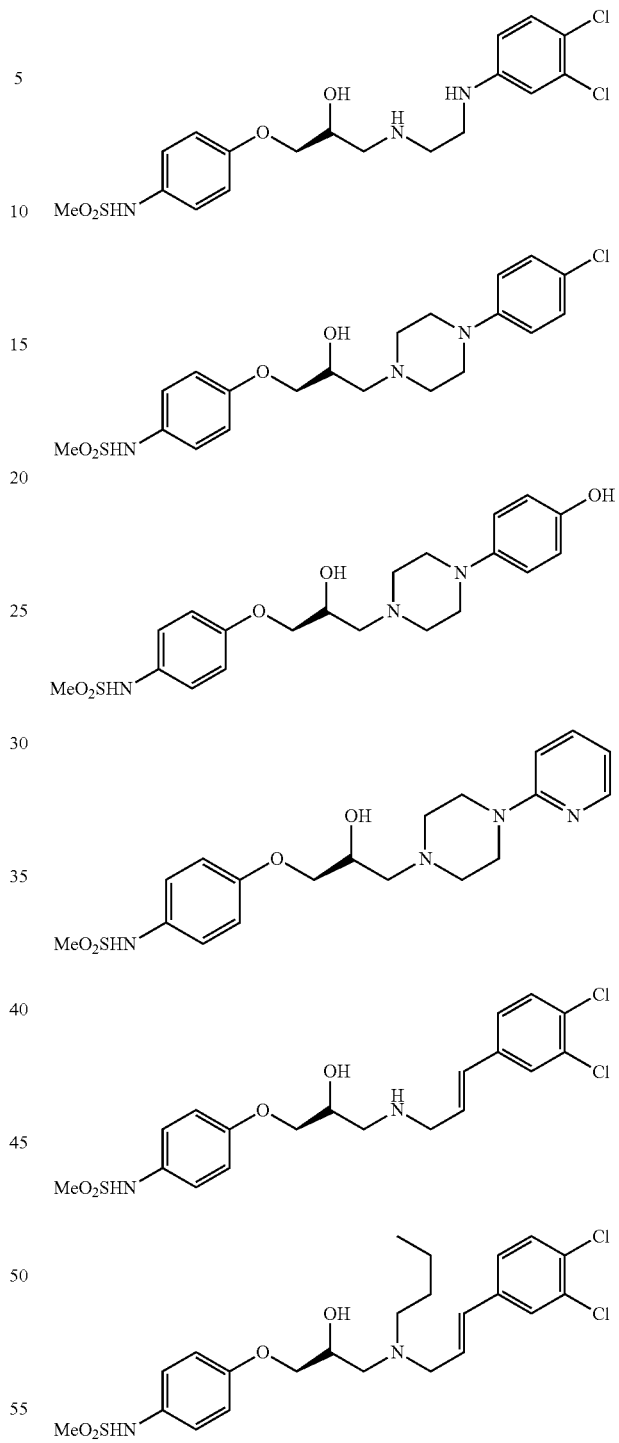
In one embodiment, the compound has a pH boost of 5 or more. In one embodiment, the compound is selected from Table 13.
TABLE 13
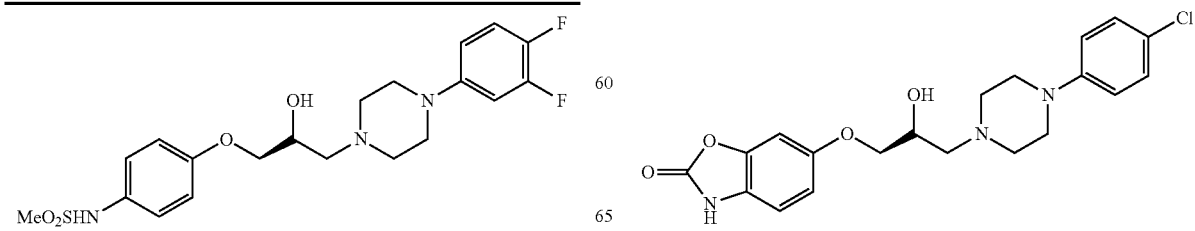

TABLE 13-continued
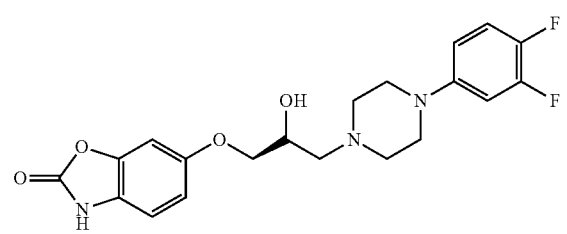
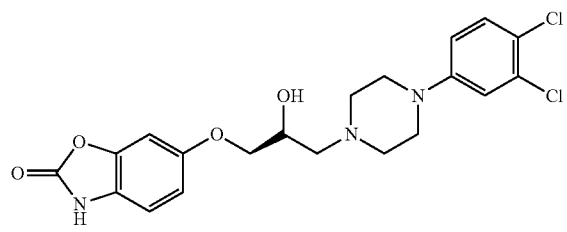
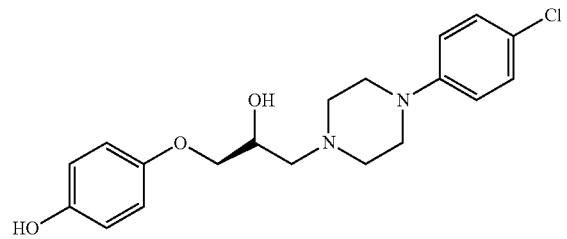
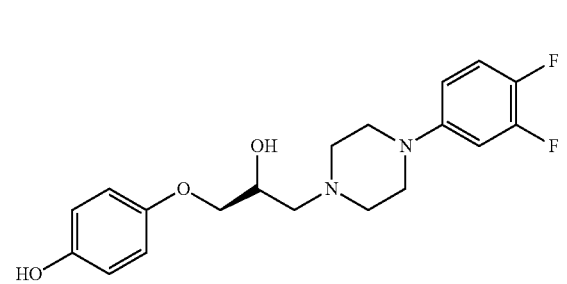
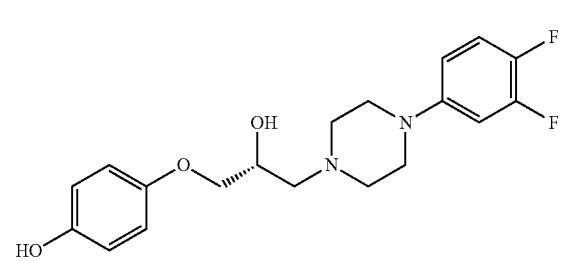 [SMILES: Oc1ccc(OC[C@H](O)CN2CCN(c3ccc(F)c(F)c3)CC2)cc1]
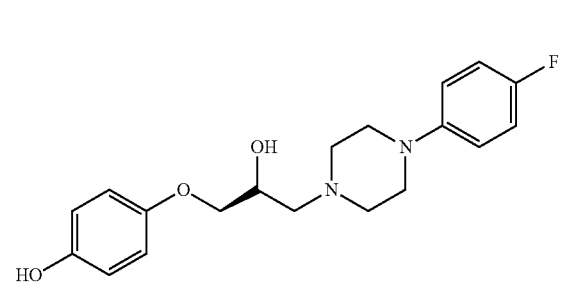
TABLE 13-continued
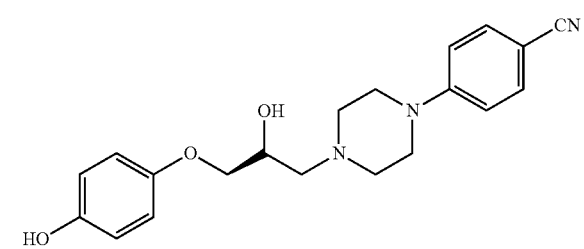
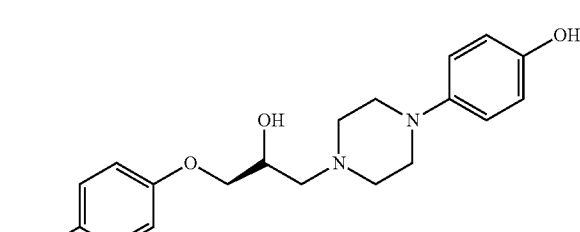
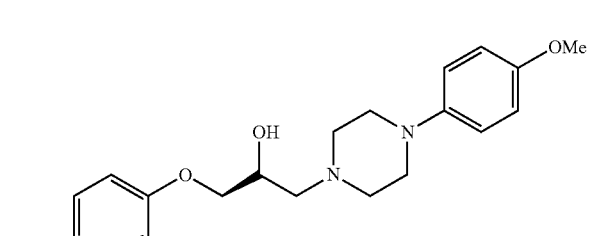
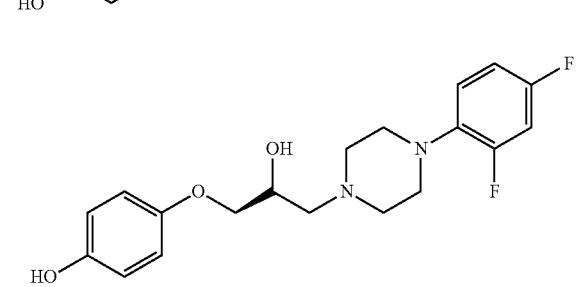
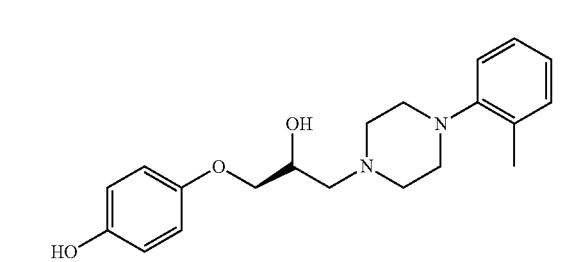
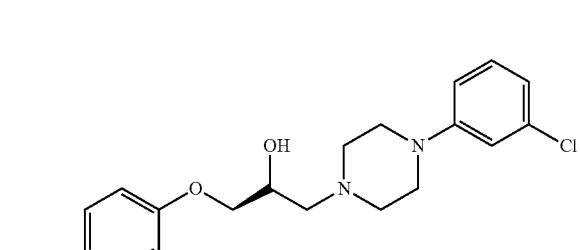

TABLE 13-continued
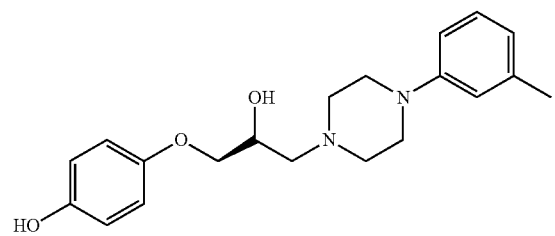
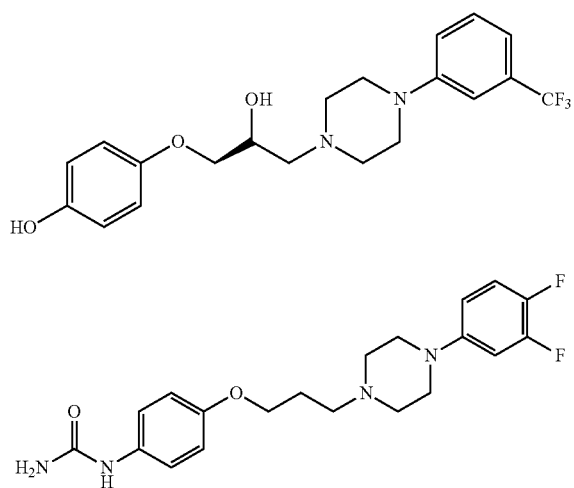
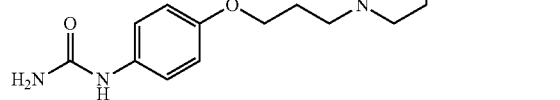
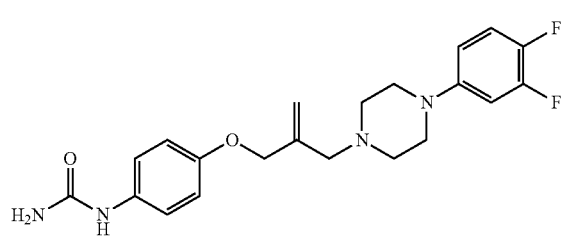 [SMILES: C=C(COc1ccc(NC(N)=O)cc1)CN1CCN(c2ccc(F)c(F)c2)CC1]
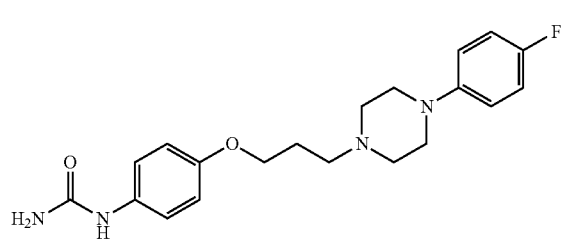 [SMILES: NC(=O)Nc1ccc(OCCCN2CCN(c3ccc(F)cc3)CC2)cc1]
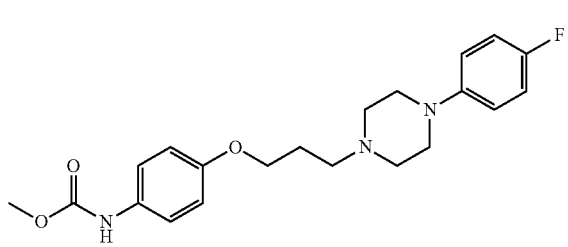 [SMILES: COC(=O)Nc1ccc(OCCCN2CCN(c3ccc(F)cc3)CC2)cc1]
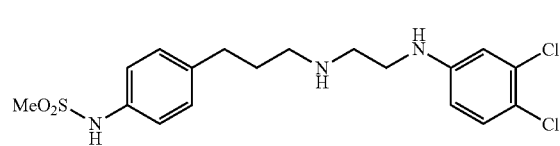
TABLE 13-continued
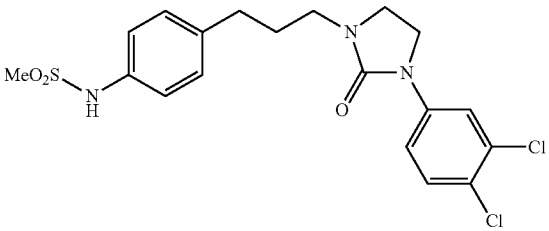 [SMILES: CS(=O)(=O)Nc1ccc(CCCN2CCN(c3ccc(Cl)c(Cl)c3)C2=O)cc1]
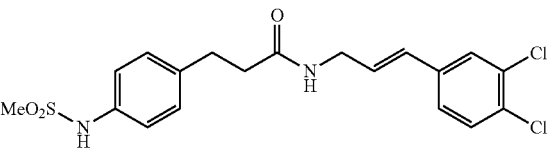 [SMILES: CS(=O)(=O)Nc1ccc(CCC(=O)NC/C=C/c2ccc(Cl)c(Cl)c2)cc1]
In one embodiment, the compound has an IC$_{50}$ of 600 nM or less and a pH boost of 5 or more. In a particular embodiment, the compound is
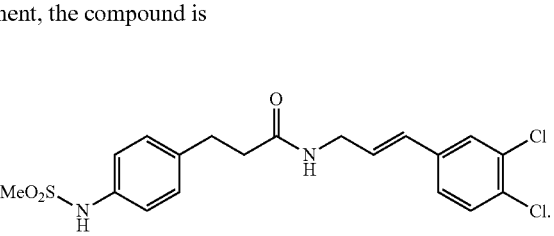
In another embodiment, the compound is
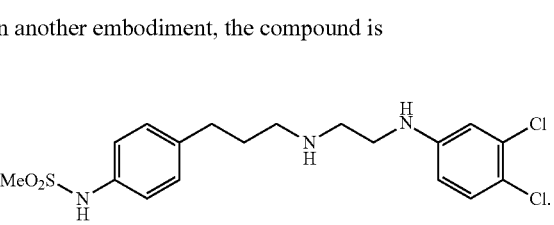
In another embodiment, the compound is,
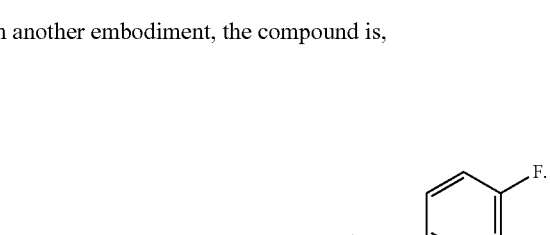
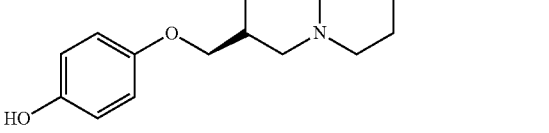

In another embodiment, the compound is,
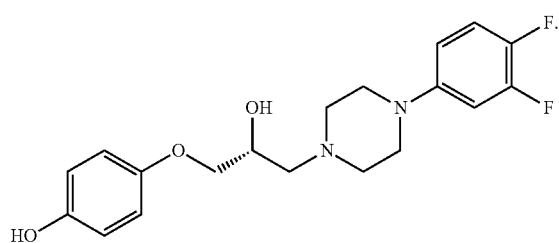 [SMILES: Oc1ccc(OC[C@H](O)CN2CCN(c3ccc(F)c(F)c3)CC2)cc1]
In a particular embodiment, the compound is
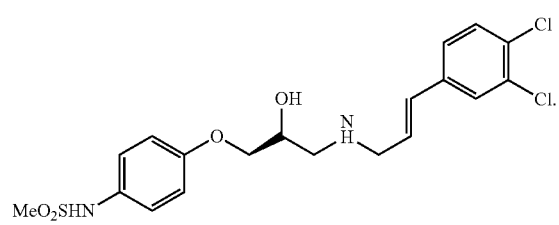
In another particular embodiment, the compound is
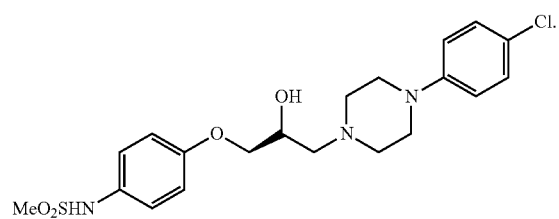
In another embodiment, the compound is,
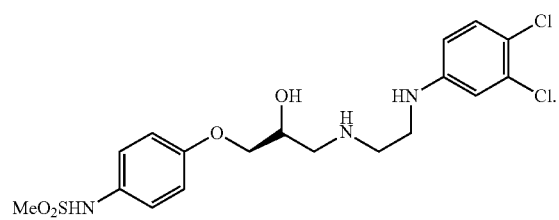
In another embodiment, the compound is,
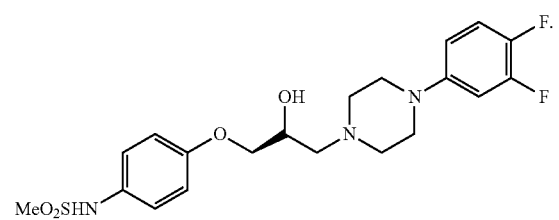
In one embodiment, the compound is selected from the group consisting of:
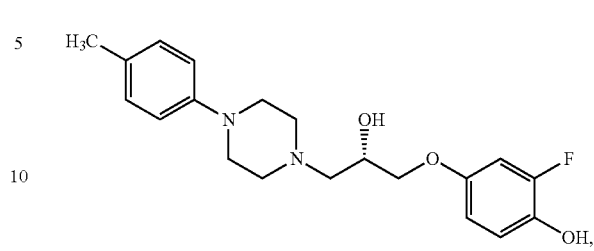
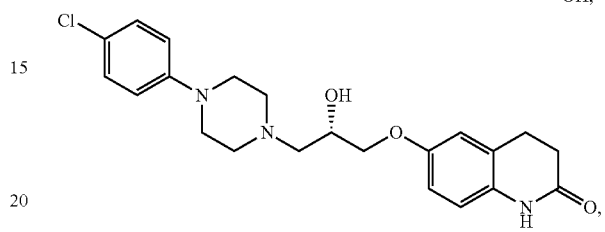
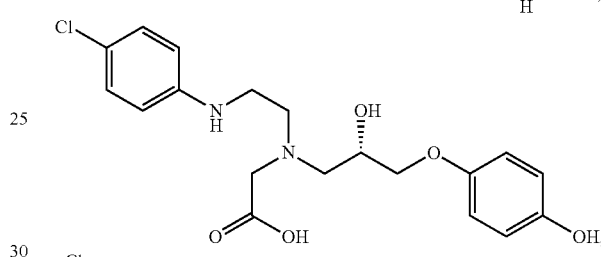
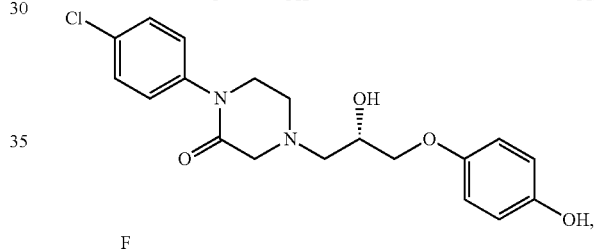
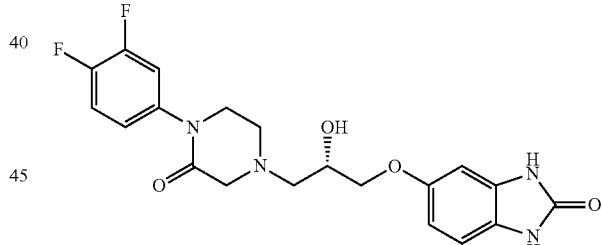
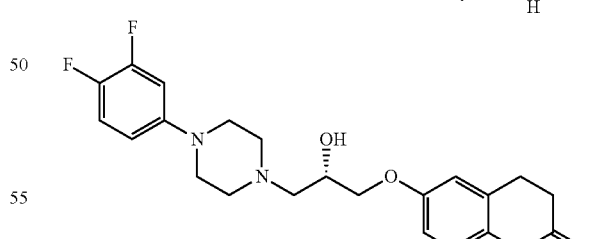
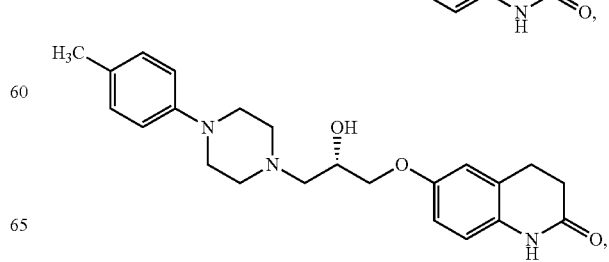

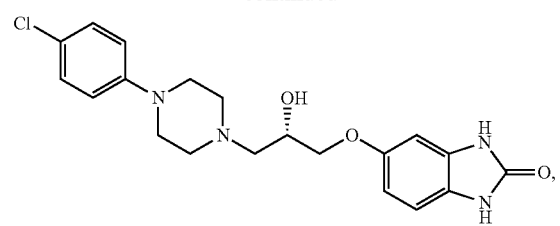
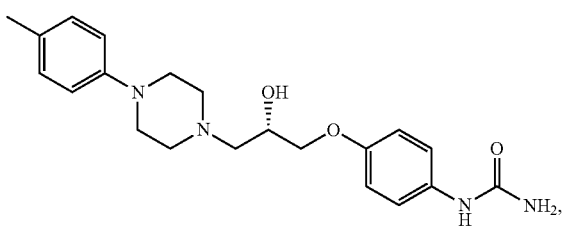
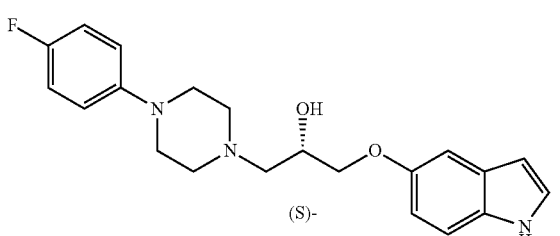
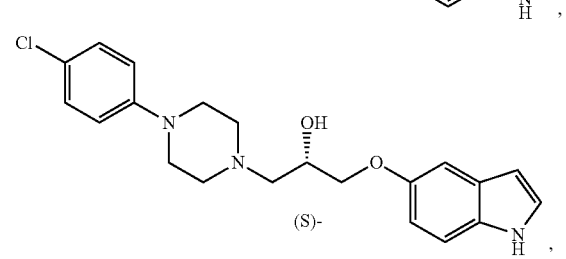
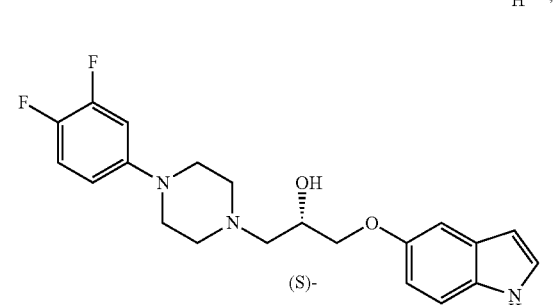
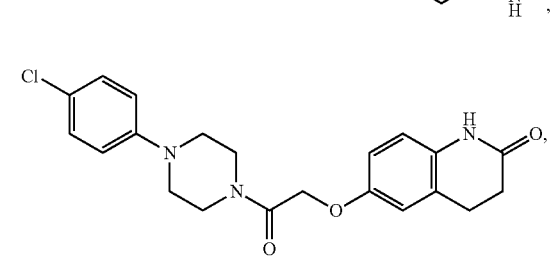
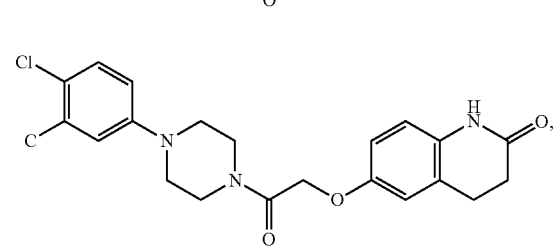
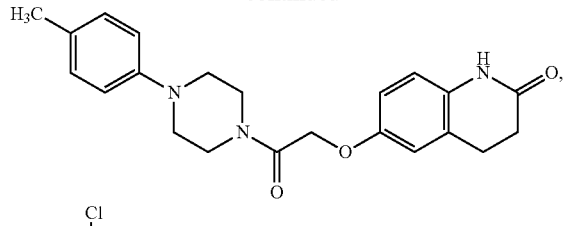
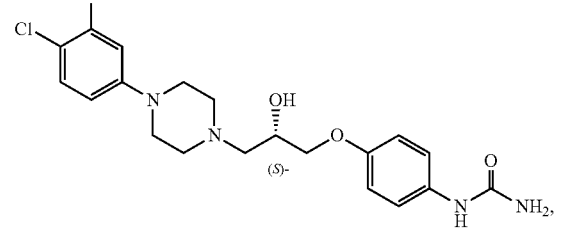
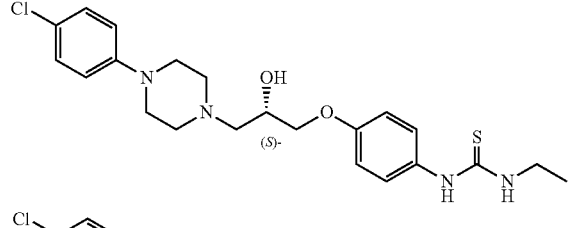
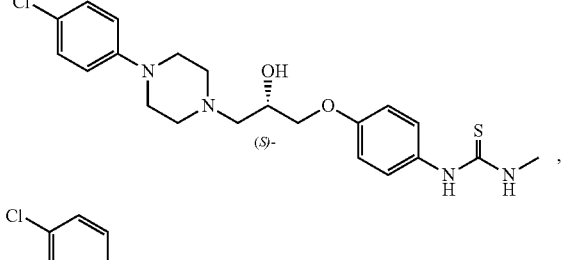
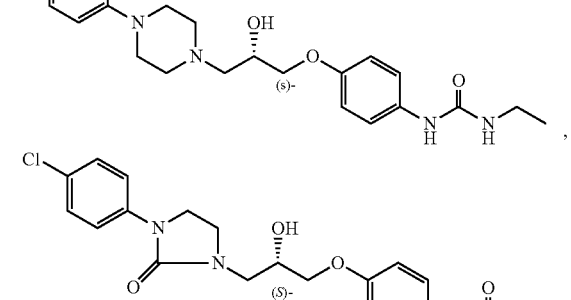
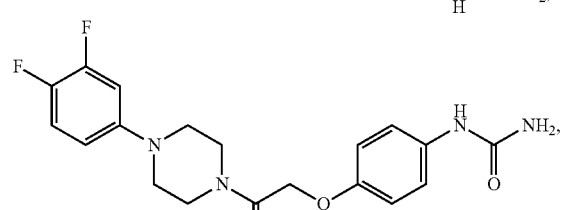
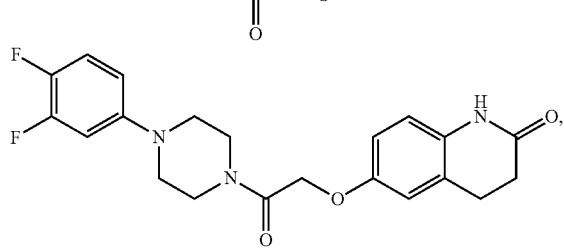

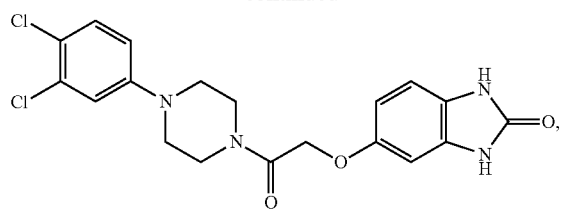
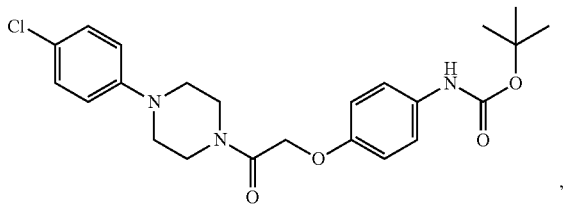
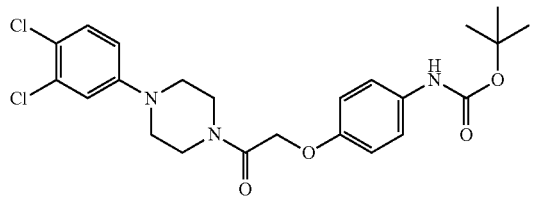
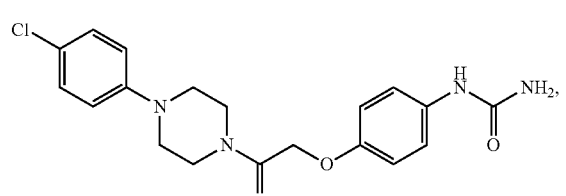
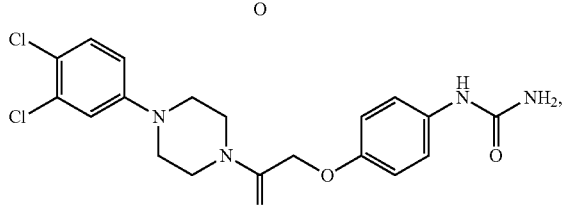
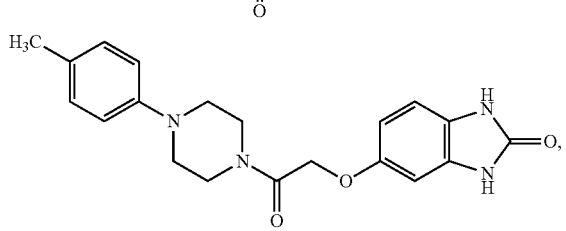
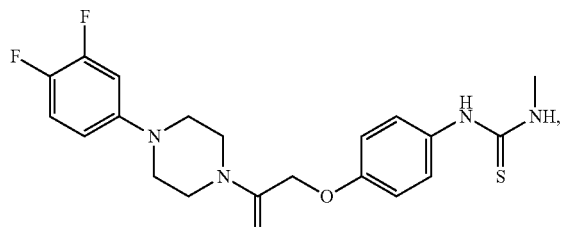
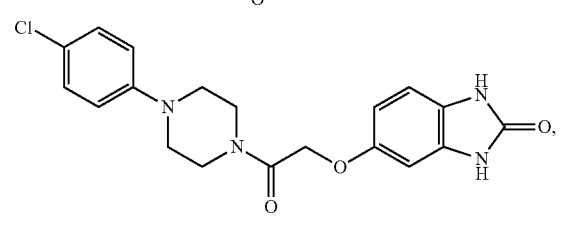
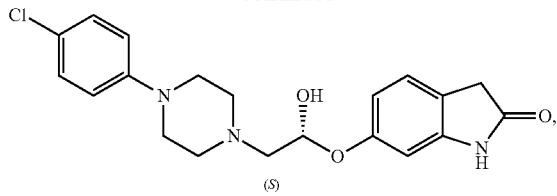
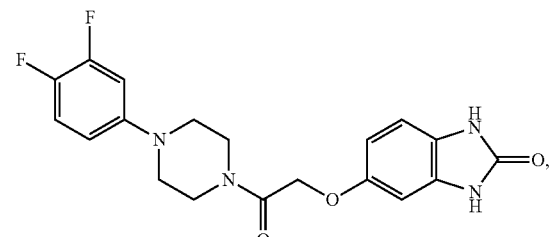
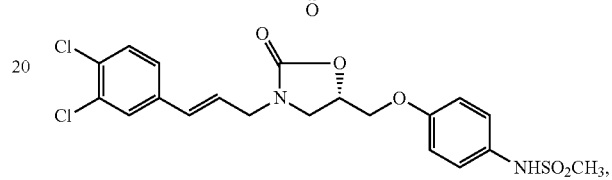
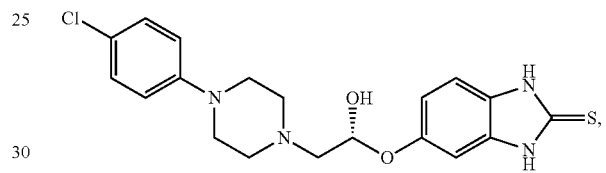
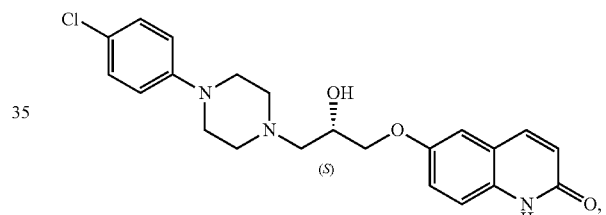
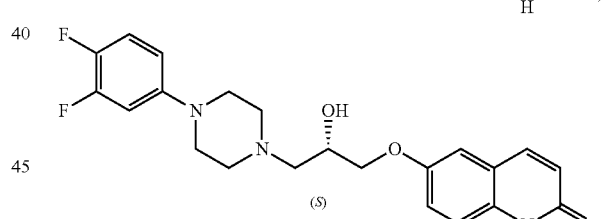
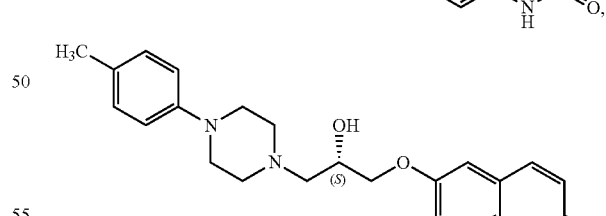
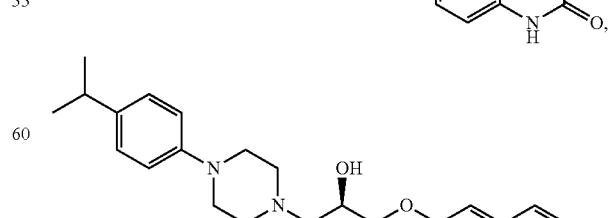
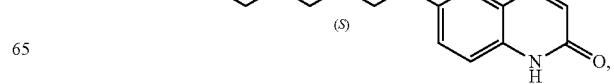

149
-continued
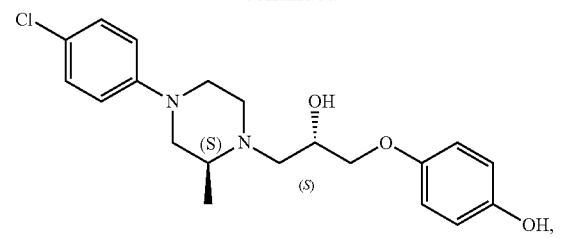
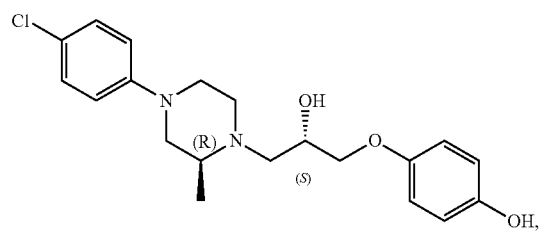
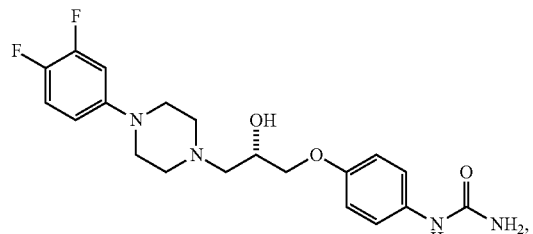
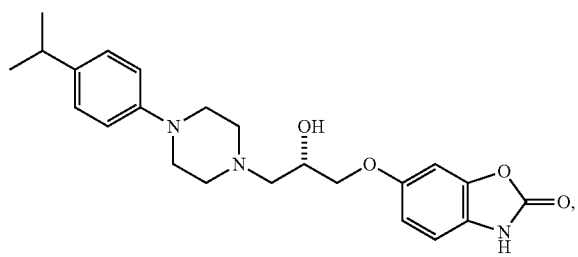
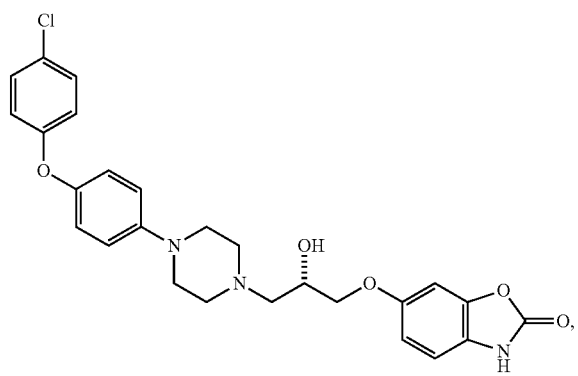
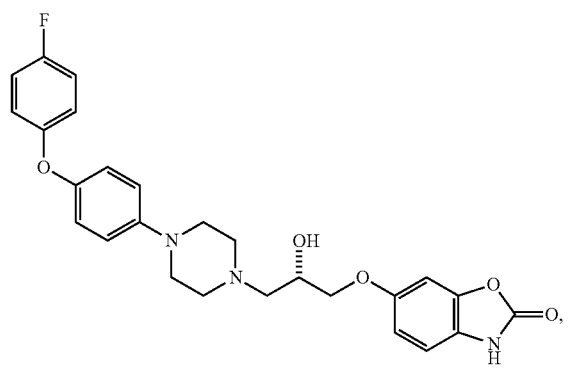
150
-continued
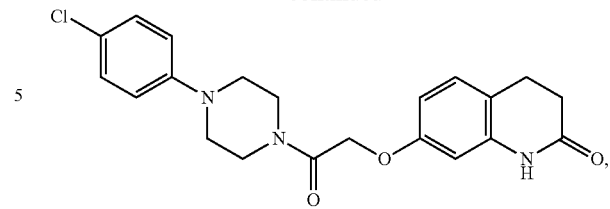
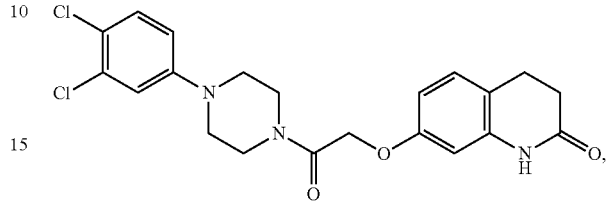
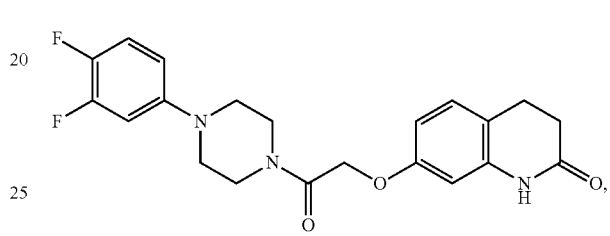
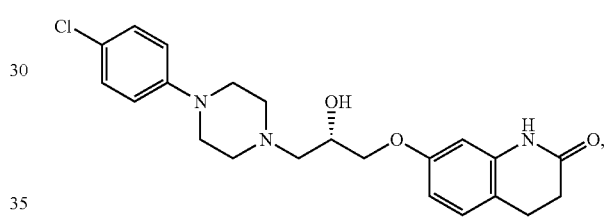
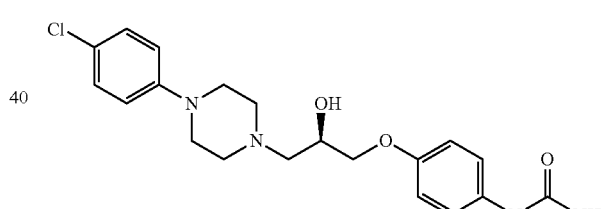
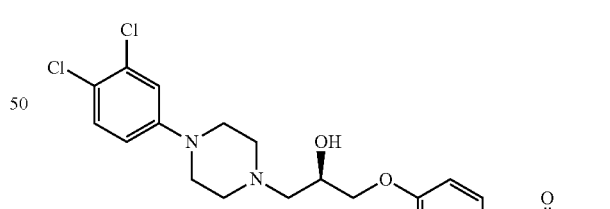
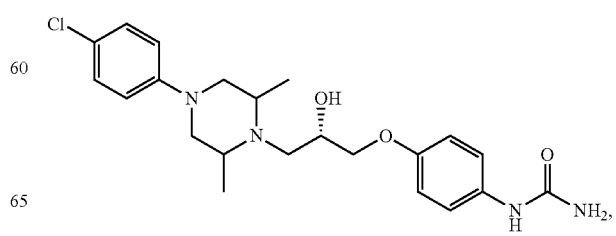

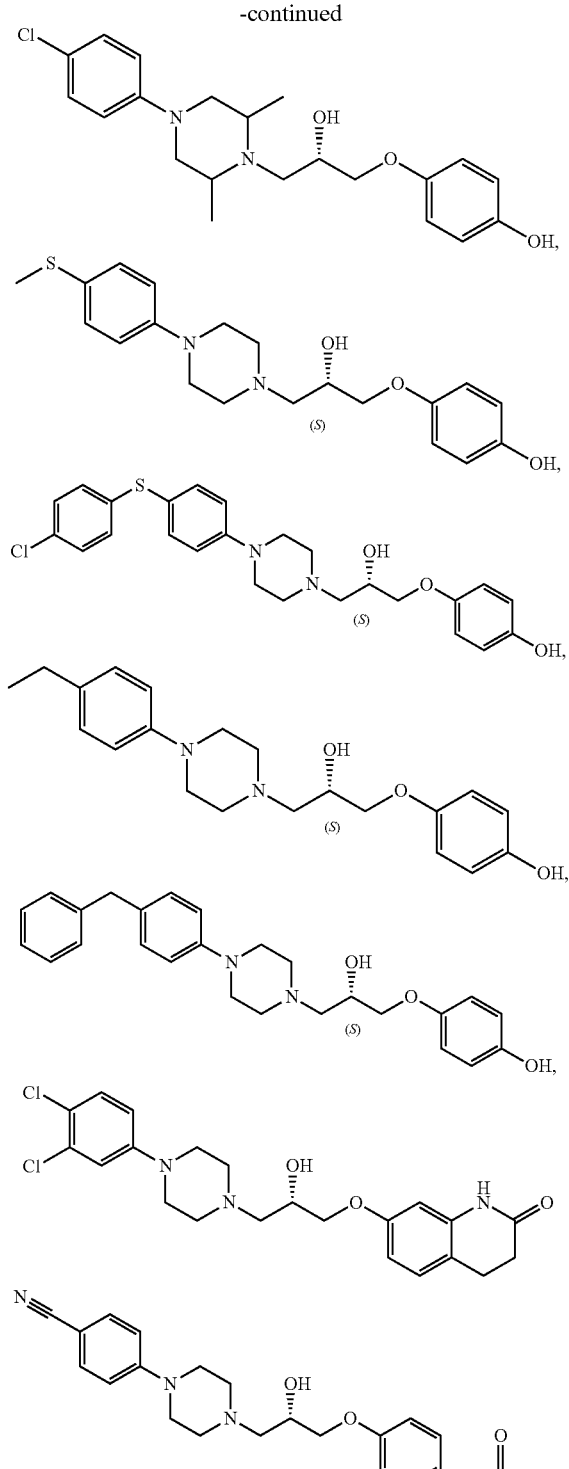
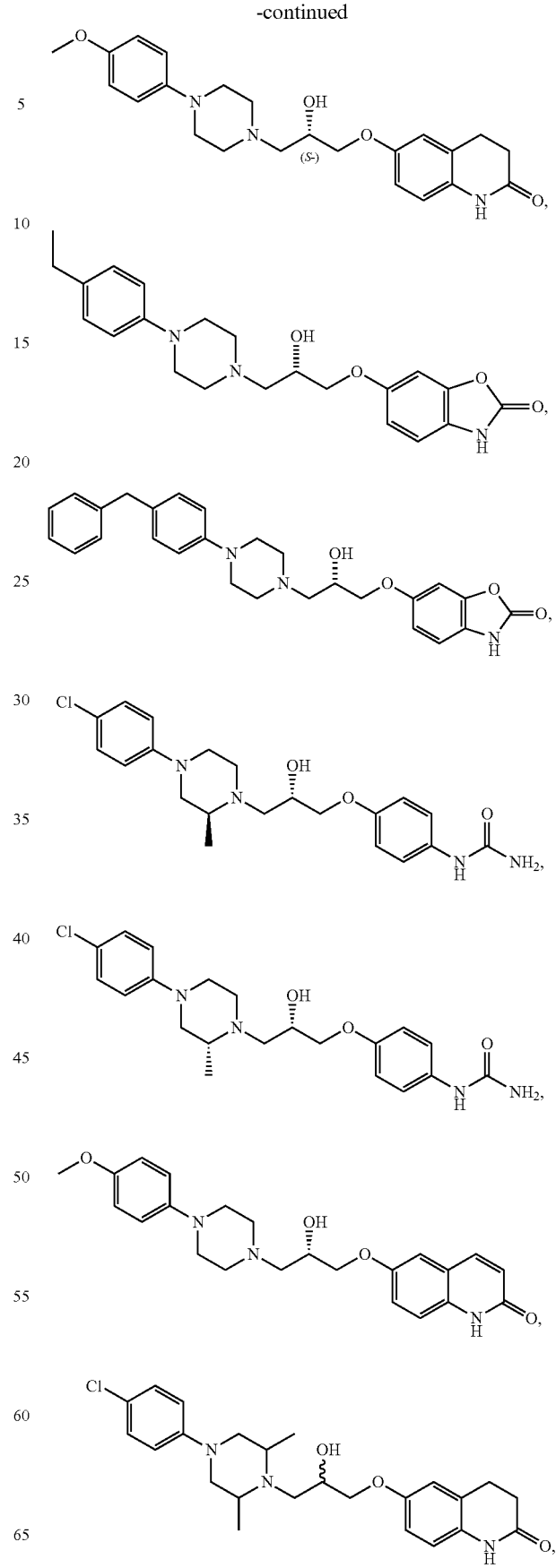

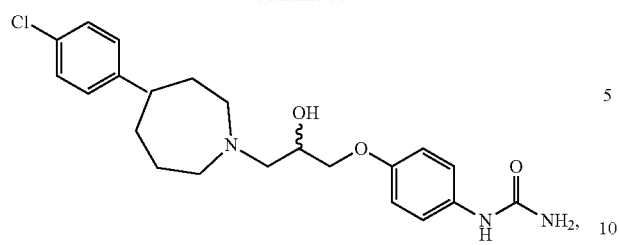
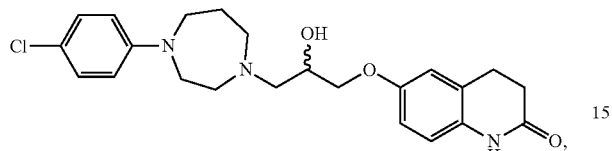
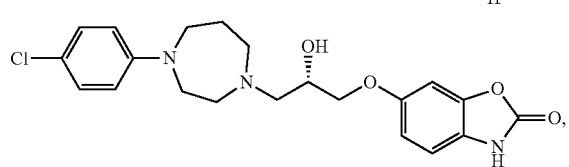
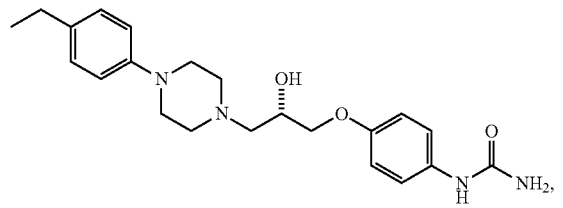
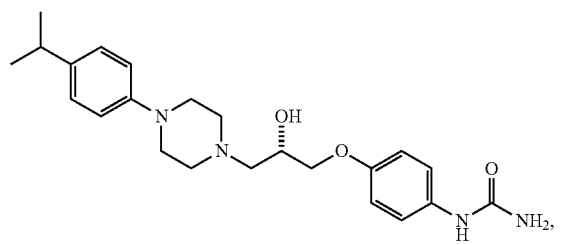
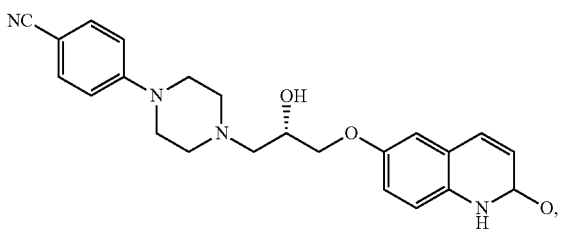
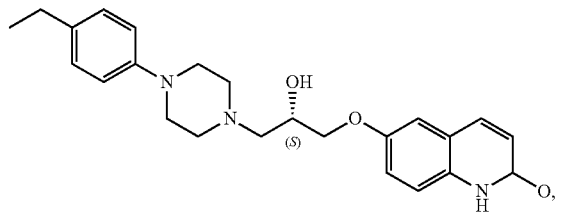
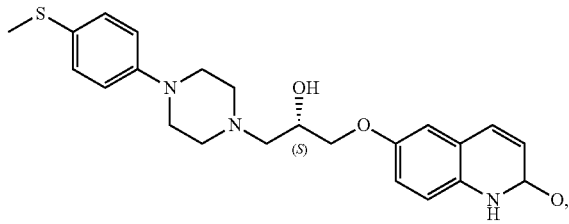
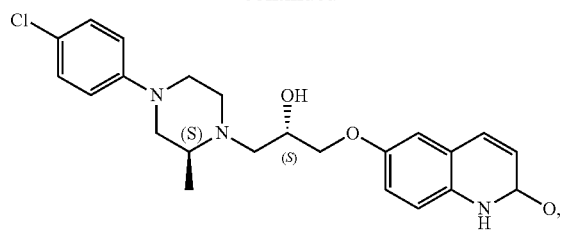
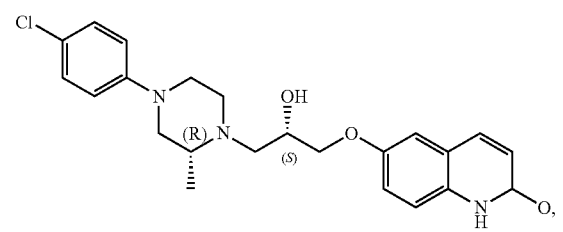
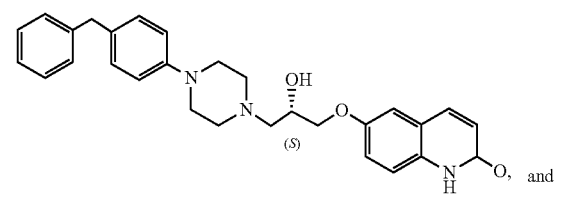
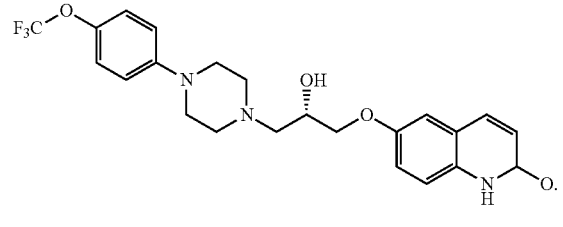
In one embodiment, the compound is selected from the group consisting of:
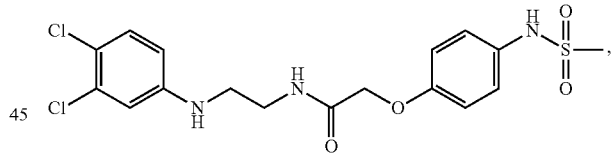
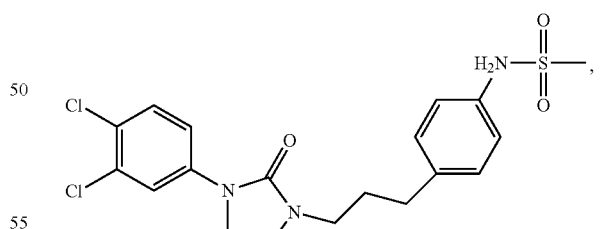
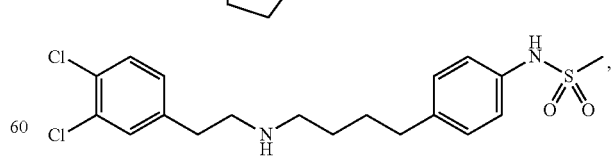
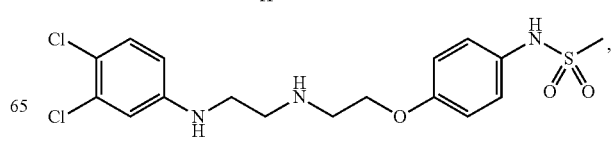

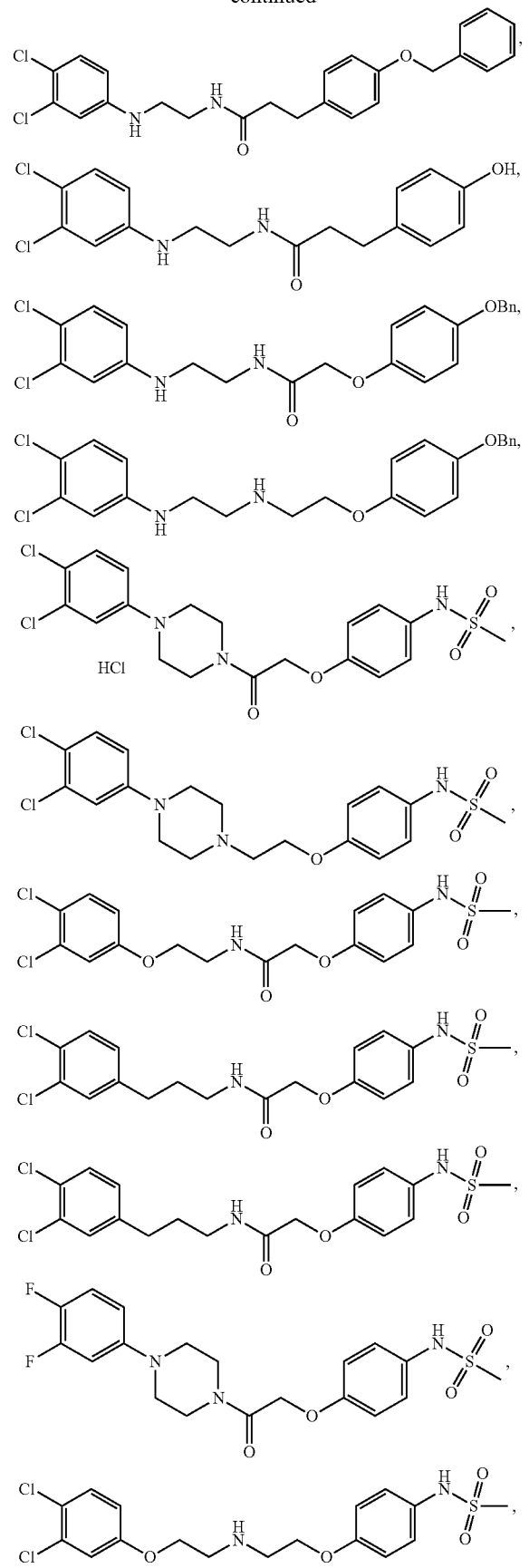
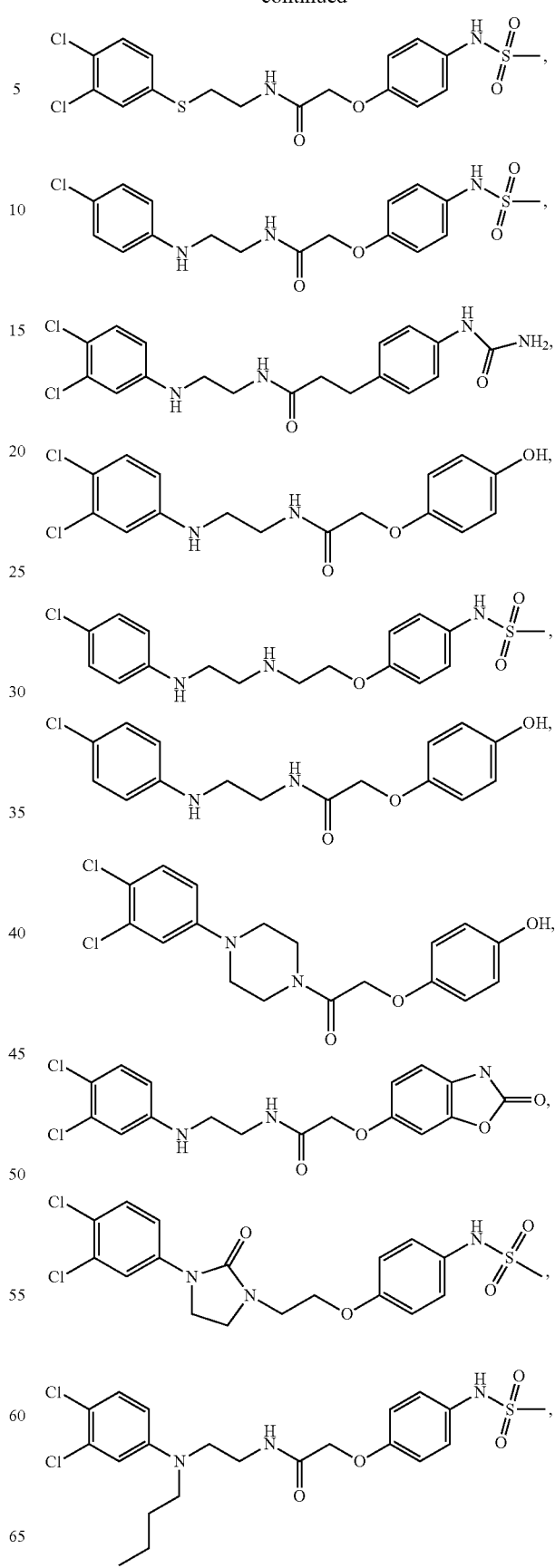

157
-continued
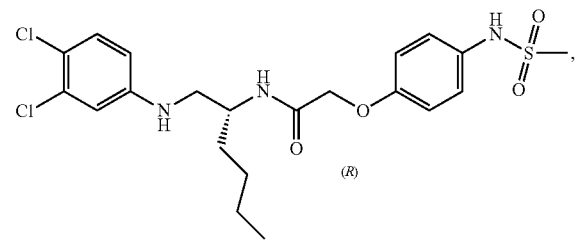
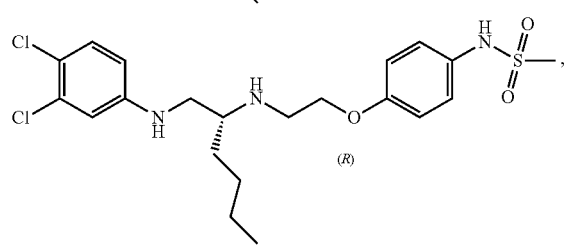
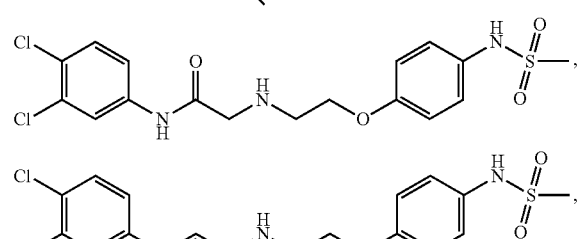
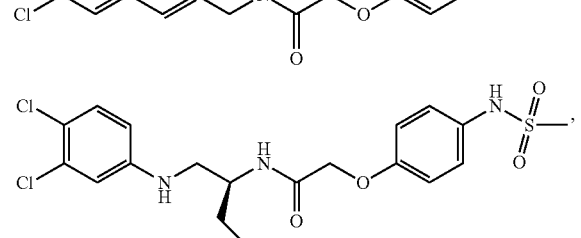
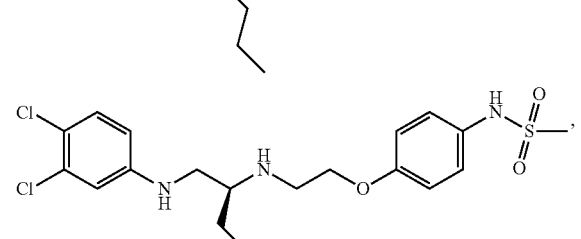
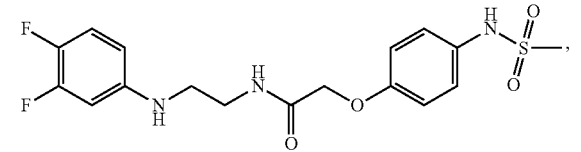
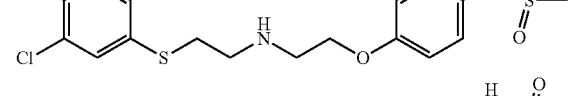
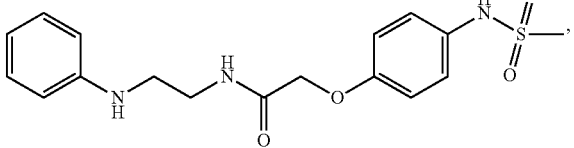
158
-continued
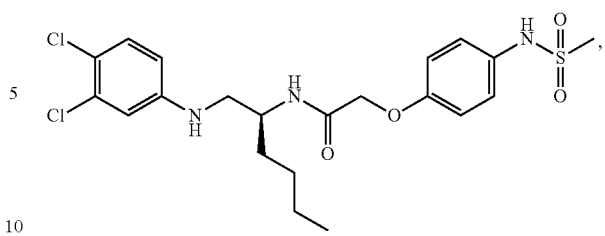
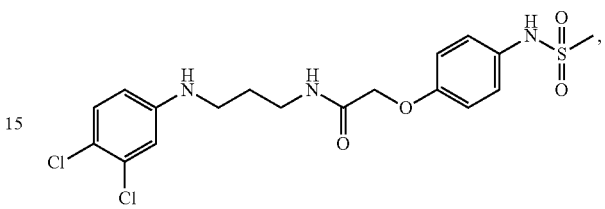
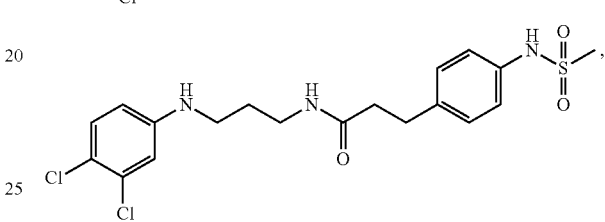
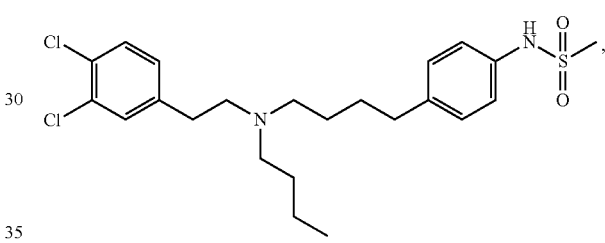
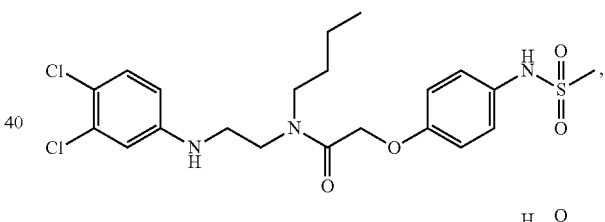
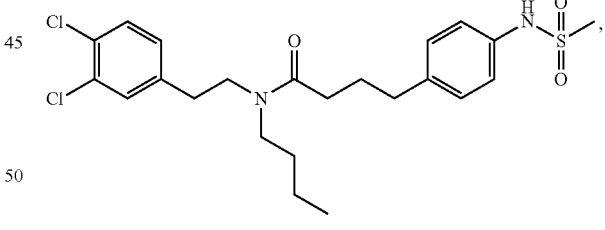
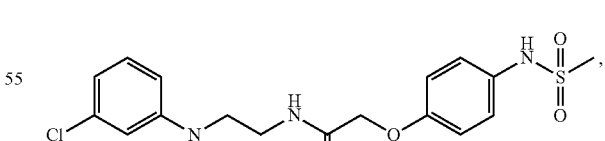
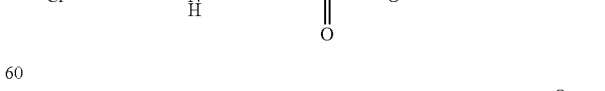
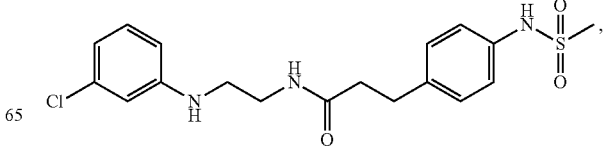

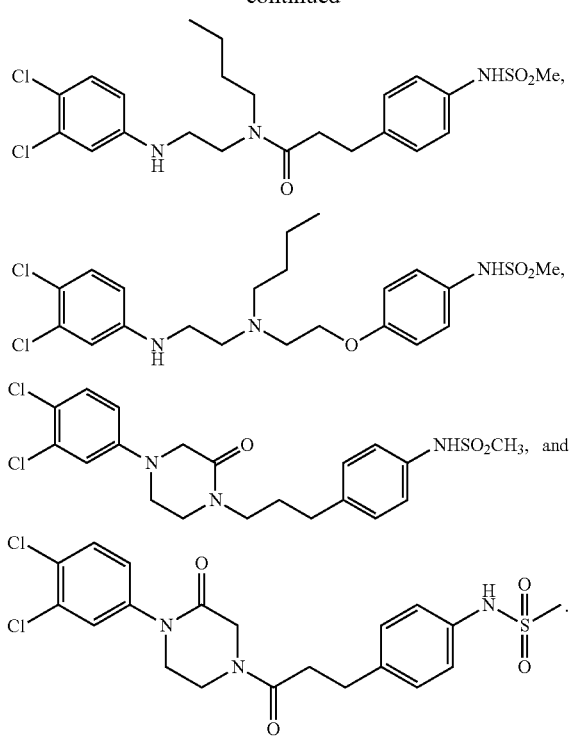
In one embodiment, the compound is
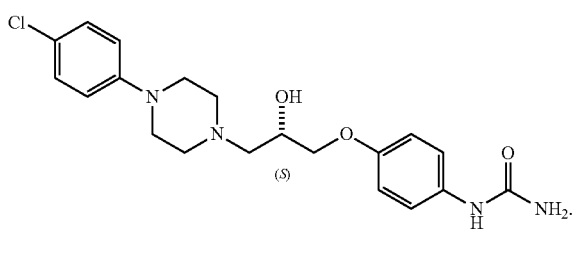
In one embodiment, the compound is selected from the group consisting of:
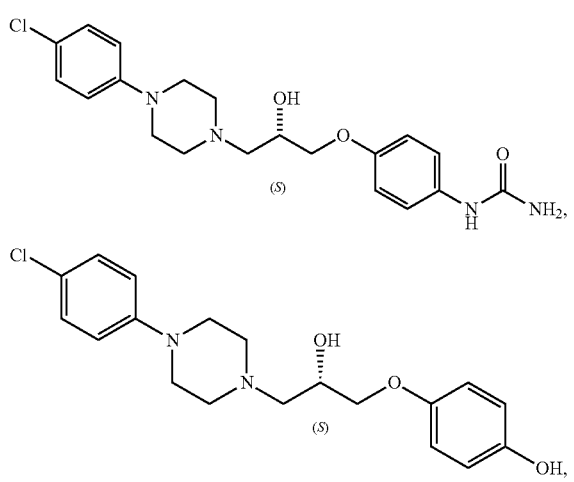
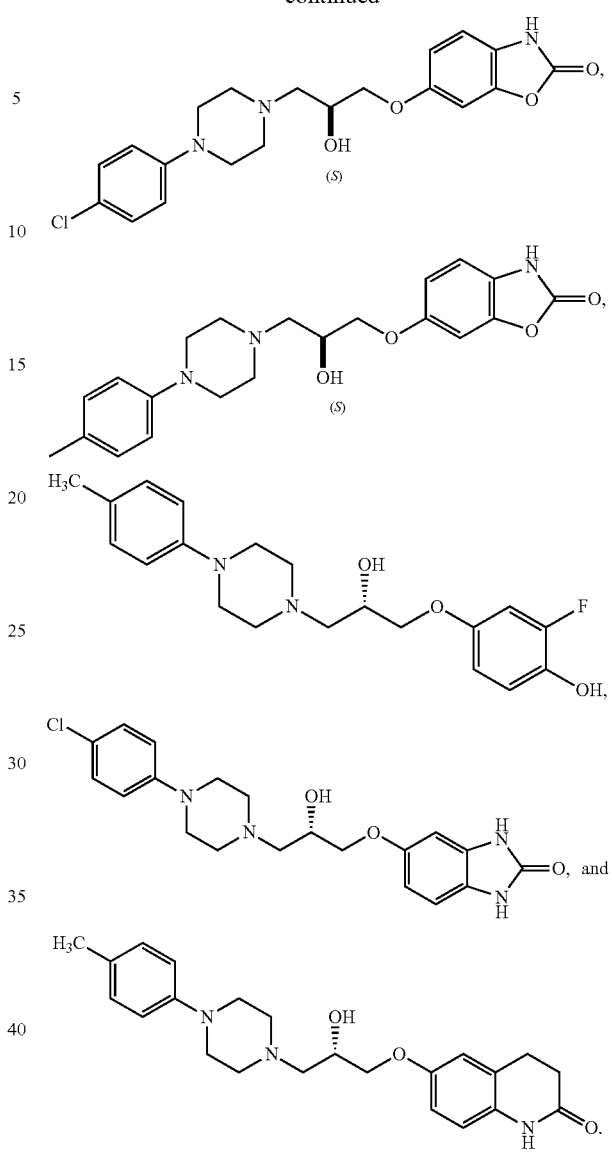
In another embodiment, the compound is selected from the group consisting of:
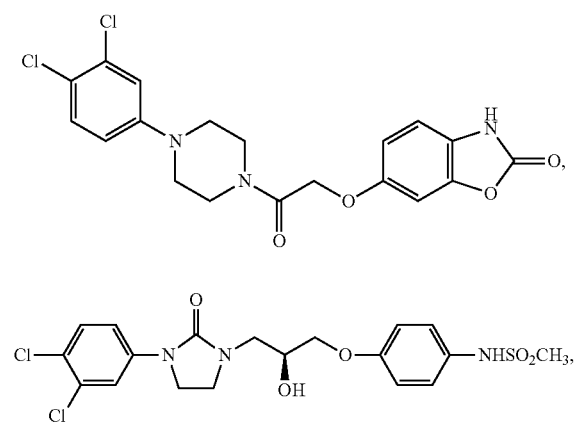

-continued

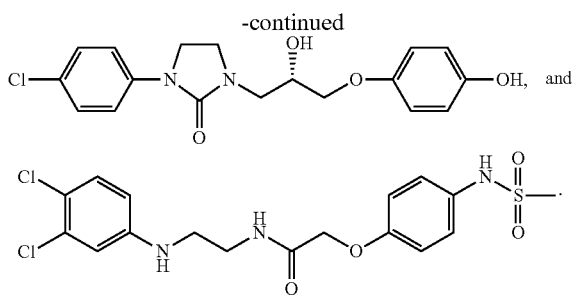

Formula II

In one embodiment, compounds, pharmaceutical compositions and methods of treatment or prophylaxis of neuropathic pain, stroke, traumatic brain injury, epilepsy, and other neurologic events or neurodegeneration resulting from NMDA receptor activation, comprising administering to a host in need thereof a compound of Formula II, or a pharmaceutically acceptable salt, ester, prodrug or derivative thereof are provided:

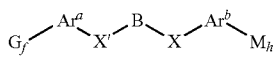

Formula II wherein:
each G is independently F, Cl, Br, I, $C_1$-$C_4$ alkyl, $C_1$-$C_4$ alkoxy, $C_6$-$C_{12}$ aralkyl, —O-aryl, —S-aryl, —NH-aryl;
f=0, 1, 2, 3, 4 or 5;
$Ar^a$ and $Ar^b$ are each independently aryl or heteroaryl;
B is selected from the group consisting of:

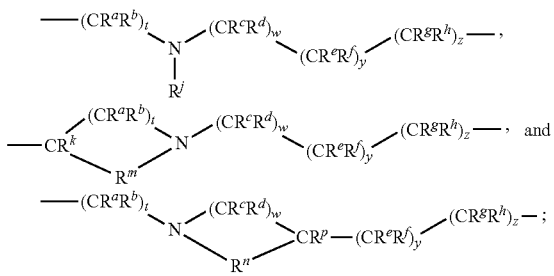

wherein $R^a$, $R^b$, $R^c$, $R^d$, $R^e$, $R^f$, $R^g$, $R^h$, $R^k$ and $R^p$ are each independently selected from H, $C_1$-$C_6$ alkyl, $C_1$-$C_6$ alkoxy, OH or halo;
$R^j$ is H, $C_1$-$C_6$ alkyl, OH or P(O)(O$C_1$-$C_4$ alkyl)$_2$;
$R_m$ is $C_1$-$C_4$ alkyl or $C_2$-$C_4$ alkenyl;
$R^n$ is $C_1$-$C_4$ alkyl, $C_2$-$C_4$ alkenyl, $C_6$-$C_{12}$ aralkyl, —CH$_2$O—, —CH($C_1$-$C_6$ alkyl)O—, —CH($C_2$-$C_{12}$ aralkyl)O—;
t, w, y and z each=0, 1, 2, or 3;
X and X' are independently selected from a bond, O, S, SO, SO$_2$, CH$_2$, NH, N($C_1$-$C_6$ alkyl), and NHC(=O);
M is OH, F, Cl, Br, I, NH$_2$, NR$^q$R$^r$, NO$_2$, O($C_1$-$C_6$ alkyl), OCF$_3$, CN, C(O)OH, C(O)O($C_1$-$C_6$ alkyl), $C_6$-$C_{12}$ aralkyl, NR$^s$C(O)CR$^t_3$, or NR$^u$C(O)NR$^v_2$, wherein each R$^q$, R$^r$, R$^s$, R$^u$ and R$^v$ is each independently H or $C_1$-$C_6$ alkyl; and each R$^t$ is independently H, $C_1$-$C_6$ alkyl or halo; or two M groups may be taken together with $Ar^b$ to form:

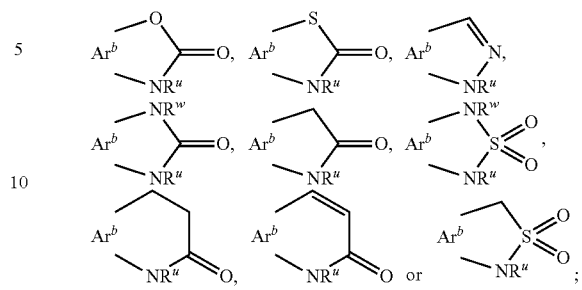

and wherein $R^u$ and $R^w$ are independently H, $C_1$-$C_6$ alkyl or $C_6$-$C_{12}$ aralkyl; and
h=1, 2, 3, 4 or 5;
wherein when B contains a piperidin-4-ol or a pyrrolidin-2-ol moiety, and $Ar^a$ and $Ar^b$ are each phenyl, M is not OH at the para position on $Ar^b$.

In one embodiment, G is F or Cl. In another embodiment, f is 1 or 2.

In one embodiment, $Ar^a$ is phenyl. In another embodiment, $Ar^b$ is phenyl. In another embodiment, $Ar^a$ and $Ar^b$ are each phenyl.

In one embodiment, $Ar^a$ is phenyl and is substituted with two G groups. In a subembodiment, both G groups are Cl. In another subembodiment, both G groups are F. In another subembodiment, one G group is Cl and the other G group is F. In one embodiment, G is selected from the group consisting of $C_6$-$C_{12}$ aralkyl, —O-aryl, —S-aryl, and —NH-aryl.

In one embodiment, B is

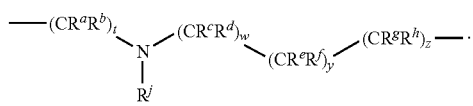

In a subembodiment, $R^a$, $R^b$, $R^c$, $R^d$, $R^e$, $R^g$ and $R^h$ are H; Rj is H, $C_1$-$C_6$ alkyl, OH or P(O)(O$C_1$-$C_4$ alkyl)$_2$; $R^f$ is H, halo or OH; t is 0, 1, 2, or 3; and w, y and z are each 1.

In one embodiment, B is

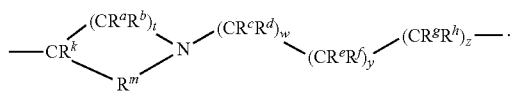

In a subembodiment, $R^a$, $R^b$, $R^c$, $R^d$, $R^e$, $R^g$ and $R^h$ are H; $R^f$ is H, halo or OH; $R^k$ is H, halo or OH; $R^m$ is $C_1$-$C_4$ alkyl; t is 1, 2, or 3; and w, y and z are each 1.

In one embodiment, B is

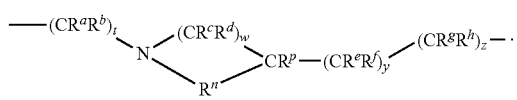

In a subembodiment, $R^a$, $R^b$, $R^c$, $R^d$, $R^e$, $R^g$ and $R^h$ are H; $R^f$ is H, halo or OH; $R^p$ is H, halo or OH; $R^n$ is —CH$_2$O—; t is 0, 1, 2, or 3; and w, y and z are each 1.

In one embodiment, the sum of w, y and z does not exceed 6. In one embodiment, the sum of w, y and z is 2, 3, 4, 5 or 6.

In one embodiment, X is a bond, O, S or CH$_2$. In another embodiment, X is O. In another embodiment, X is CH$_2$.

In one embodiment, X' is a bond, NH, S or CH$_2$. In another embodiment, X' is a bond. In another embodiment, X' is S. In another embodiment, X' is NH. In another embodiment, X' is CH$_2$.

In one embodiment, M is OH. In another embodiment, M is F or Cl. In another embodiment, M is O(C$_1$-C$_6$ alkyl), for example OCH$_3$, OCH$_2$CH$_3$, O(CH$_2$)$_2$CH$_3$, OCH(CH$_3$)$_2$ or OC(CH$_3$)$_3$. In another embodiment, M is NH$_2$. In another embodiment, M is NR$^q$R$^r$. In another embodiment, M is NO$_2$. In another embodiment, M is OCF$_3$. In one embodiment, M is CN. In one embodiment, M is C(O)OH. In one embodiment, M is C(O)O(C$_1$-C$_6$ alkyl), for example C(O)OCH$_3$, C(O)OCH$_2$CH$_3$, C(O)O(CH$_2$)$_2$CH$_3$, C(O)OCH(CH$_3$)$_2$ or C(O)OC(CH$_3$)$_3$. In one embodiment, M is C$_6$-C$_{12}$ aralkyl, for example CH$_2$-phenyl. In one embodiment, M is NR$^s$C(O)CR$^t{}_3$. In a subembodiment, R$^s$ is H. In a subembodiment, R$^t$ is H or Cl. In one embodiment, M is NR$^u$C(O)NR$^v{}_2$, for example, NHC(O)NH$_2$. In a subembodiment, R$^u$ is H and R$^v$ is H or alkyl.

In one embodiment, two M groups may be taken together with Ar$^b$ to form:

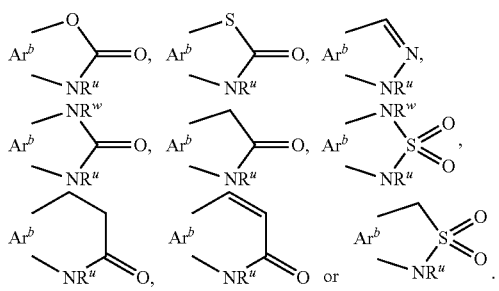

In a subembodiment, two M groups may be taken together with Ar$^b$ to form:

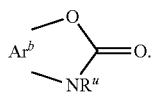

In one embodiment, R$^u$ and R$^w$ are both H. In one embodiment, h is 1 or 2.

In one embodiment, the compound is a compound of Formula II, or a pharmaceutically acceptable salt, ester, prodrug or derivative thereof, wherein:

each G is independently F, Cl, Br or I;
f is 0, 1, 2, 3, 4, or 5;
Ar$^a$ and Ar$^b$ are each independently selected from the group consisting of phenyl, pyridyl, pyrimidinyl, thiophenyl, imidazolyl, furanyl, indolyl, benzothiophenyl, benzofuranyl, benzoimidazolyl;
B is selected from the group consisting of:

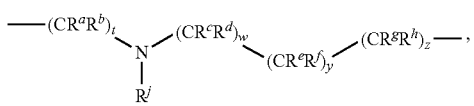

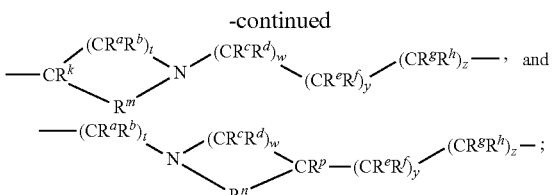

wherein R$^a$, R$^b$, R$^c$, R$^d$, R$^e$, R$^f$, R$^g$, R$^h$, R$^k$ and R$^p$ are each independently selected from H, C$_1$-C$_6$ alkyl, OH, or halo;
R$^j$ is H, C$_1$-C$_6$ alkyl, C$_7$-C$_{12}$ aralkyl, or OH;
R$^m$ is C$_1$-C$_4$ alkyl or C$_2$-C$_4$ alkenyl;
R$^n$ is C$_1$-C$_4$ alkyl, C$_2$-C$_4$ alkenyl, C$_6$-C$_{12}$ aralkyl, —CH$_2$O—, —CH(C$_1$-C$_6$ alkyl)O—, —CH(C$_2$-C$_{12}$ aralkyl)O—;
t, w, y and z each=0, 1, 2, or 3;
X is a bond, CH$_2$ or O;
X' is a bond, CH$_2$, S or NH;
M is OH, F, Cl, Br, I, NH$_2$, NR$^q$R$^r$, NO$_2$, O(C$_1$-C$_6$ alkyl), OCF$_3$, CN, C(O)OH, C(O)O(C$_1$-C$_6$ alkyl), C$_6$-C$_{12}$ aralkyl, NR$^s$C(O)CR$^t{}_3$, or NR$^u$C(O)NR$^v{}_2$; wherein each R$^q$, R$^r$, R$^s$, R$^u$ and R$^v$ is each independently H or C$_1$-C$_6$ alkyl; and each R$^t$ is independently H, C$_1$-C$_6$ alkyl or halo; or two M groups may be taken together with Ar$^b$ to form:

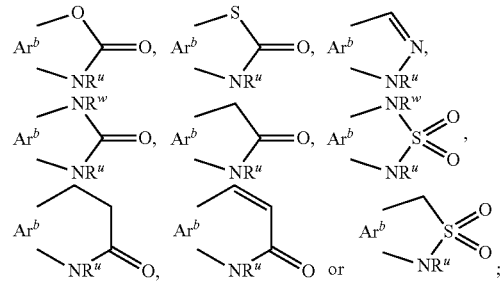

and wherein R$^u$ and R$^w$ are independently H or C$_1$-C$_4$ alkyl; and
h=1, 2 or 3.

In one embodiment, the compound is a compound of Formula II, or a pharmaceutically acceptable salt, ester, prodrug or derivative thereof, wherein:
each G is independently F, Cl, Br or I;
f=0, 1, 2, 3, 4 or 5;
Ar$^a$ and Ar$^b$ are each phenyl;
B is selected from the group consisting of:

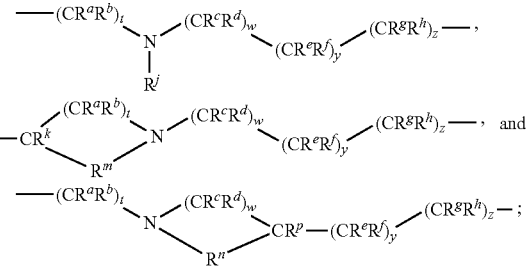

wherein R$^a$, R$^b$, R$^c$, R$^d$, R$^e$, R$^f$, R$^g$, R$^h$, R$^k$ and R$^p$ are each independently selected from H, C$_1$-C$_6$ alkyl, OH, or halo;
R$^j$ is H, C$_1$-C$_6$ alkyl, or OH;
R$^m$ is C$_1$-C$_4$ alkyl or C$_2$-C$_4$ alkenyl;

R" is $C_1$-$C_4$ alkyl, $C_2$-$C_4$ alkenyl, $C_6$-$C_{12}$ aralkyl, —$CH_2O$—, —$CH(C_1$-$C_6$ alkyl)O—, —$CH(C_2$-$C_{12}$ aralkyl)O—;

t, w, y and z each=0, 1, 2, or 3;

X is a bond, $CH_2$ or O;

X' is a bond, $CH_2$, S or NH;

M is OH, F, Cl, Br, I, $NH_2$, $NR^qR^r$, $NO_2$, $O(C_1$-$C_6$ alkyl), $OCF_3$, CN, C(O)OH, $C(O)O(C_1$-$C_6$ alkyl), $C_6$-$C_{12}$ aralkyl, $NR^sC(O)CR^t_3$; wherein each $R^q$, $R^r$, and $R^s$ is each independently H or $C_1$-$C_6$ alkyl; and each $R^t$ is independently H, $C_1$-$C_6$ alkyl or halo; or two M groups may be taken together with $Ar^b$ to form:

and wherein $R^u$ is H or $C_1$-$C_4$ alkyl; and h=1, 2 or 3.

In one embodiment, M is $NR^uC(O)NR^v_2$, for example $NHC(O)NH_2$ or $NHC(O)N(CH_3)_2$.

In another embodiment, $Ar^b$-M is selected from the group consisting of:

In one embodiment, the compound is or 6-{3-[2-(3,4-Dichloro-phenyl)-ethylamino]-2-(S)-hydroxy-propoxy}-3H-benzooxazol-2-one.

In one embodiment, the compound is

In one embodiment, the compound is selected from the compounds in Table 14.

TABLE 14

| Compound | NAME |
|---|---|
|  | 4-{3-[2-(3,4-Dichloro-phenyl)-ethylamino]-2-(S)-hydroxy-propoxy}-phenol |
|  | 4-(3-{Butyl-[2-(3,4-dichloro-phenyl)-ethyl]-amino}-2-(S)-hydroxy-propoxy)-phenol |
|  | 4-{3-[2-(3,4-Dichloro-phenyl)-ethylamino]-2-(S)-hydroxy-propoxy}-3-fluoro-phenol |

TABLE 14-continued

| Compound | NAME |
|---|---|
| (structure) | 4-{3-[2-(3,4-Dichloro-phenyl)-ethylamino]-2-(S)-hydroxy-propoxy}-2-fluoro-phenol |
| (structure) | 1-[2-(S)-Hydroxy-3-(4-hydroxy-phenoxy)-propyl]-4-phenyl-piperidin-4-ol |
| (structure) | (R)-1-(4-(2-hydroxy-3-(4-hydroxy-4-phenylpiperidin-1-yl)propoxy)phenyl)urea |
| (structure) | (S)-1-(4-(2-hydroxy-3-(4-hydroxy-4-phenylpiperidin-1-yl)propoxy)phenyl)urea |
| (structure) | (S)-1-(4-(3-(4-benzyl-4-hydroxypiperidin-1-yl)-2-hydroxypropoxy)phenyl)urea |
| (structure) | (R)-1-(4-(3-(4-benzyl-4-hydroxypiperidin-1-yl)-2-hydroxypropoxy)phenyl)urea |
| (structure) | 1-(4-(3-(4-benzyl-4-hydroxypiperidin-1-yl)-2-hydroxypropoxy)phenyl)urea |

TABLE 14-continued

| Compound | NAME |
|---|---|
| [structure] | 1-(4-(3-(4-(4-chlorobenzyl)-4-hydroxypiperidin-1-yl)-2-hydroxypropoxy)phenyl)urea |
| [structure] | 1-(4-(2-hydroxy-3-(4-hydroxy-4-phenylpiperidin-1-yl)propoxy)phenyl)urea |
| [structure] | (S)-5-(3-(4-benzyl-4-hydroxypiperidin-1-yl)-2-hydroxypropoxy)indolin-2-one |
| [structure] | (R)-5-(3-(4-benzyl-4-hydroxypiperidin-1-yl)-2-hydroxypropoxy)indolin-2-one |
| [structure] | (S)-5-(2-hydroxy-3-(4-hydroxy-4-phenylpiperidin-1-yl)propoxy)indolin-2-one |
| [structure] | (R)-5-(2-hydroxy-3-(4-hydroxy-4-phenylpiperidin-1-yl)propoxy)indolin-2-one |
| [structure] | (R)-6-(3-(4-benzyl-4-hydroxypiperidin-1-yl)-2-hydroxypropoxy)-3,4-dihydroquinolin-2(1H)-one |

TABLE 14-continued

| Compound | NAME |
| --- | --- |
| | (S)-6-(3-(4-benzyl-4-hydroxypiperidin-1-yl)-2-hydroxypropoxy)-3,4-dihydroquinolin-2(1H)-one |
| | (S)-6-(2-hydroxy-3-(4-hydroxy-4-phenylpiperidin-1-yl)propoxy)-3,4-dihydroquinolin-2(1H)-one |
| | (R)-6-(2-hydroxy-3-(4-hydroxy-4-phenylpiperidin-1-yl)propoxy)-3,4-dihydroquinolin-2(1H)-one |
| | (R)-6-(2-hydroxy-3-(4-hydroxy-4-phenylpiperidin-1-yl)propoxy)quinolin-2(1H)-one |

In one embodiment, the compound has an $IC_{50}$ value of 600 nM or less. In one embodiment, the compound has an $IC_{50}$ value of 600 nM or less at pH 6.9 or an ischemic pH. In one embodiment, the compound is selected from Table 15.

TABLE 15

TABLE 15-continued

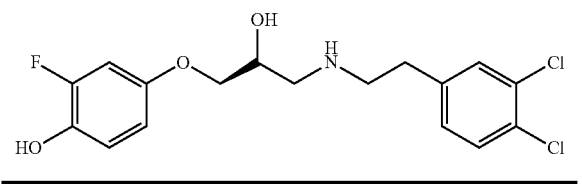

In one embodiment, the compound has a pH boost of 5 or more. In one embodiment, the compound is

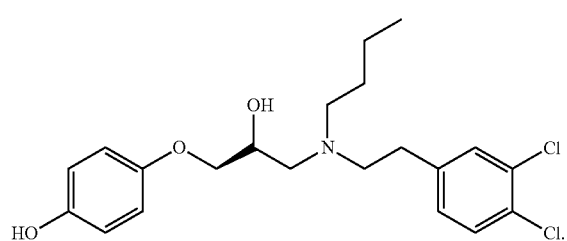

In one embodiment, the compound is selected from the group consisting of:

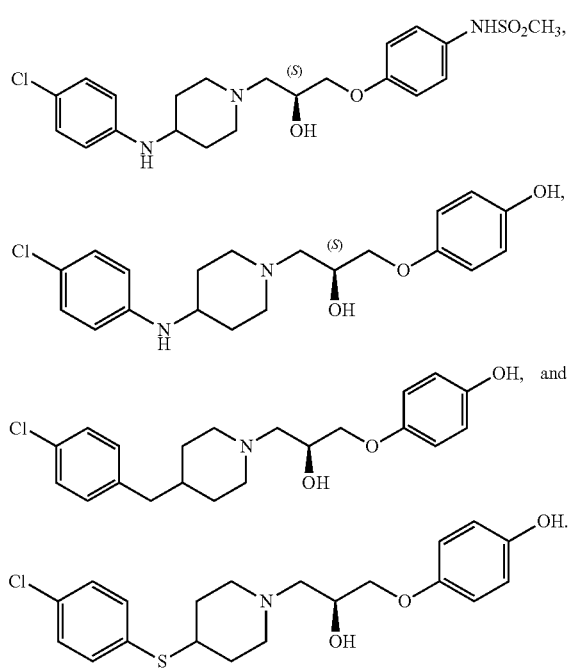

In one embodiment, the compound is

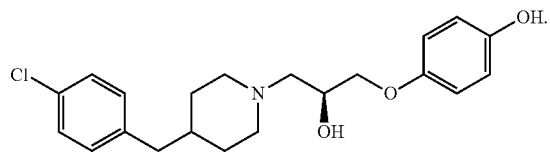 [SMILES: Oc1ccc(OC[C@@H](O)CN2CCC(Cc3ccc(Cl)cc3)CC2)cc1]

In another embodiment, the compound is selected from the group consisting of:

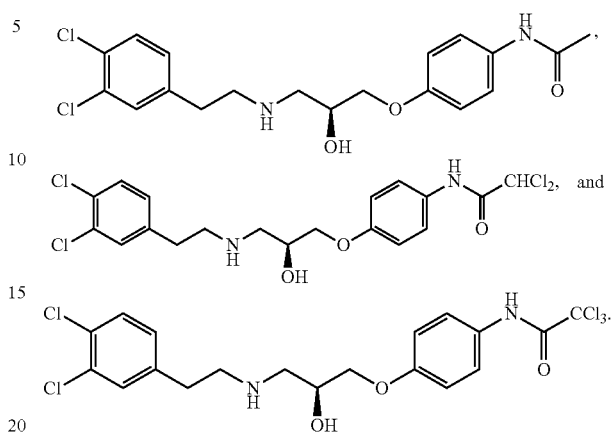

In another embodiment the compound is

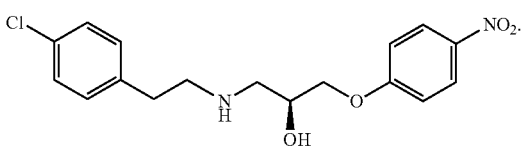 [SMILES: O=[N+]([O-])c1ccc(OC[C@@H](O)CNCCc2ccc(Cl)cc2)cc1]

In one embodiment, one or more of $R^c$, $R^d$, $R^e$, $R^f$, $R^g$, and $R^h$ is an OH group which creates a stereogenic center. In a particular subembodiment, one of $R^c$, $R^d$, $R^e$, $R^f$, $R^g$ and $R^h$ is an OH group which creates a stereogenic center. In another subembodiment, the OH group at one of $R^c$, $R^d$, $R^e$, $R^f$, $R^g$, and $R^h$ is in the R configuration. In another subembodiment, the OH group at one of $R^c$, $R^d$, $R^e$, $R^f$, $R^g$, and $R^h$ is in the S configuration.

In certain embodiments, the binding to both hERG and alpha-1 adrenergic receptors can be modulated by changing the G substituent or G substituents. In particular, for compounds wherein $Ar^a$ is phenyl, the binding to both hERG and alpha-1 adrenergic receptors can be modulated by changing the substitution at the 3 and/or 4 positions. In one embodiment, the $Ar^a$ phenyl is substituted at the 3 and/or 4 position with, for example, fluorine or chlorine. In certain embodiments, substitution at the 3 and/or 4 positions of the $Ar^a$ phenyl can increase potency.

In certain embodiments, both hERG and alpha-1 adrenergic binding can be reduced by substituting N at the $R^j$ position with $C_7$-$C_{12}$ aralkyl. In a particular subembodiment, $R^j$ is benzyl.

In certain embodiments, alpha-1 adrenergic binding is reduced when $R^j$ is $C_1$-$C_6$ alkyl.

When $Ar^b$ is phenyl, para substitution of the M substituent is particularly preferred. Additional M substitutents on the $Ar^b$ phenyl are preferred at one or more ortho positions. Additional substitution on the $Ar^b$ phenyl at one or more meta positions can reduce potency.

In certain embodiments, the $Ar^a$ phenyl is not substituted by two fluoro groups. In one embodiment, the $Ar^a$ phenyl is not substituted by two methyl groups. In one embodiment, the $Ar^a$ phenyl is not substituted by one halo group. In one embodiment, the $Ar^a$ phenyl is not substituted by one fluoro or alkyl group at the C-2 position. In one embodiment, the $Ar^a$ phenyl is not substituted by a OH or $NO_2$ group.

In one embodiment, when Ar$^a$ and Ar$^b$ are both phenyl, at least one of for h is not 0. In one embodiment, when Ar$^a$ and Ar$^b$ are both phenyl, f is not 0. In one embodiment, when Ar$^a$ and Ar$^b$ are both phenyl, h is not 0. In one embodiment, when Ar$^a$ and Ar$^b$ are both phenyl, X is not CH$_2$. In one embodiment, when Ar$^a$ and Ar$^b$ are both phenyl, X' is not CH$_2$. In another embodiment, M is not OH. In one embodiment, the compound is not

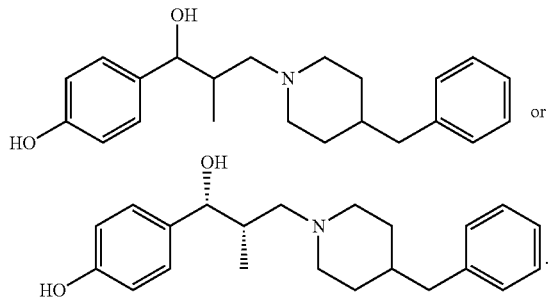

or

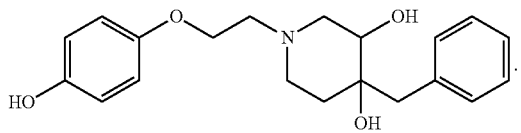 [SMILES: Oc1ccc(OCCN2CCC(O)(Cc3ccccc3)C(O)C2)cc1]

.

In one embodiment, M is not aralkoxy. In one embodiment, the compound is not

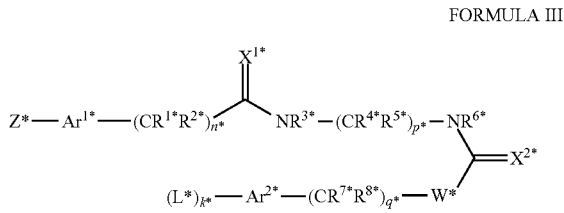

.

In one embodiment, B does not contain a piperidinyl moiety. In another embodiment, when B contains a piperidinyl moiety, and Ar$^a$ and Ar$^b$ are both phenyl, M is not OH. In one embodiment, when B contains a piperidinyl moiety, M is NR$^u$C(O)NR$^v_2$, for example, NHC(O)NH$_2$. In a subembodiment, R$^u$ is H and R$^v$ is H or alkyl. In one embodiment, when B contains a piperidinyl moiety, X is not CH$_2$. In one embodiment, when B contains a piperidinyl moiety, X' is not CH$_2$. In one embodiment, R$^k$ is not OH. In one embodiment, R$^p$ is not OH.

In one embodiment, when B contains a hydroxy-substituted-piperidinyl moiety, X is not CH$_2$. In one embodiment, when B contains a hydroxy-substituted-piperidinyl moiety, X' is not CH$_2$. In one embodiment, B does not contain a hydroxy-substituted-piperidinyl moiety.

In one embodiment, X is not SO$_2$. In another embodiment, X' is not SO$_2$. In one embodiment, when B contains a piperidinyl moiety, X is not SO$_2$. In one embodiment, when B contains a piperidinyl moiety, X' is not SO$_2$.

In one embodiment, X is not S. In another embodiment, X' is not S. In one embodiment, when B contains a piperidinyl moiety, X is not S. In one embodiment, when B contains a piperidinyl moiety, X' is not S.

In another embodiment, M is not OCH$_3$ or OCF$_3$. In another embodiment, M is not NO$_2$. In one embodiment, when B contains a nitrogen-containing heterocycle, Ar$^b$—X is not heteroaryl-NH. In another embodiment, when B contains a nitrogen-containing heterocycle, Ar$^a$—X' is not heteroaryl-NH.

In one embodiment, when B contains a nitrogen-containing heterocycle, X is not NH(C═O). In another embodiment, when B contains a nitrogen-containing heterocycle, X' is not NH(C═O).

Formula III

In one embodiment, compounds, pharmaceutical compositions and methods of treatment or prophylaxis of neuropathic pain, stroke, traumatic brain injury, epilepsy, and other neurologic events or neurodegeneration resulting from NMDA receptor activation, comprising administering to a host in need thereof a compound of Formula III, or a pharmaceutically acceptable salt, ester, prodrug or derivative thereof are provided:

FORMULA III

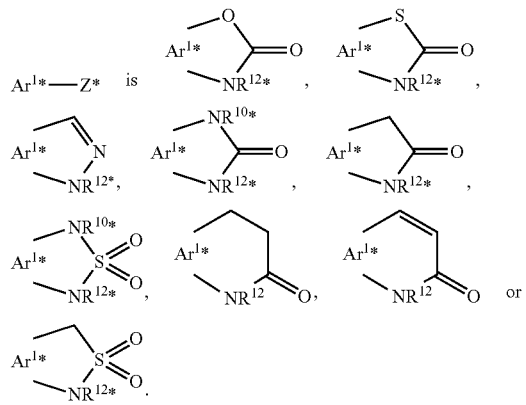

wherein:

Z* is OH, NR$^{10*}$R$^{11*}$, NR$^{12*}$SO$_2$R$^{11*}$, NR$^{12*}$C(O)NR$^{10*}$R$^{11*}$, NR$^{12*}$C(O)OR$^{10*}$, NR$^{12*}$-dihydrothiazole, or NR$^{12*}$-dihydroimidazole; wherein each R$^{10*}$, R$^{11*}$ and R$^{12*}$ is independently H, C$_1$-C$_6$ alkyl or C$_6$-C$_{12}$ aralkyl; or Ar$^{1*}$—Z* is Ar$^{1*}$ and Ar$^{2*}$ are each independently aryl or heteroaryl;

R$^{1*}$, R$^{2*}$, R$^{4*}$, R$^{5*}$, R$^{7*}$, R$^{8*}$ are independently H, OH or C$_1$-C$_4$ alkyl;

n*=1, 2, 3 or 4;

p*=0, 1, 2 or 3;

q*=0, 1 or 2;

R$^{3*}$ and R$^{6*}$ are each independently H or C$_1$-C$_4$ alkyl;

X$^{1*}$ and X$^{2*}$ are each independently O, S, N(C$_1$-C$_4$ alkyl) or C(H or C$_1$-C$_4$ alkyl)$_2$;

W* is NR$^{9*}$ or CR$^{13*}$R$^{14*}$; wherein R$^{9*}$, R$^{13*}$ and R$^{14*}$ are each independently is H or C$_1$-C$_4$ alkyl;

each L* is independently C$_1$-C$_6$ alkyl, C$_1$-C$_6$ alkoxy, C(═O)—(C$_1$-C$_6$)-alkyl, C$_1$-C$_6$ haloalkyl, hydroxy, fluoro, chloro, bromo, iodo, nitro, or cyano; or two L groups may be taken together with Ar$^{2*}$ to form a dioxolane ring or a cyclobutane ring;

k*=0, 1, 2, 3, 4 or 5;

or

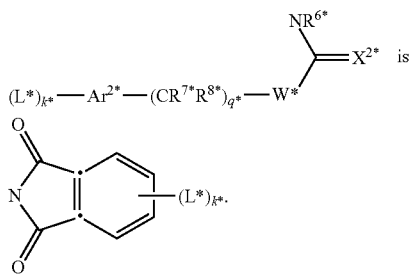

In one embodiment, $Z^*$ is OH, $NR^{12*}SO_2R^{11*}$; wherein $R^{12*}$ is H or $C_1$-$C_4$ alkyl, and $R^{11*}$ is $C_1$-$C_4$ alkyl or $C_2$-$C_{10}$ aralkyl. In one embodiment, $Z^*$ is OH. In another embodiment, $Z^*$ is $NR^{12*}SO_2R^{11*}$, for example, $NHSO_2CH_3$.

In one embodiment, $Z^*$ is $NR^{12*}C(O)NR^{10*}R^{11*}$ or

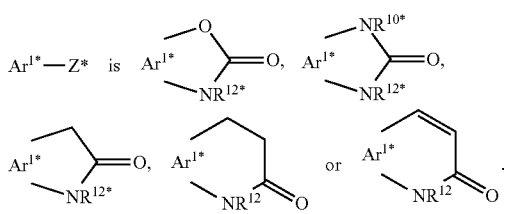

In one embodiment, $Ar^{1*}$ and $Ar^{2*}$ are each phenyl.
In one embodiment, $R^{1*}$, $R^{2*}$, $R^{4*}$, $R^{5*}$, $R^{7*}$, $R^{8*}$ are H.
In a particular embodiment, $n^*$ is 2.
In one embodiment, $p^*$ is 0, 1 or 2. In another embodiment, $p^*$ is 0. In another embodiment, $p^*$ is 1. In another embodiment, $p^*$ is 2.

In one embodiment, $q^*$ is 0. In another embodiment, $q^*$ is 1. In another embodiment, $q^*$ is 2.

In one embodiment, $R^{3*}$ and $R^{6*}$ are both H. In one embodiment, $R^{6*}$ is $C_1$-$C_4$ alkyl, for example methyl, ethyl, propyl, isopropyl, n-butyl, sec-butyl, or tert-butyl.

In one embodiment, $X^*$ is S. In one embodiment, $X^*$ is O.
In one embodiment, $W^*$ is $NR^{7*}$, for example NH. In another embodiment, $W^*$ is $CR^{13*}R^{14*}$, for example $CH_2$.

In one embodiment, each $L^*$ is independently selected from $C_1$-$C_4$ alkyl, F, Cl, Br, I, or $C_1$-$C_4$ haloalkyl, for example, Cl, $CH_3$ or $CF_3$. In one embodiment, $k^*$ is 1. In another embodiment, $k^*$ is 2.

In one embodiment, the compound is a compound of Formula III, or a pharmaceutically acceptable salt, ester, prodrug or derivative thereof, wherein:
$Z^*$ is OH, $NHSO_2CH_3$;
$Ar^{1*}$ is phenyl;
$R^{1*}$, $R^{2*}$, $R^{4*}$, $R^{5*}$ are independently H or $C_1$-$C_4$ alkyl;
$n^*=2$;
$p^*=0$, 1 or 2;
$q^*=0$, 1 or 2;
$R^{3*}$ and $R^{6*}$ are each independently H or $C_1$-$C_4$ alkyl;
$X^*$ is O or S;
$W^*$ is $NR^{7*}$ or $CR^{13*}R^{14*}$; wherein $R^{7*}$, $R^{13*}$ and $R^{14*}$ are each independently is H or $C_1$-$C_4$ alkyl;
$Ar^{2*}$ is phenyl;
each $L^*$ is independently selected from $C_1$-$C_4$ alkyl, F, Cl, Br, I, $C_1$-$C_4$ haloalkyl;
$k^*=0$, 1, 2, 3, 4 or 5;

or

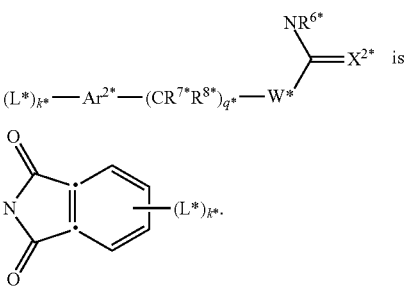

In one embodiment, the compound is selected from the group consisting of:

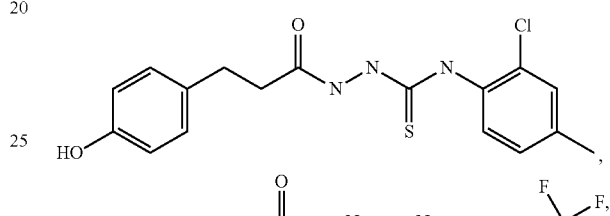

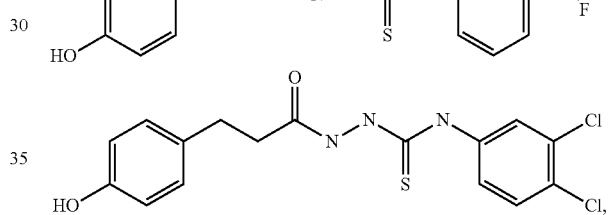

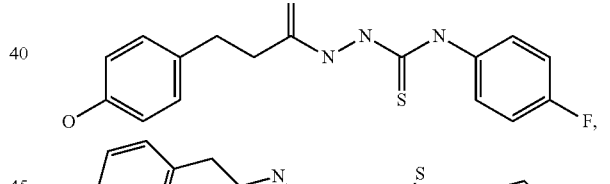

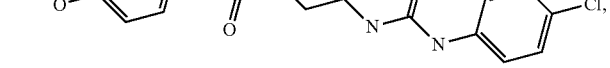

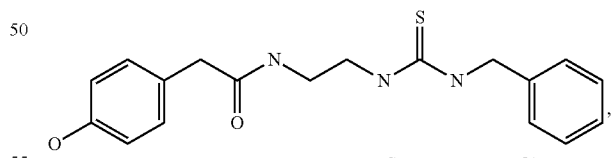

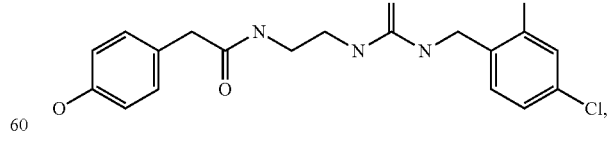

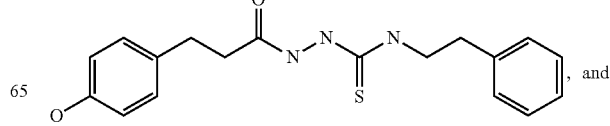

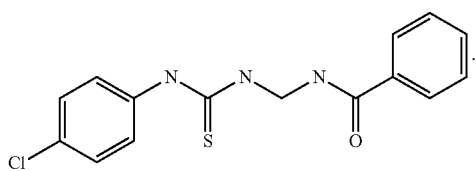

In another embodiment, the compound is selected from the group consisting of:

Formula IV

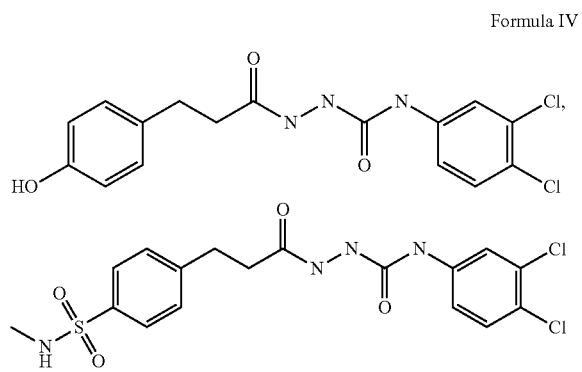
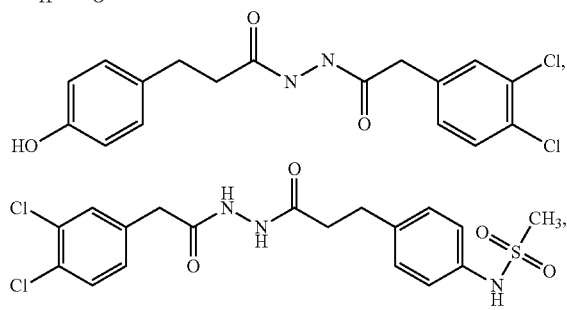
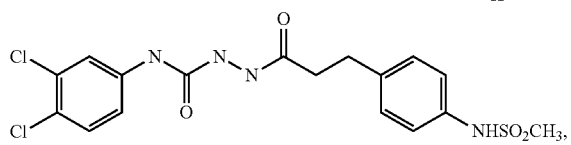
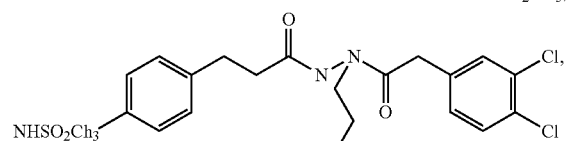
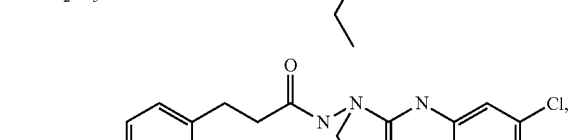
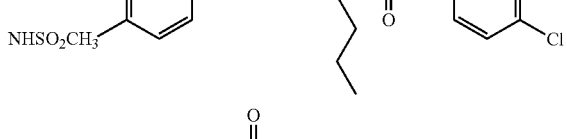
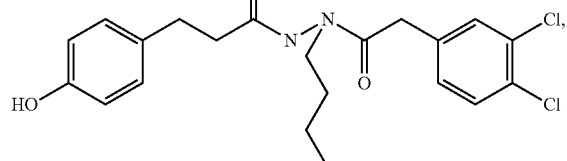

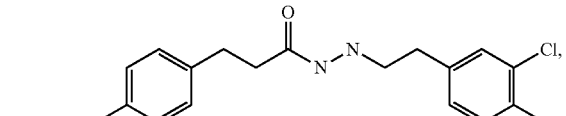
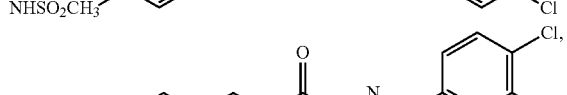
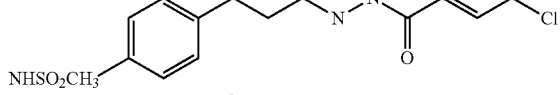
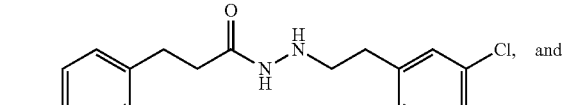
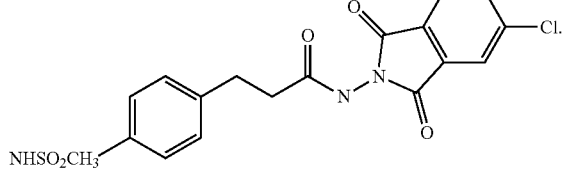

In one embodiment, compounds, pharmaceutical compositions and methods of treatment or prophylaxis of neuropathic pain, stroke, traumatic brain injury, epilepsy, and other neurologic events or neurodegeneration resulting from NMDA receptor activation, comprising administering to a host in need thereof a compound of Formula IV, or a pharmaceutically acceptable salt, ester, prodrug or derivative thereof are provided:

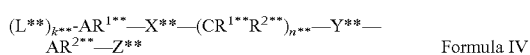

Formula IV wherein:
each $L^{}$ is independently $C_1$-$C_6$ alkyl, $C_1$-$C_6$ alkoxy, $C(=O)$—$(C_1$-$C_6)$-alkyl, $C_1$-$C_6$ haloalkyl, hydroxy, fluoro, chloro, bromo, iodo, nitro, or cyano; or two $L^{}$ groups may be taken together with $Ar^{1**}$ to form: a dioxolane ring or a cyclobutane ring;
$k^{**}=0, 1, 2, 3, 4$ or $5$;
each $Ar^{1}$ and $Ar^{2}$ is independently aryl or heteroaryl;
$X^{**}$ is S, O or $NR^3$; wherein $R^3$ is H, $C_1$-$C_6$ alkyl, or $C_6$-$C_{12}$ aralkyl;
each $R^{1}$ and $R^{2}$ is independently H, $C_1$-$C_6$ alkyl, $C_1$-$C_6$ alkoxy, $C_6$-$C_{12}$ aralkyl, $C(=O)$—$(C_1$-$C_6)$-alkyl, $C_1$-$C_6$ haloalkyl, hydroxy, fluoro, chloro, bromo, iodo, nitro, or cyano; or $CR^1R^2$ can be $C=O$ or $C=CH_2$;
$n^{**}=1, 2, 3$ or $4$;
$Y^{**}$ is a bond, O, S, SO, $SO_2$, $CH_2$, NH, $N(C_1$-$C_6$ alkyl), or $NHC(=O)$;
$Z^{}$ is OH, $NR^{6}R^{7}$, $NR^{8}SO_2(C_1$-$C_6$ alkyl), $NR^{8}C(O)NR^{6}R^{7}$, $NR^{8}C(O)O(C_1$-$C_6$ alkyl), $NR^{8}$-dihydrothiazole, or $NR^{8}$-dihydroimidazole; wherein each $R^{6}$, $R^{7}$ and $R^{8**}$ is independently H, $C_1$-$C_6$ alkyl or $C_6$-$C_{12}$ aralkyl; or

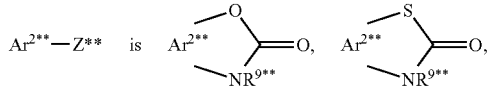

-continued

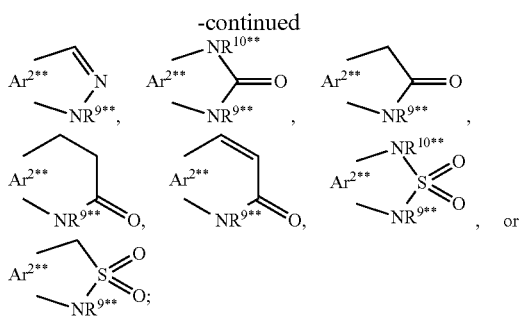

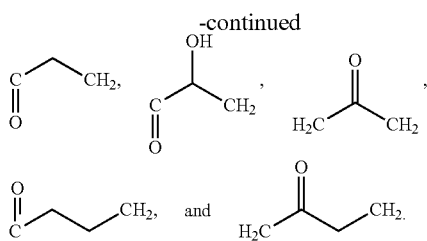

wherein $R^{9}$ and $R^{10}$ are each independently H, $C_1$-$C_6$ alkyl, aralkyl.

In particular subembodiment, $Ar^{1}$ is phenyl, pyridyl, pyrimidinyl, thiophenyl, imidazolyl, furanyl, indolyl, benzothiophenyl, benzofuranyl, or benzoimidazolyl. In one embodiment, $Ar^{2}$ is phenyl. In another embodiment, $Ar^{1}$ is benzoimidazolyl. In a particular subembodiment, $Ar^{2}$ is phenyl and $Ar^{1}$ is a heteroaryl, for example benzoimidazolyl. In one embodiment, $Ar^{1}$ is a bicyclic group wherein the $X^{**}$ group is attached to the heterocyclic ring.

In one embodiment, $X^{}$ is S. In one embodiment, $X^{}$ is O. In one embodiment, $X^{}$ is $NR^{3}$, for example NH.

In another particular subembodiment, $L^{}$ is $C_1$-$C_4$ alkyl, $C_1$-$C_4$ alkoxy, C(=O)—($C_1$-$C_4$)-alkyl, $C_1$-$C_6$ haloalkyl, hydroxy, fluoro, chloro, bromo, iodo, nitro, or cyano. In a further subembodiment, $L^{}$ is methyl, trifluoromethyl, methoxy, nitro, fluoro, chloro or hydroxy. In one further subembodiment, there are one, two or three $L^{}$ groups substituting $Ar^{1}$. In one subembodiment, $Ar^{1}$ is substituted with one fluoro group. In one subembodiment, $Ar^{1}$ is substituted with two fluoro groups. In one subembodiment, $Ar^{1}$ is substituted with one fluoro group and one chloro group. In one subembodiment, $Ar^{1}$ is substituted with one chloro group. In one subembodiment, $Ar^{1}$ is substituted with two chloro groups. In one subembodiment, $Ar^{1}$ is substituted with one methyl group. In one subembodiment, $Ar^{1**}$ is substituted with one trifluoromethyl group.

In one embodiment, each $R^{1}$ and $R^{2}$ is independently H or $C_1$-$C_4$ alkyl, for example, methyl, ethyl, n-propyl, isopropyl, n-butyl, sec-butyl or tert-butyl. In one embodiment, $R^{1}$ and $R^{2}$ are both H. In one embodiment, one $R^{1}$ or $R^{2}$ is hydroxy. In one embodiment, $n^{}$ is 2, 3, or 4. In one embodiment, $n^{}$ is 3.

In one embodiment, one $CR^{1}R^{2}$ is C=O or C=$CH_2$. In one embodiment, $(CR^{1}R^{2})_{n**}$ is selected from the group consisting of

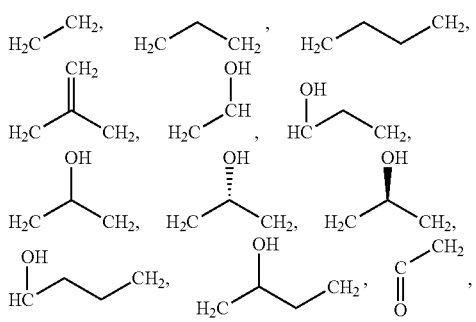

In an particular embodiment, $(CR^{1}R^{2})_{n**}$ is

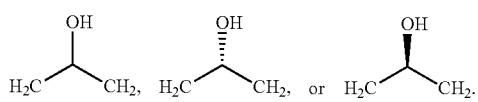

In one embodiment, $Y^{}$ is a bond, O or $CH_2$. In one embodiment, $Y^{}$ is O. In one subembodiment, $Ar^{2}$ is phenyl and is substituted with a $Z^{}$ group at the 4 position.

In one embodiment, $Z^{}$ is OH, $NR^{6}R^{7}$, $NR^{8}SO_2$($C_1$-$C_6$ alkyl), $NR^{8}C(O)NR^{6}R^{7}$, $NR^{8}C(O)O(C_1$-$C_6$ alkyl), $NR^{8}$-dihydrothiazole, or $NR^{8}$-dihydroimidazole. In one subembodiment, $Ar^{2**}$ is phenyl and is substituted with a Z group at the 4 position. In one embodiment,

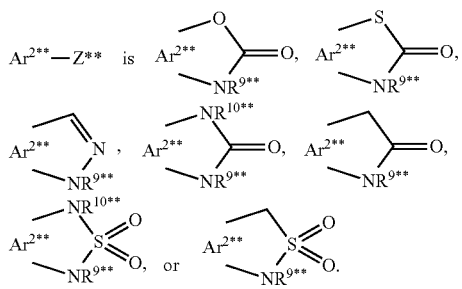

In one embodiment,

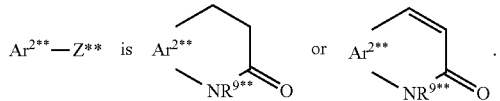

In one subembodiment,

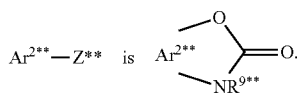

In one subembodiment, $R^{9}$ and $R^{10}$ are each H.

In another subembodiment, $Z^{}$ is $NR^{8}C(O)NR^{6}R^{7}$ or

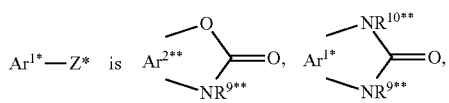

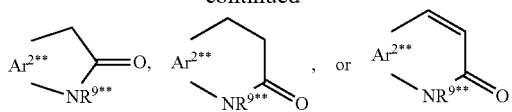

In one embodiment, the compound is a compound of Formula IV, or a pharmaceutically acceptable salt, ester, prodrug or derivative thereof, wherein:

L** is $C_1$-$C_4$ alkyl, $C_1$-$C_4$ alkoxy, C(=O)—($C_1$-$C_4$)-alkyl, $C_1$-$C_4$ haloalkyl, hydroxy, fluoro, chloro, bromo, iodo, or nitro;

k**=0, 1, 2, 3, 4 or 5;

Ar$^{1**}$ is selected from the group consisting of phenyl, pyridyl, pyrimidinyl, thiophenyl, imidazolyl, furanyl, indolyl, benzothiophenyl, benzofuranyl, or benzoimidazolyl.;

Ar$^{2**}$ is phenyl;

X** is S;

each R$^{1}$ and R$^{2}$ is independently H, hydroxy or $C_1$-$C_4$ alkyl; or CR$^{1}$R$^{2}$ is C=O;

n**=2, 3 or 4;

Y** is O;

Z is OH, NH$_2$, NHSO$_2$($C_1$-$C_4$ alkyl), NHC(O)NR$^{6}$R$^{7}$, NHC(O)O($C_1$-$C_4$ alkyl), NH-dihydrothiazole, or NH-dihydroimidazole; wherein each R$^{6}$ and R$^{7**}$ is independently H or $C_1$-$C_4$ alkyl; or

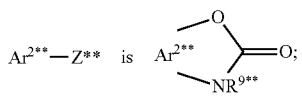

R$^{9**}$ is H or $C_1$-$C_4$ alkyl.

In one embodiment, the compound is selected from the group consisting of:

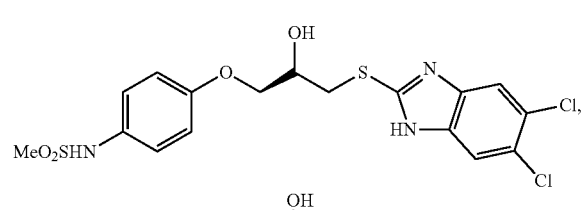

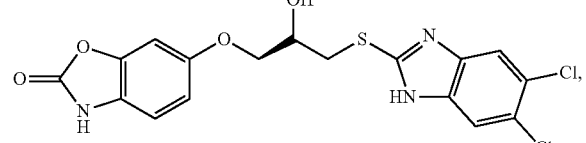

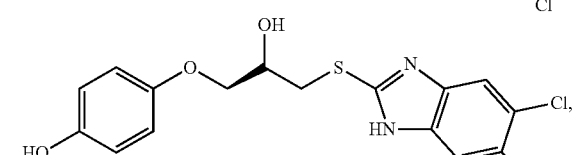

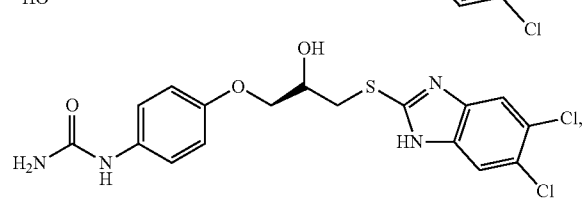

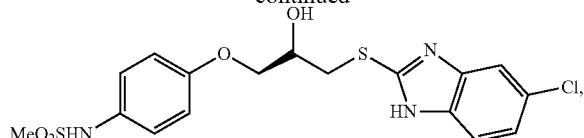

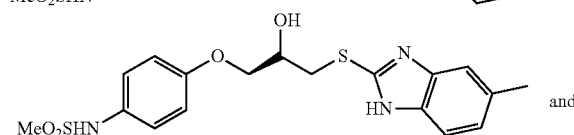

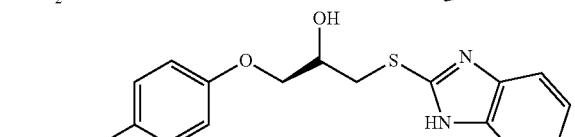

In one embodiment, the compound is

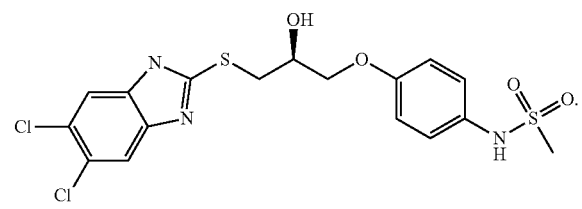 [SMILES: CS(=O)(=O)Nc1ccc(OC[C@H](O)CSc2nc3cc(Cl)c(Cl)cc3[nH]2)cc1]

In one embodiment, the compound is selected from the group consisting of:

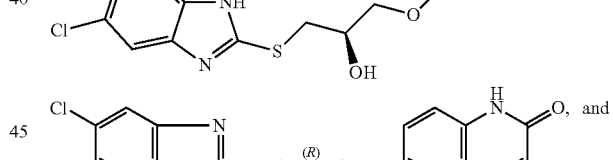

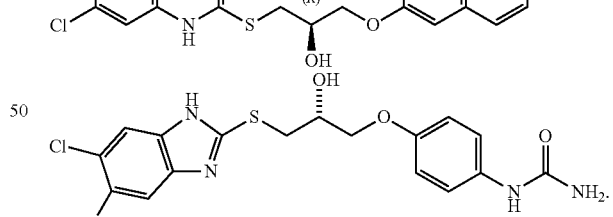

In one embodiment, the compound is

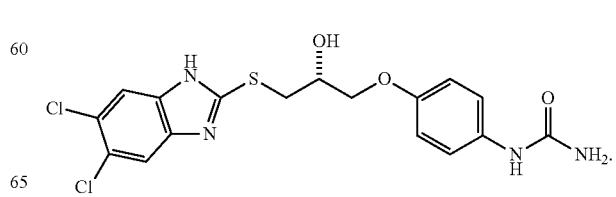

In another embodiment, the compound is selected from the group consisting of:

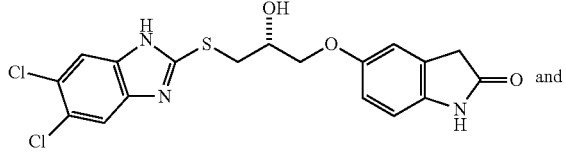 and 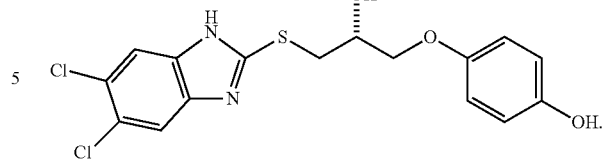

In another embodiment, the compound is selected from Table 16.

TABLE 16

| Compound | Name |
|---|---|
|  | (R)-4-(3-(5,6-dichloro-1H-benzo[d]imidazol-2-ylthio)-2-hydroxypropoxy)phenol |
|  | (R)-5-(3-(5,6-dichloro-1H-benzo[d]imidazol-2-ylthio)-2-hydroxypropoxy)indolin-2-one |
|  | (R)-6-(3-(5,6-dichloro-1H-benzo[d]imidazol-2-ylthio)-2-hydroxypropoxy)-3,4-dihydroquinolin-2(1H)-one |
|  | (R)-6-(3-(5,6-dichloro-1H-benzo[d]imidazol-2-ylthio)-2-hydroxypropoxy)quinolin-2(1H)-one |
|  | (R)-1-(4-(3-(5,6-dichloro-1H-benzo[d]imidazol-2-ylthio)-2-hydroxypropoxy)phenyl)urea |
|  | (R)-N-(4-(3-(5,6-dichloro-1H-benzo[d]imidazol-2-ylthio)-2-hydroxypropoxy)phenyl)methanesulfonamide |

TABLE 16-continued

| Compound | Name |
|---|---|
| 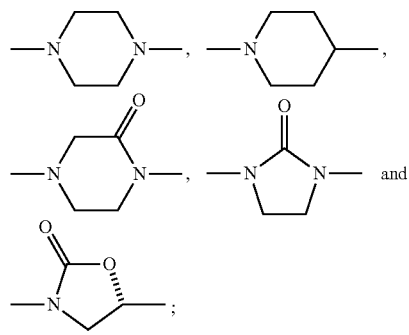 | (R)-N-(4-(2-hydroxy-3-(6-methyl-1H-benzo[d]imidazol-2-ylthio)propoxy)phenyl)methanesulfonamide |

Formula V

In one embodiment, compounds, pharmaceutical compositions and methods of treatment or prophylaxis of neuropathic pain, stroke, traumatic brain injury, epilepsy, and other neurologic events or neurodegeneration resulting from NMDA receptor activation, comprising administering to a host in need thereof a compound of Formula V, or a pharmaceutically acceptable salt, ester, prodrug or derivative thereof are provided:

Ar'—W'—B'—W"—Y'—Ar"—Z'           Formula V wherein B' is selected from the group consisting of:

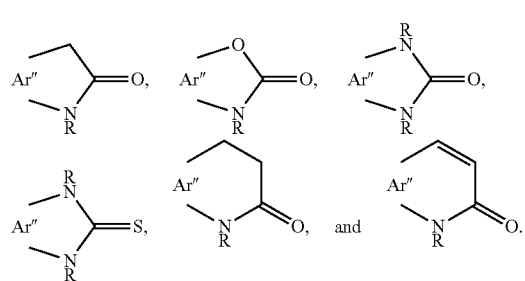

W' is a bond or $C_1$-$C_4$ alkyl;
W" is $C_1$-$C_4$ alkyl, $C_1$-$C_4$ hydroxyalkyl, $C_1$-$C_4$ haloalkyl or C(=O)—$C_1$-$C_4$ alkyl;
Y' is selected from a bond, O, S, $CH_2$ and N;
Ar' is an substituted or unsubstituted aromatic or nonaromatic cycloalkyl which optionally may include 0-3 heteroatoms;
Ar" is an aromatic or nonaromatic cycloalkyl which optionally may include 0-3 heteroatoms;
Z' is NRC(O)$NR_2$ wherein each R is independently selected from H, $C_1$-$C_6$ alkyl or $C_6$-$C_{12}$ aralkyl; or
Ar"—Z' are taken together and selected from the group consisting of:

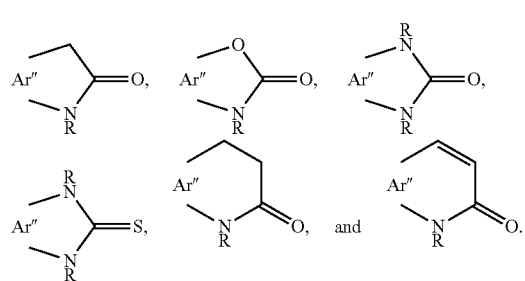

In one embodiment, Ar' is substituted by (L')$_k$' wherein each L' is independently $C_1$-$C_6$ alkyl, $C_1$-$C_6$ alkoxy, C(=O)—($C_1$-$C_6$)-alkyl, $C_1$-$C_6$ haloalkyl, alkaryl, hydroxy, —O-alkyl, —O-aryl, —SH, —S-alkyl, —S-aryl, fluoro, chloro, bromo, iodo, nitro, or cyano; or two L' groups may be taken together with Ar' to form a dioxolane ring or a cyclobutane ring; and k'=1, 2, 3, 4 or 5.

In one embodiment B' is

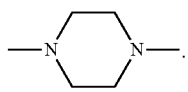

In another embodiment, B' is

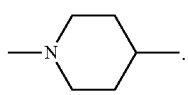

In another embodiment, B' is

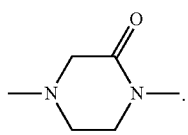

In another embodiment, B' is

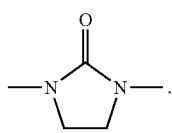

In another embodiment, B' is

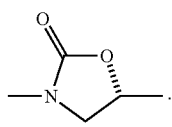

In one embodiment, W' is a bond. In another embodiment, W' is $C_1$-$C_4$ alkyl, for example methylene, ethylene, or propylene. In a particular subembodiment, W' is $CH_2$.

In one embodiment W" is $C_1$-$C_4$ alkyl, for example methylene, ethylene, propylene, methylpropylene, or butylene. In another embodiment, W" is $C_1$-$C_4$ hydroxyalkyl, for example hydroxymethylene, hydroxyethylene, or hydroxypropylene. In a particular subembodiment, W" is —$CH_2$, CH(OH)—

CH$_2$—. In another embodiment, W″ is C$_1$-C$_4$ haloalkyl, for example fluoroethylene, fluoropropylene, chloroethylene, or chloropropylene.

In another embodiment, W″ is C(=O)—C$_1$-C$_4$ alkyl, for example —C(=O)—CH$_2$— or —C(=O)—CH$_2$—CH$_2$—.

In one embodiment, Ar' is an aromatic cycloalkyl, for example phenyl. In another embodiment, Ar' is an nonaromatic cycloalkyl, for example cyclopentyl or cyclohexyl. In another embodiment, Ar' is an aromatic cycloalkyl including 1-3 heteroatoms, for example pyrrole, furan, thiophene, pyridine, pyrimidine, pyrazine, pyridazine. Heteroatoms include but are not limited to N, S and O. In another embodiment, Ar' is a nonaromatic cycloalkyl including 1-3 heteroatoms, for example pyrrolidine, pyrroline, dihydrofuran, tetrahydrofuran, dihydrothiophene, tetrahydrothiophene, piperidine, tetrahydropyran, pyran, thiane, thiiine, piperazine, oxazine, dithiane, or dioxane. In another embodiment, Ar' is an aromatic or nonaromatic cycloalkyl including 1 heteroatom. In another embodiment, Ar' is an aromatic or nonaromatic cycloalkyl including 2 heteroatoms. In another embodiment, Ar' is an aromatic or nonaromatic cycloalkyl including 3 heteroatoms.

In one embodiment, Ar″ is an aromatic cycloalkyl, for example phenyl. In another embodiment, Ar″ is an nonaromatic cycloalkyl, for example cyclopentyl or cyclohexyl. In another embodiment, Ar″ is an aromatic cycloalkyl including 1-3 heteroatoms, for example pyrrole, furan, thiophene, pyridine, pyrimidine, pyrazine, or pyridazine. In another embodiment, Ar″ is a nonaromatic cycloalkyl including 1-3 heteroatoms, for example pyrrolidine, pyrroline, dihydrofuran, tetrahydrofuran, dihydrothiophene, tetrahydrothiophene, piperidine, tetrahydropyran, pyran, thiane, thiiine, piperazine, oxazine, dithiane, or dioxane.

In another embodiment, Ar″ is an aromatic or nonaromatic cycloalkyl including 1 heteroatom. In another embodiment, Ar″ is an aromatic or nonaromatic cycloalkyl including 2 heteroatoms. In another embodiment, Ar″ is an aromatic or nonaromatic cycloalkyl including 3 heteroatoms.

In one embodiment, Z' is NRC(O)NR$_2$, for example NHC(O)NH$_2$ or NHC(O)N(CH$_3$)$_2$.

In another embodiment, Z and Ar″ are taken together and selected from the group consisting of:

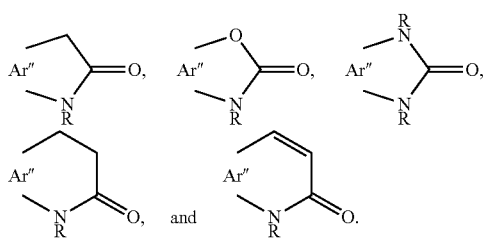

In a particular subembodiment, Ar″—Z' is

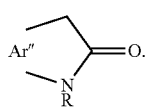

In another subembodiment, Ar″—Z' is

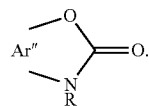

In another subembodiment, Ar″—Z' is

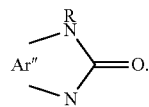

In another subembodiment, Ar″—Z' is

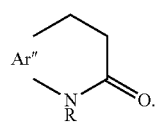

In another subembodiment, Ar″—Z' is

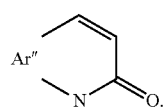

In another subembodiment, Ar″—Z' is

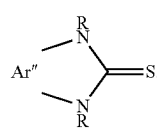

In a particular subembodiment of any of the above embodiments, R is H. In a particular subembodiment of any of the above embodiments, Ar″ is phenyl.

In one embodiment, each L' is independently halo, C$_1$-C$_6$ alkyl, or C$_1$-C$_6$ haloalkyl. In a particular subembodiment Ar' has at least one L'. In a particular subembodiment Ar' is phenyl and is substituted with one or more L' groups wherein one L' is in the para position. In a particular embodiment, at least one L' is halo, for example fluoro, chloro, bromo, or iodo. In a particular subembodiment, are least two L' are halo and may be the same or different. In another embodiment, at least one L' is C$_1$-C$_6$ alkyl, for example methyl, ethyl, propyl, isopropyl, butyl, isobutyl, pentyl, or hexyl. In another embodiment, at least one L' is C$_1$-C$_6$ haloalkyl, for example, trifluoromethyl.

In one embodiment, Ar' is unsubstituted. In another embodiment, k' is 1. In a subembodiment, when k' is 1 and Ar' is phenyl, L' is in the para position. In another embodiment, k' is 2. In a subembodiment, when k' is 2 and Ar' is phenyl, one L' is in the para position and one L' is in a meta position. In another embodiment, k' is 3. In another embodiment, k' is 4. In another embodiment, k' is 5.

In one embodiment, the compound is selected from the group consisting of:

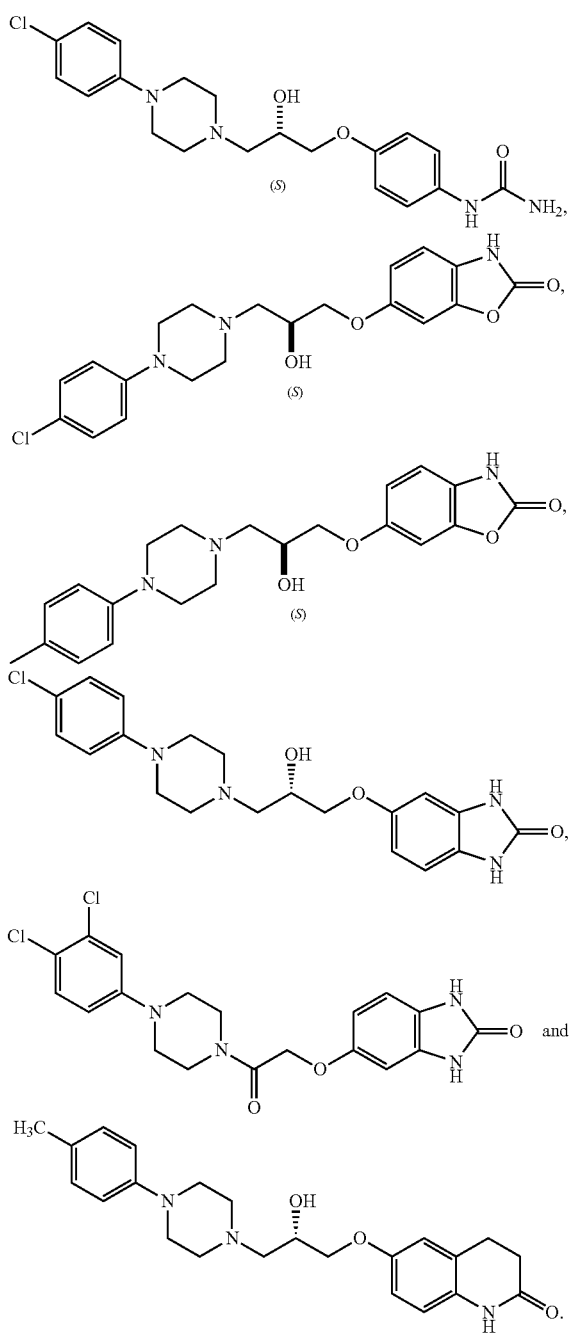

Enantiomers

In certain embodiments, the compounds are present as enantiomers. In one embodiment, the compound is provided as an enantiomer or mixture of enantiomers. In a particular embodiment, the compound is present as a racemic mixture. The enantiomer can be named by the configuration at the chiral center, such as R or S. In certain embodiments, the compound is present as a racemic mixture of R- and S-enantiomers. In certain embodiments, the compound is present as a mixture of two enantiomers. In one embodiment, the mixture has an enantiomeric excess in R. In one embodiment, the mixture has an enantiomeric excess in S. In certain other embodiments, the compound is in an enantiomeric excess of the R- or S-enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the single enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the R enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the S enantiomer.

In other embodiments, the compound is substantially in the form of a single enantiomer. In some embodiments, the compound is present substantially in the form of the R enantiomer. In some embodiments, the compound is present substantially in the form of the S enantiomer. The phrase "substantially in the form of a single enantiomer" is intended to mean at least 70% or more in the form of a single enantiomer, for example 70% or more, 75% or more, 80% or more, 85% or more, 90% or more, 95% or more, 98% or more, or 99% or more in either the R or S enantiomer.

The enantiomer can be named by the direction in which it rotates the plane of polarized light. If it rotates the light clockwise as seen by the viewer towards whom the light is traveling, the isomer can be labeled (+) and if it rotates the light counterclockwise, the isomer can be labeled (−). In certain embodiments, the compound is present as a racemic mixture of (+) and (−) isomers. In certain embodiments, the compound is present as a mixture of two isomers. In one embodiment, the mixture has an excess in (+). In one embodiment, the mixture has an excess in (−). In certain other embodiments, the compound is in an excess of the (+) or (−) isomer. The isomeric excess can be 51% or more, such as 51% or more, 55% or more, 60% or more, 65% or more, 70% or more, 75% or more, 80% or more, 85% or more, 90% or more, 95% or more, 98% or more, or 99% or more in the (+) isomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the (−) isomer.

In other embodiments, the compound is substantially in the form of a single optical isomer. In some embodiments, the compound is present substantially in the form of the (+) isomer. In other embodiments, the compound is present substantially in the form of the (−) isomer. The phrase "substantially in the form of a single optical isomer" is intended to mean at least 70% or more in the form of a single isomer, for example 70% or more, 75% or more, 80% or more, 85% or more, 90% or more, 95% or more, 98% or more, or 99% or more of either the (+) or (−) isomer.

Definitions

Whenever a term in the specification is identified as a range (i.e. $C_{1-4}$ alkyl), the range independently refers to each element of the range. As a non-limiting example, $C_{1-4}$ alkyl means, independently, $C_1$, $C_2$, $C_3$ or $C_4$ alkyl. Similarly, when one or more substituents are referred to as being "independently selected from" a group, this means that each substituent can be any element of that group, and any combination of these groups can be separated from the group. For example, if $R^1$ and $R^2$ can be independently selected from X, Y and Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "alkyl" is used herein, unless otherwise specified, refers to a substituted or unsubstituted, saturated, straight, branched, or cyclic (also identified as cycloalkyl), primary, secondary, or tertiary hydrocarbon, including but not limited to those of $C_1$ to $C_6$. Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thio, sulfonyl, ester, carboxylic acid, amide, phosphonyl, phosphinyl, thioether, oxime, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Third Edition, 2002. In certain embodiments, alkyl may be optionally substituted by one or more fluoro, chloro, bromo, iodo, hydroxy, heterocyclic, heteroaryl, carboxy, alkoxy, nitro, $NH_2$, $N(alkyl)_2$, NH(alkyl), alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—$NH_2$, —C(O)—N(H)O(H or alkyl), —S(O)$_2$—$NH_2$, —S(O)$_n$—N(H or alkyl)$_2$ and/or —S(O)$_2$—N(H or alkyl)$_2$.

The term "cycloalkyl" is used herein, unless otherwise specified, refers to a substituted or unsubstituted, saturated cyclic hydrocarbon, including but not limited to those of $C_3$ to $C_{12}$. Illustrative examples of cycloalkyl groups are cyclopropyl, cyclobutyl, cyclopentyl, cyclopentyl, and cyclohexyl. Unless otherwise specified, the cycloalkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thio, sulfonyl, ester, carboxylic acid, amide, phosphonyl, phosphinyl, thioether, oxime, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Third Edition, 2002. In certain embodiments, the cycloalkyl may be optionally substituted by one or more fluoro, chloro, bromo, iodo, hydroxy, heterocyclic, heteroaryl, carboxy, alkoxy, nitro, $NH_2$, $N(alkyl)_2$, NH(alkyl), alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—$NH_2$, —C(O)—N(H)O(H or alkyl), —S(O)$_2$—$NH_2$, —S(O)$_2$—N(H or alkyl)$_2$ and/or —S(O)$_2$—N(H or alkyl)$_2$.

The term "halo" or "halogen," refers to chloro, bromo, iodo, or fluoro.

The term "heterocyclic" refers to a non-aromatic or aromatic cyclic group wherein there is at least one heteroatom, such as oxygen, sulfur, nitrogen, or phosphorus in the ring. The term "heteroaryl" or "heteroaromatic," refers to an aromatic that includes at least one sulfur, oxygen, nitrogen or phosphorus in the aromatic ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, pteridinyl, aziridines, thiazole, isothiazole, oxadiazole, thiazine, pyridine, pyrazine, piperazine, piperidine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic or heterocyclic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. Nonlimiting examples include dihydropyridine and tetrahydrobenzimidazole. In some embodiment, the heteroaryl may be optionally substituted by one or more fluoro, chloro, bromo, iodo, hydroxy, heterocyclic, heteroaryl, carboxy, alkoxy, nitro, $NH_2$, $N(alkyl)_2$, NH(alkyl), alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—$NH_2$, —C(O)—N(H)O(H or alkyl), —S(O)$_2$—$NH_2$, —S(O)$_n$—N(H or alkyl)$_2$ and/or —S(O)$_2$—N(H or alkyl)$_2$. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-tolylsulfonyl.

The term "aryl," unless otherwise specified, refers to a carbon based aromatic ring, including phenyl, biphenyl, or naphthyl. The aryl group can be optionally substituted with one or more moieties selected from the group consisting of hydroxyl, acyl, amino, halo, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al. *Protective Groups in Organic Synthesis*, John Wiley and Sons, Third Edition, 2002. In certain embodiments, the aryl group is optionally substituted by one or more fluoro, chloro, bromo, iodo, hydroxy, heterocyclic, heteroaryl, carboxy, alkoxy, nitro, $NH_2$, $N(alkyl)_2$, NH(alkyl), alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—NH$_2$, —C(O)—N(H)O(H or alkyl), —S(O)$_2$—NH$_2$, —S(O)$_n$—N(H or alkyl)$_2$ and/or —S(O)$_2$—N(H or alkyl)$_2$.

The term "aralkyl," unless otherwise specified, refers to an aryl group as defined above linked to the molecule through an alkyl group as defined above.

The term "alkaryl," unless otherwise specified, refers to an alkyl group as defend above linked to the molecule through an aryl group as defined above. Other groups, such as acyloxyalkyl, alkoxyalkyl, alkoxycarbonyl, alkoxycarbonylalkyl, alkylaminoalkyl, alkylthioalkyl, amidoalkyl, aminoalkyl, carboxyalkyl, dialkylaminoalkyl, haloalkyl, heteroaralkyl, heterocyclicalkyl, hydroxyalkyl, sulfonamidoalkyl, sulfonylalkyl and thioalkyl are named in a similar manner.

The term "alkoxy," unless otherwise specified, refers to a moiety of the structure —O-alkyl, wherein alkyl is as defined above.

The term "acyl," refers to a group of the formula C(O)R' or "alkyl-oxy", wherein R' is an alkyl, aryl, alkaryl or aralkyl group, or substituted alkyl, aryl, aralkyl or alkaryl.

The term "alkenyl" The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to (C$_2$-C$_8$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "carbonyl" refers to a functional group composed of a carbon atom double-bonded to an oxygen atom: —C═O, Similarly, C(O) or C(═O) refers to a carbonyl group.

The term "amino" refers to —NH$_2$, —NH(alkyl) or —N(alkyl)$_2$.

The term "thio" indicates the presence of a sulfur group. The prefix thio- denotes that there is at least one extra sulfur atom added to the chemical. The prefix 'thio-' can also be placed before the name of a compound to mean that an oxygen atom in the compound has been replaced by a sulfur atom. Although typically the term "thiol" is used to indicate the presence of —SH, in instances in which the sulfur atom would be have improper valance a radical if the hydrogen is improperly designated, the terms 'thio' and 'thiol' are used interchangeably, unless otherwise indicated.

The term "amido" indicates a group (H or alkyl)-C(O)—NH—.

The term "carboxy" designates the terminal group —C(O)OH.

The term "sulfonyl" indicates an organic radical of the general formula (H or alkyl) -S(═O)$_2$—(H or alkyl'), where there are two double bonds between the sulfur and oxygen.

The term "pharmaceutically acceptable salt" refers to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is H or alkyl and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

It should be understood that the various possible stereoisomers of the groups mentioned above and herein are within the meaning of the individual terms and examples, unless otherwise specified. As an illustrative example, "1-methyl-butyl" exists in both (R) and the (S) form, thus, both (R)-1-methyl-butyl and (S)-1-methyl-butyl is covered by the term "1-methyl-butyl", unless otherwise specified.

Methods of Use

The compounds described herein can generally be used to treat neuropathic pain, stroke, traumatic brain injury, epilepsy, and other neurologic events or neurodegeneration resulting from NMDA receptor activation. Methods are provided for the treatment neuropathic pain, stroke, traumatic brain injury, epilepsy, and other neurologic events or neurodegeneration resulting from NMDA receptor activation comprising administering to a host in need thereof an effective amount of a compound of Formula I, II, III, IV or V, or a pharmaceutical composition thereof. In specific embodiments, the compound is of Formula I or V, or a salt or ester thereof.

In one embodiment, a method of treatment for neuropathic pain, stroke, traumatic brain injury, epilepsy, and other neurologic events or neurodegeneration resulting from NMDA receptor activation comprising administering a neuroprotective agent of Formula I is provided. Compositions and methods comprising the compounds described herein are useful for treating neuropathic pain, stroke, traumatic brain injury, epilepsy, and other neurologic events or neurodegeneration resulting from NMDA receptor activation. In one embodiment, methods are useful in the treatment of neuropathic pain. In another embodiment, the methods are useful in preventing neurodegeneration in patients with Parkinson's, Alzheimer's, Huntington's chorea, ALS, and other neurodegenerative conditions known to the art to be responsive to treatment using NMDA receptor blockers.

The compounds of the invention can generally be administered to a host at risk of, or suffering from, neuropathic pain, stroke, traumatic brain injury, epilepsy, and other neurologic events or neurodegeneration resulting from NMDA receptor activation. In one embodiment, the compounds are administered for the treatment or prophylaxis of an neuropathic pain, stroke, traumatic brain injury, epilepsy, and other neurologic events or neurodegeneration resulting from NMDA receptor activation.

In additional aspects of the present invention, methods are provided to treat patients by administering a compound selected according to the methods or processes described herein. Any disease, condition or disorder which induces a region with a reduced pH (below pH 7.6) can be treated according to the methods described herein.

Certain NMDA receptor antagonists described herein have enhanced activity in tissue having lower-than-normal pH. The tissue can be brain tissue. In certain embodiments, the reduced pH is due to pathological conditions such as hypoxia resulting from stroke, traumatic brain injury, global ischemia, such as global ischemia that may occur during cardiac surgery, hypoxia, including hypoxia that may occur following cessation of breathing, pre-eclampsia, spinal cord trauma, epilepsy, status epilepticus, neuropathic pain, inflammatory pain, chronic pain, vascular dementia and glioma tumors. Because tumors produce an acidic environment, drugs activated by low pH can be useful in slowing tumor growth because they have enhanced activity only at the site of the tumor. In some embodiments, the compounds are useful in the treatment of tumor growth. In certain embodiments, the compounds reduce tumor mass. In one embodiment, the compounds are useful in the treatment or prophylaxis of a neurologic event involving acidification of brain or spinal cord tissue. In another embodiment, the NMDA receptor antagonists of this invention are useful both in the treatment of stroke and head trauma, and for use as prophylactic agents for at risk patients. The acid generated by ischemic tissue during stroke is harnessed as a switch to activate the neuroprotective agents described herein. In this way side effects are minimized in unaffected tissue since drug at these sites are less active. These compounds may be used to reduce the amount of neuronal death associated with stroke and head trauma. They may be given chronically to individuals with epilepsy or who are at risk for stroke or head trauma, preoperatively in high risk heart/brain surgery, etc., in order to lengthen the window of opportunity for subsequent therapy.

In one embodiment, methods are provided to attenuate the progression of an ischemic or excitotoxic cascade associated with a drop in pH by administering a compound described herein. In addition, methods are provided to decrease infarct volume associated with a drop in pH by administering a compound selected according to the processes or methods described herein. Further, a method is provided to decrease cell death associated with a drop in pH by administering a compound selected according to the processes or methods described herein. Still further, methods are provided to decrease behavioral deficits associated with an ischemic event associated with a drop in pH by administering a compound selected according to the processes or methods described herein.

In additional aspects of the present invention, methods are provided to treat patients in need thereof by administering a compound or composition described herein. Any disease, condition or disorder which induces a low pH can be treated according to the methods described herein.

In one embodiment, methods are provided to treat patients with ischemic injury or hypoxia, or prevent or treat the neuronal toxicity associated with ischemic injury or hypoxia, by administering a compound or composition described herein. In one particular embodiment, the ischemic injury is stroke. In another particular embodiment, the ischemic injury is vasospasm after subarachnoid hemorrhage. In other embodiments, the ischemic injury is selected from, but not limited to, one of the following: traumatic brain injury, cognitive deficit after bypass surgery, cognitive deficit after carotid angioplasty; and/or neonatal ischemia following hypothermic circulatory arrest.

In another embodiment, methods are provided to treat patients with neuropathic pain or related disorders by administering a compound or composition described herein. In certain embodiments, the neuropathic pain or related disorder can be selected from the group including, but not limited to: peripheral diabetic neuropathy, postherpetic neuralgia, complex regional pain syndromes, peripheral neuropathies, chemotherapy-induced neuropathic pain, cancer neuropathic pain, neuropathic low back pain, HIV neuropathic pain, trigeminal neuralgia, and/or central post-stroke pain.

In another embodiment, methods are provided to treat patients with brain tumors by administering a compound selected according to the methods or processes described herein. In a further embodiment, methods are provided to treat patients with neurodegenerative diseases by administering a compound selected according to the methods or processes described herein. In one embodiment, the neurodegenerative disease can be Parkinson's disease. In another embodiment, the neurodegenerative disease can be Alzheimer's, Huntington's and/or Amyotrophic Lateral Sclerosis.

Further, compounds selected according to the methods or processes described herein can be used prophylactically to prevent or protect against such diseases or neurological conditions, such as those described herein. In one embodiment, patients with a predisposition for an ischemic event, such as a genetic predisposition, can be treated prophylactically with the methods and compounds described herein. In another embodiment, patients that exhibit vasospasms can be treated prophylactically with the methods and compounds described herein. In a further embodiment, patients that have undergone cardiac bypass surgery can be treated prophylactically with the methods and compounds described herein.

In one embodiment, methods are provided to treat patients with ischemic injury or hypoxia, or prevent or treat the neuronal toxicity associated with ischemic injury or hypoxia, by administering a compound selected according to the methods or processes described herein. In one particular embodiment, the ischemic injury can be stroke. In other embodiments, the ischemic injury can be selected from, but not limited to, one of the following: traumatic brain injury, cognitive deficit after bypass surgery, cognitive deficit after carotid angioplasty; and/or neonatal ischemia following hypothermic circulatory arrest.

In another particular embodiment, the ischemic injury can be vasospasm after subarachnoid hemorrhage. A subarachnoid hemorrhage refers to an abnormal condition in which blood collects beneath the arachnoid mater, a membrane that covers the brain. This area, called the subarachnoid space, normally contains cerebrospinal fluid. The accumulation of blood in the subarachnoid space and the vasospasm of the vessels which results from it can lead to stroke, seizures, and other complications. The methods and compounds described herein can be used to treat patients experiencing a subarachnoid hemorrhage. In one embodiment, the methods and compounds described herein can be used to limit the toxic effects of the subarachnoid hemorrhage, including, for example, stroke and/or ischemia that can result from the subarachnoid hemorrhage. In a particular embodiment, the methods and compounds described herein can be used to treat patients with traumatic subarachnoid hemorrhage. On one embodiment, the traumatic subarachnoid hemorrhage can be due to a head injury. In another embodiment, the patients can have a spontaneous subarachnoid hemorrhage.

In another embodiment, methods are provided to treat patients with neuropathic pain or related disorders by administering a compound selected according to the methods or processes described herein. In certain embodiments, the neuropathic pain or related disorder can be selected from the group including, but not limited to: peripheral diabetic neuropathy, postherpetic neuralgia, complex regional pain syndromes, peripheral neuropathies, chemotherapy-induced neuropathic pain, cancer neuropathic pain, neuropathic low back pain, HIV neuropathic pain, trigeminal neuralgia, and/or central post-stroke pain.

Neuropathic pain can be associated with signals generated ectopically and often in the absence of ongoing noxious events by pathologic processes in the peripheral or central nervous system. This dysfunction can be associated with common symptoms such as allodynia, hyperalgesia, intermittent abnormal sensations, and spontaneous, burning, shooting, stabbing, paroxysmal or electrical-sensations, paresthesias, hyperpathia and/or dysesthesias, which can also be treated by the compounds and methods described herein.

Further, the compounds and methods described herein can be used to treat neuropathic pain resulting from peripheral or central nervous system pathologic events, including, but not limited to trauma, ischemia; infections or from ongoing metabolic or toxic diseases, infections or endocrinologic disorders, including, but not limited to, diabetes mellitus, diabetic neurophathy, amyloidosis, amyloid polyneuropathy (primary and familial), neuropathies with monoclonal proteins, vasculitic neuropathy, HIV infection, herpes zoster—shingles and/or postherpetic neuralgia; neuropathy associated with Guillain-Barre syndrome; neuropathy associated with Fabry's disease; entrapment due to anatomic abnormalities; trigeminal and other CNS neuralgias; malignancies; inflammatory conditions or autoimmune disorders, including, but not limited to, demyelinating inflammatory disorders, rheumatoid arthritis, systemic lupus erythematosus, Sjogren's syndrome; and cryptogenic causes, including, but not limited to idiopathic distal small-fiber neuropathy. Other causes of neuropathic pain that can be treated according to the methods and compositions described herein include, but are not limited to, exposure to toxins or drugs (such as arsenic, thallium, alcohol, vincristine, cisplatinum and dideoxynucleosides), dietary or absorption abnormalities, immuno-globulinemias, hereditary abnormalities and amputations (including mastectomy). Neuropathic pain can also result from compression of nerve fibers, such as radiculopathies and carpal tunnel syndrome.

In another embodiment, methods are provided to treat patients with brain tumors by administering a compound selected according to the methods or processes described herein. In a further embodiment, methods are provided to treat patients with neurodegenerative diseases by administering a compound selected according to the methods or processes described herein. In one embodiment, the neurodegenerative disease can be Parkinson's disease. In another embodiment, the neurodegenerative disease can be Alzheimer's, Huntington's and/or Amyotrophic Lateral Sclerosis.

In another embodiment, the methods provided herein can be used prophylactically to prevent or protect against such diseases or neurological conditions, such as those described herein. In one embodiment, patients with a predisposition for an ischemic event, such as a genetic predisposition, can be treated prophylactically with the methods and compounds described herein. In another embodiment, patients that exhibit vasospasms can be treated prophylactically with the methods and compounds described herein. In further embodiment, patients that have undergone cardiac bypass surgery can be treated prophylactically with the methods and compounds described herein.

In addition, methods are provided to treat the following diseases or neurological conditions, including, but not limited to: chronic nerve injury, chronic pain syndromes, such as, but not limited to diabetic neuropathy, ischemia, ischemia following transient or permanent vessel occlusion, seizures, spreading depression, restless leg syndrome, hypocapnia, hypercapnia, diabetic ketoacidosis, fetal asphyxia, spinal cord injury, traumatic brain injury, status epilepticus, epilepsy, hypoxia, perinatal hypoxia, concussion, migraine, hypocapnia, hyperventilation, lactic acidosis, fetal asphyxia during parturition, brain gliomas, and/or retinopathies by administering a compound selected according to the methods or processes described herein.

Further provided are methods to attenuate the progression of an ischemic, hypoxic or excitotoxic cascade associated with a drop in pH by administering an effective amount of a compound that exhibits the properties described herein. In addition, methods are provided to decrease infarct volume associated with a drop in pH by administering a compound that exhibits the properties described herein. Further, a method is provided to decrease cell death associated with a drop in pH by administering a compound that exhibits the properties described herein. Still further, methods are provided to decrease behavioral deficits associated with an ischemic event associated with a drop in pH by administering a compound that exhibits the properties described herein.

In one embodiment, the use of the compounds of the invention reduces symptoms of neuropathic pain, stroke, traumatic brain injury, epilepsy, and other neurologic events or neurodegeneration resulting from NMDA receptor activation.

Side Effects

In an additional aspect of the methods and processes described herein, the compound does not exhibit substantial toxic an/or psychotic side effects. Toxic side effects include, but are not limited to, agitation, hallucination, confusion, stupor, paranoia, delirium, psychotomimetic-like symptoms, rotarod impairment, amphetamine-like stereotyped behaviors, stereotypy, psychosis memory impairment, motor impairment, anxiolytic-like effects, increased blood pressure, decreased blood pressure, increased pulse, decreased pulse, hematological abnormalities, electrocardiogram (ECG) abnormalities, cardiac toxicity, heart palpitations, motor stimulation, psychomotor performance, mood changes, short-term memory deficits, long-term memory deficits, arousal, sedation, extrapyramidal side-effects, ventricular tachycardia. Lengthening of cardiac repolarisation, ataxia, cognitive deficits and/or schizophrenia-like symptoms.

In one embodiment, the compounds are selective NMDA receptor blockers. General blocking of NMDA receptors throughout the brain causes adverse effects such as ataxia, memory deficits, hallucinations and other neurological problems. The compounds provided herein can selectively block NR2B-containing NMDA receptors, have varying activity against receptors containing NR2A or NR2D, and may also be selective for other members of the NMDA receptor family (NR2C, NR3A and NR3B). IIn one embodiment, the compounds are NMDA receptors antagonists selective for NR2B, NR2A, NR2C, NR2D, NR3A, and/or NR3B and do not interact with other receptors or ion channels at therapeutic concentrations. In one embodiment, the compound is a selective NR1/NR2A NMDA receptor and/or a NR1/NR2B NMDA receptor antagonist. In one particular embodiment, the compounds can bind to the NR2B subunit of the NMDA receptor. In another particular embodiment, the compounds are selective for the NR2B subunit of the NMDA receptor. In one embodiment, the compound is not an NMDA receptor glutamate site antagonist. In another embodiment, the compound is not an NMDA receptor glycine site antagonist.

The compounds selected or identified according to the processes and methods described herein generally avoid substantial side effects associated with other classes of NMDA receptor antagonists. In one embodiments, such compounds do not substantially exhibit the side effects associated with NMDA antagonists of the glutamate site, such as selfotel, D-CPPene (SDZ EAA 494) and AR-R15896AR (ARL 15896AR), including, agitation, hallucination, confusion and stupor (Davis et al. (2000) Stroke 31(2):347-354; Diener et al. (2002), J Neurol 249(5):561-568); paranoia and delirium (Grotta et al. (1995), J Intern Med 237:89-94); psychotomimetic-like symptoms (Loscher et al. (1998), Neurosci Lett 240(1):33-36); poor therapeutic ratio (Dawson et al. (2001), Brain Res 892(2):344-350); amphetamine-like stereotyped behaviors (Potschka et al. (1999), Eur J Pharmacol 374(2): 175-187). In another embodiment, such compounds do not exhibit the side effects associated with NMDA antagonists of the glycine site, such as HA-966, L-701,324, d-cycloserine, CGP-40116, and ACEA 1021, including significant memory impairment and motor impairment (Wlaz, P (1998), Brain Res Bull 46(6):535-540). In a still further embodiment, such compounds do not exhibit the side effects of NMDA high affinity receptor channel blockers, such as MK-801 and ketamine, including, psychosis-like effects (Hoffman, D C (1992), J Neural Transm Gen Sect 89:1-10); cognitive deficits (decrements in free recall, recognition memory, and attention; Malhotra et al (1996), Neuropsychopharmacology 14:301-307); schizophrenia-like symptoms (Krystal et al (1994), Arch Gen Psychiatry 51:199-214; Lahti et al. (2001), Neuropsychopharmacology 25:455-467), and hyperactivity and increased stereotpy (Ford et al (1989) Physiology and behavior 46: 755-758.

In a further additional or alternative embodiment, the compound has a therapeutic index equal to or greater than at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 40:1, at least 50:1, at least 75:1, at least 100:1 or at least 1000:1. The therapeutic index can be defined as the ratio of the dose required to produce toxic or lethal effects to dose required to produce therapeutic responses. It can be the ratio between the median toxic dose (the dosage at which 50% of the group exhibits the adverse effect of the drug) and the median effective dose (the dosage at which 50% of the population respond to the drug in a specific manner). The higher the therapeutic index, the more safe the drug is considered to be. It simply indicates that it would take a higher dose to invoke a toxic response that it does to cause a beneficial effect.

The side effect profile of compounds can be determined by any method known to those skilled in the art. In one embodiment, motor impairment can be measured by, for example, measuring locomotor activity and/or rotorod performance. Rotorod experiments involve measuring the duration that an animal can remain on an accelerating rod. In another embodiment, memory impairment can be assessed, for example, by using a passive avoidance paradigm; Sternberg memory scanning and paired words for short-term memory, or delayed free recall of pictures for long-term memory. In a further embodiment, anxiolytic-like effects can be measured, for example, in the elevated plus maze task. In other embodiments, cardiac function can be monitored, blood pressure and/or body temperature measured and/or electrocardiograms conducted to test for side effects. In other embodiments, psychomotor functions and arousal can be measured, for example by analyzing critical flicker fusion threshold, choice reaction time, and/or body sway. In other embodiments, mood can be assessed using, for example, self-ratings. In further embodiments, schizophrenic symptoms can be evaluated, for example, using the PANSS, BPRS, and CGI, side-effects were assessed by the HAS and the S/A scale.

In one embodiment, the compound does not exhibit substantial toxic side effects, such as, for example, motor impairment or cognitive impairment. In a particular embodiment, the compound has a therapeutic index equal to or greater than at least 2. In another embodiment, the compound is at least 10 times more selective for binding to an NMDA receptor than any other glutamate receptor. In certain embodiments, the compound activates hERG receptors at an $IC_{50}$ at least 10 times the $IC_{50}$ of inhibition of an NMDA receptor at either pH 6.9 or 7.6 or both. In certain embodiments, the compound activates adrenergic receptors, in particular a adrenergic such as α1 adrenergic receptors at an $IC_{50}$ at least 10 times the $IC_{50}$ of inhibition of an NMDA receptor at either pH 6.9 or 7.6 or both. In specific embodiments the ratio of $IC_{50}$'s between either hERG activation or adrenergic receptor activation and NMDA receptor antagonism is greater than 50, or greater than 100, or greater than 500.

Pharmaceutical Compositions

Mammals, and specifically humans, suffering from neuropathic pain, stroke, traumatic brain injury, epilepsy, and other neurologic events or neurodegeneration resulting from NMDA receptor activation, or any of the above-described conditions, and in particular suffering from neuropathic pain, can be treated by either targeted or systemic administration, via oral, inhalation, topical, trans- or sub-mucosal, subcutaneous, parenteral, intramuscular, intravenous or transdermal administration of a composition comprising an effective amount of the compounds described herein or a pharmaceutically acceptable salt, ester or prodrug thereof, optionally in a pharmaceutically acceptable carrier.

The compounds or composition is typically administered by oral administration. Alternatively, compounds can be administered by inhalation. In another embodiment, the compound is administered transdermally (for example via a slow release patch), or topically. In yet another embodiment, the compound is administered subcutaneously, intravenously, intraperitoneally, intramuscularly, parenterally, or submucosally. In any of these embodiments, the compound is administered in an effective dosage range to treat the target condition.

In one embodiment, compounds of the present invention are administered orally. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

When the compound is administered orally in the form of a dosage unit such as a tablets, pills, capsules, troches and the like, these can contain any of the following ingredients, or compounds of a similar nature: a binder (such as microcrystalline cellulose, gum tragacanth or gelatin); an excipient (such as starch or lactose), a disintegrating agent (such as alginic acid, Primogel, or corn starch); a lubricant (such as magnesium stearate or Sterotes); a glidant (such as colloidal silicon dioxide); a sweetening agent (such as sucrose or saccharin); and/or a flavoring agent (such as peppermint, methyl salicylate, or orange flavoring). When the dosage unit form is a capsule, it can contain, in addition to material of the above type, a liquid carrier (such as a fatty oil). In addition, dosage unit forms can contain various other materials which modify the physical form of the dosage unit, for example, coatings of sugar, shellac, or other enteric agents.

The compound or its salts can also be administered orally as a component of an elixir, suspension, syrup, wafer, chewing gum or the like. A syrup may contain, in addition to the active compounds, a sweetening agent (such as sucrose, saccharine, etc.) and preservatives, dyes and colorings and flavors.

The compounds of the invention may be also administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: suspending agents, e.g., microcrystalline cellulose, sodium carboxymethylcellulose, hydroxypropyl-methyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. Polysorbate 80; and antimicrobial preservatives, e.g., benzalkonium chloride, phenylethyl alcohol and potassium sorbate.

In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or gas pressure such as the dry-powder inhaler disclosed in the Schering Corporation International Patent Application No. PCT/US92/05225, published 7 Jan. 1993 as well as the Turbuhaler™ (available from Astra Pharmaceutical Products, Inc.) or the Rotahaler™ (available from Allen & Hanburys) which may be used to deliver the aerosolized particles as a finely milled powder in large aggregates either alone or in combination with some pharmaceutically acceptable carrier e.g. lactose; and nebulizers.

Solutions or suspensions used for parenteral, intradermal, subcutaneous, or topical application can include at least some of the following components: a sterile diluent (such as water for injection, saline solution, fixed oils, polyethylene glycols, glycerine, propylene glycol or other synthetic solvents); antibacterial agents (such as benzyl alcohol or methyl parabens); antioxidants (such as ascorbic acid or sodium bisulfate); chelating agents (such as ethylenediaminetetraacetic acid); buffers (such as acetates, citrates or phosphates); and/or agents for the adjustment of tonicity (such as sodium chloride or dextrose). The pH of the solution or suspension can be adjusted with acids or bases, such as hydrochloric acid or sodium hydroxide.

A parenteral preparation can be enclosed in ampoules, disposable syringes or multiple dose vials made of glass or plastic.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

If administered intravenously, carriers can be physiological saline, bacteriostatic water, Cremophor EL™ (BASF, Parsippany, N.J.) or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid (s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Dosing

The compound is administered for a sufficient time period to alleviate the undesired symptoms and the clinical signs associated with the condition being treated. In one embodiment, the compounds are administered less than three times daily. In one embodiment, the compounds are administered in one or two doses daily. In one embodiment, the compounds are administered once daily. In some embodiments, the compounds are administered in a single oral dosage once a day.

The active compound is included in the pharmaceutically acceptable carrier or diluent in an amount sufficient to deliver to a patient a therapeutic amount of compound in vivo in the absence of serious toxic effects. An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

Typical systemic dosages for the herein described conditions are those ranging from 0.01 mg/kg to 1500 mg/kg of body weight per day as a single daily dose or divided daily doses. Preferred dosages for the described conditions range from 0.5-1500 mg per day. A more particularly preferred dosage for the desired conditions ranges from 5-750 mg per day. Typical dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as a single daily dose or divided daily doses. In one embodiment, the daily dose is between 10 and 500 mg/day. In another embodiment, the dose is between about 10 and 400 mg/day, or between about 10 and 300 mg/day, or between about 20 and 300 mg/day, or between about 30 and 300 mg/day, or between about 40 and 300 mg/day, or between about 50 and 300 mg/day, or between about 60 and 300 mg/day, or between about 70 and 300 mg/day, or between about 80 and 300 mg/day, or between about 90 and 300 mg/day, or between about 100 and 300 mg/day, or about 200 mg/day. In one embodiment, the compounds are given in doses of between about 1 to about 5, about 5 to about 10, about 10 to about 25 or about 25 to about 50 mg/kg. Typical dosages for topical application are those ranging from 0.001 to 100% by weight of the active compound.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

Combination Treatment

The compound can also be mixed with other active materials which do not impair the desired action, or with materials that supplement the desired action. The active compounds can be administered in conjunction, i.e. combination or alternation, with other medications used in the treatment or prevention neuropathic pain, stroke, traumatic brain injury, epilepsy, and other neurologic events or neurodegeneration resulting from NMDA receptor activation. In another embodiment, the compounds can be administered in conjunction (combination or alternation) with other medications used in treatment or prophylaxis of inflammatory conditions. In certain embodiments, the combination can be synergistic although in other embodiments the combination is not synergistic.

Emergency treatment for an ischemic stroke, particularly when the stroke is diagnosed within 3 hours of the start of symptoms, include thrombolytic, or clot-dissolving, medications such as tissue plasminogen activator (t-PA). Other treatments of an ischemic stroke involve administering to the patient an antiplatelet medication (aspirin, clopidogrel, dipyridamole), or anticoagulant medication (warfarin), dependent on the cause. Dextrorphan, a pharmacologically active metabolite of the cough suppressant dextromethorphan, is an NMDA antagonists studied in human stroke patients. Selfotel, a competitive NMDA antagonist, has also been tested in human patients, however it trends toward higher mortality within treated patients than within placebo-treated cohorts, and therefore, trials were stopped prematurely. A trial of another NMDA receptor antagonist, aptiganel HCl (Cerestat), was terminated. A large, 1367-patient, efficacy trial with the agent GV150526 was completed in 2000. (http://www.emedicine.com/neuro/topic488.htm, Lutsep & Clark "Neuroprotective Agents in Stroke", Apr. 30, 2004).

EXAMPLES

The following examples are provided to illustrate the present invention and are not intended to limit the scope thereof. Those skilled in the art will readily understand that known variations of the conditions and processes of the following preparative procedures can be used to manufacture the desired compounds. The materials required for the embodiments and the examples are known in the literature, readily commercially available, or can be made by known methods from the known starting materials by those skilled in the art.

Examples 1 and 2

N-(4-{3-[4-(3,4-Difluoro-phenyl)-piperazin-1-yl]-2-(S)-hydroxy-propoxy}-phenyl)-methanesulfonamide (Compound 1) and N-(4-{3-[2-(3,4-Dichloro-phenylamino)-ethylamino-]-2-(S)-hydroxy-propoxy}-phenyl)-methanesulfonamide (Compound 2)

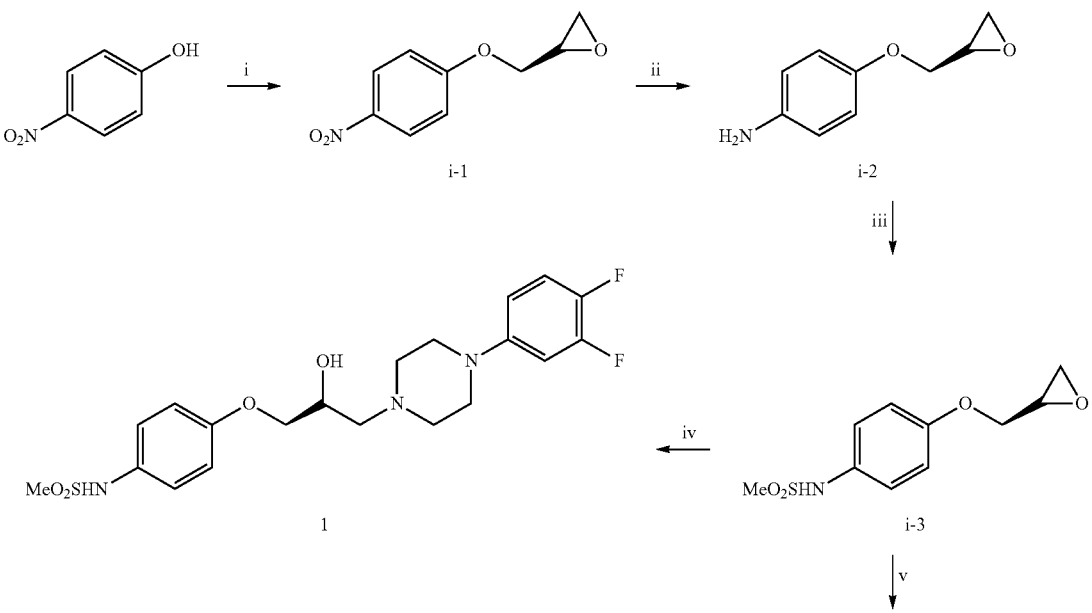

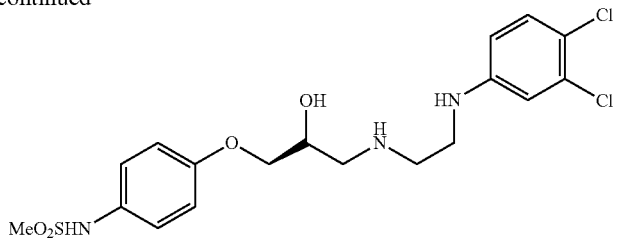

2

Step (i). 3-(4-Nitro-phenoxy)-2-(S)-propyleneoxide (i-1). 4-Nitrophenol (6.6 mmol) was dissolved in 5 ml anhydrous DMF. Cesium fluoride (19.9 mmol) was added to the reaction. The reaction mixture was stirred for 1 hour at room temperature and (S)-Glycidyl nosylate (6.6 mmol) was added to the reaction mixture. The reaction stirred for 24 hours at room temperature. Water (150 mL) was added and the solution was extracted with ethyl acetate. The organic phase was dried over MgSO$_4$ and evaporated. The residue was purified with column chromatograph using ethylacetate:hexane (50:50) solvent system to give the desired product i-1 This step can be substituted with (R)-Glycidyl nosylate to get the R isomer.

Step (ii). 3-(4-Amino-phenoxy)-2-(S)-propyleneoxide (i-2). (S)-Glycidyl-4-nitrophenyl ether (2.6 mmol, i-1) and 5% Pd/C(en)[{Sajiki et all, Chemistry—a europian journal 6(12):2200-2204 (2000).] (10% of the weight of starting material) in 5 ml anhydrous THF was hydrogenated at ambient pressure and temperature for 3 hours. The reaction mixture was filtered by using membrane filter (13, 0.22 μm) and the filtrate was concentrated in vacuum. The compound was afforded as a crude mixture of amino reduction compound i-2.

Step (iii). 3-(4-methansulfonylamido-phenoxy)-2-(S)-propyleneoxide (i-3). (S)-Glycidyl-4-aminophenyl ether (2 4 mmol, i-2) dissolved in 20 ml anhydrous DCM and N,N-diisopropyl-N-ethylamine (2.6 mmol) was added at 0° C. After stirring 15 minutes methanesulfonyl chloride (2.6 mmol) was added drop wise to the reaction mixture at 0° C. After stirring over night, the reaction extracted with water and washed with brine. Organic phase dried over magnesium sulfate and evaporated. The residue was purified with flash chromatography using Ethyl acetate:DCM (30:70) solvent system to give the desired product i-3.

Step (iv). N-(4-{3-[4-(3,4-Difluoro-phenyl)-piperazin-1-yl]-2-(S)-hydroxy-propoxy}-phenyl)-methanesulfonamide (Compound 1). Compound i-3 (2.00 mmol) and N-(3,4-Difluorophenyl)piperazine (2.00 mmol) were heated under reflux conditions in 20 ml ethanol for 8 hours. Then solvent was evaporated and residue was purified with flash chromatography using dichloromethane:methanol (90:10) solvent system to get compound 1. Compound 1 was dissolved in ethanol and bubbled HCl gas to get the HCl salt of the compound 1.

Step (v). N-(4-{3-[2-(3,4-Dichloro-phenylamino)-ethylamino]-2-(S)-hydroxy-propoxy}-phenyl)-methanesulfonamide (Compound 2). The epoxide (i-3, 1.58 mmol) was dissolved in EtOH (20 ml), and then the 3,4-dichloro-ethylene diamine (1.58 mmol) (preparation: Isabel Perillo, M. Cristina Caterina, Julieta López, Alejandra Salerno. Synthesis 2004, 6, 851-856) was added and the solution refluxed for 16 hours. The solvent was evaporated and the product purified with column chromatography using 10% MeOH/DCM+1% NH$_4$OH to give compound 2.

The following compounds were synthesized according to the procedures provided in examples 1 and 2.

| COMPOUND | NAME AND PHYSICAL DATA |
|---|---|
| | N-(4-{3-[4-(3,4-Dichloro-phenyl)-piperazin-1-yl]-2-(S)-hydroxy-propoxy}-phenyl)-methanesulfonamide<br>MS: 475.14486 |
| | N-(4-{3-[4-(4-Chloro-phenyl)-piperazin-1-yl]-2-(S)-hydroxy-propoxy}-phenyl)-methanesulfonamide<br>MS: 440.14017 |

| COMPOUND | NAME AND PHYSICAL DATA |
|---|---|
| 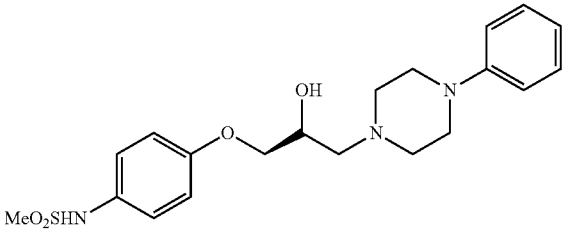 | N-(4-{3-[4-phenyl-piperazin-1-yl]-2-(S)-hydroxy-propoxy}-phenyl)-methanesulfonamide<br>MS: 406.20183 |
| 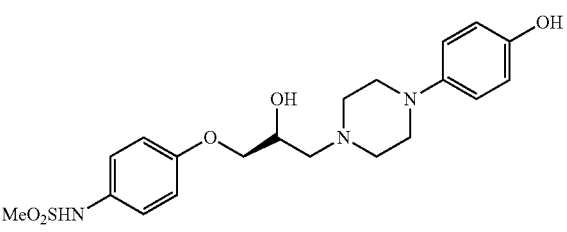 | N-(4-{3-[4-(4-Hydroxy-phenyl)-piperazin-1-yl]-2-(S)-hydroxy-propoxy}-phenyl)-methanesulfonamide |
| 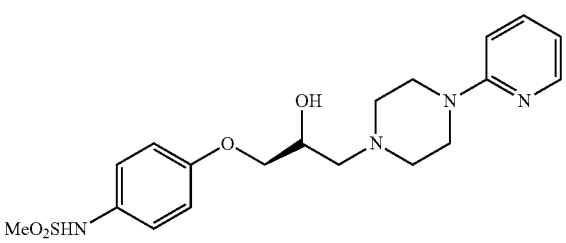 | N-(4-{3-[4-(2-Pyridyl)-piperazin-1-yl]-2-(S)-hydroxy-propoxy}-phenyl)-methanesulfonamide |
| 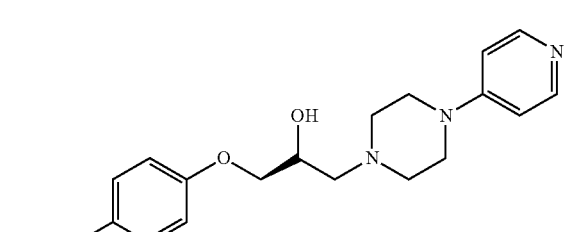 | N-(4-{3-[4-(4-Pyridyl)-piperazin-1-yl]-2-(S)-hydroxy-propoxy}-phenyl)-methanesulfonamide |
| 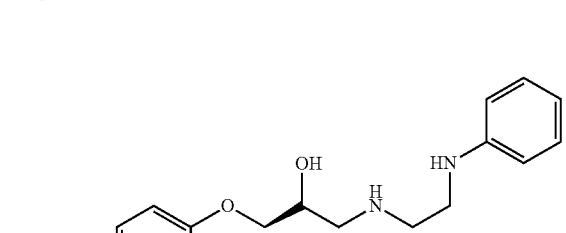 | N-{4-[2-(S)-Hydroxy-3-(2-phenylamino-ethylamino)-propoxy]-phenyl}-methanesulfonamide |
| 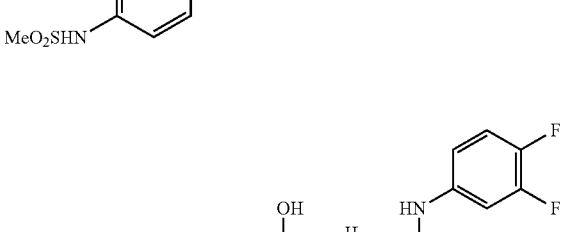 | N-{4-[2-(S)-Hydroxy-3-(2-(3,4-difluoro-phenyl)amino-ethylamino)-propoxy]-phenyl}-methanesulfonamide<br>MS: 416.15842 |

| COMPOUND | NAME AND PHYSICAL DATA |
|---|---|
| | N-(4-{3-[3-(3,4-Dichloro-phenyl)-allylamino]-2-(S)-hydroxy-propoxy}-phenyl)-methanesulfonamide<br>MS: 446.09479 |
| | N-[4-(3-{Butyl-[3-(3,4-dichloro-phenyl)-allyl]-amino}-2-(S)-hydroxy-propoxy)-phenyl]-methanesulfonamide<br>MS: 501.13871 |
| | N-(4-{3-[3-(3,4-Difluoro-phenyl)-allylamino]-2-(S)-hydroxy-propoxy}-phenyl)-methanesulfonamide<br>MS: 413.58425 |

Example 3

6-{3-[4-(4-Chloro-phenyl)-piperazin-1-yl]-2-(S)-hydroxy-propoxy}-3H-benzooxazol-2-one (Compound 3)

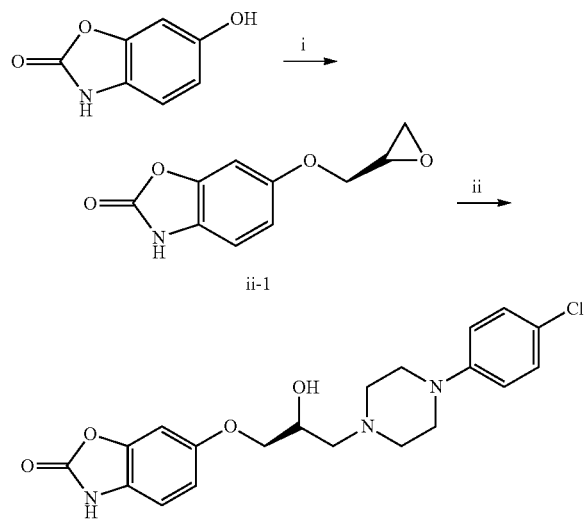

Step (i). 6-(2-(S)-Oxiranylmethoxy)-3H-benzooxazol-2-one (ii-1). 5-hydroxy-benzoxazole (310 mg) and cesium carbonate (780 mg) were combined in 6 mL of N,N-dimethylformamide. The reaction was stirred for room temperature for 1 hour. (S)-glycidal nosylate (520 mg) was added, and the reaction stirred at room temperature overnight. The reaction was quenched with $NH_4Cl$(aq) solution and extracted with ethyl acetate. The organic layer was washed with $NH_4Cl$(aq) and NaCl(aq) solutions, separated, and dried over $Na_2SO_4$(s). Filtration and solvent removal was followed by absorption onto silica gel. Elution with an ethyl acetate/methanol mixture (4:1) followed by solvent removal gave 445 mg of a yellow, oily solid.

Step (ii). 6-{3-[4-(4-Chloro-phenyl)-piperazin-1-yl]-2-(S)-hydroxy-propoxy}-3H-benzooxazol-2-one (Compound 3). To a solution of 300 mg of epoxide (ii-1) in 10 mL of absolute ethanol was added 300 mg of 4-(4-chlorophenyl)-piperazine. The solution was heated to 70° C. for 8 hours. The reaction was cooled and the solvent removed under vacuum. The residue was purified by column chromatography on silica gel using ethyl acetate as solvent. Obtained 240 mg of a light brown solid (45% yield). 1HNMR (d6-DMSO, 400 MHz): δ 2.37 (dq, 2H, J=6 Hz, J=13 Hz), 2.51 (m, 4H), 3.02 (m, 4H), 3.68 (q, 1H, J=8 Hz 3.84 (dd, 1H, J=4 Hz, J=14 Hz), 4.02 (bs, 1H), 5.07 (d, 1H, J=5 Hz), 6.61 (dd, 1H, J=2 Hz, J=9 Hz 6.73 (d, 1H, J=2 Hz 6.91 (d, 2H, J=9 Hz 7.05 (d, 1H, J=8 Hz 7.21 (d, 2H, J=9 Hz 9.43 (s, 1H); MS (m/z): 404 (M+H), 406 (M+2+H); HRMS Calcd. for C20H23ClN3O4: 404.13771. Found: 404.13673.

The following compounds were synthesized according to the procedure in Example 3.

| COMPOUND | NAME AND PHYSICAL DATA |
|---|---|
| 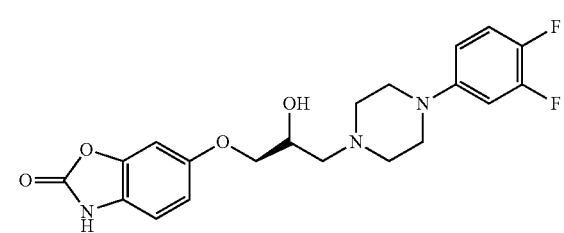 | 6-{3-[4-(3,4-Dichloro-phenyl)-piperazin-1-yl]-2-(S)-hydroxy-propoxy}-3H-benzooxazol-2-one<br>MS: 406.15664 |
| 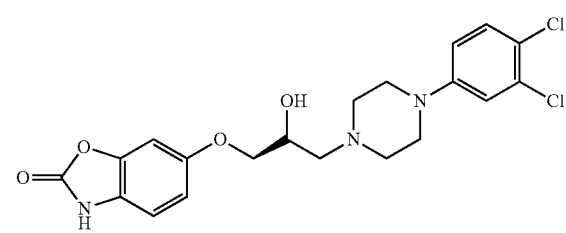 | 6-{3-[4-(3,4-Dichloro-phenyl)-piperazin-1-yl]-2-(S)-hydroxy-propoxy}-3H-benzooxazol-2-one |
| 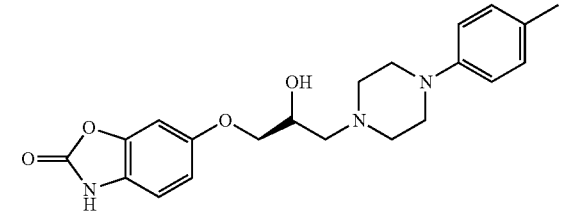 | 6-{3-[4-(4-Methyl-phenyl)-piperazin-1-yl]-2-(S)-hydroxy-propoxy}-3H-benzooxazol-2-one<br>MS: 384.19077 |
| 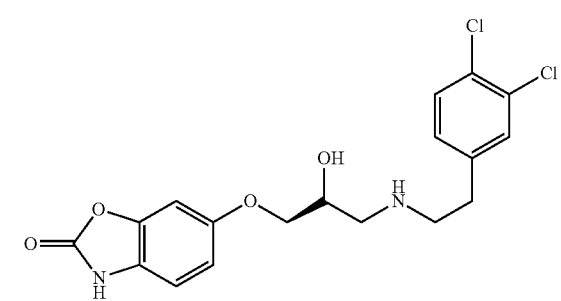 | 6-{3-[2-(3,4-Dichloro-phenyl)-ethylamino]-2-(S)-hydroxy-propoxy}-3H-benzooxazol-2-one |
| 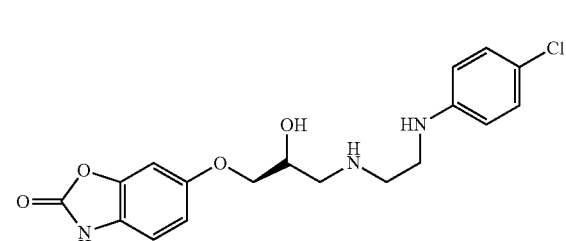 | 6-{3-[2-(4-Chloro-phenylamino)-ethylamino]-2-(S)-hydroxy-propoxy}-3H-benzooxazol-2-one<br>MS: 378.12089 |

Example 4

4-{3-[4-(3,4-Dichloro-phenyl)-piperazin-1-yl]-2-(S)-hydroxy-propoxy}-phenol (Compound 4)

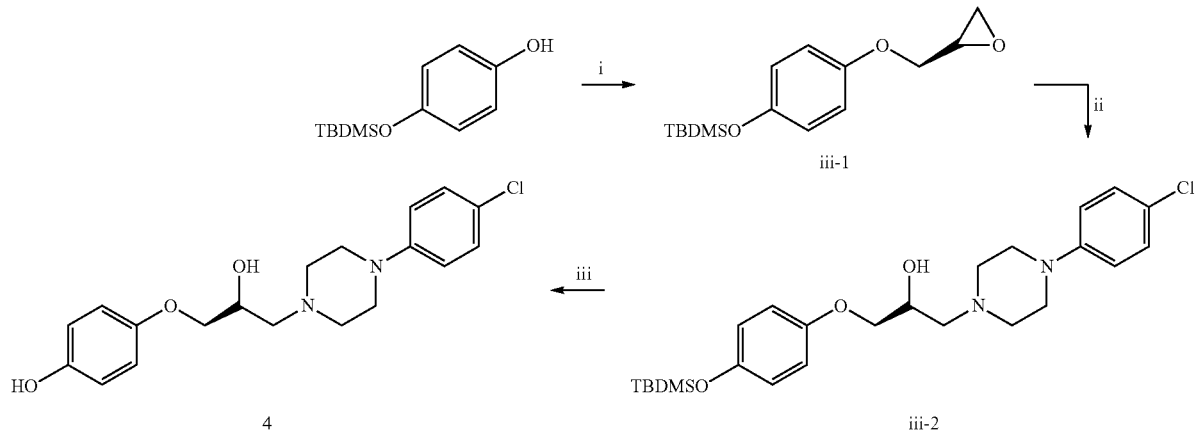

Step (i). 3-(4-tert-Butyldimethylsilyloxy-phenoxy)-2-(S)-propyleneoxide (iii-1). 4-(tert-Butyldimethylsiloxy)phenol (1.45 g, 6.25 mmol) in 5 ml anhydrous THF was added dropwise to the suspension of NaH (0.158 g, 6.25 mmol) in 5 ml THF. After stirring at room temperature for 2 hours glycidyl nosylate (1.30 g, 5 mmol) and then 15-crown-5 (25 mol %) were added to the reaction mixture. After stirring 24 hours reaction was poured to ice-water and extracted with ethyl acetate. Organic phase was washed with water and brine, then dried over sodium sulfate and evaporated. Product was purified by column chromatography using EtOAc:Hexane (1:9) (yield: 1.06 g 76%). $^1$H-NMR (400 MHz, CDCl$_3$) δ 0.17 (6H, s), 0.98 (9H, s), 2.75 (1H, dd, J=2.4, 4.4 Hz), 2.89 (1H, q, J=4.4 Hz), 3.33-3.36 (1H, m), 3.90 (1H, dd, J=5.6, 10.8 Hz), 4.16 (1H, dd, J=3.6, 11.2 Hz), 6.69-6.81 (4H, m).

Step (ii). 4-{3-[4-(3,4-Dichloro-phenyl)-piperazin-1-yl]-2-(S)-hydroxy-propoxy}-phenoxy-tert-butyldimethyl silane (iii-2). Compound iii-1 (0.280 g, 1 mmol) and 1-(4-chlorophenyl)piperazine (0.200 g, 1 mmol) were dissolved in 5 ml EtOH and refluxed for 90 minutes. Solvent was evaporated and the material was used in the next step without purification.

Step (iii). 4-{3-[4-(3,4-Dichloro-phenyl)-piperazin-1-yl]-2-(S)-hydroxy-propoxy}-phenol (Compound 4). Compound iii-2 was dissolved in 5 ml THF and 2 ml TBAF in 1.0M THF solution was added, and stirred for 2 hours. Quenched with ammonium chloride solution, extracted with EtOAc. Organic phase was dried over sodium sulfate and evaporated. Product was purified using column chromatography using EtOAc:MeOH (95:5). 1H-NMR (400 MHz, DMSO-d6) δ 2.36-2.61 (6H, m), 3.11 (4H, t, J=4.8 Hz), 3.76 (1H, dd, J=4.0, 6.0 Hz), 386 (1H, dd, J=4.4, 10.0 Hz), 3.91-3.95 (1H, m), 4.85 (1H, d, J=4.8 Hz), 6.66 (1H, dd, J=2.4, 6.8 Hz), 6.75 (1H, dd, J=2.4, 6.8 Hz), 6.92 (1H, dd, J=2.4, 6.8 Hz), 7.21 (1H, dd, J=2.4, 6.8 Hz), 8.90 (1H, s). HRMS: 362.1397 calculated. 362.14696 found.

The following compounds were synthesized according to Example 4.

| COMPOUND | NAME AND PHYSICAL DATA |
|---|---|
| ![structure] | 4-{3-[4-(3,4-Dichloro-phenyl-piperazin-1-yl]-2-(S)-hydroxy-propoxy}-phenol<br>MS: 397.10811 |
| ![structure] | 4-{3-[4-(3,4-Difluoro-phenyl)-piperazin-1-yl]-2-(S)-hydroxy-propoxy}-phenol<br>MS: 365.16672 |

| COMPOUND | NAME AND PHYSICAL DATA |
|---|---|
| | 4-{3-[4-(3,4-Difluoro-phenyl)-piperazin-1-yl]-2-(R)-hydroxy-propoxy}-phenol<br>MS: 365.16657 |
| | 4-{3-[4-(4-Fluoro-phenyl)-piperazin-1-yl]-2-(S)-hydroxy-propoxy}-phenol<br>MS: 347.17602 |
| | 4-{3-[4-(3,4-Dimethyl-phenyl)-piperazin-1-yl]-2-(S)-hydroxy-propoxy}-phenol<br>MS: 357.21716 |
| | 4-{3-[4-(4-Methyl-phenyl)-piperazin-1-yl]-2-(S)-hydroxy-propoxy}-phenol<br>MS: 343.20093 |
| | 4-{3-[4-(4-Cyano-phenyl)-piperazin-1-yl]-2-(S)-hydroxy-propoxy}-phenol<br>MS: 354.18073 |
| | 4-{3-[4-(4-Bromo-phenyl)-piperazin-1-yl]-2-(S)-hydroxy-propoxy}-phenol<br>MS: 407.09663 |

| COMPOUND | NAME AND PHYSICAL DATA |
|---|---|
| | 4-{3-[4-(4-Hydroxy-phenyl)-piperazin-1-yl]-2-(S)-hydroxy-propoxy}-phenol<br>MS: 345.18061 |
| | 4-{3-[4-(4-Methoxy-phenyl)-piperazin-1-yl]-2-(S)-hydroxy-propoxy}-phenol<br>MS: 359.19608 |
| | 4-{3-[4-(4-Trifluoromethyl-phenyl)-piperazin-1-yl]-2-(S)-hydroxy-propoxy}-phenol<br>MS: 397.17327 |
| | 4-{3-[4-(4-Biphenyl)-piperazin-1-yl]-2-(S)-hydroxy-propoxy}-phenol<br>MS: 405.21643 |
| | 4-{3-[4-(2,4-Difluoro-phenyl)-piperazin-1-yl]-2-(S)-hydroxy-propoxy}-phenol<br>MS: 365.16651 |
| | 4-{3-[4-(2-Fluoro-phenyl)-piperazin-1-yl]-2-(S)-hydroxy-propoxy}-phenol<br>MS: 347.17595 |

-continued

| COMPOUND | NAME AND PHYSICAL DATA |
|---|---|
| | 4-{3-[4-(2-Chloro-phenyl)-piperazin-1-yl]-2-(S)-hydroxy-propoxy}-phenol<br>MS: 363.14695 |
| | 4-{3-[4-(2-Chloro-phenyl)-piperazin-1-yl]-2-(S)-hydroxy-propoxy}-phenol<br>MS: 343.20108 |
| | 4-{3-[4-(2-Cyano-phenyl)-piperazin-1-yl]-2-(S)-hydroxy-propoxy}-phenol<br>MS: 354.18070 |
| | 4-{3-[4-Phenyl-piperazin-1-yl]-2-(S)-hydroxy-propoxy}-phenol<br>MS: 329.18547 |
| | 4-{3-[4-(3-Fluoro-phenyl)-piperazin-1-yl]-2-(S)-hydroxy-propoxy}-phenol<br>MS: 347.17608 |
| | 4-{3-[4-(3-Chloro-phenyl)-piperazin-1-yl]-2-(S)-hydroxy-propoxy}-phenol<br>MS: 363.14741 |

| COMPOUND | NAME AND PHYSICAL DATA |
|---|---|
| | 4-{3-[4-(3-Methyl-phenyl)-piperazin-1-yl]-2-(S)-hydroxy-propoxy}-phenol<br>MS: 343.20109 |
| | 4-{3-[4-(3-Trifluoromethyl-phenyl)-piperazin-1-yl]-2-(S)-hydroxy-propoxy}-phenol<br>MS: 397.17269 |
| | 4-{3-[2-(3,4-Dichloro-phenyl)-ethylamino]-2-(S)-hydroxy-propoxy}-phenol<br>MS: 357.10159 |
| | 4-(3-{Butyl-[2-(3,4-dichloro-phenyl)-ethyl]-amino}-2-(S)-hydroxy-propoxy)-phenol<br>MS: 413.12769 |
| | 4-{3-[2-(3,4-Dichloro-phenyl)-ethylamino]-2-(S)-hydroxy-propoxy}-3-fluoro-phenol<br>MS: 375.03418 |
| | 4-{3-[2-(3,4-Dichloro-phenyl)-ethylamino]-2-(S)-hydroxy-propoxy}-2-fluoro-phenol<br>MS: 375.03409 |
| | 1-[2-(S)-Hydroxy-3-(4-hydroxy-phenoxy)-propyl]-4-phenyl-piperidin-4-ol<br>MS: 344.18509 |

Example 5a (4-{3-[4-(3,4-Difluoro-phenyl)-piperazin-1-yl]-propoxy}-phenyl)-urea (Compound 5)

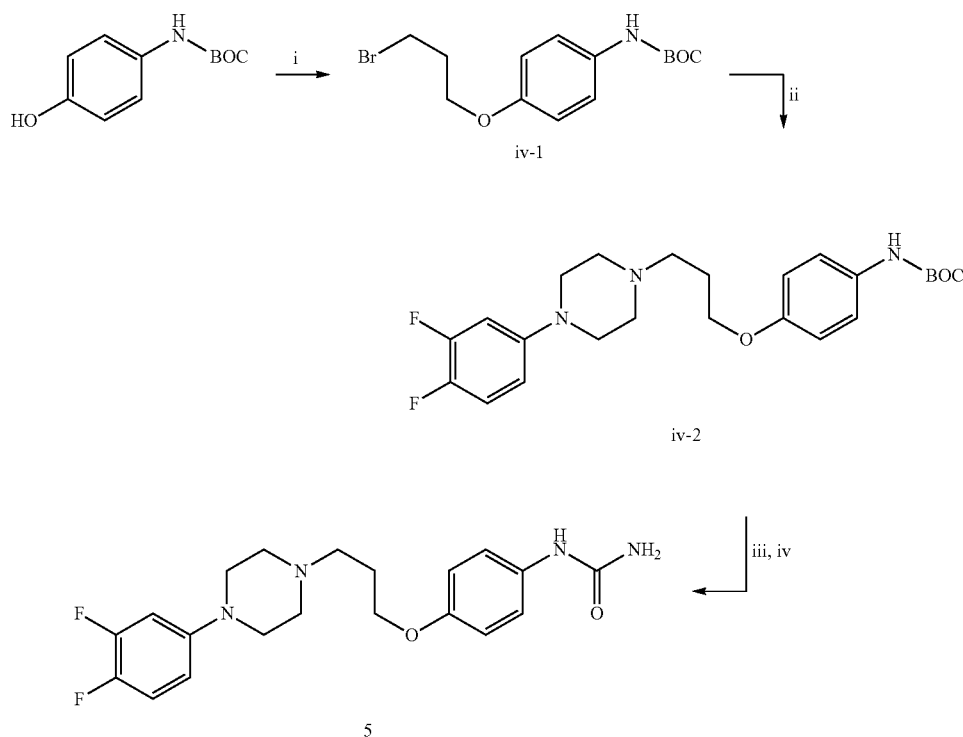

Step (i). [4-(3-Bromo-propoxy)-phenyl]-carbamic acid tert-butyl ester (iv-1). To a solution of 2.1 g of 4-t-butylcarbonylamino-phenol in 20 mL of acetonitrile was added 3.25 g of cesium carbonate. The reaction was stirred for one hour, and then 1.5 mL of 1,3-dibromopropane was added and the reaction stirred for 20 hours. The reaction was then quenched with $NH_4Cl$(aq.) solution. The mixture was extracted with ethyl acetate and washed with $NH_4Cl$(aq.) and NaCl(aq.) solutions. The organic layer was separated and dried over $Na_2SO_4$(s). Filtration and solvent removal gave a light brown oily solid. Hexanes were added and the resulting solids filtered and washed with Hexanes three times. Drying gave 2.4 g of an off-white solid.

Step (ii). (4-{3-[4-(3,4-Difluoro-phenyl)-piperazin-1-yl]-propoxy}-phenyl)-carbamic acid tert-butyl ester (iv-2). To 305 mg of 4-(3,4-Difluoro-phenyl)-piperazine and 335 mg of compound iv-1 was added 5 mL of acetonitrile. The reaction was heated to 65° C. overnight. The reaction was cooled, and then extracted with ethyl acetate. The organic layers were washed with $NaHCO_3$(aq.) twice, and the organic layers separated and dried over $Na_2SO_4$(s). Filtration and solvent removal gave an light brown solid. Dilution with hexanes, filtration, and washing with hexanes gave 458 mg of a white solid (iv-2). MS (m/z): 430 (M+H); HRMS: Obsd for $C_{24}H_{33}FN_3O_3$: 430.24951.

Step (iii). Compound iv-2 (430 mg) was dissolved in 6 mL of dichloromethane. Next, 4 mL of trifluoroacetic acid was added and the reaction was stirred for 6 hours. Then $NaHCO_3$(s) was added until the bubbling stopped. Then water was added to the reaction mixture and the reaction was extracted with dichloromethane and washed with $NaHCO_3$ (aq.) twice. The organics were dried over $Na_2SO_4$(s), and then the solution was filtered and the solvent removed under vacuum. The residue was used in the next step without any purification.

Step (iv). (4-{3-[4-(3,4-Difluoro-phenyl)-piperazin-1-yl]-propoxy}-phenyl)-urea (Compound 5). The aniline from the previous step was dissolved in 10 mL of N,N-dimethyl formamide. Next, 1 mL of trimethylsilyl isocyanate was added, and the reaction was stirred at room temperature overnight. The reaction was then quenched with $NaHCO_3$(aq.) solution. The reaction was extracted with ethyl acetate and washed with $NaHCO_3$(aq.) solution twice. The organic layer was separated and dried over $Na_2SO_4$(s). Filtration and solvent removal gave a brown solid. Filtration over a plug of silica gel with ethyl acetate/methanol (4:1) was followed by solvent removal. Trituration of the resulting solids with ethyl ether and filtration gave 98 mg of an off-white solid. MS (m/z): 391 (M+H); HRMS: calcd. for $C_{20}H_{25}F_2N_4O_2$: 391.19456. Found: 391.19184.

The following compounds were synthesized according to the methods and variations of described for Example 5.

| COMPOUND | NAME AND PHYSICAL DATA |
|---|---|
| | (4-{2-[4-(3,4-Difluoro-phenyl)-piperazin-1-ylmethyl]-allyloxy}-phenyl)-urea<br>MS: 403.19326 |
| | (4-{3-[4-(4-Fluoro-phenyl)-piperazin-1-yl]-propoxy}-phenyl)-urea<br>MS: 373.20319 |
| | 1-Ethyl-3-(4-{3-[4-(4-fluoro-phenyl)-piperazin-1-yl]-propoxy}-phenyl)-urea |
| | (4-{3-[4-(4-Fluoro-phenyl)-piperazin-1-yl]-propoxy}-phenyl)-carbamic acid methyl ester<br>MS: 388.20251 |
Example 5b
(4-{3-[4-(4-Chloro-phenyl)-piperazin-1-yl]-2-(S)-hydroxy-propoxy}-phenyl)-urea.
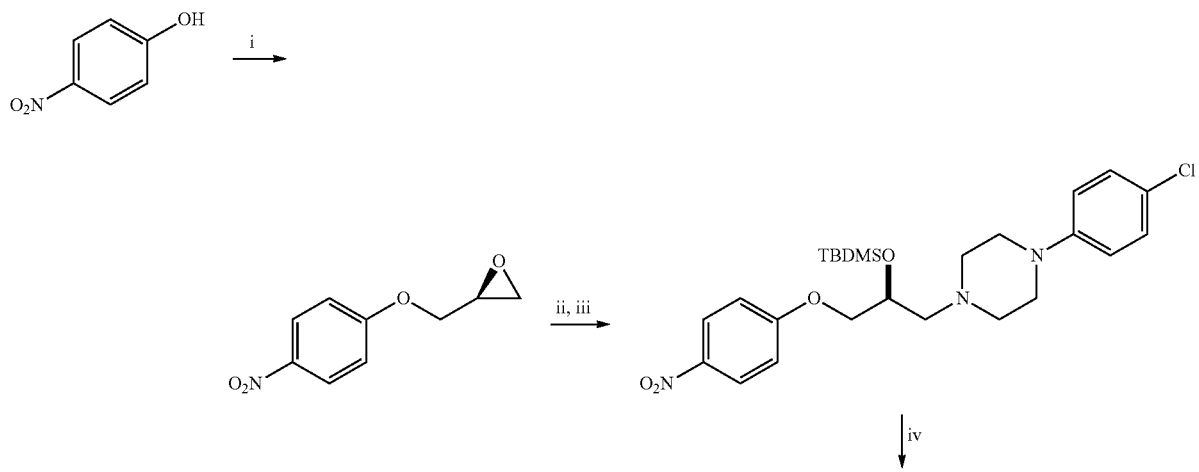

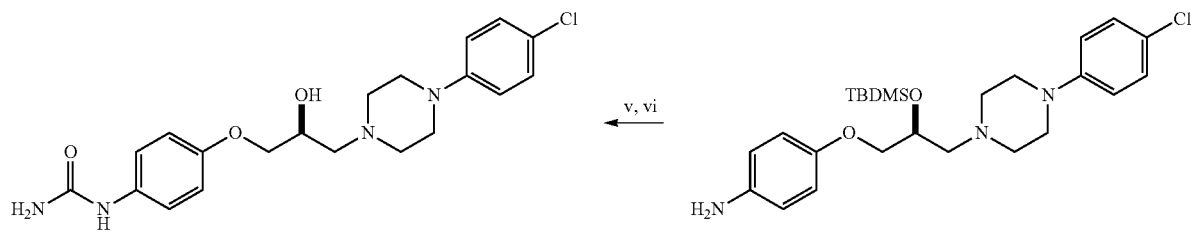

Step (ii). Epoxide ring opening with p-chlorophenyl-piperazine. To a solution of 1.1 g of p-chloro-phenyl-piperazine in 10 mL of ethanol was added 0.95 g of the S-epoxide. The solution was heated for 18 hours at 70° C. The reaction was cooled, and extracted with dichloromethane. The organic layers were washed twice with NaHCO$_3$(aq.) solution. The organic layers were separated, and then dried over Na$_2$SO$_4$(s). Filtration and solvent removal gave an oily residue. Next, ethyl ether was triturated in and the resulting solids filtered and dried. Obtained 1.49 g of piperazine compound as a light yellow solid. $^1$H NMR (400 MHz, CDCl$_3$): 2.64 (m, 4H), 2.86 (m, 2H), 3.08 (m, 1H), 3.19 (m, 4H), 4.12 (m, 2H), 4.18 (m, 1H), 6.85 (d, 2H, J=8 Hz), 7.01 (d, 2H, J=11 Hz), 8.21 (d, 2H, J=9 Hz); ms (m/z): 392 (M+H). HRMS: m/z 392.13665—theoretical for C$_{19}$H$_{23}$O$_4$N$_3$Cl—392.13716.

Step (iii). Silyl ether formation p-chlorophenyl-piperazine. To a solution of 1.2 g of alcohol i-2 in dichloromethane was added 600 mg of t-butyldimethylsilyl chloride, 1 mL of diisopropylethyl amine, and 600 mg of 4-N,N-dimethylaminopyridine. The reaction was stirred for 1 day, then 150 mg of t-butyldimethylsilyl chloride was added. Stirring for a third day was followed by addition of a third alloquat of 150 mg of t-butyldimethylsilyl chloride. Stirring for an additional day was followed by solvent removal and absorption onto silica gel. The residue was filtered with a 3:1-Hexane-ethyl acetate mixture and the solvent was removed under vacuum. 1.1 g of a yellow, oily solid was obtained. $^1$H NMR (CDCl$_3$): δ 0.08 (s, 3H), 0.11 (s, 3H), 0.88 (s, 9H), 2.52 (m, 2H), 2.65 (m, 4H), 3.13 (t, 4H, J=4 Hz), 3.98 (dd, 1H, J=7 Hz, J=9 Hz), 4.16 (m, 1H), 4.22 (dd, 1H, J=3 Hz, J=9 Hz), 6.81 (d, 2H, J=9 Hz), 6.96 (d, 2H, J=9 Hz), 7.18 (d, 2H, J=9 Hz), 8.18 (d, 2H, J=9 Hz); MS (m/z): 506 (M+H); HRMS: Calcd. for C$_{25}$H$_{37}$ClN$_3$O$_4$Si: 506.22419. Found: 506.22577.

Step (iv). Nitro group reduction. To a solution of 25 mg of silyl ether i-3 in 6 mL of N,N-dimethylformamide was added 1 g of tin(II)chloride hydrate. The reaction was heated to 65° C. for 20 hours. The reaction was cooled and quenched by pouring over NaHCO$_3$(aq.) solution. The mixture bubbled and was allowed to subside. Ethyl acetate was added, and the materials filtered through celite. The organic layer was extracted with NaHCO3(aq.) solution. The aqueous layers were re-extracted with ethyl acetate and the organic layers were combined and dried over sodium sulfate. Filtration, solvent removal, and column chromatography gave 210 mg of a clear oil. Repetition with 450 mg of nitro compound i-3 gave 290 mg of aniline.

Step (v). Urea formation. To a solution of 500 mg of aniline in 6 mL of N,N-dimethyl formamide was added 1 mL of trimethylsilyl isocyanate. The reaction was stirred for 2 days. An additional 0.5 mL of trimethylsilyl isocyanate was added and followed by stirring for 2 more days. The reaction was extracted with ethyl acetate, and washed with NaHCO$_3$(aq.) solution. The organic layer was separated and dried over Na$_2$SO$_4$(s). Filtration, solvent removal, and column chromatography gave 410 mg of a waxy, white solid. 1H NMR (d$^6$-DMSO): δ 0.04 (s, 3H), 0.07 (s, 3H), 0.83 (s, 9H), 2.39 (m, 2H), 2.48 (m, 4H), 3.08 (t, 4H, J=4 Hz), 3.75 (dd, 1H, J=7 Hz, J=10 Hz), 3.98 (dd, 1H, J=3 Hz, J=10 Hz), 4.08 (m, 1H), 5.69 (s, 2H), 6.76 (d, 2H, J=9 Hz), 6.89 (d, 2H, J=9 Hz), 7.18 (d, 2H, J=9 Hz), 7.23 (d, 2H, J=9 Hz), 8.28 (s, 1H).

Step (vi). Desilylation. 400 mg of silyl ether i-5 was dissolved in 10 mL of tetrahydrofuran. Next, 2 mL of a tetrabutylammonium fluoride solution (1M, in THF, Aldrich) was added. The reaction was stirred overnight, and then saturated NH$_4$Cl(aq.) solution was added. The mixture was diluted with ethyl acetate, and the resulting solids filtered. The solids were washed with water, ethyl acetate, and ethyl ether (three times each). Drying gave 220 mg of an off-white powder. $^1$H NMR (d$^6$-DMSO): 2.42 (m, 2H), 2.54 (m, 4H), 3.08 (t, 4H, J=4 Hz), 3.77 (dd, 1H, J=6 Hz, J=9 Hz), 3.89 (m, 2H), 4.85 (d, 1H, J=5 Hz), 5.68 (s, 2H), 6.78 (d, 2H, J=9 Hz), 6.89 (d, 2H, J=9 Hz), 7.18 (d, 2H, J=9 Hz), 7.23 (d, 2H, J=9 Hz), 8.27 (s, 1H); MS (m/z): 405 (M+H), 407 (M+2+H); HRMS: calcd for C$_{20}$H$_{26}$N$_4$O$_3$$^{35}$Cl: 405.16934. observed: 405.16872. The p-toluene sulfonate salt was formed by taking 70 mg of the free base and mixing in 50 mg of p-toluene sulfonic acid hydrate. The mixture was diluted with 5 mL tetrahydrofuran and 3 mL ethanol and heated to 60° C. until all solids had dissolved. The mixture was cooled, and 90% of the solvent removed under vacuum. Next, ethanol was added and allowed to stand at room temperature for several hours. The resulting solids were filtered, washed with ethanol three times and dried. Obtained 80 mg of a fluffy, white solid. $^1$H NMR (d$^6$-DMSO): 2.25 (s, 3H), 2.99 (m, 2H), 3.09 (m, 2H), 3.22 (m, 2H), 3.58 (m, 2H), 3.79 (m, 2H), 3.87 (m, 2H), 4.28 (s, 1H), 5.74 (s, 2H), 5.97 (s, 1H), 6.81 (d, 2H, J=8 Hz), 6.99 (d, 2H, J=8 Hz), 7.08 (d, 2H, J=7 Hz), 7.27 (t, 4H, J=8 Hz), 7.44 (d, 2H, J=8 Hz), 8.36 (s, 1H), 9.58 (s, 1H); Anal. Calc. For C$_{20}$H$_{25}$N$_4$O$_3$Cl-pTsOH—H2O: C, 54.49, H, 5.93, N, 9.41. Found: C, 54.82, H, 5.77, N, 9.42.

Example 5c

Synthesis of R and S Hydroxy-Propyl Urea Piperazines

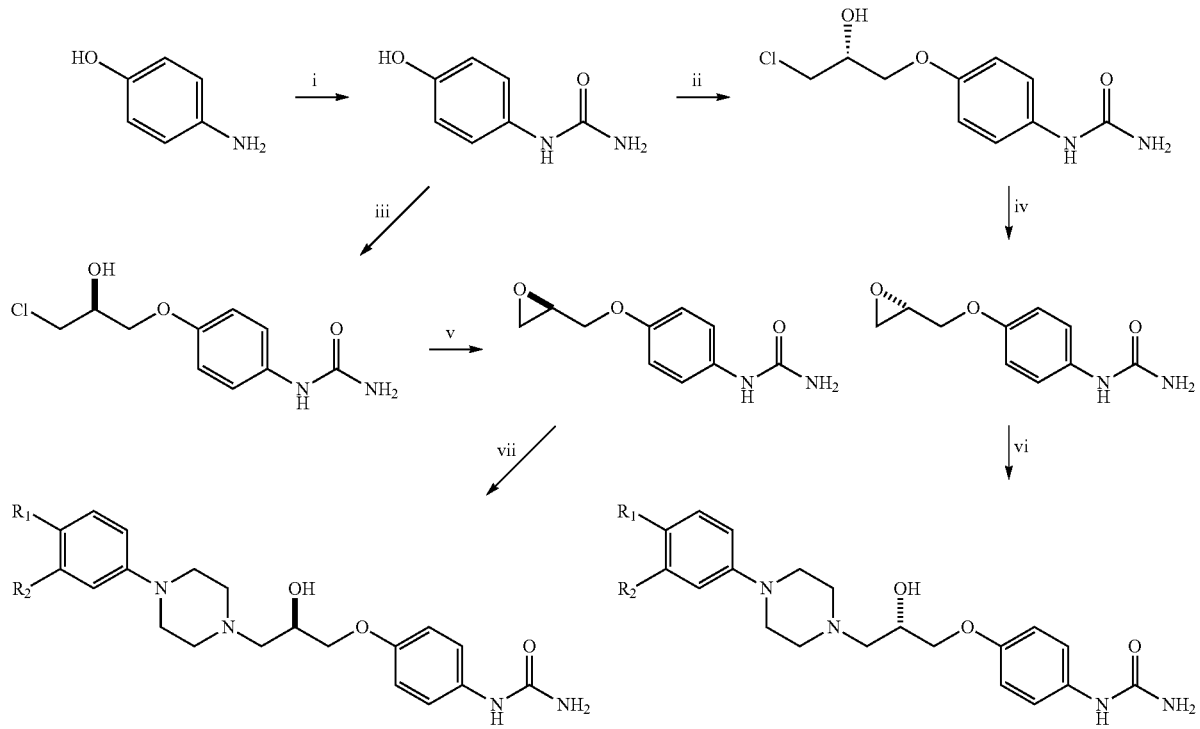

Step (i). Preparation of 1-(4-hydroxyphenyl)urea.

To a solution of 10.92 g of 4-hydroxy-aniline in 100 mL of tetrahydrofuran at 65° C. was added 20 mL of trimethylsilyl isocyanate (85%, Aldrich). The solution was heated at 65° C. for 6 hours. The solution was cooled to room temperature, and then 100 mL of ethanol and 10 g of silica gel were added. The reaction was stirred at room temperature overnight. The solvent was removed under vacuum. The solids were diluted with a 1:1 mixture of dichloromethane and ethanol (500 mL). After all the solids had dissolved, the solution was filtered over a plug of silica gel. The solvent was removed under vacuum. Next, dichloromethane was added and the solids were filtered and washed with dichloromethane three times. The resulting solids were then dried. The reaction gave 15.5 g of a fine white powder (100% yield). $^1$H NMR (d$^6$-DMSO): δ 5.62 (s, 2H), 6.58 (d, 2H, J=9 Hz), 7.1 (d, 2H, J=9 Hz), 8.12 (s, 1H), 8.91 (s, 1H); MS: 187 (M+Cl); HRMS: 187.02821.

Step (ii). Preparation of (R)-1-(4-(3-chloro-2-hydroxypropoxy)phenyl)urea. (T. Fujioka et al. *Chem. Pharm. Bull.* 44(8), 1996, 1596-1598.)

To a solution of 1.52 g (10 mmoles) of 1-(4-hydroxyphenyl)urea in 10 mL of methanol and 10 mL of water was added 0.5 mL of triethylamine, followed by 8 mL of (R)-epichlorohydrin. The reaction was homogeneous, and was stirred at room temperature for 20 hours. The reaction was diluted with 50 mL of water and extracted with 5×100 mL portions of ethyl acetate. The organics were washed with dilute HCl (aq.) and NaCl (aq.) solutions. The organics were separated and dried over Na$_2$SO$_4$(s). Filtration and solvent removal gave an oily residue, which was absorbed onto silica gel. The crude product was then subjected to purification by column chromatography with a gradiant based on a 90:10:1 mixture of dichloromethane:methanol:NH$_4$OH and dichloromethane. The fractions of interest were combined and the solvent removed under vacuum. The resulting pink solid was dried under vacuum to give 1.62 g of fluffy white solid (66% yield). $^1$H NMR: (d$^6$-DMSO): δ 3.62 (dd, 1H, J=6 Hz, J=11 Hz), 3.71 (dd, 1H, J=5 Hz, J=11 Hz), 3.86 (d, 2H, J=5 Hz), 3.96 (m, 1H), 5.49 (d, 1H, J=6 Hz), 5.69 (s, 2H), 6.78 (d, 2H, J=9 Hz), 7.24 (d, 2H, J=9 Hz), 8.29 (s, 1H); MS: 279 (M+Cl); HRMS: 279.03124.

Step (iii). Preparation of (S)-1-(4-(3-chloro-2-hydroxypropoxy)phenyl)urea.

Following the exact procedure of the R-enantiomer, 1.52 g (10 mmoles) of 1-(4-hydroxyphenyl)urea and 8 mL of (S)-epichlorohydrin gave 1.39 g (57% yield) of light pink solid. The compound had identical $^1$HNMR and MS spectra to the (R)-enantiomer.

Step (iv). (S)-1-(4-(oxiran-2-ylmethoxy)phenyl)urea. (T. Fujioka et al. *Chem. Pharm. Bull.* 44(8), 1996, 1596-1598.) To a solution of 1.62 g of the (R)-chlorohydrin (3) in 70 mL of isopropanol and 10 mL of water at 0° C. was added a solution of 2 g of KOH dissolved in 12 mL of water. The reaction was stirred for 2 hours at 0° C., during which time a white precipitate formed. After 2.5 hours, 100 mL of ethyl acetate was added and the reaction was allowed to warm to room temperature. The organic layer was washed with NaCl (aq.) solution. The aqueous layer was extracted with 4×100 mL of ethyl acetate, and the organic layers were combined and dried over Na$_2$SO$_4$(s). Filtration and solvent removal gave a white residue. Ethyl ether was added and the solids were filtered and washed with ethyl ether three times. Drying gave 1.23 g of a white, fluffy solid (89% yield). $^1$H NMR (d$^6$-DMSO): δ 2.65 (dd, 1H, J=3 Hz, J=5 Hz), 2.79 (t, 1H, J=5 Hz), 3.25 (m, 1H), 3.71 (dd, 1H, J=7 Hz, J=12 Hz), 4.2 (dd, 1H, J=3 Hz, J=12

Hz), 5.7 (s, 2H), 6.79 (d, 2H, J=9 Hz), 7.25 (d, 2H, J=9 Hz), 8.3 (s, 1H); MS: 243 (M+Cl); HRMS: 243.05458.

Step (v). (R)-1-(4-(oxiran-2-ylmethoxy)phenyl)urea.

Using the same procedure as for the (S)-enantiomer, 1.39 g of the S-chlorohydrin gave 1.11 g (93% yield) of the R-epoxide as a fluffy, white solid. This compound had identical $^1$H NMR and MS as the S-enantiomer.

Specific exemplary syntheses for step (vi):

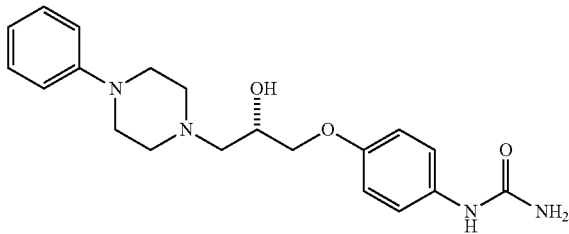 [SMILES: NC(=O)Nc1ccc(OC[C@@H](O)CN2CCN(c3ccccc3)CC2)cc1]

(S)-1-(4-(2-hydroxy-3-(4-phenylpiperazin-1-yl)propoxy)phenyl)urea. A mixture of 0.1 g of (S)-1-(4-(oxiran-2-ylmethoxy)phenyl)urea, 0.14 g of N-phenyl-piperazine, and 6 mL of abosolute ethanol was heated to 70° C. for 20 hrs. The reaction was cooled, and the resulting precipitate collected by filtration. The solids were washed three times with ethanol, and dried. 0.126 g of the title compound was obtained as a fluffy white powder was obtained. $^1$H NMR (d$^6$-DMSO): δ 2.36 (dd, 1H, J=6 Hz, J=13 Hz), 2.48 (m, 1H), 2.55 (m, 4H), 3.08 (t, 4H, J=5 Hz), 3.78 (dd, 1H, J=6 Hz, J=9 Hz), 3.89 (m, 1H), 3.93 (m, 1H), 4.84 (d, 1H, J=5 Hz), 5.68 (s, 2H), 6.73 (t, 1H, J=8 Hz), 6.78 (d, 2H, J=9 Hz), 6.88 (d, 2H, J=8 Hz), 7.16 (t, 2H, J=8 Hz), 7.24 (d, 2H, J=9 Hz), 8.27 (s, 1H); MS: 371 (M+H); HRMS: Observed: 371.20723; HPLC: 100% peak area composition; retention time=6.64 min.

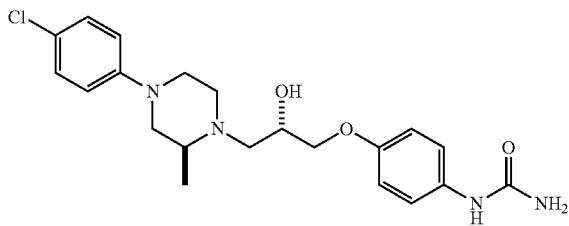 [SMILES: C[C@H]1CN(c2ccc(Cl)cc2)CCN1C[C@H](O)COc1ccc(NC(N)=O)cc1]

1-(4-((S)-3-((S)-4-(4-chlorophenyl)-2-methylpiperazin-1-yl)-2-hydroxypropoxy)phenyl)urea. A solution of 0.5 mmol of the (S)-epoxide and 0.6 mmol of (3S)-1-(4-chlorophenyl)-3-methylpiperazine in 5 ml ethanol was refluxed for overnight. The solvent was evaporated and product was purified with the column chromatography using dichloromethane:methanol:NH$_4$OH (90:10:1). After the column it was crystallized with ethyl acetate to give 0.109 g (52% yield). $^1$H NMR (400 MHz, d6-DMSO): δ 1.01 (3H, d, J=6.0 Hz), 2.16 (1H, dd, J=5.6, 12.8 Hz), 2.34-2.51 (3H, m), 2.78-2.89 (2H, m), 2.99 (1H, d, J=11.6 Hz), 3.38 (2H, d, J=11.2 Hz), 3.75-3.79 (1H, m), 3.88-3.92 (2H, m), 4.84, (1H, d, J=5.2 Hz), 5.67 (2H, s), 6.78 (2H, d, J=7.2 Hz), 6.88 (2H, d, J=9.2 Hz), 7.17 (2H, d, J=7.2 Hz), 7.23 (2H, d, J=9.2 Hz), 8.25 (1H, s); MS: 419 (M+H); HRMS=419.18431; HPLC=96% peak area at 7.7 min. retention time.

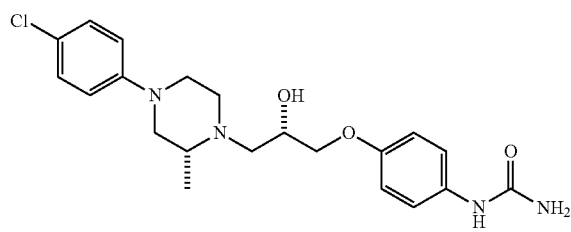 [SMILES: C[C@@H]1CN(c2ccc(Cl)cc2)CCN1C[C@H](O)COc1ccc(NC(N)=O)cc1]

1-(4-((S)-3-((R)-4-(4-chlorophenyl)-2-methylpiperazin-1-yl)-2-hydroxypropoxy)phenyl)urea. A solution of 0.5 mmol of the (S)-epoxide and 0.6 mmol of (3R)-1-(4-chlorophenyl)-3-methylpiperazine in 5 ml ethanol was refluxed overnight. The solvent was evaporated and product was purified with the column chromatography using dichloromethane:methanol:NH$_4$OH (90:10:1). After the column it was crystallized with ethyl acetate to give 0.099 g (47% yield). $^1$H NMR (400 MHz, d$^6$-DMSO) δ 1.05 (3H, d, J=6.0 Hz), 2.37 (1H, dd, J=4.8, 13.2 Hz), 2.46-2.53 (2H, m), 2.71 (1H, dd, J=6.8, 13.2 Hz), 2.78 (1H, t, J=8.8 Hz), 2.95 (1H, d, J=12.0 Hz), 3.40 (2H, d, J=8.8 Hz), 3.80-3.83 (1H, m), 3.89, (2H, d, J=6.4 Hz), 4.78 (1H, d, J=4.4 Hz), 5.71 (2H, s), 6.82 (2H, d, J=8.8 Hz), 6.91 (2H, d, J=8.8 Hz), 7.20 (2H, d, J=8.8 Hz), 7.27 (2H, d, J=8.8 Hz), 8.29 (1H, s); MS: 419 (M+H); HRMS=419.18437; HPLC=95% peak area at 7.6 min. retention time.

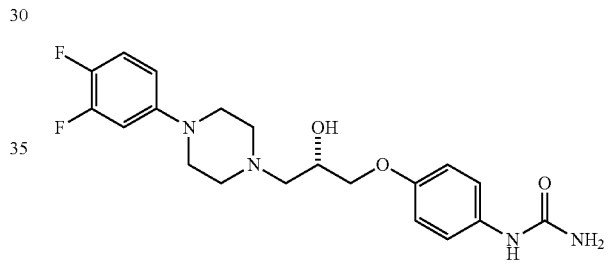

(S)-1-(4-(3-(4-(3,4-difluorophenyl)piperazin-1-yl)-2-hydroxypropoxy)phenyl)urea. A solution of 0.106 g of (S)-epoxide, 0.135 g of N-(3,4-difluorophenyl)-piperazine and 6 mL of absolute ethanol was heated at 70° C. for 18 hours. The reaction was cooled, and the resulting precipitate filtered. The solids were washed with ethanol and ethyl ether three times each. Drying gave 0.12 g of a white solid. $^1$H NMR (d$^6$-DMSO): 2.36 (dd, 1H, J=7 Hz, J=13 Hz), 2.45 (m, 1H), 2.53 (m, 4H), 3.06 (m, 4H), 3.77 (dd, 1H, J=6 Hz, J=9 Hz), 3.88 (m, 1H), 3.91 (m, 1H), 4.83 (d, 1H, J=4 Hz), 5.67 (s, 2H), 6.67 (m, 1H), 6.78 (d, 2H, J=9 Hz), 6.93 (m, 1H), 7.19 (quart, 1H, J=10 Hz), 7.23 (d, 2H, J=9 Hz), 8.26 (s, 1H); MS: 407 (M+H); HRMS: 407.18890; HPLC: 100% peak area at 7.1 min. retention time.

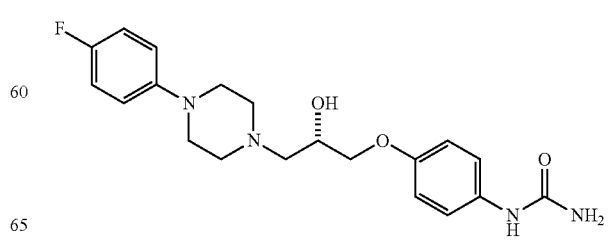

(S)-1-(4-(3-(4-(4-fluorophenyl)piperazin-1-yl)-2-hydroxypropoxy)phenyl)urea. A solution of 0.11 g of (S)-epoxide, 0.14 g of N-(4-fluorophenyl)-piperazine, and 6 mL of ethanol was heated to 70° C. for 20 hours. The solution was cooled to room temperature. The solids were filtered, washed with ethanol three times, and dried. Gave 0.164 g of a white powder. 1H NMR (d6-DMSO): d 2.36 (dd, 1H, J=6 Hz, J=13 Hz), 2.47 (m, 1H), 2.55 (m, 4H), 3.02 (t, 4H, J=5 Hz), 3.77 (dd, 1H, J=6 Hz, J=9 Hz), 3.88 (m, 1H), 3.92 (m, 1H), 4.84 (d, 1H, J=5 Hz), 5.68 (s, 2H), 6.78 (d, 2H, J=9 Hz), 6.89 (m, 2H), 6.99 (t, 2H, J=8 Hz), 7.23 (d, 2H, J=9 Hz), 8.27 (s, 1H); MS: 389. (M+H); HRMS: 389.19782; HPLC: 99.2% peak area at 6.5 min. retention time.

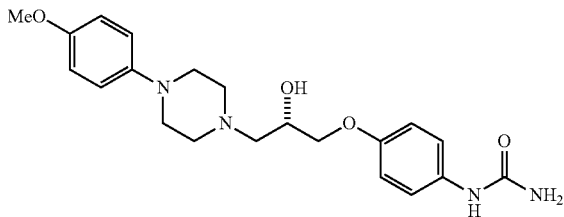 [SMILES: COc1ccc(N2CCN(C[C@H](O)COc3ccc(NC(N)=O)cc3)CC2)cc1]

(S)-1-(4-(2-hydroxy-3-(4-(4-methoxyphenyl)piperazin-1-yl)propoxy)phenyl)urea. A solution of 0.11 g of (S)-epoxide, 0.155 g of N-(4-methoxyphenyl)-piperazine, and 6 mL of ethanol was heated to 70° C. for 20 hours. The solution was cooled to room temperature. The solids were filtered, washed with ethanol three times, and dried. Gave 0.18 g of a white powder. $^1$H NMR (d$^6$-DMSO): δ 2.36 (dd, 1H, J=7 Hz, J=13 Hz), 2.45 (m, 1H), 2.55 (m, 4H), 2.96 (t, 4H, J=5 Hz), 3.64 (s, 3H), 3.77 (dd, 1H, J=6 Hz, J=9 Hz), 3.87 (m, 1H), 3.93 (m, 1H), 4.83 (d, 1H, J=5 Hz), 5.68 (s, 2H), 6.78 (m, 4H), 6.83 (d, 2H, J=9 Hz), 7.23 (d, 2H, J=9 Hz), 8.27 (s, 1H); MS: 401 (M+H); HRMS: 401.21861; HPLC: 99% peak area at 6.2 min.

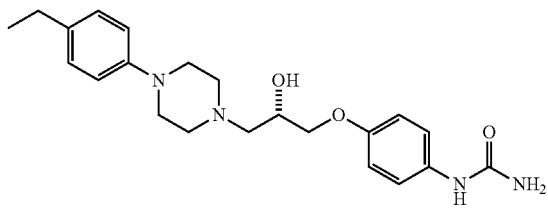 [SMILES: CCc1ccc(N2CCN(C[C@H](O)COc3ccc(NC(N)=O)cc3)CC2)cc1]

(S)-1-(4-(3-(4-(4-ethylphenyl)piperazin-1-yl)-2-hydroxypropoxy)phenyl)urea. A solution of 0.08 g of (S)-epoxide, 0.12 g of N-(4-ethylphenyl)-piperazine, and 5 mL of absolute ethanol were heated at 70° C. for 30 hours. The solution was cooled to room temperature. The solvent was removed under vacuum, and the residue subjected to column chromatography on silica gel with a dichloromethane/dichloromethane:methanol:NH$_4$OH (90:10:1) gradiant. Combination of the fractions and solvent removal, followed by drying under vacuum gave 0.064 g of a white solid. $^1$H NMR (d$^6$-DMSO): δ 1.09 (t, 3H, J=8 Hz), 2.36 (dd, 1H, J=6 Hz, J=12 Hz), 2.44 (m, 1H), 2.54 (m, 4H), 3.03 (t, 4H, J=5 Hz), 3.77 (dd, 1H, J=6 Hz, J=10 Hz), 3.89 (m, 1H), 3.92 (m, 1H), 4.83 (d, 1H, J=5 Hz), 5.67 (s, 2H), 6.78 (d, 2H, J=9 Hz), 6.8 (d, 2H, J=8 Hz), 7.01 (d, 2H, J=9 Hz), 7.23 (d, 2H, J=10 Hz), 8.26 (s, 1H); MS: 399 (M+H); HRMS: 399.23896; HPLC: 100% peak area; retention time at 7.8 min. Elemental -formula+0.25 H$_2$O— theory: C, 65.57, H, 7.63, N, 13.9. Found: C, 65.58, H, 7.51, N, 13.98.

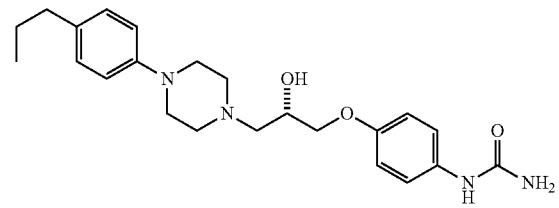 [SMILES: CCCc1ccc(N2CCN(C[C@H](O)COc3ccc(NC(N)=O)cc3)CC2)cc1]

(S)-1-(4-(3-(4-(4-propylphenyl)piperazin-1-yl)-2-hydroxypropoxy)phenyl)urea. A solution of 0.11 g of (S)-epoxide, 0.154 g of N-(4-propylphenyl)-piperazine, and 6 mL of ethanol was heated to 70° C. for 20 hours. The solution was cooled to room temperature. The solids were filtered, washed with ethanol three times, and dried. Gave 0.094 g of a white powder. $^1$H NMR (d$^6$-DMSO): δ 0.83 (t, 3H, J=7 Hz), 1.49 (hextet, 2H, J=7 Hz), 2.38 (m, 3H), 2.54 (m, 4H), 3.03 (t, 4H, J=5 Hz), 3.77 (dd, 1H, J=6 Hz, J=9 Hz), 3.89 (m, 1H), 3.92 (m, 1H), 4.83 (d, 1H, J=5 Hz), 5.68 (s, 2H), 6.78 (d, 2H, J=9 Hz), 6.8 (d, 2H, J=8 Hz), 6.98 (d, 2H, J=8 Hz), 7.24 (d, 2H, J=9 Hz), 8.27 (s, 1H); MS: 413 (M+H); HRMS: 413.25406; HPLC: 99% peak area at 8.6 min. retention time.

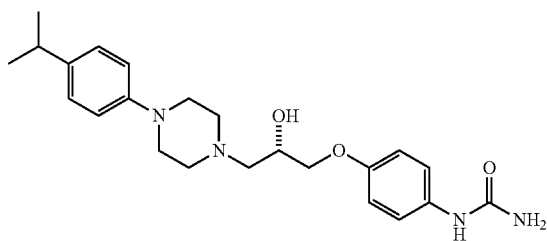 [SMILES: CC(C)c1ccc(N2CCN(C[C@H](O)COc3ccc(NC(N)=O)cc3)CC2)cc1]

(S)-1-(4-(3-(4-(4-isopropyl-phenyl)piperazin-1-yl)-2-hydroxypropoxy)phenyl)urea. A solution of 0.08 g of (S)-epoxide, 0.16 g of N-(4-isopropylphenyl)-piperazine, and 5 mL of absolute ethanol were heated at 70° C. for 30 hours. The solution was cooled to room temperature. The solvent was removed under vacuum, and the residue subjected to column chromatography on silica gel with a dichloromethane: dichloromethane:methanol:NH$_4$OH (90:10:1) gradient. The fractions were combined and the solvent removed under vacuum. Ethyl ether was added to the solids and they were filtered, washed with ethyl ether three times, and then dried. 0.046 g of a white solid was obtained. $^1$H NMR (400 MHz, d$^6$-DMSO): δ 1.11 (d, 6H, J=7 Hz), 2.36 (dd, 1H, J=7 Hz, J=13 Hz), 2.45 (m, 1H), 2.54 (m, 4H), 2.74 (quint, 1H, J=7 Hz), 3.03 (t, 4H, J=5 Hz), 3.77 (dd, 1H, J=6 Hz, J=10 Hz), 3.88 (m, 1H), 3.92 (m, 1H), 4.84 (d, 1H, J=5 Hz), 5.68 (s, 2H), 6.8 (t, 4H, J=10 Hz), 7.03 (d, 2H, J=8 Hz), 7.24 (d, 2H, J=9 Hz), 8.27 (s, 1H); MS: 413 (M+H); HRMS: 413.25458; HPLC: 100% peak area at a retention time of 8.25 min.; Elemental analysis—Theory: C, 66.96, H, 7.82, N, 13.58. Found, C, 66.98, H, 7.82, N, 13.48.

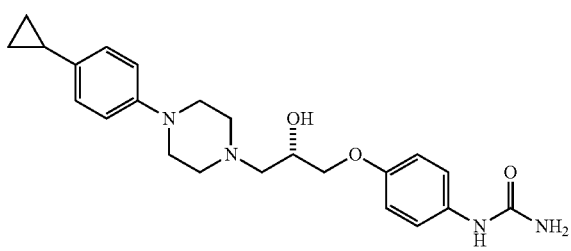 [SMILES: NC(=O)Nc1ccc(OC[C@@H](O)CN2CCN(c3ccc(C4CC4)cc3)CC2)cc1]

(S)-1-(4-(3-(4-(4-cyclopropylphenyl)piperazin-1-yl)-2-hydroxypropoxy)phenyl)urea. A solution of 0.1 g of (S)-epoxide, 0.15 g of N-(4-cyclopropylphenyl)-piperazine, and 6 mL of absolute ethanol were heated at 70° C. for 20 hours. The solution was cooled to room temperature. The solvent was removed under vacuum, and the residue subjected to column chromatography on silica gel with a dichloromethane/dichloromethane: methanol:NH$_4$OH (90:10:1) gradiant. The fractions were combined and the solvent removed under vacuum. Ethanol was added to the solids and they were filtered, washed with ethanol three times, and then dried. 0.067 g of a white solid was obtained. $^1$H NMR: (d$^6$-DMSO): δ 0.5 (quart, 2H, J=4 Hz), 0.8 (m, 2H), 1.76 (m, 1H), 2.35 (dd, 1H, J=6 Hz, J=12 Hz), 2.46 (m, 1H), 2.54 (m, 4H), 3.01 (t, 4H, J=5 Hz), 3.77 (dd, 1H, J=6 Hz, J=10 Hz), 3.88 (m, 1H), 3.91 (m, 1H), 4.83 (d, 1H, J=5 Hz), 5.68 (s, 2H), 6.78 (m, 4H), 6.88 (d, 2H, J=8 Hz), 7.23 (d, 2H, J=9 Hz), 8.27 (s, 1H); MS: 411 (M+H); HRMS: 411.23895; HPLC: 100% peak area at 7.8 min. retention time; Elemental analysis: Theory: C, 67.29, H, 7.37, N, 13.65. Found: C, 67.27, H, 7.36, N, 13.54.

(S)-1-(4-(3-(4-(4-isobutylphenyl)piperazin-1-yl)-2-hydroxypropoxy)phenyl)urea

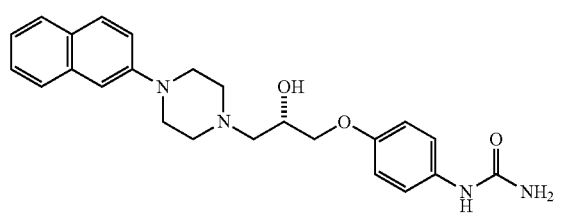 [SMILES: NC(=O)Nc1ccc(OC[C@@H](O)CN2CCN(c3ccc4ccccc4c3)CC2)cc1]

(S)-1-(4-(3-(4-(2-naphthyl)piperazin-1-yl)-2-hydroxypropoxy)phenyl)urea. A solution of 0.11 g of (S)-epoxide, 0.175 g of N-(2-naphthyl)-piperazine, and 6 mL of ethanol was heated to 70° C. for 20 hours. The solution was cooled to room temperature. The solids were filtered, washed with ethanol three times, and dried. Gave 0.197 g of a white powder. $^1$H NMR (d$^6$-DMSO): δ 2.39 (dd, 1H, J=7 Hz, J=12 Hz), 2.49 (m, 1H), 2.61 (m, 4H), 3.79 (dd, 1H, J=6 Hz, J=10 Hz), 3.9 (m, 1H), 3.96 (m, 1H), 4.86 (d, 1H, J=5 Hz), 5.68 (s, 2H), 6.79 (d, 2H, J=9 Hz), 7.11 (d, 1H, J=2 Hz), 7.23 (m, 4H), 7.34 (m, 3H), 7.69 (m, 4H), 8.27 (s, 1H); MS: 421 (M+H); HRMS: 421.22338; HPLC: 99.9% peak area at 7.8 min. retention time.

Specific Exemplary Syntheses for Step (vii):

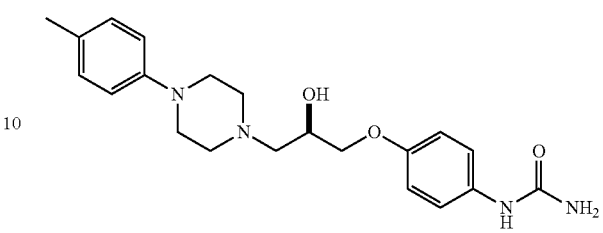

(R)-1-(4-(3-(4-(4-methylphenyl)piperazin-1-yl)-2-hydroxypropoxy)phenyl)urea. A solution of 0.11 g of (R)-epoxide, 0.13 g of N-(4-methylphenyl)-piperazine, and 5 mL of absolute ethanol were heated at 70° C. for 30 hours. The solution was cooled to room temperature. The solution was filtered. The solids were washed with ethanol three times and dried. Gave 0.157 g of a white solid.

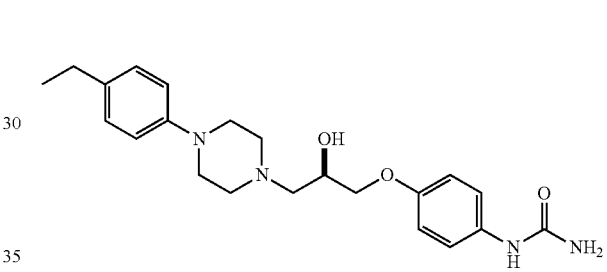

(R)-1-(4-(3-(4-(4-ethylphenyl)piperazin-1-yl)-2-hydroxypropoxy)phenyl)urea. A solution of 0.11 g of (S)-epoxide, 0.15 g of N-(4-ethylphenyl)-piperazine, and 5 mL of absolute ethanol were heated at 70° C. for 30 hours. The solution was cooled to room temperature. The solids were filtered, washed with ethanol and ethyl ether three times each. Drying gave 0.1 g of a white solid.

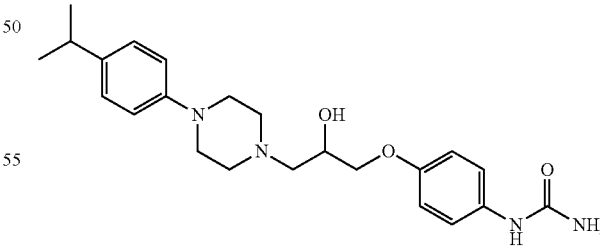

(R)-1-(4-(3-(4-(4-isopropylphenyl)piperazin-1-yl)-2-hydroxypropoxy)phenyl)urea. A solution of 0.11 g of (S)-epoxide, 0.175 g of N-(4-ethylphenyl)-piperazine, and 5 mL of absolute ethanol were heated at 70° C. for 30 hours. The solution was cooled to room temperature. The resulting solids were filtered, washed with ethanol and ethyl ether three times each. Drying gave 0.094 g of a white solid.

Examples 6, 7, and 8

N-[2-(3,4-Dichloro-phenylamino)-ethyl]-3-(4-methanesulfonylamino-phenyl)-propionamide (Compound 6), N-(4-{3-[2-(3,4-Dichloro-phenylamino)-ethylamino]-propyl}-phenyl)-methanesulfonamide (Compound 7), and N-(4-(3-(3-(3,4-dichlorophenyl)-2-oxoimidazolidin-1l)propyl)phenyl)methanesulfonamide (Compound 8)

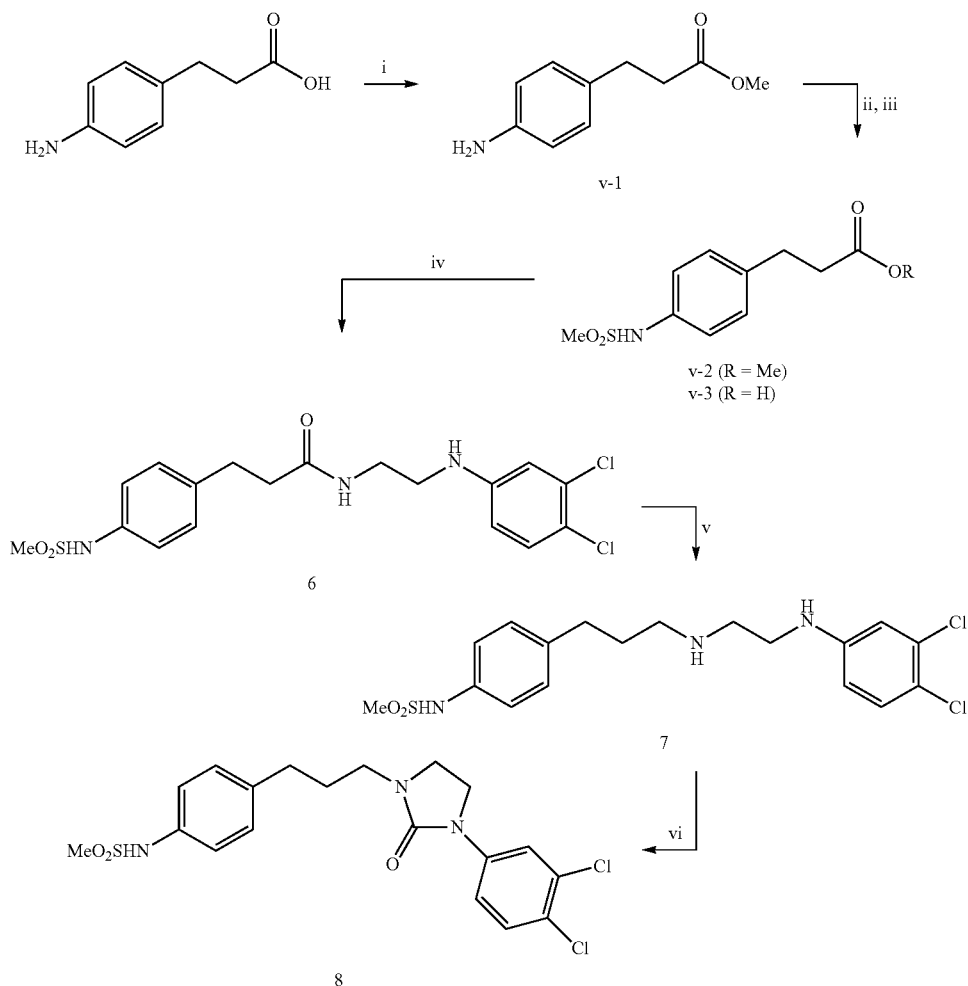

Step (i) Methyl 3-(4-aminophenyl)propanoate (v-1). Thionyl chloride (14.6 ml, 200 mmol, 3.3 equiv) was added dropwise to a solution of dry methanol (60 ml, 1453 mmol, 24 equiv) at −10° C. After stirring for 10 minutes, 3-(4-aminophenyl)propanoic acid (10.0 g, 61 mmol) was added to give a yellow suspension. The solution stirred for 1 hour and was slowly warmed to room temperature. The resulting solution was concentrated to give a yellow solid. The solid was suspended in ethyl acetate, and $NaHCO_3$ (aq.) was added until the salt dissolved fully. Solid sodium bicarbonate was added to give pH 8. The layers were separated and the organics were washed with brine (aq.). The resulting solution was dried over $MgSO_4$, filtered, and concentrated to give a yellow solid (10.6 g, 98%). $^1H$ NMR (300 MHz, $CDCl_3$) 7.00 (d, J=8.3 Hz, 2H), 6.63 (d, J=8.3 Hz, 2H), 3.67 (s, 3H), 3.59 (bs, $NH_2$, 2H), 2.85 (t, J=7.6 Hz, 2H), 2.58 (t, J=8.3 Hz, 2H). $^{13}C$ NMR (300 MHz, $CDCl_3$) 173.8, 144.9, 130.7, 129.3, 115.5, 51.8, 36.4, 30.4. M.S. (ESI) m/z=180.102 (M+H).

Step (ii). Methyl 3-(4-(methylsulfonamido)phenyl)propanoate (v-2). The ester (7.38 g, 41.2 mmol) was dissolved in pyridine (17.0 ml, excess). After cooling to 0° C., methanesulfonyl chloride (4.55 ml, 57.7 mmol, 1.4 equiv) was added dropwise. The reaction was warmed to room temperature and stirred overnight. The reaction was quenched with water and diluted with DCM. The layers were separated and the organics were washed with brine. The resulting solution was concentrated to give a red solid. The crude material was purified using silica gel chromatography (1 EtOAc/1 Hexanes) to give a white solid (87%). $^1H$ NMR: ($CDCl_3$, 400 MHz) 7.20 (d, J=8.6 Hz, 2H), 7.15 (d, J=8.6 Hz, 2H), 6.45 (bs, NH, 1H), 3.68 (s, 3H), 3.00 (s, 3H), 2.94 (t, J=7.6 Hz, 2H), 2.63 (t, J=7.5 Hz, 2H). $^{13}C$ NMR ($CDCl_3$, 400 MHz): 173.4, 137.6, 135.2, 129.4, 121.4, 51.7, 38.5, 35.5, 30.1. M.S. (ESI) m/z=257.56 (M+H)

Step (iii). 3-(4-(methylsulfonamido)phenyl)propanoic acid (v-3). The sulfonamide ester (1.16 g, 4.5 mmol) was dissolved in methanol (50 ml). To this solution, 1.0 N NaOH (17.0 ml, 17.0 mmol, 3.8 equiv) was added. The mixture was stirred at room temperature overnight. TLC indicated the reaction was finished. The pH of the solution was adjusted to 3 with a solution of aqueous HCl. The volume of methanol was reduced by rotary evaporation (40 mbar), upon which the product crashed out of solution. The yellow crystals were filtered off and dried (0.900 g, 82%). $^1$H NMR (400 MHz, CD$_3$OD) 7.21 (d, J=8.6 Hz, 2H), 7.17 (d, J=8.6 Hz, 2H), 2.91 (s, 3H), 2.89 (t, J=7.6 Hz, 2H), 2.59 (t, J=7.6 Hz, 2H). $^{13}$C NMR (400 MHz, CD$_3$OD) 176.7, 139.0, 137.7, 130.5, 122.3, 39.1, 36.8, 31.4. M.S. (ESI) m/z=242.05 (M−H).

Step (iv). N-(2-(3,4-dichlorophenylamino)ethyl)-3-(4-(methylsulfonamido)phenyl)propanamide Compound 6). The carboxylic acid (0.700 g, 2.88 mmol) was dissolved in DMF (30.0 ml) and cooled to 0° C. To this solution, DMAP (0.352 g, 2.28 mmol, 1.1 equiv), and EDCI (0.552 g, 2.88 mmol, 1.0 equiv) were added to give a clear suspension. After stirring for 30 minutes, the amine (0.590 g, 2.88 mmol, 1.0 equiv) in THF (5.0 ml) was added dropwise to give a brown solution. The mixture was warmed to room temperature and stirred overnight. The reaction was monitored by TLC. To quench the reaction, 20 mL of 1.0 N HCl was added and the solution was extracted with 3×30 mL of EtOAc. The orgainic layer was dried with MgSO$_4$, filtered, and concentrated to give red oil. The crude material was purified by taking the residue up in DCM and stirring. Immediately a white powder precipitated out (0.920 g, 74%). $^1$H NMR (400 MHz, CD$_3$OD) 7.14-7.10 (mult, 5H), 6.72 (d, J=2.9 Hz, 1H), 6.51 (dd, J$_1$=8.9 Hz, J$_2$=2.6 Hz, 1H), 3.27 (t, 2H), 3.10 (t, J=6.4 Hz, 2H), 2.88 (s, 3H), 2.87 (t, J=6.5 Hz, 2H), 2.46, (t, J=6.4 Hz, 2H). $^{13}$C NMR (300 MHz, CDCl$_3$) 175.8, 150.0, 138.7, 138.3, 131.7, 130.5, 122.3, 114.4, 113.6, 44.0, 39.8, 39.2, 39.0, 32.3. M.S. Calc'd 429.0681. Found (HRMS) 431.08143 (M+H). E.A. Calc'd: C, 50.24; H, 4.92; N, 9.76. Found: C 49.94, H 4.91, N 9.74.

Step (v). N-(4-(3-(2-(3,4-dichlorophenylamino)ethylamino)propyl)phenyl)methanesulfonamide (Compound 7). The sulfonamide amide ((0.500 g, 1.2 mmol) was dissolved in THF (30.0 ml). After cooling to 0° C., a solution of Lithium Aluminum hydride (2.0 M solution in THF, 2.3 ml, 4.6 mmol, 4.0 equiv) was added dropwise. After stirring for 10 minutes at 0° C., the ice bath was removed and the reaction mixed was warmed to room temperature and stirred overnight. The mixture was diluted with DCM and water to give an emulsion. Rochelle's salt (sat'd solution) was added and the mixture stirred for 20 minutes before filtering over a pad of celite. The resulting liquid was separated, and the organics were washed with brine, dried over MgSO$_4$ and concentrated to give a white foam (0.358 g, 74%). The free base was converted to the HCl salt by bubbling HCl (g) through a solution of substrate dissolved in ethanol. The white powder precipitated out and was filtered off $^1$H NMR (300 MHz, CDCl$_3$) 7.20-7.11 (mult, 5H), 6.69 (d, J=2.8 Hz, 1H), 6.46 (dd, J$_1$=8.8 Hz, J$_2$=2.8 Hz), 4.36 (bs, 1H, NH), 3.156 (mult, 2H), 3.00 (s, 3H), 2.88 (t, J=6.2 Hz, 2H), 2.66 (t, J=7.1 Hz, 4H), 1.86-1.79 (mult, 3H). $^{13}$C NMR (300 MHz, CDCl$_3$) 148.1, 139.4, 134.8, 132.8, 130.7, 129.7, 121.6, 119.7, 113.9, 112.9, 49.0, 48.2, 43.2, 39.3, 32.9, 31.5. M.S. Calc'd 416.088. Found (HRMS): 416.069.

Step (vi). N-(4-(3-(3-(3,4-dichlorophenyl)-2-oxoimidazolidin-1I)propyl)phenyl)methanesulfonamide (Compound 8). The starting material diamine (0.113 g, 0.27 mmol) was dissolved in THF (10.0 ml). To this solution 1,1-carbonyldiimidazole (0.048 g, 0.30 mmol, 1.1 equiv) was added. The mixture stirred at room temperature overnight. After completion, the solution was evaporated to dryness and the residue was taken up in ethyl acetate, washed with brine (1×) and dried over Na$_2$SO$_4$, filtered, and concentrated to give a clear oil. The crude material was purified using silica gel chromatography (100% EtOAc) to give a white foam (0.070 g, 58%). $^1$H (400 MHz, CDCl$_3$) 7.72 (s, 1H), 7.16 (d, J=8.6 Hz, 2H), 7.07 (d, J=8.6 Hz, 2H), 7.02 (s, 1H), 6.64 (d, J=2.9 Hz, 1H), 6.41 (dd, J$_1$=8.5 Hz, J$_2$=2.9 Hz), 3.64 (t, J=6.0 Hz, 2H), 3.40-3.36 (mult, 4H), 2.97 (s, 3H), 2.57 (t, J=7.3 Hz, 2H), 1.26 (t, J=7.3 Hz, 2H). $^{13}$C (75 MHz, CDCl$_3$) 152.6, 147.1, 137.3, 136.8, 135.6, 130.9, 129.5, 121.6, 118.0, 113.6, 112.5. M.S. (ESI) Calc'd: 441.0681. Found: 442.07527 (M+H).

Compounds in the following table were synthesized according to variations in methods described for Examples 6, 7, and 8.

| COMPOUND | NAME |
| --- | --- |
|  | N-[2-(3,4-Dichloro-phenylamino)-ethyl]-2-(4-methanesulfonylamino-phenoxy)-acetamide |
|  | N-(4-{2-[2-(3,4-Dichloro-phenylamino)-ethylamino]-ethoxy}-phenyl)-methanesulfonamide |
|  | N-(4-{3-[4-(3,4-Dichloro-phenyl)-piperazin-1-yl]-3-oxo-propyl}-phenyl)-methanesulfonamide |

-continued

| COMPOUND | NAME |
|---|---|
| | N-(4-{3-[4-(3,4-DiFluoro-phenyl)-piperazin-1-yl]-3-oxo-propyl}-phenyl)-methanesulfonamide |
| | N-(4-{3-[4-(3,4-Dichloro-phenyl)-piperazin-1-yl]-propyl}-phenyl)-methanesulfonamide |
| | N-(4-{2-[4-(3,4-Dichloro-phenyl)-piperazin-1-yl]-2-oxo-ethoxy}-phenyl)-methanesulfonamide |
| | 6-{2-[4-(3,4-Dichloro-phenyl)-piperazin-1-yl]-2-oxo-ethoxy}-3H-benzooxazol-2-one |
| | 6-{2-[4-(3,4-DiFluoro-phenyl)-piperazin-1-yl]-2-oxo-ethoxy}-3H-benzooxazol-2-one |
| | 6-{2-[4-(4-Chloro-phenyl)-piperazin-1-yl]-2-oxo-ethoxy}-3H-benzooxazol-2-one |
| | N-[2-(3,4-Dichloro-phenylamino)-ethyl]-2-(2-oxo-2,3-dihydro-benzooxazol-6-yloxy)-acetamide |

| COMPOUND | NAME |
|---|---|
| | N-[3-(3,4-Dichloro-phenyl)-allyl]-2-(4-methanesulfonylamino-phenoxy)-acetamide |
| | N-[2-(3,4-Dichloro-phenylamino)-ethyl]-2-(4-hydroxy-phenoxy)-acetamide |
| | N-[2-(3,4-Dichloro-phenylamino)-ethyl]-3-(4-hydroxy-phenyl)-propionamide |
| | N-[2-(3,4-Dichloro-phenylamino)-ethyl]-2-(3-fluoro-4-hydroxy-phenoxy)-acetamide |

Example 9

General synthesis for quinolinone derivatives. Preparation of (S)-6-(3-(4-(4-chlorophenyl)piperazin-1-yl)-2-hydroxypropoxy)-3,4-dihydroquinolin-2(1H)-one

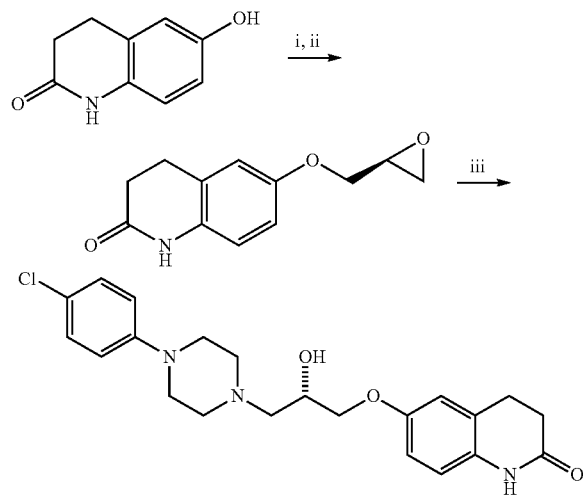

Steps (i) and (ii). Preparation of (S)-6-(oxiran-2-yl-methoxy)-3,4-dihydroquinolin-2(1H)-one. Reactions were performed according to the literature (Uno, T. et all; Chem. Pharm. Bull. 43(10) 1724-1733 (1995). Either stereoisomer could be formed from (S) or (R) epichlorohydrin and 6-hydroxy-3,4-dihydroquinolin-2(1H)-one.

Step (iii). A solution of 2 mmol of the quinolinone epoxide and 3 mmol 1-(4-chlorophenyl)piperazine in 10 ml ethanol was refluxed overnight. The solid was precipitated during the reflux which was filtered, and dried to give 0.42 g of a white solid (51% yield). $^1$H-NMR (400 MHz, CDCl$_3$) δ 2.55-2.65 (6H, m), 2.81-2.86 (2H, m), 2.93 (2H, t, J=7.6 Hz), 2.95-3.23 (4H, m), 3.48 (1H, bs), 3.94-3.99 (2H, m), 4.09-4.15 (1H, m), 6.69-6.77 (3H, m), 6.84 (2H, d, J=8.8 Hz), 7.21 (2H, d, J=8.8 Hz), 8.31 (1H, s); MS416 (M+H); HRMS416.17306; Elemental Analysis for C$_{22}$H$_{26}$ClN$_3$O$_3$; Calculated: C, 63.53; H, 6.30; N, 10.10. Found: C, 63.27; H, 6.29; N, 10.05.

Example 10

Preparation of (S)-5-(3-(4-(4-chlorophenyl)piperazin-1-yl)-2-hydroxypropoxy)-1H-benzo[d]imidazol-2(3H)-one

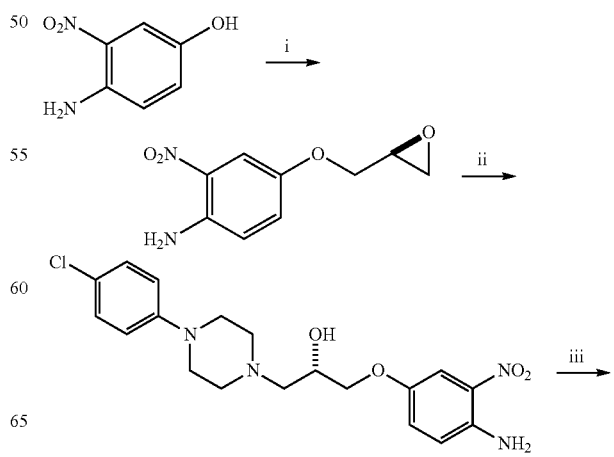

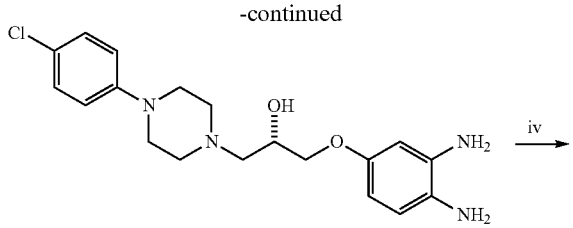

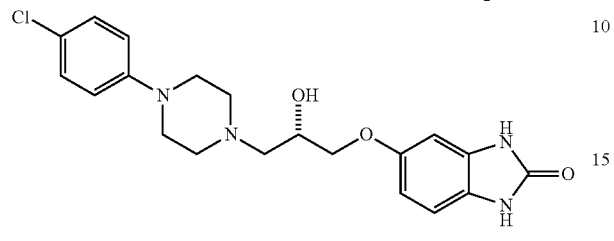

Step (i). A solution of 2-amino-3-nitrophenol (5.08 g, 33 mmol) and (2S)-(+)-glycidyl 3-nitrobenzenesulfonate (8.54 g, 33 mmol) in 75 mL of acetone was treated with $K_2CO_3$ (5.00 g, 36.3 mmol) and stirred at reflux for 18 hours. The suspension was cooled to ambient temperature; the solids were filtered; and the filtrate concentrated in vacuo to dryness. The resulting solids were partitioned between dichloromethane and water, and the aqueous layer extracted once with DCM. The organic layers were combined and dried over $Na_2SO_4$ and concentrated in vacuo to give an orange solid (0.3 g, 86.7% yield). $^1$H-NMR (400 MHz, CDCl$_3$) δ 3.45 (1H, t, J=4.8 Hz), 3.86-4.03 (1H, m), 4.64-4.67 (1H, m), 4.79 (1H, dd, J=2.4, 10.8 Hz), 5.14 (1H, t, J=5.6), 7.45 (1H, d, J=9.2 Hz), 7.62 (1H, dd, J=4.8, 9.2 Hz), 8.36 12H, d, J=6.8 Hz).

Step (ii). A solution of 2.54 mmol of (S)-2-nitro-4-(oxiran-2-ylmethoxy)aniline and 3.0 mmol of 1-(4-chlorophenyl)piperazine in 10 ml ethanol was refluxed overnight. The solvent was evaporated and product was purified with column chromatography using DCM:MeOH:NH$_4$OH (95:5:0.5). Gave 1.033 g (100% yield).

Step (iii). (S)-1-(4-amino-3-nitrophenoxy)-3-(4-(4-chlorophenyl)piperazin-1-yl)propan-2-ol (1.033 g, 2.54 mmol) was suspended in 40 ml ethanol and 30 ml water at room temperature and treated with excesses of sodium bicarbonate (2.56 g, 30.48 mmol) and sodium hydrosulfite (6.24 g, 30.48 mmol). The orange reaction mixture slowly became colorless in 3-4 hours, and the mixture was left to stir at room temperature for overnight. The suspension was filtered, and the filtrate concentrated in vacuo to a leave a white solid. This residue was partitioned between DCM and water, and the organic layer washed two times with brine. The combined organic extracts were concentrated in vacuo to give light brown solid (0.43 g, 45% yield). The compound was used directly for the next step without further purification.

Step (iv). The compound from step iii (0.430 g, 1.14 mmol) was suspended in mixture of 8 ml toluene and 14.25 ml 2N HCl at room temperature with vigorous stirring. An excess of triphosgene (3.61 g, 11.93 mmol) was added, and the stirring continued for overnight. The biphasic mixture was cautiously quenched and neutralized with sodium bicarbonate, causing an pinkish-white precipitate to form at the interface. The precipitate was filtered and purified with column chromatography using DCM:MeOH:NH$_4$OH (90:10:1) to give 0.283 g of a brown solid (47% yield). $^1$H-NMR (400 MHz, d$_6$-DMSO): δ 2.32-2.45 (1H, m), 2.53-2.64 (4H, m), 3.11 (4H, t, J=5.2 Hz), 3.79-3.83 (1H, m), 3.91 (1H, dd, J=4.0, 9.6 Hz), 3.94-4.01 (1H, m), 4.89 (1H, d, J=4.4 Hz), 6.51 (1H, d, J=2.4 Hz), 6.54 (1H, s), 6.79 (1H, d, J=8.4 Hz), 6.93 (2H, d, J=9.6 Hz), 7.22 (2H, d, J=9.2 Hz), 10.39 (1H, s), 10.52 (1H, s); HRMS=403.15259; HPLC=2.804 retention time (99% purity); Elemental analysis for $C_{20}H_{23}ClN_4O_3$ x 0.75 mol H2O: Calculated: C, 57.69; H, 5.93; N, 13.46. Found: C, 57.63; H, 5.63; N, 13.45.

Example 11

Preparation of (S)-6-(3-(4-(4-chlorophenyl)piperazin-1-yl)-2-hydroxypropoxy)quinolin-2(1H)-one

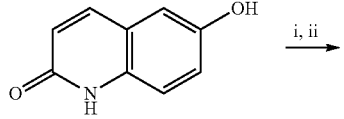

Steps i and ii. Steps i and ii: Preparation of (S)-6-(oxiran-2-ylmethoxy)-quinolin-2(1H)-one. Reactions were performed according to the literature (Uno, T. et all; Chem. Pharm. Bull. 43(10) 1724-1733 (1995). Either stereoisomer could be formed from (S) or (R) epichlorohydrin and 6-hydroxy-3,4-dihydroquinolin-2(1H)-one.

Step (iii). A solution of 2 mmol the (5)-dihydroquinolinone epoxide and 3 mmol 1-(4-chlorophenyl)piperazine in 10 ml ethanol was refluxed overnight. The solid was precipitated during the reflux which was filtered, washed with ethanol, and dried to give 0.314 g of a white solid (76% yield). $^1$H-NMR (400 MHz, dmso-d$_6$) δ 2.42 (1H, dd, J=6.4, 12.8 Hz), 2.53-2.64 (4H, m), 3.11 (4H, t, J=5.2 Hz), 3.88-3.92 (1H, m), 4.00 (2H, d, J=6.4 Hz), 4.94 (1H, d, J=4.4 Hz), 6.48 (1H, d, J=9.6 Hz), 6.92 (2H, d, J=9.2 Hz), 7.15-7.25 (5H, m), 7.83 (1H, d, J=9.6 Hz), 11.64 (1H, s); HRMS=414.15720; HPLC=8.196 retention time (99% purity); Elemental analysis: $C_{22}H_{24}ClN_3O_3$; Calculated: C, 63.84; H, 5.84; N, 10.15. Found: C, 63.42; H, 5.80; N, 10.11.

Example 12

Preparation of (S)-5-(3-(4-(4-chlorophenyl)piperazin-1-yl)-2-hydroxypropoxy)indolin-2-one

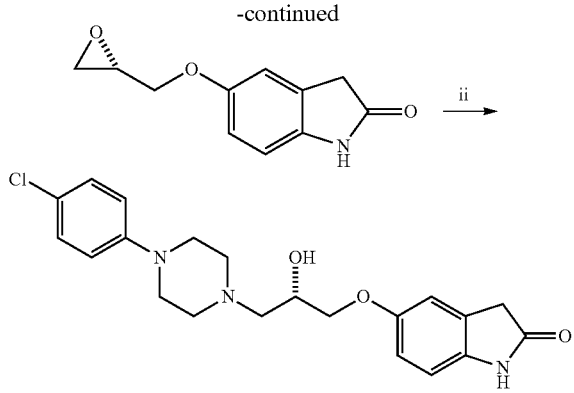

Step (i). Diethylazodicarboxylate (40% solution in toluene, 1.9 mL, 4.4 mmol) was added to a mixture of 5-hydroxy-oxindole (0.65 g, 4.4 mmol), triphenylphosphine (1.14 g, 4.4 mmol), and (S)-glycidol (0.29 mL, 4.4 mmol) in anhydrous tetrahydrofuran at 0° C. After the addition, the mixture was stirred at 20° C. for 16 h. The volatiles were evaporated on a rotavap and the residue was purified on silica gel using hexane/ethyl acetate solvent mixture. Yield: 0.4 g (impure). $^1$H NMR (400 MHz, CDCl$_3$): δ 8.29 (b.s, 1H), 6.92 (s, 1H), 6.78 (s, 2H), 4.22 (m, 1H), 3.88 (m, 1H), 3.52 (s, 2H), 3.36 (m, 1H), 2.91 (m, 1H), 2.76 (m, 1H).

Step (ii). A mixture of (S)-indolinone epoxide (0.35 g, 1.7 mmol) and 4-chlorophenylpiperazine (0.35 g, 1.8 mmol) in ethanol (10 mL) was heated at 70° C. for 16 hours. The reaction mixture was cooled to room temperature and volatiles were evaporated. The residue was purified on silica gel using a dichloromethane:methanol:ammonia solvent mixture. Gave 0.17 g (25%) of a brown solid. $^1$H NMR (400 MHz, d$^6$-DMSO): δ 10.19 (b.s), 7.21 (d, 2H), 6.92 (d, 2H), 6.88 (s, 1H), 6.77 (d, 1H), 6.68 (d, 1H), 4.88 (d, 1H), 3.96 (m, 1H), 3.91 (m, 1H), 3.80 (m, 1H), 3.43 (s, 2H), 3.11 (m, 4H), 2.58 (m, 4H), 2.41 (m, 1H). ES-MS m/z 402.16 (C$_2$M$_{24}$ClN$_3$O$_3$+1)$^+$. Analysis Calculated for C$_{21}$H$_{24}$ClN$_3$O$_3$: % C, 62.76; % H 6.02; % N 10.46. found: % C, 62.62; % H, 6.06; % N, 10.36.

Example 13

Preparation of (R)-6-(3-(5,6-dichloro-1H-benzo[d]imidazol-2-ylthio)-2-hydroxypropoxy)benzo[d]oxazol-2(3H)-one

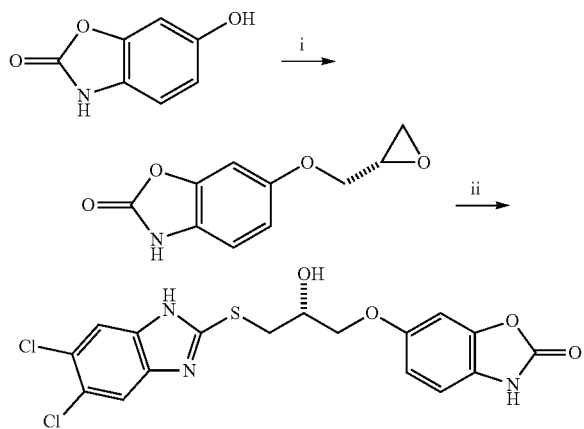

Step i. (S)-6-(oxiran-2-ylmethoxy)benzo[d]oxazol-2(3H)-one. A mixture of 0.6 g of 6-hydroxy-2-benzoxazolinone and 0.75 g of potassium carbonate was diluted with 8 mL of N,N-dimethylformamide. The reaction was stirred at room temperature for 1 hour, and then 1.2 g of (S)-glycidyl nosylate was added. The reaction was stirred for 3 days at room temperature. The reaction was then quenched with water, extracted with NaHCO$_3$(aq.) solution and ethyl acetate. The organic layer was separated and dried over Na$_2$SO$_4$(s). Filtration and solvent removal gave a residue that was subjected to column chromatography (hexanes-ethyl acetate gradient). Fraction combination and solvent removal gave 0.39 g of a white solid (47% yield). $^1$H NMR (d$^6$-DMSO): δ 2.6 (quart, 1H, J=3 Hz), 2.76 (t, 1H, J=4 Hz), 3.23 (m, 1H), 3.71 (dd, 1H, J=6 Hz, J=15 Hz), 4.11 (dd, 1H, J=3 Hz, J=15 Hz), 6.59 (dd, 1H, J=2 Hz, J=9 Hz), 6.73 (d, 1H, J=2 Hz), 7.06 (d, 1H, J=8 Hz), 9.48 (s, 1H).

Step (ii). Preparation of (R)-6-(3-(5,6-dichloro-1H-benzo[d]imidazol-2-ylthio)-2-hydroxypropoxy)benzo[d]oxazol-2(3H)-one. 5,6-Dichloro-2-thiabenzimidazole. $^1$H NMR (d6-DMSO): δ 3.59 (dd, 1H, J=6 Hz, J=8 Hz), 3.7 (d, 2H, J=6 Hz), 3.93 (t, 1H, J=25 Hz), 4.93 (M, 2h), 6.17 (dd, 1H, J=2 Hz, J=8 Hz), 6.3 (d, 1H, J=3 Hz), 6.94 (d, 1H, J=8 Hz), 7.7 (s, 2H), 9.4 (s, 1H), 9.59 (s, 1H), 12.98 (s, 1H); MS (m/z): 426 (M+H), 428 (M+2+H); HRMS: Calcd. for C$_{17}$H$_{14}$$^{35}$Cl$_2$N$_3$O$_4$5: 426.00821. Found: 426.00739.

The following compounds were prepared using similar procedures.

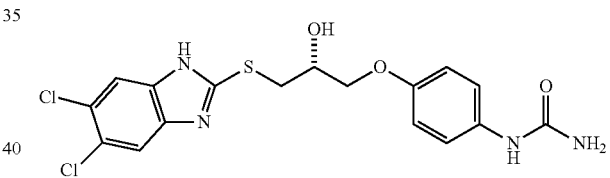

(R)-1-(4-(3-(5,6-dichloro-1H-benzo[d]imidazol-2-ylthio)-2-hydroxypropoxy)phenyl)urea. To a solution of 0.19 g of 5,6-dichloro-1H-benzo[d]imidazole-2-thiol in 4 mL of N,N-dimethylformamide was added 0.36 g of cesium carbonate. The reaction was stirred at room temperature for 2 hours. Next, 0.1 g of the (S)-epoxide was added, and the reaction heated to 60° C. for 18 hours. The reaction was cooled, extracted with ethyl acetate and washed with NaHCO$_3$ (aq.) solution. The aqueous layer was re-extracted with ethyl acetate, and the organic layers combined and dried over Na$_2$SO$_4$(s). Filtration and solvent removal gave a dark yellow solid. Column chromatography with an ethyl acetate/methanol gradient gave an off-white solid after fraction combination and solvent removal. The solids were heated with ethyl acetate to 70° C. for 15 minutes. The solution was cooled, filtered, and the solids were washed with ethyl acetate. Drying gave 0.099 g of a white solid. $^1$H NMR (d$^6$-DMSO): δ 3.31 (bs, 1H), 3.38 (dd, 1H, J=7 Hz, J=13 Hz), 3.55 (dd, 1H, J=5 Hz, J=13 Hz), 3.91 (m, 2H), 4.09 (m, 1H), 5.68 (s, 2H), 6.79 (d, 2H, J=9 Hz), 7.24 (d, 2H, J=9 Hz), 7.64 (s, 2H), 8.27 (s, 1H); MS: 429 (M+H+2), 427 (M+H); HRMS: 427.03926; HPLC: 100% peak area at 7.1 min. retention time.

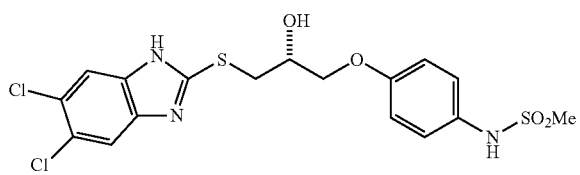 [SMILES: CS(=O)(=O)Nc1ccc(OC[C@@H](O)CSc2nc3cc(Cl)c(Cl)cc3[nH]2)cc1]

(R)—N-(4-(3-(5,6-dichloro-1H-benzo[d]imidazol-2-ylthio)-2-hydroxypropoxy)phenyl)methanesulfonamide.

mide was stirred at room temperature for one hour. Next, 0.25 g of the sulfonamide (S) epoxide was added and the reaction was heated to 60° C. for 8 hours. The reaction was cooled, and diluted with water. The aqueous phase was extracted with ethyl acetate, and Physical data: $^1$H NMR (d$^6$-DMSO): δ 2.34 (s, 3H), 2.84 (s, 3H), 3.36 (dd, 1H, J=8 Hz, J=13 Hz), 3.5 (dd, 1H, J=5 Hz, J=13 Hz), 3.95 (m, 2H), 4.1 (quint, 1H, J=6 Hz), 5.7 (bs, 1H), 6.89 (d, 2H, J=9 Hz), 6.9 (m, 1H), 7.1 (d, 2H, J=9 Hz), 7.17 (bs, 1H), 7.26 (d, 1H, J=6 Hz), 9.39 (bs, 1H); MS m/z: 408 (M+H); HRMS: Calcd. for $C_{18}H_{22}N_3O_4S_2$: 408.10517. Found: 408.10416.

| Compound | Name |
|---|---|
| ![structure] | (R)-4-(3-(5,6-dichloro-1H-benzo[d]imidazol-2-ylthio)-2-hydroxypropoxy)phenol |
| ![structure] | (R)-5-(3-(5,6-dichloro-1H-benzo[d]imidazol-2-ylthio)-2-hydroxypropoxy)indolin-2-one |
| ![structure] | (R)-6-(3-(5,6-dichloro-1H-benzo[d]imidazol-2-ylthio)-2-hydroxypropoxy)-3,4-dihydroquinolin-2(1H)-one |
| ![structure] | (R)-6-(3-(5,6-dichloro-1H-benzo[d]imidazol-2-ylthio)-2-hydroxypropoxy)quinolin-2(1H)-one |

Physical data: $^1$H NMR (d$^6$-DMSO): δ 2.84 (s, 3H), 3.99 (dd, 1H, J=7 Hz, J=13 Hz), 3.56 (dd, 1H, J=5 Hz, J=14 Hz), 3.96 (m, 2H), 4.12 (m, 1H), 6.9 (d, 2H, J=9 Hz), 7.1 (d, 2H, J=9 Hz), 7.65 (s, 2H), 9.38 (bs, 1H); MS: 462 (M+H), 464 (M+2+H); FIRMS: calcd. for $C_{12}H_{18}{}^{35}Cl_2N_3O_4S_2$: 462.01158. Observed: 462.01045.

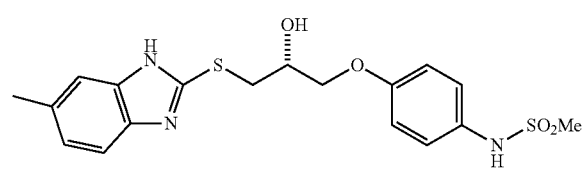 [SMILES: Cc1ccc2nc(SC[C@H](O)COc3ccc(NS(C)(=O)=O)cc3)[nH]c2c1]

(R)—N-(4-(2-hydroxy-3-(6-methyl-1H-benzo[d]imidazol-2-ylthio)propoxy)phenyl)methanesulfonamide. A solution of 0.25 g of 6-methyl-1H-benzo[d]imidazol-2-thiol and 0.5 g of cesium carbonate in 5 mL of N,N-dimethylforma- Example 14

Expression of Glutamate Receptors in *Xenopus laevis* Oocytes cRNA was synthesized from linearized template cDNA for rat glutamate receptor subunits according to manufacturer specifications (Ambion). Quality of synthesized cRNA was assessed by gel electrophoresis, and quantity was estimated by spectroscopy and gel electrophoresis. Stage V and VI oocytes were surgically removed from the ovaries of large, well-fed and healthy *Xenopus laevis* anesthetized with 3-amino-benzoic acid ethyl ester (3 gm/l) as previously described. Clusters of isolated oocytes were incubated with 292 U/ml Worthington (Freehold, N.J.) type IV collagenase or 1.3 mg/ml collagenase (Life Technologies, Gaithersburg, Md.; 17018-029) for 2 hr in Ca$^{2+}$-free solution comprised of (in mM) 115 NaCl, 2.5 KCl, and 10 HEPES, pH 7.5, with slow agitation to remove the follicular cell layer. Oocytes were then washed extensively in the same solution supplemented with 1.8 mM CaCl$_2$ and maintained in Barth's solution comprised of (in mM): 88 NaCl, 1 KCl, 2.4 NaHCO$_3$, 10 HEPES, 0.82 MgSO$_4$, 0.33 Ca(NO$_3$)$_2$, and 0.91 CaCl$_2$ and supplemented with 100 µg/ml gentamycin, 10 µg/ml streptomycin, and 10 µg/ml penicillin. Oocytes were manually defolliculated and injected within 24 hrs of isolation with 3-5 ng of NR1 subunit cRNA and 7-10 ng of NR2 cRNA subunit in a 50 nl volume, or 5-10 ng of AMPA or kainate receptor cRNAs in a 50 nl volume, and incubated in Barth's solution at 18° C. for 1-7 d. Glass injection pipettes had tip sizes ranging from 10-20 microns, and were backfilled with mineral oil.

Example 15

Two Electrode Voltage Clamp Recording from *Xenopus laevis* Oocytes

Two electrode voltage-clamp recordings were made 2-7 days post-injection as previously described. Oocytes were placed in a dual-track plexiglass recording chamber with a single perfusion line that splits in a Y-configuration to perfuse two oocytes. Dual recordings were made at room temperature (23° C.) using two Warner OC725B two-electrode voltage clamp amplifiers, arranged as recommended by the manufacturer. Glass microelectrodes (1-10 Megaohms) were filled with 300 mM KCl (voltage electrode) or 3 M KCl (current electrode). The bath clamps communicated across silver chloride wires placed into each side of the recording chamber, both of which were assumed to be at a reference potential of 0 mV. Oocytes were perfused with a solution comprised of (in mM) 90 NaCl, 1 KCl, 10 HEPES, and 0.5 BaCl$_2$; pH was adjusted by addition of 1-3 M NaOH of HCl. Oocytes were recorded under voltage clamp at −40 mV. Final concentrations for control application of glutamate (50 µM) plus glycine (30 µM) were achieved by adding appropriate volumes from 100 and 30 mM stock solutions, respectively. In addition, 10 µM final EDTA was obtained by adding a 1:1000 dilution of 10 mM EDTA, in order to chelate contaminant divalent ions such as Zn$^{2+}$. Concentration-response curves for experimental compounds were obtained by applying in successive fashion maximal glutamate/glycine, followed by glutamate/glycine plus variable concentrations of experimental compounds. Dose response curves consisting of 4 to 8 concentrations were obtained in this manner. The baseline leak current at −40 mV was measured before and after recording, and the full recording linearly corrected for any change in leak current. Oocytes with glutamate-evoked responses smaller than 50 nA were not included in the analysis. The level of inhibition by applied experimental compounds was expressed as a percent of the initial glutamate response, and averaged together across oocytes from a single frog. Each experiment consisted of recordings from 3 to 10 oocytes obtained from a single frog. Results from 3-6 experiments were pooled, and the average percent responses at antagonist concentrations were fitted by the equation, $$\text{Percent Response} = (100-\text{minimum})/(1+([\text{conc}]/IC_{50})^{nH}) + \text{minimum}$$

where minimum is the residual percent response in saturating concentration of the experimental compounds, IC$_{50}$ is the concentration of antagonist that causes half of the achievable inhibition, and nH is a slope factor describing steepness of the inhibition curve. Minimum was constrained to be greater than or equal to 0.

TABLE A

| ASSAY RESULTS FOR COMPOUNDS PREPARED IN EXAMPLES 1 AND 2. | | |
|---|---|---|
| COMPOUND | IC$_{50}$ at pH 6.9 (nM) | IC$_{50}$ at pH 7.6 (nM) |
| [structure: MeO$_2$SHN-phenyl-O-CH$_2$-CH(OH)-CH$_2$-N(piperazine)-N-(3,4-difluorophenyl)] | 31 | 557 |
| [structure: MeO$_2$SHN-phenyl-O-CH$_2$-CH(OH)-CH$_2$-NH-CH$_2$-CH$_2$-NH-(3,4-dichlorophenyl)] | 12 | 62 |
| [structure: MeO$_2$SHN-phenyl-O-CH$_2$-CH(OH)-CH$_2$-N(piperazine)-N-(3,4-dichlorophenyl)] | 296 | 1,020 |

TABLE A-continued

ASSAY RESULTS FOR COMPOUNDS PREPARED IN EXAMPLES 1 AND 2.

| COMPOUND | IC$_{50}$ at pH 6.9 (nM) | IC$_{50}$ at pH 7.6 (nM) |
| --- | --- | --- |
| MeO$_2$SHN-C$_6$H$_4$-O-CH$_2$-CH(OH)-CH$_2$-N(piperazine)-C$_6$H$_4$-Cl | 32 | 270 |
| MeO$_2$SHN-C$_6$H$_4$-O-CH$_2$-CH(OH)-CH$_2$-N(piperazine)-C$_6$H$_5$ | 213 | 1,020 |
| MeO$_2$SHN-C$_6$H$_4$-O-CH$_2$-CH(OH)-CH$_2$-N(piperazine)-C$_6$H$_4$-OH | 2,400 | 28,000 |
| MeO$_2$SHN-C$_6$H$_4$-O-CH$_2$-CH(OH)-CH$_2$-N(piperazine)-2-pyridyl | 1,810 | 12,700 |
| MeO$_2$SHN-C$_6$H$_4$-O-CH$_2$-CH(OH)-CH$_2$-N(piperazine)-4-pyridyl | >30,000 | >30,000 |
| MeO$_2$SHN-C$_6$H$_4$-O-CH$_2$-CH(OH)-CH$_2$-NH-CH$_2$-CH$_2$-NH-C$_6$H$_5$ | 55 | 133 |

TABLE A-continued

ASSAY RESULTS FOR COMPOUNDS PREPARED IN EXAMPLES 1 AND 2.

| COMPOUND | IC$_{50}$ at pH 6.9 (nM) | IC$_{50}$ at pH 7.6 (nM) |
|---|---|---|
| [structure] | 108 | 199 |
| [structure] | 7 | 38 |
| [structure] | 163 | 2,580 |
| [structure] | 38 | 71 |

TABLE B

ASSAY RESULTS FOR COMPOUNDS PREPARED IN EXAMPLE 3.

| COMPOUND | IC$_{50}$ at pH 6.9 (nM) | IC$_{50}$ at pH 7.6 (nM) |
|---|---|---|
| [structure] | 79 | 726 |

TABLE B-continued
ASSAY RESULTS FOR COMPOUNDS PREPARED IN EXAMPLE 3.
| COMPOUND | IC$_{50}$ at pH 6.9 (nM) | IC$_{50}$ at pH 7.6 (nM) |
|---|---|---|
| 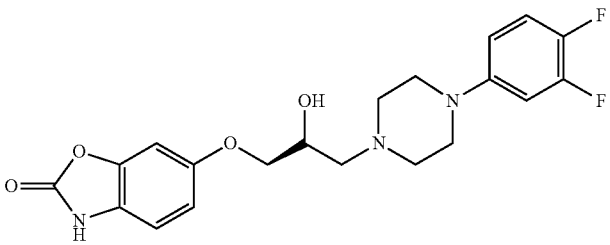 | 145 | 1,700 |
| 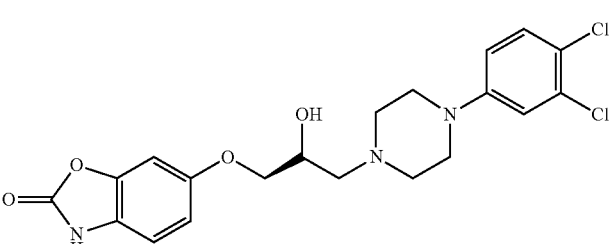 | 185 | 1,500 |
| 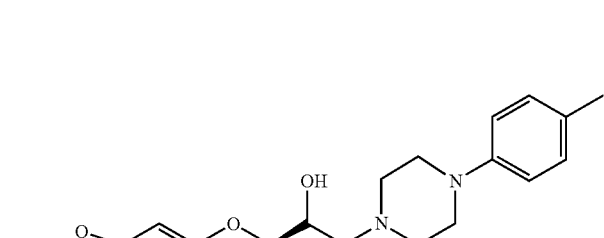 | 72 | 644 |
| 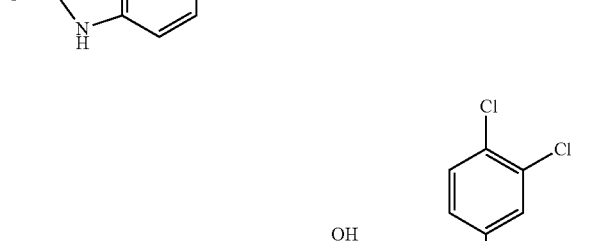 | 185 | 446 |
| 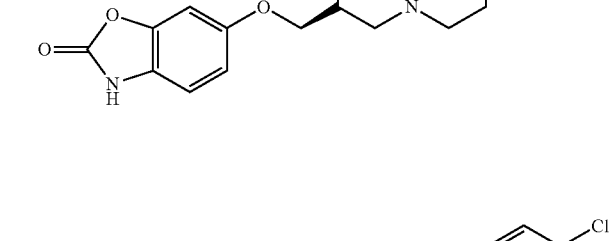 | 25 | 97 |

TABLE C
ASSAY RESULTS FOR COMPOUNDS PREPARED ACCORDING TO EXAMPLE 4.
| COMPOUND | IC$_{50}$ at pH 6.9 (nM) | IC$_{50}$ at pH 7.6 (nM) |
|---|---|---|
| 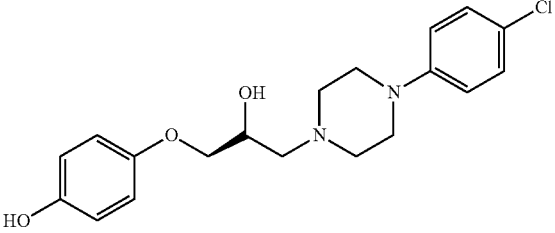 | 80 | 814 |
| 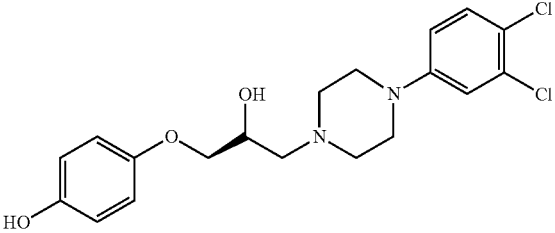 | 131 | 611 |
| 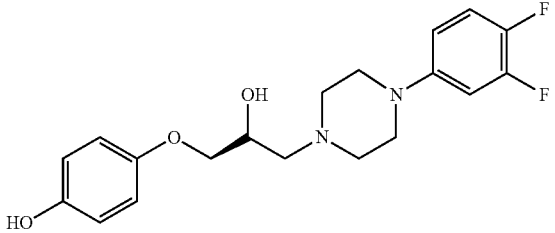 | 87 | 980 |
| 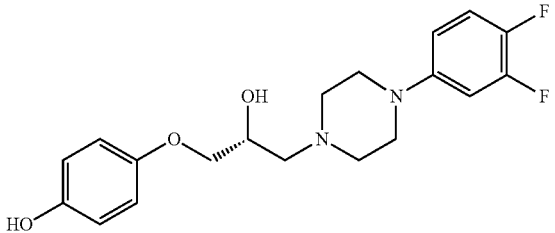 [SMILES: Oc1ccc(OC[C@H](O)CN2CCN(c3ccc(F)c(F)c3)CC2)cc1] | 50 | 272 |
| 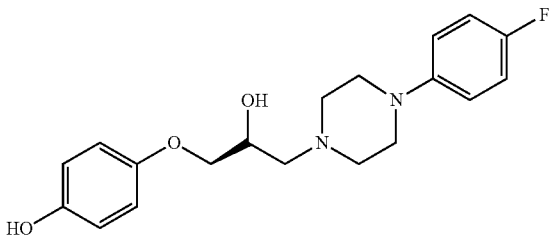 | 87 | 529 |
| 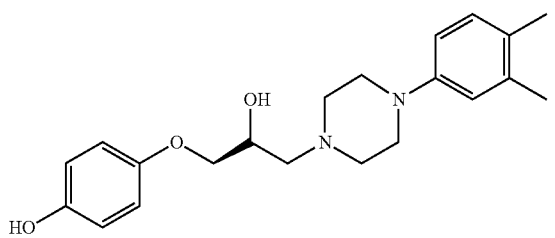 | 1,500 | 5,790 |

TABLE C-continued
ASSAY RESULTS FOR COMPOUNDS PREPARED ACCORDING TO EXAMPLE 4.
| COMPOUND | IC$_{50}$ at pH 6.9 (nM) | IC$_{50}$ at pH 7.6 (nM) |
|---|---|---|
| 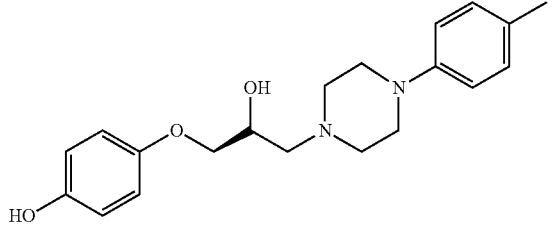 | 70 | 260 |
| 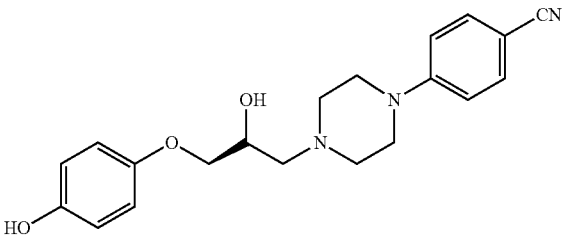 | 460 | 4,370 |
| 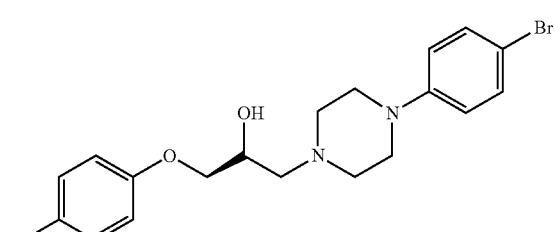 | 73 | 204 |
| 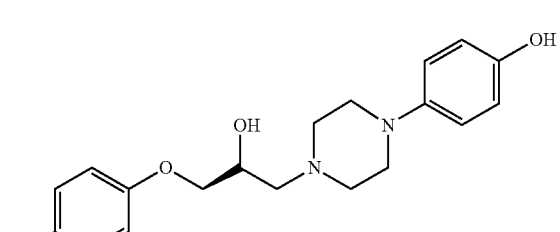 | 576 | 4,700 |
| 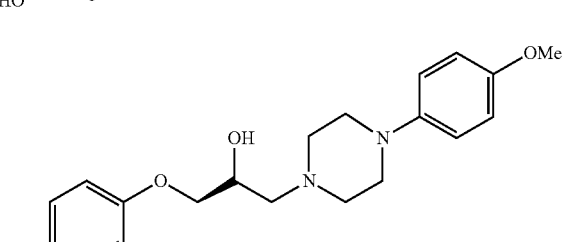 | 562 | 9,740 |
| 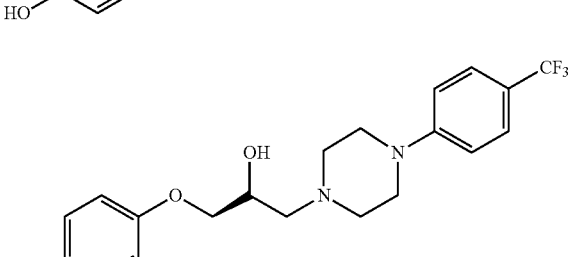 | 113 | 448 |

TABLE C-continued
ASSAY RESULTS FOR COMPOUNDS PREPARED ACCORDING TO EXAMPLE 4.
| COMPOUND | IC$_{50}$ at pH 6.9 (nM) | IC$_{50}$ at pH 7.6 (nM) |
|---|---|---|
| 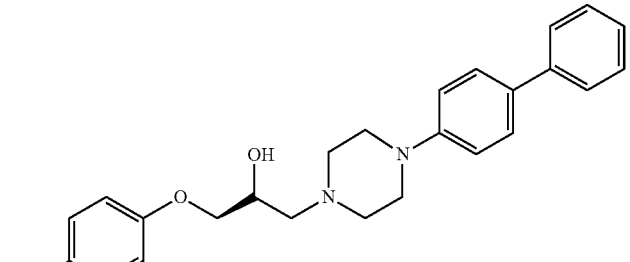 | 6,950 | 191,300 |
| 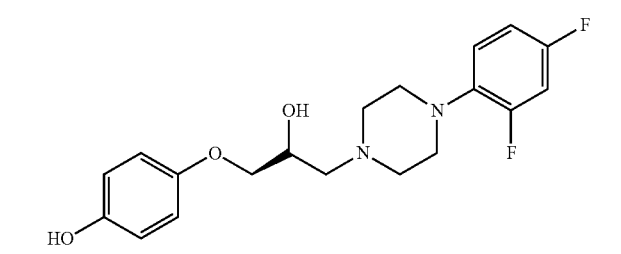 | 529 | 3,560 |
| 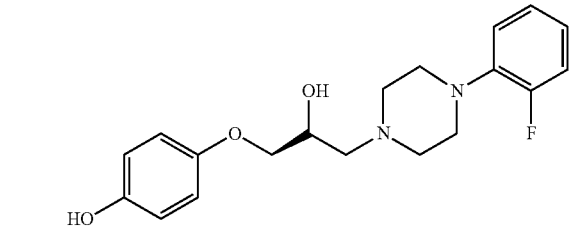 | 541 | 1,730 |
| 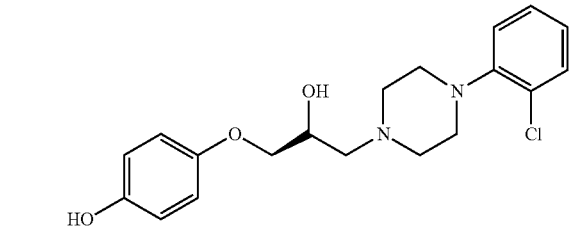 | 978 | 4,390 |
| 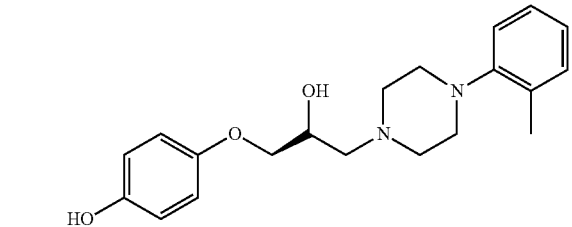 | 430 | 3,930 |
| 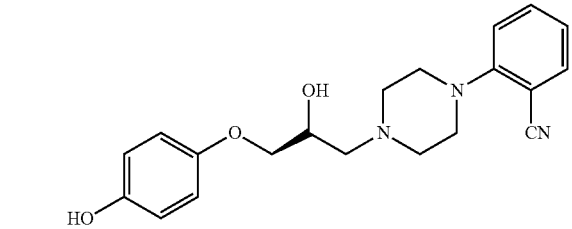 | 3,210 | 8,330 |

TABLE C-continued

ASSAY RESULTS FOR COMPOUNDS PREPARED ACCORDING TO EXAMPLE 4.

| COMPOUND | IC$_{50}$ at pH 6.9 (nM) | IC$_{50}$ at pH 7.6 (nM) |
| --- | --- | --- |
| (4-hydroxyphenoxy)-CH$_2$-CH(OH)-CH$_2$-(4-phenylpiperazin-1-yl) | 217 | 476 |
| (4-hydroxyphenoxy)-CH$_2$-CH(OH)-CH$_2$-(4-(3-fluorophenyl)piperazin-1-yl) | 211 | 598 |
| (4-hydroxyphenoxy)-CH$_2$-CH(OH)-CH$_2$-(4-(3-chlorophenyl)piperazin-1-yl) | 257 | 4,800 |
| (4-hydroxyphenoxy)-CH$_2$-CH(OH)-CH$_2$-(4-(3-methylphenyl)piperazin-1-yl) | 341 | 1,740 |
| (4-hydroxyphenoxy)-CH$_2$-CH(OH)-CH$_2$-(4-(3-trifluoromethylphenyl)piperazin-1-yl) | 386 | 3,790 |
| (4-hydroxyphenoxy)-CH$_2$-CH(OH)-CH$_2$-NH-CH$_2$CH$_2$-(3,4-dichlorophenyl) | 197 | 501 |

TABLE C-continued

ASSAY RESULTS FOR COMPOUNDS PREPARED ACCORDING TO EXAMPLE 4.

| COMPOUND | IC$_{50}$ at pH 6.9 (nM) | IC$_{50}$ at pH 7.6 (nM) |
|---|---|---|
| [structure] | 585 | 6,500 |
| [structure] | 116 | 330 |
| [structure] | 114 | 549 |
| [structure] | 191 | 298 |

TABLE D

ASSAY RESULTS FOR COMPOUNDS MADE ACCORDING TO EXAMPLE 5.

| COMPOUND | IC$_{50}$ at pH 6.9 | IC$_{50}$ at pH 7.6 |
|---|---|---|
| [structure] | 82 | 696 |
| [structure] | 557 | 10,400 |

TABLE D-continued

ASSAY RESULTS FOR COMPOUNDS MADE ACCORDING TO EXAMPLE 5.

| COMPOUND | IC$_{50}$ at pH 6.9 | IC$_{50}$ at pH 7.6 |
| --- | --- | --- |
| (structure) | 117 | 625 |
| (structure) | 46 | 452 |
| (structure) | 19 | 60 |
| (structure) | 3,030 | 15,700 |
| (structure) | 1,540 | 16,200 |

TABLE E

ASSAY RESULTS FOR COMPOUNDS MADE ACCORDING TO EXAMPLES 6, 7, AND 8.

| COMPOUND | IC$_{50}$ at pH 6.9 | IC$_{50}$ at pH 7.6 |
|---|---|---|
| MeO$_2$S-NH-C$_6$H$_4$-CH$_2$CH$_2$C(O)NH-CH$_2$CH$_2$-NH-C$_6$H$_3$(3,4-Cl$_2$) | 30 | 55 |
| MeO$_2$S-NH-C$_6$H$_4$-(CH$_2$)$_3$-NH-CH$_2$CH$_2$-NH-C$_6$H$_3$(3,4-Cl$_2$) | 2 | 21 |
| MeO$_2$S-NH-C$_6$H$_4$-(CH$_2$)$_3$-[imidazolidin-2-one]-N-C$_6$H$_3$(3,4-Cl$_2$) | 160 | 809 |
| MeO$_2$S-NH-C$_6$H$_4$-O-CH$_2$-C(O)NH-CH$_2$CH$_2$-NH-C$_6$H$_3$(3,4-Cl$_2$) | 13 | 58 |
| MeO$_2$S-NH-C$_6$H$_4$-O-CH$_2$CH$_2$-NH-CH$_2$CH$_2$-NH-C$_6$H$_3$(3,4-Cl$_2$) | 14 | 36 |
| MeO$_2$S-NH-C$_6$H$_4$-CH$_2$CH$_2$C(O)-[piperazine]-N-C$_6$H$_3$(3,4-Cl$_2$) | 670 | 5,330 |
| MeO$_2$S-NH-C$_6$H$_4$-CH$_2$CH$_2$C(O)-[piperazine]-N-C$_6$H$_3$(3,4-F$_2$) | 2,200 | 8,400 |
| MeO$_2$S-NH-C$_6$H$_4$-(CH$_2$)$_3$-[piperazine]-N-C$_6$H$_3$(3,4-Cl$_2$) | 230 | 2,730 |

TABLE E-continued

ASSAY RESULTS FOR COMPOUNDS MADE ACCORDING TO EXAMPLES 6, 7, AND 8.

| COMPOUND | $IC_{50}$ at pH 6.9 | $IC_{50}$ at pH 7.6 |
| --- | --- | --- |
| MeO2S-NH-C6H4-O-CH2-C(O)-N(piperazine)N-(3,4-dichlorophenyl) | 40 | 129 |
| 2-oxo-benzoxazol-6-yl-O-CH2-C(O)-N(piperazine)N-(3,4-dichlorophenyl) | 41 | 45 |
| 2-oxo-benzoxazol-6-yl-O-CH2-C(O)-N(piperazine)N-(3,4-difluorophenyl) | 307 | 467 |
| 2-oxo-benzoxazol-6-yl-O-CH2-C(O)-N(piperazine)N-(4-chlorophenyl) | 189 | 243 |
| 2-oxo-benzoxazol-6-yl-O-CH2-C(O)-NH-CH2CH2-NH-(3,4-dichlorophenyl) | 80 | 150 |
| MeO2S-NH-C6H4-CH2CH2-C(O)-NH-CH=CH-(3,4-dichlorophenyl) | 10 | 70 |
| HO-C6H4-O-CH2-C(O)-NH-CH2CH2-NH-(3,4-dichlorophenyl) | 280 | 515 |

TABLE E-continued

ASSAY RESULTS FOR COMPOUNDS MADE ACCORDING TO EXAMPLES 6, 7, AND 8.

| COMPOUND | $IC_{50}$ at pH 6.9 | $IC_{50}$ at pH 7.6 |
|---|---|---|
| (structure) | 210 | 339 |

Example 16

In Vitro Binding Studies for Secondary Effects

Compounds were evaluated for binding to the human ether-a-go-go potassium channel (hERG) expressed in HEK293 cells by displacement of $^3$[H]-astemizole according to the methods by Finlayson et al. (K. Finlayson., L. Turnbull, C. T. January, J. Sharkey, J. S. Kelly; [3H]Dofetilide binding to HERG transfected membranes: a potential high throughput preclinical screen. *Eur. J. Pharmacol.* 2001, 430, 147-148). Compounds were incubated at 1 or 10 µM final concentration, in duplicate, and the amount of displaced $^3$[H]-astemizole determined by liquid scintillation spectroscopy. In some cases, a seven concentration (each concentration in duplicate) displacement curve was generated to determine an $IC_{50}$.

Binding to the rat alpha-1 adrenergic receptor in rat brain membranes was determined by displacement of $^3$[H]-prazosin (P. Greengrass and R. Bremner; Binding characteristics of 3H-prazosin to rat brain a-adrenergic receptors. *Eur. J. Pharmacol.* 1979, 55: 323-326). Compounds were incubated at 0.3 or 3 µM final concentration, in duplicate, and the amount of displaced $^3$[H]-prazosin determined by liquid scintillation spectroscopy.

Binding $IC_{50}$ values were determined from displacement curves (four-six concentrations, each concentration in duplicate) fit by a non-linear, least squares, regression analysis using MathIQ (ID Business Solutions Ltd., UK). The binding Ki's were determined from the $IC_{50}$ according to the method of Cheng and Prusoff (Y. Cheng and W. H. Prusoff; Relationship between the inhibition constant (K1) and the concentration of inhibitor which causes 50 percent inhibition (IC50) of an enzymatic reaction. *Biochem. Pharmacol.* 1973, 22: 3099-3108).

TABLE F

COMPARISON OF IC50 VALUES FOR NMDA ANTAGONISM AT PH 6.9 AND 7.6 AND HERG AND A1 ADRENERGIC RECEPTORS

| Compound | $IC_{50}$ pH 6.9 (nM) | $IC_{50}$ pH 7.6 (nM) | hERG Ki (nM) | α1 $IC_{50}$ (nM) |
|---|---|---|---|---|
| 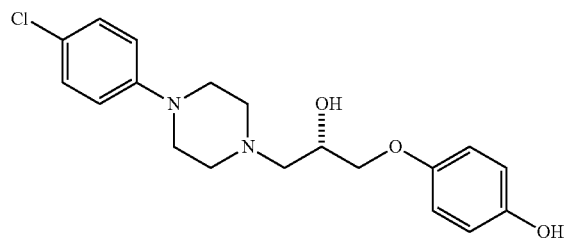 [SMILES: Oc1ccc(OC[C@@H](O)CN2CCN(c3ccc(Cl)cc3)CC2)cc1] | 74 | 555 | 39,000 | 720 |
| 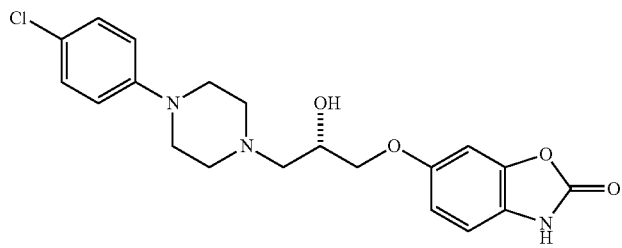 [SMILES: O=c1[nH]c2ccc(OC[C@@H](O)CN3CCN(c4ccc(Cl)cc4)CC3)cc2o1] | 51 | 447 | 1,600 | 620 |

TABLE F-continued

COMPARISON OF IC50 VALUES FOR NMDA ANTAGONISM AT PH 6.9 AND 7.6 AND hERG AND A1 ADRENERGIC RECEPTORS

| Compound | IC$_{50}$ pH 6.9 (nM) | IC$_{50}$ pH 7.6 (nM) | hERG Ki (nM) | α1 IC$_{50}$ (nM) |
|---|---|---|---|---|
| [structure: 4-chlorophenyl-piperazine-CH2-CH(OH)-CH2-O-C6H4-NHSO2Me] | 32 | 270 | 553 | 350 |
| [structure: 4-chlorophenyl-piperazine-CH2-CH(OH)-CH2-O-C6H4-NHC(O)NH2] | 46 | 452 | 13,000 | 340 |
| [structure: 4-chlorophenyl-piperazine-CH2-CH(OH)-CH2-O-indazol-5-yl] | 410 | 3,830 | ~1,000 | ~300 |
| [structure: 4-chlorophenyl-piperazine-CH2-CH(OH)-CH2-O-2-oxoquinolin-6-yl] | 69 | 550 | ~7,500 | ~350 |
| [structure: 4-chlorophenyl-piperazine-CH2-CH(OH)-CH2-O-2-oxobenzimidazol-5-yl] | 14 | 103 | ~7,500 | ~350 |

TABLE F-continued

COMPARISON OF IC50 VALUES FOR NMDA ANTAGONISM AT PH 6.9 AND 7.6 AND hERG AND A1 ADRENERGIC RECEPTORS

| Compound | $IC_{50}$ pH 6.9 (nM) | $IC_{50}$ pH 7.6 (nM) | hERG Ki (nM) | α1 $IC_{50}$ (nM) |
|---|---|---|---|---|
| 4-Cl-phenyl-piperazine-CH2-CH(OH)-CH2-O-(5-indole) | >10,000 | >10,000 | — | — |
| 4-Cl-phenyl-piperazine-CH2-CH(OH)-CH2-O-(5-oxindole) | 370 | 29 | ~10,000 | ~100 |
| 4-Cl-phenyl-piperazine-CH2-CH(OH)-CH2-O-(5-benzimidazole-2-thione) | 16 | 76 | ~7,500 | ~150 |
| 4-Cl-phenyl-piperazine-CH2-CH(OH)-CH2-O-(6-dihydroquinolin-2-one) | 12 | 66 | ~5,000 | ~100 |

Example 17

Metabolic Stability

Compounds were incubated with pooled human (from at least 10 donors) or rat liver microsomes, 1.0 mg/ml microsomal protein, and 1 mM NADPH, in buffer at 37 C. in a shaking water bath according to the method of Clarke and Jeffrey (S. E. Clarke and P. Jeffrey; Utility of metabolic stability screening: comparison of in vitro and in vivo clearance. *Xenobiotica* 2001. 31: 591-598). At 60 min the samples were extracted and analyzed for the presence of the parent compound by LC-MS/MS. The parent material remaining in the sample at 60 min is compared to that at 0 min and expressed as a percentage. A control compound, testosterone, was run in parallel.

Example 18

Plasma Half-Life and Brain Exposure

Rats (n=3 per dose) were administered compounds at a doses of 1-4 mg/kg in a single bolus i.v. infusion (2 ml/kg body weight) via the tail vein formulated in 2% dimethyl acetamide/98% 2-hydroxy-propyl cyclodextrin (5%). Animals were fasted overnight prior to dose administration and food returned to the animals two hours after dosing. Following IV dosing, blood samples (ca 200 µL) were collected into separate tubes containing anticoagulant (K-EDTA) via the orbital plexus at various times post administration. Plasma samples were prepared immediately after collection by centrifugation for ten minutes using a tabletop centrifuge, and stored at −80° C. Brain tissue was weighed, homogenized on ice in 50 mM phosphate buffer (2 ml per brain) and the homogenate stored at −80° C. Plasma and brain homogenate samples were extracted by the addition of 5 volumes of cold acetonitrile, mixed well by vortexing and centrifuged at 4000 rpm for 15 minutes. The supernatant fractions were analyzed by LC-MS/MS operating in multiple reaction monitoring mode (MRM). The amount of parent compound in each sample was calculated by comparing the response of the analyte in the sample to that of a standard curve.

TABLE G

PLASMA STABILITY RESULTS

| Compound | PK- i.v. t½ (hr) | i.v. Cmax ng/ml | AUC (0-last h) i.v. XMPK (hr * ng/mL) | Dosing | Formulation |
|---|---|---|---|---|---|
| 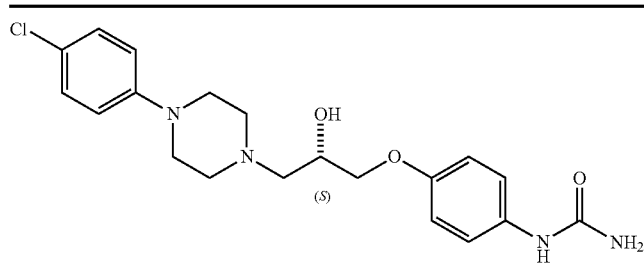 | 2.7 | 252 | 1031* | (a) 1 MPK, 0-4 hr i.v.; | 2% DMA/98% 2-HPBCD (5% in Water) |
| 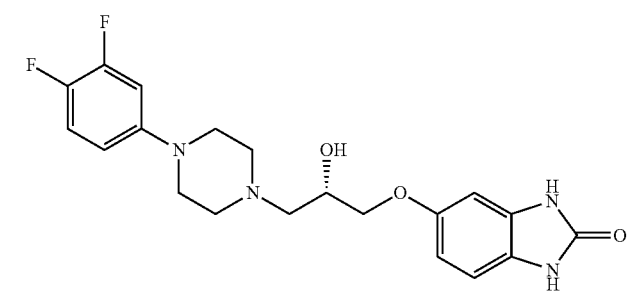 [SMILES: O=c1[nH]c2ccc(OC[C@@H](O)CN3CCN(c4ccc(F)c(F)c4)CC3)cc2[nH]1] | 2.4 | 241 | 452 | (b) 1 MPK, 0-6 hr i.v.; | 5% DMA/95% 2-HPBCD (5% in Water) |
| 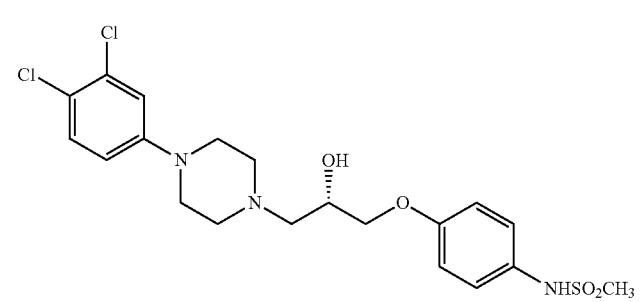 | 2.6 | 1069 | 2351 | (b) 3 MPK, 0-4 hr i.v.; | 2% DMA/98% 2-HPBCD (5% in Water) |
| 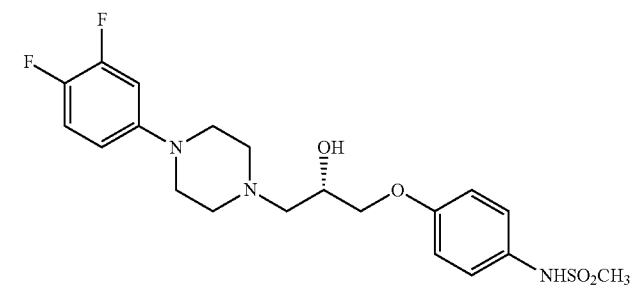 | >2 i.p.** | 13403 (30 m), 13057 (2 hr), | | 60 MPK, i.p. NP/ Ricerca | 5% DMA/95% 2-HPBCD (5% in Water) |
| 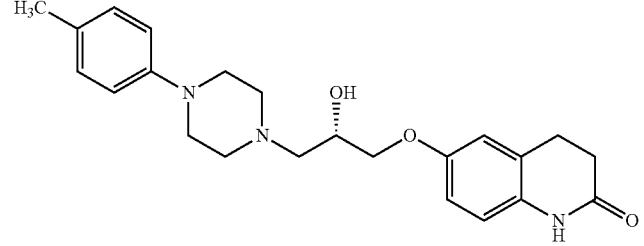 [SMILES: Cc1ccc(N2CCN(C[C@H](O)COc3ccc4c(c3)CCC(=O)N4)CC2)cc1] | 0.8 | 464 | 347 | (b) 1 MPK, 0-6 hr i.v.; | 5% DMA/95% 2-HPBCD (5% in Water) |

TABLE G-continued
PLASMA STABILITY RESULTS
| Compound | PK-i.v. t½ (hr) | i.v. Cmax ng/ml | AUC (0-last h) i.v. XMPK (hr * ng/mL) | Dosing | Formulation |
|---|---|---|---|---|---|
| 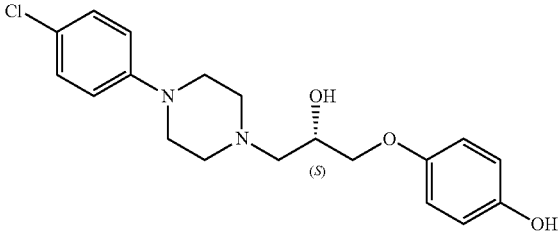 | 0.6 | 193 | 187 | (a) 1 MPK, 0-4 hr i.v.; | 2% DMA/98% 2-HPBCD (5% in Water) |
| 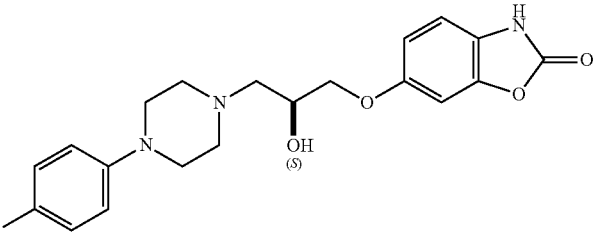 | 0.6 | 288 | 217 | (a) 1 MPK, 0-4 hr i.v.; | 2% DMA/98% 2-HPBCD (5% in Water) |
| 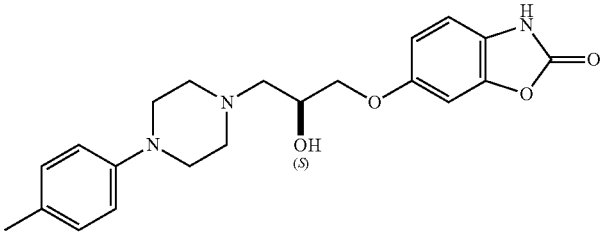 | 0.6 | 568 | 364 | (a) 1 MPK, 0-4 hr i.v.; | 2% DMA/98% 2-HPBCD (5% in Water) |
| 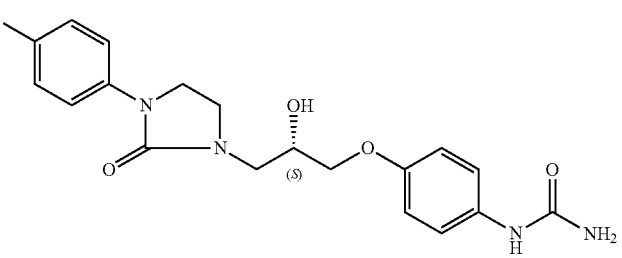 | 1.14 | 715 | 787.4 | (b) 1 MPK, 0-6 hr i.v.; 5 MPK, 0-6 hr | 10% DMA/10% EtOH/30% 2-HPBCD/ 50% water |
| 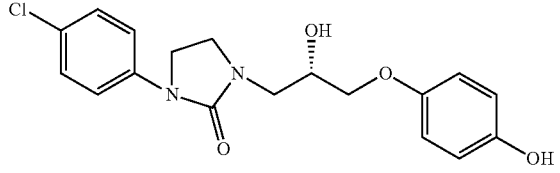 [SMILES: O=C1N(C[C@H](O)COc2ccc(O)cc2)CCN1c1ccc(Cl)cc1] | ≤0.8 hr | 377 (30 m) | | 3 MPK i.v. (Ricerca) | 2% DMA/98% 2-HPBCD (5% in Water) |
| 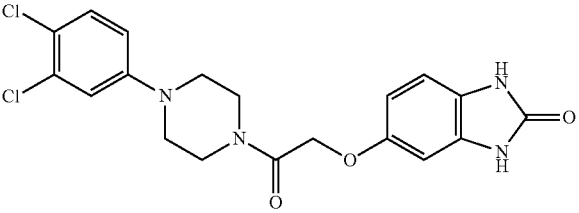 [SMILES: O=C(COc1ccc2[nH]c(=O)[nH]c2c1)N1CCN(c2ccc(Cl)c(Cl)c2)CC1] | 1.84 | 575.7 | 1096 | (b) 1 MPK, 0-6 hr i.v.; 5 MPK, 0-6 hr | 10% DMA/10% EtOH/30% 2-HPBCD/ 50% water |

US 9,079,852 B2

287                                                                                          288

TABLE G-continued

PLASMA STABILITY RESULTS

| Compound | PK-i.v. t½ (hr) | i.v. Cmax ng/ml | AUC (0-last h) i.v. XMPK (hr * ng/mL) | Dosing | Formulation |
|---|---|---|---|---|---|
| 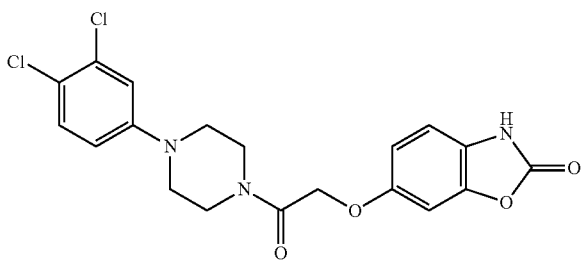 [SMILES: O=C(COc1ccc2[nH]c(=O)oc2c1)N1CCN(c2ccc(Cl)c(Cl)c2)CC1] | ~0.83 i.p. | 960 (15 m) | | 10 MPK i.p., (NeurOp/Yerkes) | 50% DMSO/50% saline |
| 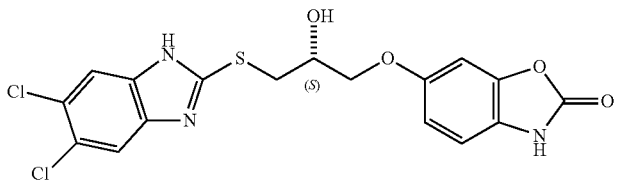 | ≤0.8 hr | 398 (30 m) | | 3 MPK i.v. (Ricerca) | 2% DMA/98% 2-HPBCD (5% in Water) |
| 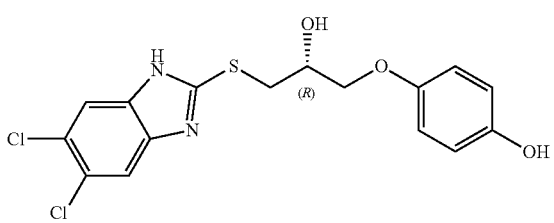 | ~0.5 hr | 413 (30 m) | | 3 MPK i.v. (Ricerca) | 2% DMA/98% 2-HPBCD (5% in Water) |

TABLE H

BRAIN PENETRATION

| Compound | RATIO: Brain:plasma (Direct) | Dosing | Formulation | BBB Pene Classification |
|---|---|---|---|---|
| 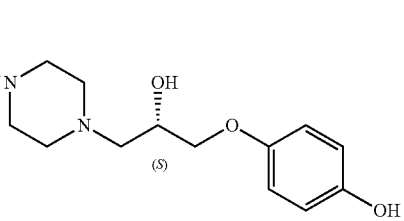 | 10.2 (avg); 11 (30 m), 9.5 (1 hr), | 3 MPK i.v. | 2% DMA/98% 2-HPBCD (5% in Water) | High |
| 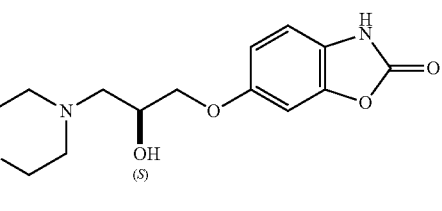 | 2.3 (avg); 2.3 (30 m), 2.9 (1 hr), 1.7 (2 hr) | 3 MPK i.v. (Ricerca) | 2% DMA/98% 2-HPBCD (5% in Water) | Moderate |

TABLE H-continued

BRAIN PENETRATION

| Compound | RATIO: Brain:plasma (Direct) | Dosing | Formulation | BBB Pene Classification |
|---|---|---|---|---|
| 3,4-difluorophenyl-piperazine-CH2-CH(OH)-CH2-O-C6H4-NHSO2CH3 | 0.77 (avg); 0.7 (30 m), 0.7 (2 hr), 0.9 (4 hr) | 60 MPK i.p. NP/Ricerca | 5% DMA/95% 2-HPBCD (5% in Water) | Moderate |
| (S)-4-chlorophenyl-piperazine-CH2-CH(OH)-CH2-O-C6H4-NHC(O)NH2 | 0.42 (avg); 0.24 (30 m), 0.53 (1 hr), 0.49 (6 hr) | 3 MPK i.v. @ 6 hr, 1 MPK @ 0.5 hr and 2 hr (Ricerca) | 2% DMA/98% 2-HPBCD (5% in Water) | Low |
| 4-chlorophenyl-imidazolidinone-CH2-CH(OH)-CH2-O-C6H4-OH | 0.59 (avg); 0.68 (30 m), 0.49 (1 hr), | 3 MPK i.v. (Ricerca) | 2% DMA/98% 2-HPBCD (5% in Water) | High |
| (S)-4-chlorophenyl-imidazolidinone-CH2-CH(OH)-CH2-O-C6H4-NHC(O)NH2 | Below Detection limit (~0) | 1 MPK i.v.; (Absorption) | 10% DMA/10% EtOH/30% 2-HPBCD/50% water | Low |
| 3,4-dichlorophenyl-piperazine-C(O)-CH2-O-benzoxazolone | 0.33 (avg); 0.25 (15 m), 0.49 (30 m), 0.30 (1 hr), 0.36 (2 hr) | 10 MPK i.p., (NeurOp/ Yerkes) | 50% DMSO/50% saline | Moderate |
| 3,4-dichlorophenyl-piperazine-C(O)-CH2-O-benzoxazolone | 0.07 (avg.); 0.04 (15 m), 0.06 (30 m), 0.07 (1 hr), 0.10 (3 hr) | 1 MPK i.v.; (Absorption) | 10% DMA/10% EtOH/30% 2-HPBCD/50% water | Moderate |

TABLE H-continued

| | BRAIN PENETRATION | | | |
|---|---|---|---|---|
| Compound | RATIO: Brain:plasma (Direct) | Dosing | Formulation | BBB Pene Classification |
| [5,6-dichloro-1H-benzimidazol-2-yl]-S-CH2-CH(OH)-CH2-O-(4-hydroxyphenyl), (R) | 0.25 (avg); 0.15 (30 m), 0.35 (1 hr), BLQ (2 hr) | 3 MPK i.v. (Ricerca) | 2% DMA/98% 2-HPBCD (5% in Water) | High |
| [5,6-dichloro-1H-benzimidazol-2-yl]-S-CH2-CH(OH)-CH2-O-(benzoxazol-2(3H)-one-6-yl), (S) | BLQ (avg); BLQ (30 m), BLQ (1 hr), | 3 MPK i.v. (Ricerca) | 2% DMA/98% 2-HPBCD (5% in Water) | Moderate |

TABLE I

| | ORAL ABSORPTION | | | | | | |
|---|---|---|---|---|---|---|---|
| Compound | % Absorbed (% F) | p.o. Cmax | p.o. Tmax hr | p.o. t½ hr | AUC (0-last h) p.o. (hr * ng/mL) | Dosing | Formulation |
| 4-(4-chlorophenyl)piperazine-CH2-CH(OH)-CH2-O-(4-ureidophenyl), (S) | 145.7** | 1556.6 | 2.67 | 6.46 | 8451 | 10 MPK, 0-8 hr p.o. | 2% DMA/98% 2-HPBCD (5% in Water) |
| 4-(3,4-difluorophenyl)piperazine-CH2-CH(OH)-CH2-O-(benzimidazol-2(3H)-one-5-yl) | 82.2 | 558 | 0.5 | 3.04 | 1856 | 5 MPK, 0-6 hr p.o. | 5% DMA/95% 2-HPBCD (5% in Water) |
| 4-(4-methylphenyl)piperazine-CH2-CH(OH)-CH2-O-(3,4-dihydroquinolin-2(1H)-one-6-yl) | 31.6 | 407 | 0.33 | 0.85 | 549 | 5 MPK, 0-6 hr p.o. | 5% DMA/95% 2-HPBCD (5% in Water) |

TABLE I-continued

ORAL ABSORPTION

| Compound | % Absorbed (% F) | p.o. Cmax | p.o. Tmax hr | p.o. t½ hr | AUC (0-last h) p.o. (hr * ng/mL) | Dosing | Formulation |
|---|---|---|---|---|---|---|---|
| *(structure: tolyl-piperazine-CH2-CH(OH)-CH2-O-benzoxazolone, (S))* | 7.9** | 57.8 | 6.7 | nc | 284 | 10 MPK, 0-8 hr p.o. | 2% DMA/ 98% 2-HPBCD (5% in Water) |
| *(structure: 4-chlorophenyl-piperazine-CH2-CH(OH)-CH2-O-benzoxazolone, (S))* | 6.2** | 30.6 | 8 | nc | 132 | 10 MPK, 0-8 hr p.o. | 2% DMA/ 98% 2-HPBCD (5% in Water) |
| *(structure: 4-chlorophenyl-piperazine-CH2-CH(OH)-CH2-O-phenol, (S))* | 3.3** | 10.2 | 5.3 | nc | 56.4 | 10 MPK, 0-8 hr p.o. | 2% DMA/ 98% 2-HPBCD (5% in Water) |

We claim:

1. A method of treatment or reducing the symptoms of neuropathic pain, stroke, traumatic brain injury, epilepsy, and other neurologic events or neurodegeneration resulting from NMDA receptor activation comprising administering to a host in need thereof an effective amount of a compound of Formula I, or a pharmaceutically acceptable salt, ester, prodrug or derivative thereof:

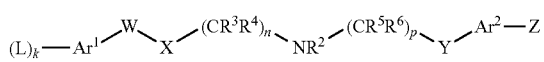

Formula I wherein:
each L is independently $C_1$-$C_6$ alkyl, $C_1$-$C_6$ alkoxy, C(=O)—($C_1$-$C_6$)-alkyl, $C_1$-$C_6$ haloalkyl, alkaryl, hydroxy, —O-alkyl, —O-aryl, —SH, —S-alkyl, —S-aryl, fluoro, chloro, bromo, iodo, nitro, or cyano; or two L groups may be taken together with $Ar^1$ to form: a dioxolane ring or a cyclobutane ring;
k=0, 1, 2, 3, 4 or 5;
each $Ar^1$ and $Ar^2$ is independently aryl or heteroaryl;
W is a bond, $C_1$-$C_4$ alkyl, or $C_2$-$C_4$ alkenyl;
X is a bond, $NR^1$ or O;
each $R^1$ and $R^2$ is independently H, $C_1$-$C_6$ alkyl, $C_2$-$C_6$ alkenyl or $C_6$-$C_{12}$ aralkyl; or $R^1$ and $R^2$ can be taken together to form a 5-8 membered ring;
each $R^3$ and $R^4$ is independently H, $C_1$-$C_6$ alkyl, $C_1$-$C_6$ alkoxy, C(=O)—($C_1$-$C_6$)-alkyl, $C_1$-$C_6$ haloalkyl, hydroxy, fluoro, chloro, bromo, iodo, nitro, or cyano; or $CR^3R^4$ is C=O;
n=1, 2, 3 or 4;
p=2, 3 or 4;
each $R^5$ and $R^6$ is independently H, $C_1$-$C_6$ alkyl, $C_1$-$C_6$ alkoxy, C(=O)—($C_1$-$C_6$)-alkyl, $C_1$-$C_6$ haloalkyl, hydroxy, fluoro, chloro, bromo, iodo, nitro, or cyano; or $CR^5R^6$ is C=O or C=$CH_2$;
or wherein —$NR^2$—$(CR^5R^6)_p$— can be

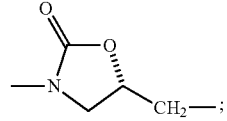

Y is a bond, O, S, SO, $SO_2$, $CH_2$, NH, N($C_1$-$C_6$ alkyl), or NHC(=O);
Z is OH, $NR^6R^7$, $NR^8SO_2$($C_1$-$C_6$ alkyl), $NR^8C(O)NR^6R^7$, $NR^8C(S)NR^6R^7$, $NR^8C(O)O(C_1$-$C_6$ alkyl), $NR^8$-dihydrothiazole, or $NR^8$-dihydroimidazole; wherein each $R^6$, $R^7$ and $R^8$ is independently H, $C_1$-$C_6$ alkyl or $C_6$-$C_{12}$ aralkyl; or $Ar^2$—Z is

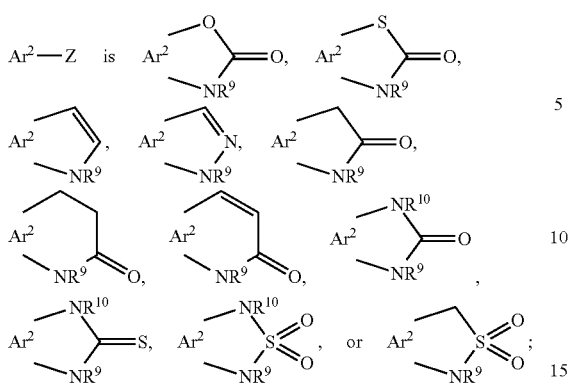

wherein $R^9$ and $R^{10}$ are each independently H, $C_1$-$C_6$ alkyl, aralkyl;

wherein when X is a bond, Y is O and $Ar^2$ is phenyl, Z is not $NR^8SO_2(C_1$-$C_6$ alkyl); and when X is O, —$NR^2$—$(CR^5R^6)_p$— is not —NH—C(=O)—, optionally in a pharmaceutically acceptable carrier;
wherein other neurologic events or neurodegeneration resulting from NMDA receptor activation are selected from the group consisting of Parkinson's disease, Alzheimer's disease, Huntington's chorea, Amyotrophic Lateral Sclerosis, ischemic injury, hypoxia, pre-eclampsia, spinal cord trauma, status epilepticus, inflammatory pain, chronic pain, vascular dementia, glioma tumors, acidification of brain or spinal cord tissue, and head trauma.

2. The method of claim 1, wherein the administration is for treatment of a host suffering from neuropathic pain.

3. The method of claim 1, wherein the administration is for reducing neuronal injury in a host suffering from a stroke or a traumatic brain injury.

4. A method of treatment or reducing the symptoms neuropathic pain, stroke, traumatic brain injury, epilepsy, and other neurologic events or neurodegeneration resulting from NMDA receptor activation comprising administering to a host in need thereof an effective amount of a compound of Formula V or a pharmaceutically acceptable salt, ester, prodrug or derivative thereof:

Ar'—W'—B'—W''—Y'—Ar''—Z'    Formula V wherein B' is selected from the group consisting of:

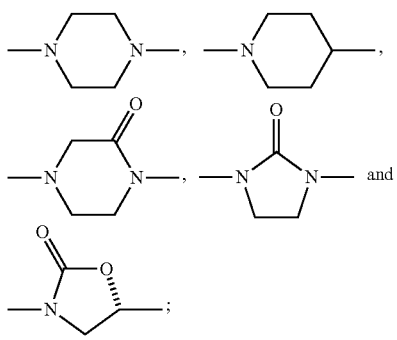

W' is a bond or $C_1$-$C_4$ alkyl;
W'' is $C_1$-$C_4$ alkyl, $C_1$-$C_4$ hydroxyalkyl, $C_1$-$C_4$ haloalkyl or C(=O)—$C_1$-$C_4$ alkyl;
Y' is selected from a bond, O, S, $CH_2$ and N;

Ar' is a substituted or unsubstituted aromatic or nonaromatic cycloalkyl which optionally may include 0-3 heteroatoms;

Ar'' is an aromatic or nonaromatic cycloalkyl which optionally may include 0-3 heteroatoms;

Z' is NRC(O)$NR_2$; wherein each R is independently selected from H, $C_1$-$C_6$ alkyl or $C_6$-$C_{12}$ aralkyl; or Ar'—Z' are taken together and selected from the group consisting of:
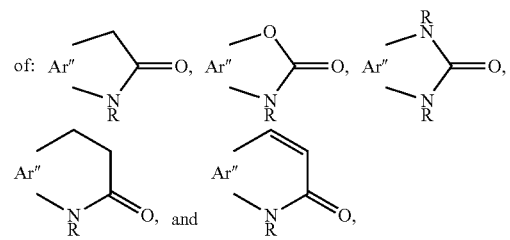

optionally in a pharmaceutically acceptable carrier;
wherein other neurologic events or neurodegeneration resulting from NMDA receptor activation are selected from the group consisting of Parkinson's disease, Alzheimer's disease, Huntington's chorea, Amyotrophic Lateral Sclerosis, ischemic injury, hypoxia, pre-eclampsia, spinal cord trauma, status epilepticus, inflammatory pain, chronic pain, vascular dementia, glioma tumors, acidification of brain or spinal cord tissue, and head trauma.

5. The method of claim 1, wherein X is $NR_1$.

6. The method of claim 5, wherein $R^1$ and $R^2$ are taken together to form a 5-8 membered ring so that —$NR^1$—$(CR^3R^4)_n$—$NR^2$— is

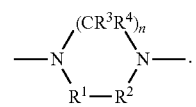

7. The method of claim 6, wherein

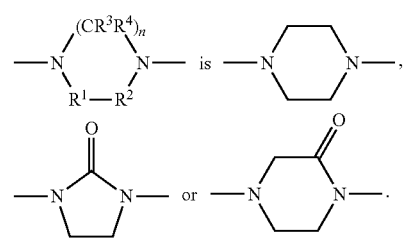

8. The method of claim 1, wherein —$NR^2$—$(CR^5R^6)_p$—is

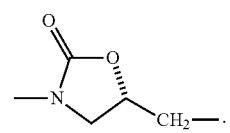

9. The method of claim 1, wherein W is a bond.
10. The method of claim 1, wherein Y is O.

11. The method of claim 1, wherein Z is $NR^8C(O)NR^6R^7$.

12. The method of claim 1, wherein

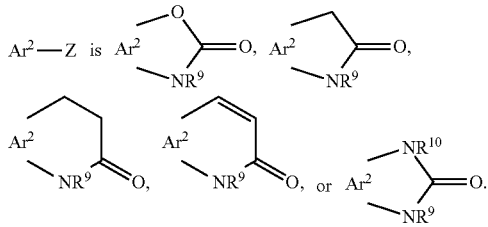

13. The method of claim 1, wherein the compound is present substantially in the form of a single enantiomer.

14. The method of claim 4, wherein B' is

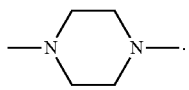

15. The method of claim 4, wherein W" is $-CH_2$ or $CH(OH)-CH_2-$.

16. The method of claim 4, wherein Ar" is phenyl.

17. The method of claim 4, wherein Z' is $NRC(O)NR_2$.

18. The method of claim 4, wherein Z and Ar" are taken together and selected from the group consisting of:

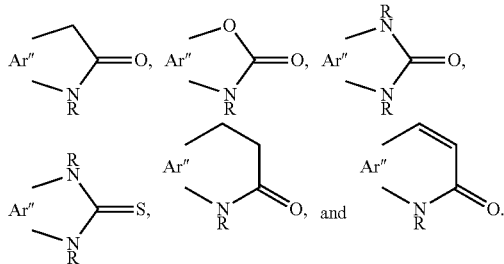

19. The method of claim 4, wherein Ar' is substituted with $(L')_{k'}$ and each L' is independently $C_1$-$C_6$ alkyl, $C_1$-$C_6$ alkoxy, $C(=O)-(C_1$-$C_6)$-alkyl, $C_1$-$C_6$ haloalkyl, alkaryl, hydroxy, —O-alkyl, —O-aryl, —SH, —S-alkyl, —S-aryl, fluoro, chloro, bromo, iodo, nitro, or cyano; or two L' groups may be taken together with Ar' to form: a dioxolane ring or a cyclobutane ring; and k'=0, 1, 2, 3, 4 or 5.

20. The method of claim 19, wherein an L' group is in the para position on Ar'.

21. The method of claim 20, wherein L' in the para position is a halogen.

22. The method of claim 20, wherein L' in the para position is a $C_1$-$C_6$ alkyl.

23. The method of claim 4, wherein the compound is selected from the group consisting of:

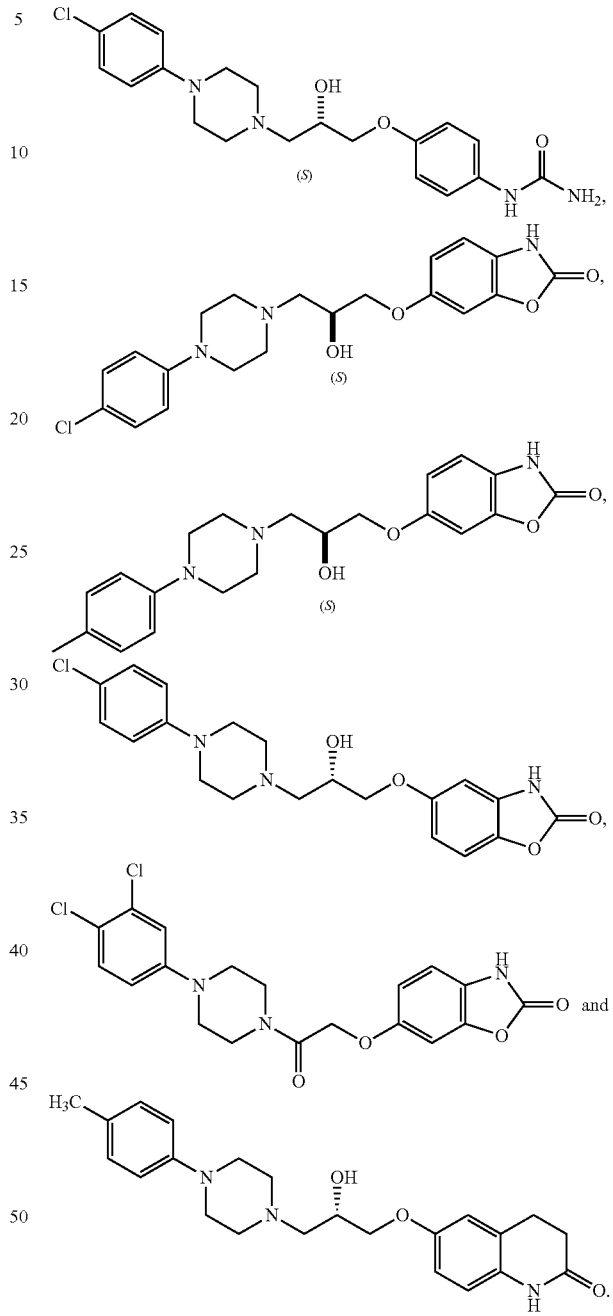

* * * * *